US008507174B2

(12) United States Patent
Takahashi et al.

(10) Patent No.: US 8,507,174 B2
(45) Date of Patent: Aug. 13, 2013

(54) POSITIVE RESIST COMPOSITION, PATTERN FORMING METHOD USING THE COMPOSITION, AND COMPOUND FOR USE IN THE COMPOSITION

(75) Inventors: Hidenori Takahashi, Haibara-gun (JP); Kenji Wada, Haibara-gun (JP); Sou Kamimura, Haibara-gun (JP)

(73) Assignee: FUJIFILM Corporation, Tokyo (JP)

( * ) Notice: Subject to any disclaimer, the term of this patent is extended or adjusted under 35 U.S.C. 154(b) by 482 days.

(21) Appl. No.: 12/673,096

(22) PCT Filed: Aug. 11, 2008

(86) PCT No.: PCT/JP2008/064419
§ 371 (c)(1),
(2), (4) Date: Feb. 11, 2010

(87) PCT Pub. No.: WO2009/022681
PCT Pub. Date: Feb. 19, 2009

(65) Prior Publication Data
US 2011/0183258 A1 Jul. 28, 2011

(30) Foreign Application Priority Data

Aug. 10, 2007 (JP) ................. 2007-209034
Sep. 21, 2007 (JP) ................. 2007-245331
Jan. 15, 2008 (JP) ................. 2008-005705
Mar. 21, 2008 (JP) ................. 2008-074740

(51) Int. Cl.
*G03F 7/039* (2006.01)
*G03F 7/20* (2006.01)
*G03F 7/30* (2006.01)

(52) U.S. Cl.
USPC ........ 430/270.1; 430/311; 430/326; 430/905; 558/52; 560/150; 560/155; 560/171; 560/174; 560/176; 549/378; 549/396

(58) Field of Classification Search
None
See application file for complete search history.

(56) References Cited

U.S. PATENT DOCUMENTS

| 4,405,708 | A | * | 9/1983 | van Pelt et al. ............. 430/281.1 |
| 4,480,910 | A | | 11/1984 | Takanashi |
| 6,245,492 | B1 | * | 6/2001 | Huang et al. ................ 430/326 |
| 6,576,392 | B1 | | 6/2003 | Sato |
| 6,794,108 | B1 | * | 9/2004 | Sato et al. .................. 430/270.1 |
| 8,088,550 | B2 | * | 1/2012 | Tarutani et al. ............ 430/270.1 |
| 2005/0014090 | A1 | | 1/2005 | Hirayama |
| 2005/0147920 | A1 | * | 7/2005 | Lin et al. ..................... 430/311 |
| 2006/0154171 | A1 | | 7/2006 | Hirayama |
| 2007/0134588 | A1 | * | 6/2007 | Kanda et al. ............... 430/270.1 |
| 2007/0178394 | A1 | | 8/2007 | Hirayama |
| 2009/0035692 | A1 | * | 2/2009 | Tarutani et al. ............ 430/270.1 |
| 2009/0130605 | A1 | | 5/2009 | Hirayama |
| 2011/0183258 | A1 | | 7/2011 | Takahashi et al. |

FOREIGN PATENT DOCUMENTS

| EP | 1447403 A1 | 8/2004 |
| EP | 1717261 A1 | 11/2006 |
| JP | 57-153433 A | 9/1982 |
| JP | 6-041221 A | 2/1994 |
| JP | 7-220990 A | 8/1995 |
| JP | 08 248561 A | 9/1996 |
| JP | 8-248561 A | 9/1996 |
| JP | 9-034106 A | 2/1997 |
| JP | 11-158118 A | 6/1999 |
| JP | 2000-035665 A | 2/2000 |
| JP | 2000-122291 A | 4/2000 |
| JP | 2000-227659 A | 8/2000 |
| JP | 2001 022069 A | 1/2001 |
| JP | 3173368 B | 3/2001 |
| JP | 2001-114825 A | 4/2001 |
| JP | 2001-206917 A | 7/2001 |
| JP | 2002-075857 A | 3/2002 |
| JP | 2002-323768 A | 11/2002 |
| JP | 2007-114431 A | 5/2007 |
| JP | 2009 075427 A | 4/2009 |
| WO | 2004/068242 A1 | 8/2004 |
| WO | 2004/077158 A1 | 9/2004 |

OTHER PUBLICATIONS

JPO English abstract for JP 9-34106 (1997).*
Machine-assisted English translation of JP 8-248561, provided by JPO (1996).*
International Search Report (PCT/ISA/210) dated Oct. 14, 2008 in PCT/JP2008/064419.
International Preliminary Examination Report (PCT/ISA/237) dated Aug. 11, 2008 in PCT/JP2008/064419.
Lin, "Semiconductor Foundry, Lithography, and Partners," Proceedings of SPIE, vol. 4688, pp. 11-24 (2002).
Park et al, "A Novel Photoresist Based on Polymeric Acid Amplifiers," Chemical Letters, pp. 1036-1037 (2000).
Ichimura, "Nonlinear Organic Reactions to Proliferate Acidic and Basic Molecules and Their Applications," The Chemical Record, vol. 2, pp. 46-55 (2002).
Arimitsu et al, "Autocatalytic Fragmentation of Acetoacetate Derivatives as Acid Amplifiers to Proliferate Acid Molecules," Journal of the American Chemical Society, vol. 120, pp. 37-45 (1998).
Fukuchi et al, "Catalytic asymmetric aldol reactions of enolizable carbon pronucleophiles with formaldehyde and ethyl gyloxylate," Advanced Synthesis and Catalysis, vol. 349, pp. 509-512 (2007).
Extended European Search Report issued on May 19, 2011 in European Patent Application No. 08827323.0.
Office Action dated Mar. 12, 2012 in European Patent Application No. 08827323.0.
Office Action dated Mar. 13, 2012 in Japanese Patent Application No. 2008-074740.

* cited by examiner

*Primary Examiner* — Sin J. Lee
(74) *Attorney, Agent, or Firm* — Sughrue Mion, PLLC

(57) ABSTRACT

A positive resist composition comprising (A) a compound capable of generating an acid upon irradiation with an actinic ray or radiation, (B) a resin capable of increasing the solubility in an alkali developer by the action of an acid, and (C) a compound having a specific structure, which decomposes by the action of an acid to generate an acid, a pattern forming method using the positive resist composition, and a compound for use in the positive resist composition are provided as a positive resist composition exhibiting good performance in terms of pattern profile, line edge roughness, pattern collapse, sensitivity and resolution in normal exposure (dry exposure), immersion exposure and double exposure, a pattern forming method using the positive resist composition and a compound for use in the positive resist composition.

18 Claims, 1 Drawing Sheet

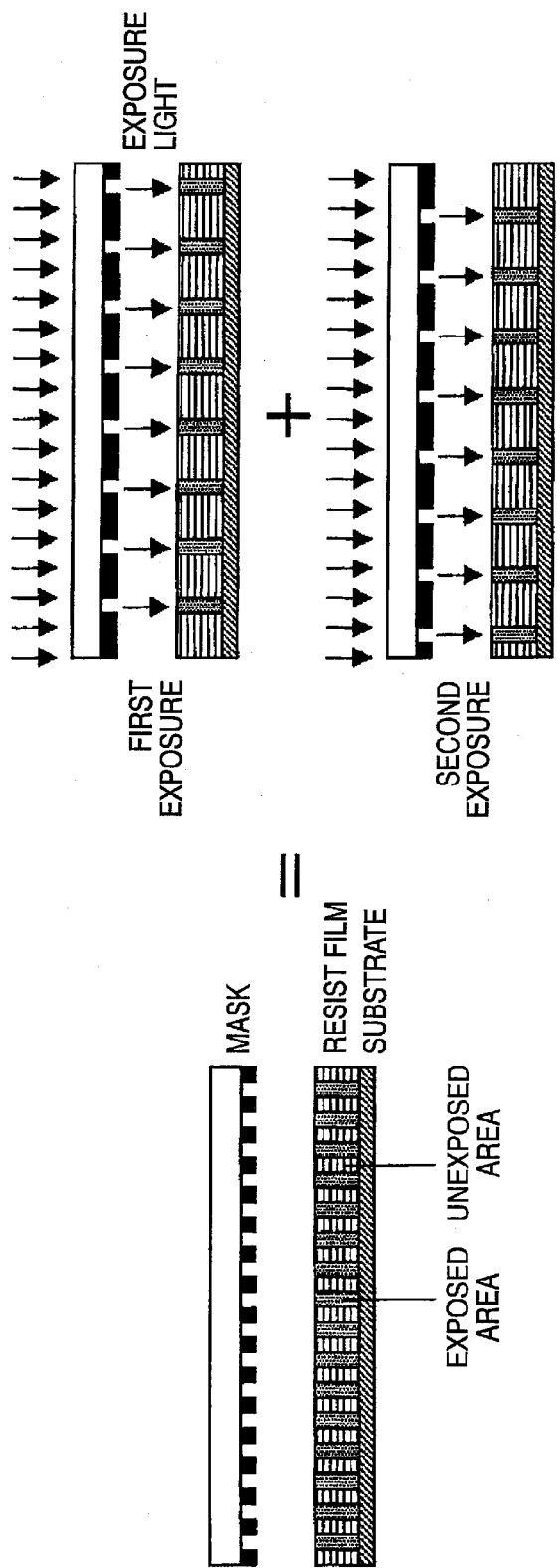

POSITIVE RESIST COMPOSITION, PATTERN FORMING METHOD USING THE COMPOSITION, AND COMPOUND FOR USE IN THE COMPOSITION

TECHNICAL FIELD

The present invention relates to a positive resist composition capable of changing its property by undergoing a reaction upon irradiation with an actinic ray or radiation, a pattern forming method using the positive resist composition, and a compound for use in the positive resist composition. More specifically, the present invention relates to a positive resist composition for use in the process of producing a semiconductor such as IC, in the production of a circuit board for liquid crystal, thermal head and the like, in other photofabrication processes, or in a lithographic printing plate or an acid-curable composition, and also relates to a pattern forming method using the positive resist composition and a compound for use in the positive resist composition.

BACKGROUND ART

A chemical amplification resist composition is a pattern forming material of forming a pattern on a substrate by producing an acid in the exposed area upon irradiation with an actinic ray or radiation such as far ultraviolet light and through a reaction using the acid as a catalyst, changing the developer solubility of the area irradiated with an actinic ray or radiation and that of the non-irradiated area.

A so-called immersion method of filling a high refractive-index liquid (hereinafter sometimes referred to as an "immersion liquid") between a projection lens and a sample has been conventionally known as a technique for enhancing the resolution in an optical microscope.

As for the "effect of immersion", assuming that $NA_0 = \sin\theta$, the resolution and depth of focus in immersion can be expressed by the following formulae:

(Resolution)=$k_1 \cdot (\lambda_0/n)/NA_0$ (Depth of focus)=$\pm k_2 \cdot (\lambda_0/n)/NA_0^2$ wherein $\lambda_0$ is the wavelength of exposure light in air, n is the refractive index of the immersion liquid based on air, and $\theta$ is the convergence half-angle of beam.

That is, the effect of immersion is equal to use of an exposure wavelength of 1/n. In other words, when the projection optical system has the same NA, the depth of focus can be made n times larger by the immersion. This is effective for all pattern profiles and furthermore, can be combined with the super-resolution technology under study at present, such as phase-shift method and modified illumination method.

Examples of the apparatus where the effect above is applied to transfer of a fine image pattern of a semiconductor device is described in, for example, Patent Documents 1 and 2.

Recent technical progress in the immersion exposure is reported, for example, in Non-Patent Document 1 and Patent Document 3. In the case of using an ArF excimer laser as a light source, pure water (refractive index at 193 nm: 1.44) is considered to be most promising as the immersion liquid in view of safety in handling as well as transmittance and refractive index at 193 nm. In the case of using an $F_2$ excimer laser as a light source, a fluorine-containing solution is being studied from the aspect of balance between transmittance and refractive index at 157 nm, but a solution satisfied in terms of environmental safety and refractive index has not yet been found. Considering the degree of immersion effect and the perfection of resist, the immersion exposure technique is expected to be most soon mounted on an ArF exposure machine.

Also, it is pointed out that when the chemical amplification resist is applied to immersion exposure, the resist layer comes into contact with the immersion liquid at the exposure, as a result, the resist layer deteriorates or a component adversely affecting the immersion liquid bleeds out from the resist layer. Patent Document 4 describes a case where when a resist for ArF exposure is dipped in water before and after exposure, the resist performance is changed, and this is indicated as a problem in the immersion exposure.

As regards the medium filled between a projection lens and a semiconductor substrate, which is used in the immersion exposure, water having a refractive index of 1.44 is employed in view of easy availability and safety and by using an exposure machine having a projection lens with NA of 1.2 to 1.35, pattern formation of a semiconductor device in a design dimension up to a 45 nm generation is considered to be possible.

The generation next to the design dimension of 45 nm is a 32 nm generation, and it is considered that NA of 1.65 is necessary for the pattern formation of a 32 nm-generation semiconductor device and in this case, the medium filled between a projection lens and a semiconductor substrate must have a refractive index of 1.8 or more.

Meanwhile, the material of a projection lens having NA of 1.65 is required to have a refractive index of 1.9 or more, and LuAg is currently supposed to be a promising candidate therefor, but its problem of absorbing a large amount of light passed has not yet been solved.

Furthermore, a candidate medium having a refractive index of 1.8 or more has also not yet been found.

For these reasons, there is attracting attention a method where a special pattern forming method using an exposure machine with a projection lens having NA of 1.2 to 1.35 is used for the pattern formation of a 32 nm-generation semiconductor device.

Several methods have been proposed for this special pattern forming method, and one of these methods is a double exposure process.

The double exposure process is, as described in Patent Document 5, a process of exposing the same photoresist film two times, and this is a method where the pattern in the exposure field is divided into two pattern groups and the exposure is preformed in twice for respective pattern groups divided.

Patent Document 5 indicates that this method inevitably requires a property like a two-photon absorption resist, that is, a property of the photosensitivity or developer solubility being changed in proportion to the square of exposure intensity, but a resist having such a property has not yet been developed.

Also, a compound capable of decomposing by the action of an acid to generate an acid is described in Non-Patent Documents 2 and 3.

On the other hand, in respect of the pattern forming method for a 32-nm generation semiconductor device, development of lithography using electron beam, X-ray or UV light is also proceeding.

In particular, the electron beam lithography is positioned as a next-generation or next-next-generation pattern formation technique, and a positive resist assured of high sensitivity and high resolution is demanded. Above all, the elevation of sensitivity is very important so as to shorten the wafer processing time, but in the positive resist for electron beam, when higher sensitivity is sought for, this incurs not only reduction in the resolution but also worsening of the line edge roughness, and development of a resist satisfying all of these properties at the same time is strongly desired. The line edge roughness as used herein means that the resist edge at the interface between the pattern and the substrate irregularly fluctuates in the direction perpendicular to the line direction due to resist characteristics and when the pattern is viewed from right above, the edge gives an uneven appearance. This unevenness is transferred in the etching step using the resist as a mask and gives rise to deterioration of electrical properties and in turn, reduction in the yield. Particularly, in the ultrafine region of 0.25 µm or less, the line edge roughness is a very important problem to be solved. The high sensitivity is in a trade-off relationship with high resolution, good pattern profile and good line edge roughness and it is very important how to satisfy these properties all at the same time.

In the case of using an EUV light source, the light belongs to an extreme-ultraviolet wavelength region and has high energy, and a concerted photochemical reaction such as negative conversion ascribable to EUV light is brought about, which gives rise to a problem such as reduction in the contrast. Accordingly, it is an important task also in the lithography using X-ray or EUV light to satisfy all of high sensitivity, high resolution and the like, and this task needs to be solved.

As regards the resist suitable for such a lithography process using electron beam, X-ray or EUV light, a chemical amplification resist utilizing an acid catalytic reaction is mainly employed from the standpoint of elevating the sensitivity, and in the case of a positive resist, a chemical amplification resist composition containing, as main components, an acid generator and a phenolic resin having a property of being insoluble or sparingly soluble in an alkali developer and becoming soluble in an alkali developer by the action of an acid (hereinafter simply referred to as a "phenolic acid-decomposable resin") is effectively used.

With respect to such a positive resist for electron beam, X-ray or EUV light, as described, for example, in Patent Documents 6 to 11, some resist compositions containing a phenolic acid-decomposable resin have been heretofore known.

Also, as described in Patent Documents 12 and 13, a radiation-sensitive resin composition having blended therein a compound capable of decomposing by the action of an acid to generate an acid is known.

However, these techniques have not succeeded so far by any combination in satisfying all of high sensitivity, high resolution, good pattern profile and good line edge roughness in the ultrafine region.

Patent Document 1: JP-A-57-153433 (the term "JP-A" as used herein means an "unexamined published Japanese patent application")
Patent Document 2: JP-A-7-220990
Patent Document 3: International Publication No. 04/077158, pamphlet
Patent Document 4: International Publication No. 04/068242, pamphlet
Patent Document 5: JP-A-2002-75857
Patent Document 6: JP-A-2002-323768
Patent Document 7: JP-A-6-41221
Patent Document 8: Japanese Patent No. 3,173,368
Patent Document 9: JP-A-2000-122291
Patent Document 10: JP-A-2001-114825
Patent Document 11: JP-A-2001-206917
Patent Document 12: JP-A-2000-35665
Patent Document 13: JP-A-2007-114431

Non-Patent Document 1: Proc. SPIE, Vol. 4688, page 11 (2002)
Non-Patent Document 2: Chem. Lett., 1036 (2000)
Non-Patent Document 3: The Chemical Record, Vol. 2, 46-55 (2002)

DISCLOSURE OF THE INVENTION

Problems that the Invention is to Solve

An object of the present invention is to provide a positive resist composition ensuring good performance in terms of pattern profile, line edge roughness, pattern collapse, sensitivity and resolution not only in normal exposure (dry exposure) but also in immersion exposure, a pattern forming method using the positive resist composition, and a compound for use in the positive resist composition. Another object of the present invention is to provide a positive resist composition suitable for double exposure, ensuring good performance in terms of pattern profile, line edge roughness, pattern collapse, sensitivity and resolution in double exposure, a pattern forming method using the positive resist composition, and a compound for use in the positive resist composition.

Still another object of the present invention is to solve the technical task of enhancing the performance in the microfabrication of a semiconductor device, where electron beam, X-ray or EUV light is used, and provide a positive resist composition for electron beam, X-ray or EUV light, which can satisfy all of high sensitivity, high resolution, good pattern profile and good line edge roughness, and a pattern forming method using the composition.

Means for Solving the Problems

The present invention is as follows.
(1) A positive resist composition, comprising:
(A) a compound capable of generating an acid upon irradiation with an actinic ray or radiation;
(B) a resin capable of increasing a solubility in an alkali developer by an action of an acid; and
(C) a compound represented by the following formula (I), which decomposes by an action of an acid to generate an acid:

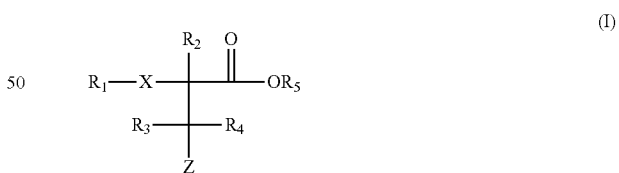

wherein $R_1$ represents an alkyl group, a cycloalkyl group, an alkoxy group, an aryl group or an aryloxy group;
$R_2$ represents an alkyl group or a cycloalkyl group;
$R_1$ and $R_2$ may combine with each other to form a monocyclic or polycyclic hydrocarbon structure;
each of $R_3$ and $R_4$ independently represents a hydrogen atom or an alkyl group;
$R_5$ represents a group capable of leaving by an action of an acid;
X represents $—SO_2—$, $—SO—$ or $—CO—$; and
Z represents a residue of an organic acid represented by ZH.

(2) The positive resist composition as described in (1) above,
wherein the compound of component (C) is represented by the following formula (Ia) or (Ib):

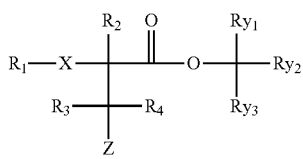

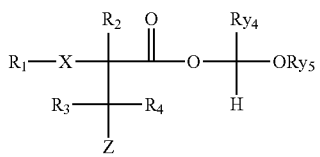

wherein $R_1$ represents an alkyl group, a cycloalkyl group, an alkoxy group, an aryl group or an aryloxy group;

$R_2$ represents an alkyl group or a cycloalkyl group;

$R_1$ and $R_2$ may combine with each other to form a monocyclic or polycyclic hydrocarbon structure;

each of $R_3$ and $R_4$ independently represents a hydrogen atom or an alkyl group;

X represents $-SO_2-$, $-SO-$ or $-CO-$;

Z represents a residue of an organic acid represented by ZH;

each of $Ry_1$ to $Ry_3$ independently represents an alkyl group or a cycloalkyl group, and at least two members out of $Ry_1$ to $Ry_3$ may combine with each other to form a monocyclic or polycyclic hydrocarbon structure, provided that at least one of $Ry_1$ to $Ry_3$ represents a cycloalkyl group or at least two members out of $Ry_1$ to $Ry_3$ are combined to form a monocyclic or polycyclic hydrocarbon structure;

$Ry_4$ represents a hydrogen atom, an alkyl group or a cycloalkyl group;

$Ry_5$ represents a cycloalkyl group; and $Ry_4$ and $Ry_5$ may combine with each other to form a monocyclic or polycyclic hydrocarbon structure.

(3) The positive resist composition as described in (1) above,
wherein the compound of component (C) is represented by the following formula (II):

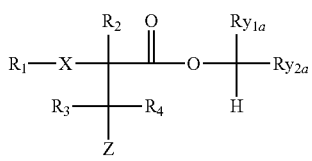

wherein $R_1$ represents an alkyl group, a cycloalkyl group, an alkoxy group, an aryl group or an aryloxy group;

$R_2$ represents an alkyl group or a cycloalkyl group;

$R_1$ and $R_2$ may combine with each other to form a monocyclic or polycyclic hydrocarbon structure;

each of $R_3$ and $R_4$ independently represents a hydrogen atom or an alkyl group;

$Ry_{1a}$ represents a hydrogen atom, an alkyl group, a cycloalkyl group, an alkoxy group, an aryl group, or an alkylene group bonded to $Ry_{2a}$;

$Ry_{2a}$ represents an aryl group or an aryloxy group;

X represents $-SO_2-$, $-SO-$ or $-CO-$; and

Z represents a residue of an organic acid represented by ZH.

(4) The positive resist composition as described in (3) above,
wherein the compound of component (C), is represented by the following formula (IIa) or (IIb):

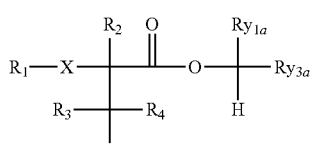

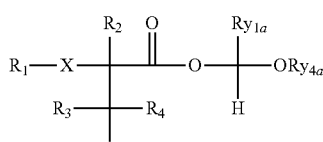

wherein $R_1$ represents an alkyl group, a cycloalkyl group, an alkoxy group, an aryl group or an aryloxy group;

$R_2$ represents an alkyl group or a cycloalkyl group;

$R_1$ and $R_2$ may combine with each other to form a monocyclic or polycyclic hydrocarbon structure;

each of $R_3$ and $R_4$ independently represents a hydrogen atom or an alkyl group;

$Ry_{1a}$ represents a hydrogen atom, an alkyl group, a cycloalkyl group, an alkoxy group, an aryl group, or an alkylene group bonded to $Ry_{3a}$ or $Ry_{4a}$;

$Ry_{3a}$ represents an aryl group;

$Ry_{4a}$ represents an aryl group;

X represents $-SO_2-$, $-SO-$ or $-CO-$; and

Z represents a residue of an organic acid represented by ZH.

(5) The positive resist composition as described in (1) above,
wherein ZH is selected from a sulfonic acid, a carboxylic acid, an imide acid and a methide acid.

(6) The positive resist composition as described in (1) above, which further comprises:
a hydrophobic resin.

(7) A pattern forming method, comprising:
steps of forming a resist film from the positive resist composition as described in any one of (1) to (6) above; and subjecting the resist film to exposure and development.

(8) A pattern forming method, comprising:
steps of forming a resist film from the positive resist composition as described in any one of (1) to (6) above: and subjecting the resist film to immersion exposure and development.

(9) A pattern forming method, comprising:
steps of forming a resist film from the positive resist composition as described in any one of (1) to (6) above; forming a hydrophobic resin-containing topcoat on the resist film; and subjecting the resist film to immersion exposure and development.

(10) A pattern forming method, comprising:
steps of forming a resist film from the positive resist composition as described in any one of (1) to (6) above; and subjecting the resist film to double exposure and development.

(11) A pattern forming method, comprising:
steps of forming a resist film from the positive resist composition as described in any one of (1) to (6) above; and subjecting the resist film to immersion double exposure and development.

(12) A pattern forming method, comprising:
steps of forming a resist film from the positive resist composition as described in any one of (1) to (6) above; forming a hydrophobic resin-containing topcoat on the resist film; and subjecting the resist film to immersion double exposure and development.

(13) A compound represented by the following formula (I):

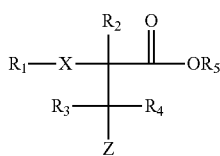
(I)

wherein $R_1$ represents an alkyl group, a cycloalkyl group, an alkoxy group, an aryl group or an aryloxy group;
$R_2$ represents an alkyl group or a cycloalkyl group;
$R_1$ and $R_2$ may combine with each other to form a monocyclic or polycyclic hydrocarbon structure;
each of $R_3$ and $R_4$ independently represents a hydrogen atom or an alkyl group;
$R_5$ represents a group capable of leaving by an action of an acid;
X represents —SO$_2$—, —SO— or —CO—; and
Z represents a residue of an organic acid represented by ZH.

(14) A compound represented by the following formula (Ia) or (Ib):

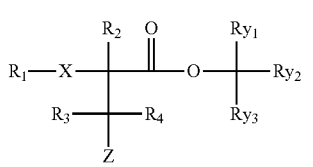
(Ia)

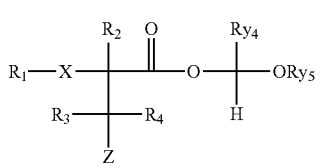
(Ib)

wherein $R_1$ represents an alkyl group, a cycloalkyl group, an alkoxy group, an aryl group or an aryloxy group;
$R_2$ represents an alkyl group or a cycloalkyl group;
$R_1$ and $R_2$ may combine with each other to form a monocyclic or polycyclic hydrocarbon structure;
each of $R_3$ and $R_4$ independently represents a hydrogen atom or an alkyl group;
X represents —SO$_2$—, —SO— or —CO—;
Z represents a residue of an organic acid represented by ZH;
each of $Ry_1$ to $Ry_3$ independently represents an alkyl group or a cycloalkyl group, and at least two members out of $Ry_1$ to $Ry_3$ may combine with each other to form a monocyclic or polycyclic hydrocarbon structure, provided that at least one of $Ry_1$ to $Ry_3$ represents a cycloalkyl group or at least two members out of $Ry_1$ to $Ry_3$ are combined to form a monocyclic or polycyclic hydrocarbon structure;
$Ry_4$ represents a hydrogen atom, an alkyl group or a cycloalkyl group;
$Ry_5$ represents a cycloalkyl group; and
$Ry_4$ and $Ry_5$ may combine with each other to form a monocyclic or polycyclic hydrocarbon structure.

(15) The compound as described in (13) above,
wherein ZH is selected from a sulfonic acid, a carboxylic acid, an imide acid and a methide acid.

(16) A compound represented by the following formula (II):

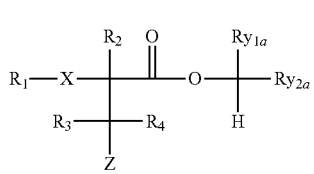
(II)

wherein $R_1$ represents an alkyl group, a cycloalkyl group, an alkoxy group, an aryl group or an aryloxy group;
$R_2$ represents an alkyl group or a cycloalkyl group;
$R_1$ and $R_2$ may combine with each other to form a monocyclic or polycyclic hydrocarbon structure;
each of $R_3$ and $R_4$ independently represents a hydrogen atom or an alkyl group;
$Ry_{1a}$ represents a hydrogen atom, an alkyl group, a cycloalkyl group, an alkoxy group, an aryl group, or an alkylene group bonded to $Ry_{2a}$;
$Ry_{2a}$ represents an aryl group or an aryloxy group;
X represents —SO$_2$—, —SO— or —CO—; and
Z represents a residue of an organic acid represented by ZH.

(17) A compound represented by the following formula (IIa) or (IIb):

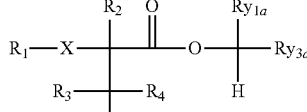
(IIa)

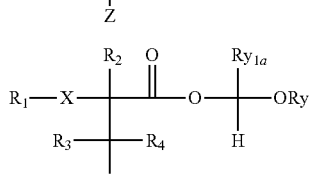
(IIb)

wherein $R_1$ represents an alkyl group, a cycloalkyl group, an alkoxy group, an aryl group or an aryloxy group;
$R_2$ represents an alkyl group or a cycloalkyl group;
$R_1$ and $R_2$ may combine with each other to form a monocyclic or polycyclic hydrocarbon structure;
each of $R_3$ and $R_4$ independently represents a hydrogen atom or an alkyl group;
$Ry_{1a}$ represents a hydrogen atom, an alkyl group, a cycloalkyl group, an alkoxy group, an aryl group, or an alkylene group bonded to $Ry_{3a}$ or $Ry_{4a}$;
$Ry_{3a}$ represents an aryl group;
$Ry_{4a}$ represents an aryl group;
X represents —SO— or —CO—; and
Z represents a residue of an organic acid represented by ZH.

(18) The compound as described in (16) above,
wherein ZH is an organic acid selected from a sulfonic acid, a carboxylic acid, an imide acid and a methide acid.

Furthermore, the preferred embodiment of the present invention includes the following constructions.

(19) The positive resist composition as described in (1) above,
wherein the compound of component (A) is a sulfonium salt of fluoro-substituted alkanesulfonic acid, fluorine-substituted benzenesulfonic acid, fluorine-substituted imide acid or fluorine-substituted methide acid.

(20) The positive resist composition as described in (1) above,
wherein the resin of component (B) contains an acid-decomposable repeating unit having a monocyclic or polycyclic alicyclic hydrocarbon structure.

(21) The positive resist composition as described in (20) above,
wherein the resin of component (B) further contains a repeating unit having a lactone structure.

(22) The positive resist composition as described in (20) above,
wherein the resin of component (B) further contains a repeating unit having a hydroxyl group or a cyano group.

(23) The positive resist composition as described in (20) above,
wherein the resin of component (13) further contains a repeating unit having a carboxyl group.

(24) The positive resist composition as described in (20) above,
wherein the resin of component (B) further contains a repeating unit having a hexafluoroisopropanol structure.

(25) The positive resist composition as described in (1) above,
wherein the resin of component (B) contains a hydroxystyrene-based repeating unit.

(26) The positive resist composition as described in (1) above, which further comprises:
a dissolution inhibiting compound having a molecular weight of 3,000 or less and being capable of decomposing by an action of an acid to increase a solubility in an alkali developer.

(27) The positive resist composition as described in (1) above, which further comprises:
a basic compound and/or a fluorine-containing and/or silicon-containing surfactant.

(28) The positive resist composition as described in (27) above,
wherein the basic compound is a compound having a structure selected from an imidazole structure, a diazabicyclo structure, an onium hydroxide structure, an onium carboxylate structure, a trialkylamine structure, an aniline structure and a pyridine structure, an alkylamine derivative having a hydroxyl group and/or an ether bond, or an aniline derivative having a hydroxyl group and/or an ether bond.

Advantage of the Invention

According to the present invention, a positive resist composition ensuring good performance in terms of pattern profile, line edge roughness, pattern collapse, sensitivity and resolution not only in normal exposure (dry exposure) but also in immersion exposure, a pattern forming method using the positive resist composition, and a compound for use in the positive resist composition can be provided. Also, a positive resist composition suitable for double exposure, ensuring good performance in terms of pattern profile, line edge roughness, pattern collapse, sensitivity and resolution in double exposure, a pattern forming method using the positive resist composition, and a compound for use in the positive resist composition can be provided.

Furthermore, according to the present invention, a positive resist composition for electron beam, X-ray or EUV light, which can satisfy all of high sensitivity, high resolution, good pattern profile and good line edge roughness particularly in the electron beam, X-ray or EUV exposure, and a pattern forming method using the composition can be provided.

BRIEF DESCRIPTION OF THE DRAWING

FIG. 1 is a schematic view showing the state in the double exposure process according to the present invention.

BEST MODE FOR CARRYING OUT THE INVENTION

The best mode for carrying out the present invention is described below.

Incidentally, in the present invention, when a group (atomic group) is denoted without specifying whether substituted or unsubstituted, the group includes both a group having no substituent and a group having a substituent. For example, an "alkyl group" includes not only an alkyl group having no substituent (unsubstituted alkyl group) but also an alkyl group having a substituent (substituted alkyl group).

(A) Compound Capable of Generating an Acid Upon Irradiation with an Actinic Ray or Radiation The positive resist composition of the present invention contains a compound capable of generating an acid upon irradiation with an actinic ray or radiation (hereinafter sometimes referred to as an "acid generator").

The acid generator which can be used may be appropriately selected from a photo-initiator for cationic photopolymerization, a photo-initiator for radical photopolymerization, a photo-decoloring agent for dyes, a photo-discoloring agent, a compound known to generate an acid upon irradiation with an actinic ray or radiation and used for a microresist and the like, and a mixture thereof.

Examples thereof include a diazonium salt, a phosphonium salt, a sulfonium salt, an iodonium salt, an imidosulfonate, an oxime sulfonate, a diazodisulfone, a disulfone and an o-nitrobenzyl sulfonate.

Also, a compound where such a group or compound capable of generating an acid upon irradiation with an actinic ray or radiation is introduced into the main or side chain of the polymer, for example, compounds described in U.S. Pat. No. 3,849,137, German Patent 3,914,407, JP-A-63-26653, JP-A-55-164824, JP-A-62-69263, JP-A-63-146038, JP-A-63-163452, JP-A-62-153853 and JP-A-63-146029, may be used.

Furthermore, compounds capable of generating an acid by the effect of light described, for example, in U.S. Pat. No. 3,779,778 and European Patent 126,712 may also be used.

Out of the acid generators, preferred compounds include compounds represented by the following formulae (ZI), (ZII) and (ZIII):

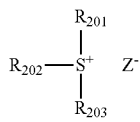

ZI

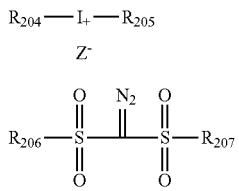

in formula (ZI), each of $R_{201}$, $R_{202}$ and $R_{203}$ independently represents an organic group.

The number of carbons in the organic group as $R_{201}$, $R_{202}$ and $R_{203}$ is generally from 1 to 30, preferably from 1 to 20.

Two members out of $R_{201}$ to $R_{203}$ may combine to form a ring structure, and the ring may contain an oxygen atom, a sulfur atom, an ester bond, an amide bond or a carbonyl group. Examples of the group formed by combining two members out of $R_{201}$ to $R_{203}$ include an alkylene group (e.g., butylene, pentylene).

$Z^-$ represents a non-nucleophilic anion.

Examples of the non-nucleophilic anion as $Z^-$ include sulfonate anion, carboxylate anion, sulfonylimide anion, bis(alkylsulfonyl)imide anion and tris(alkylsulfonyl)methyl anion.

The non-nucleophilic anion is an anion having an extremely low ability of causing a nucleophilic reaction, and this anion can suppress decomposition with aging due to an intramolecular nucleophilic reaction. Thanks to this anion, the aging stability of the resist is enhanced.

Examples of the sulfonate anion include an aliphatic sulfonate anion, an aromatic sulfonate anion and a camphorsulfonate anion.

Examples of the carboxylate anion include an aliphatic carboxylate anion, an aromatic carboxylate anion and an aralkylcarboxylate anion.

The aliphatic moiety in the aliphatic sulfonate anion may be an alkyl group or a cycloalkyl group but is preferably an alkyl group having a carbon number of 1 to 30 or a cycloalkyl group having a carbon number of 3 to 30, and examples thereof include a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbornyl group and a boronyl group.

The aromatic group in the aromatic sulfonate anion is preferably an aryl group having a carbon number of 6 to 14, and examples thereof include a phenyl group, a tolyl group and a naphthyl group.

The alkyl group, cycloalkyl group and aryl group in the aliphatic sulfonate anion and aromatic sulfonate anion may have a substituent. Examples of the substituent of the alkyl group, cycloalkyl group and aryl group in the aliphatic sulfonate anion and aromatic sulfonate anion include a nitro group, a halogen atom (e.g., fluorine, chlorine, bromine, iodine), a carboxyl group, a hydroxyl group, an amino group, a cyano group, an alkoxy group (preferably having a carbon number of 1 to 15), a cycloalkyl group (preferably having a carbon number of 3 to 15), an aryl group (preferably having a carbon number of 6 to 14), an alkoxycarbonyl group (preferably having a carbon number of 2 to 7), an acyl group (preferably having a carbon number of 2 to 12), an alkoxycarbonyloxy group (preferably having a carbon number of 2 to 7), an alkylthio group (preferably having a carbon number of 1 to 15), an alkylsulfonyl group (preferably having a carbon number of 1 to 15), an alkyliminosulfonyl group (preferably having a carbon number of 2 to 15), an aryloxysulfonyl group (preferably having a carbon number of 6 to 20), an alkylaryloxysulfonyl group (preferably having a carbon number of 7 to 20), a cycloalkylaryloxysulfonyl group (preferably having a carbon number of 10 to 20), an alkyloxyalkyloxy group (preferably having a carbon number of 5 to 20), and a cycloalkylalkyloxyalkyloxy group (preferably having a carbon number of 8 to 20). As for the aryl group or ring structure in each group, examples of the substituent further include an alkyl group (preferably having a carbon number of 1 to 15).

Examples of the aliphatic moiety in the aliphatic carboxylate anion include the same alkyl groups and cycloalkyl groups as in the aliphatic sulfonate anion.

Examples of the aromatic group in the aromatic carboxylate anion include the same aryl groups as in the aromatic sulfonate anion.

The aralkyl group in the aralkylcarboxylate anion is preferably an aralkyl group having a carbon number of 6 to 12, and examples thereof include a benzyl group, a phenethyl group, a naphthylmethyl group, a naphthylethyl group and a naphthylmethyl group.

The alkyl group, cycloalkyl group, aryl group and aralkyl group in the aliphatic carboxylate anion, aromatic carboxylate anion and aralkylcarboxylate anion may have a substituent. Examples of the substituent of the alkyl group, cycloalkyl group, aryl group and aralkyl group in the aliphatic carboxylate anion, aromatic carboxylate anion and aralkylcarboxylate anion include the same halogen atoms, alkyl groups, cycloalkyl groups, alkoxy groups and alkylthio groups as in the aromatic sulfonate anion.

Examples of the sulfonylimide anion include saccharin anion.

The alkyl group in the bis(alkylsulfonyl)imide anion and tris(alkylsulfonyl)methyl anion is preferably an alkyl group having a carbon number of 1 to 5, and examples thereof include a methyl group, an ethyl group, a propyl group, an isopropyl group, an n-butyl group, an isobutyl group, a sec-butyl group, a pentyl group and a neopentyl group. Examples of the substituent of such an alkyl group include a halogen atom, a halogen atom-substituted alkyl group, an alkoxy group, an alkylthio group, an alkyloxysulfonyl group, an aryloxysulfonyl group and a cycloalkylaryloxysulfonyl group, with a fluorine atom-substituted alkyl group being preferred.

Other examples of the non-nucleophilic anion include fluorinated phosphorus, fluorinated boron and fluorinated antimony.

The non-nucleophilic anion of is preferably an aliphatic sulfonate anion substituted by a fluorine atom at the a-position of the sulfonic acid, an aromatic sulfonate anion substituted by a fluorine atom or a fluorine atom-containing group, a bis(alkylsulfonyl)imide anion with the alkyl group being substituted by a fluorine atom, or a tris(alkylsulfonyl)methide anion with the alkyl group being substituted by a fluorine atom. The non-nucleophilic anion is more preferably a perfluoroaliphatic sulfonate anion having a carbon number of 4 to 8, or a benzenesulfonate anion having a fluorine atom, still more preferably nonafluorobutanesulfonate anion, perfluorooctanesulfonate anion, pentafluorobenzenesulfonate anion or 3,5-bis(trifluoromethyl)benzenesulfonate anion.

Examples of the organic group as $R_{201}$, $R_{202}$ and $R_{203}$ include the corresponding groups in the compounds (ZI-1), (ZI-2) and (ZI-3) described later.

The compound may be a compound living a plurality of structures represented by formula (ZI), for example, may be a compound having a structure where at least one of $R_{201}$ to $R_{203}$ in a compound represented by formula (ZI) is bonded to at least one of $R_{201}$ to $R_{203}$ in another compound represented by formula (ZI).

The component (ZI) is more preferably a compound (ZI-1), (ZI-2) or (ZI-3) described below.

The compound (ZI-1) is an arylsulfonium compound where at least one of $R_{201}$ to $R_{203}$ in formula (ZI) is an aryl group, that is, a compound having arylsulfonium as the cation.

In the arylsulfonium compound, all of $R_{201}$ to $R_{203}$ may be an aryl group or a part of $R_{201}$ to $R_{203}$ may be an aryl group with the remaining being an alkyl group or a cycloalkyl group.

Examples of the arylsulfonium compound include a triarylsulfonium compound, a diarylalkylsulfonium compound, an aryldialkylsulfonium compound, a diarylcycloalkylsulfonium compound and an myldicycloalkylsulfonium compound.

The aryl group in the arylsulfonium compound is preferably a phenyl group or a naphthyl group, more preferably a phenyl group. The aryl group may be an aryl group having a heterocyclic structure containing an oxygen atom, a nitrogen atom, a sulfur atom or the like. Examples of the aryl group having a heterocyclic structure include a pyrrole residue (a group formed by removing one hydrogen atom from a pyrrole), a furan residue (a group formed by removing one hydrogen atom from a furan), a thiophene residue (a group formed by removing one hydrogen atom from a thiophene), an indole residue (a group formed by removing one hydrogen atom from an indole), a benzofuran residue (a group formed by removing one hydrogen atom from a benzofuran) and a benzothiophene residue (a group formed by removing one hydrogen atom from a benzothiophene). In the case where the arylsulfonium compound has two or more aryl groups, these two or more aryl groups may be the same or different.

The alkyl or cycloalkyl group which is present, if desired, in the arylsulfonium compound is preferably a linear or branched alkyl group having a carbon number of 1 to 15 or a cycloalkyl group having a carbon number of 3 to 15, and examples thereof include a methyl group, an ethyl group, a propyl group, an n-butyl group, a sec-butyl group, a tert-butyl group, a cyclopropyl group, a cyclobutyl group and a cyclohexyl group.

The aryl group, alkyl group and cycloalkyl group of $R_{201}$ to $R_{203}$ may have, as the substituent, an alkyl group (for example, having a carbon number of 1 to 15), a cycloalkyl group (for example, having a carbon number of 3 to 15), an aryl group (for example, having a carbon number of 6 to 14), an alkoxy group (for example, having a carbon number of 1 to 15), a halogen atom, a hydroxyl group or a phenylthio group. The substituent is preferably a linear or branched alkyl group having a carbon number of 1 to 12, a cycloalkyl group having a carbon number of 3 to 12, or a linear, branched or cyclic alkoxy group having a carbon number of 1 to 12, more preferably an alkyl group having a carbon number of 1 to 4, or an alkoxy group having a carbon number of 1 to 4. The substituent may be substituted on any one of three members $R_{201}$ to $R_{203}$ or may be substituted on all of these three members. In the case where $R_{201}$ to $R_{203}$ are an aryl group, the substituent is preferably substituted at the p-position of the aryl group.

The compound (ZI-2) is described below.

The compound (ZI-2) is a compound where each of $R_{201}$ to $R_{203}$ in formula (ZI) independently represents an aromatic ring-free organic group. The aromatic ring as used herein includes an aromatic ring containing a heteroatom.

The aromatic ring-free organic group as $R_{201}$ to $R_{203}$ has a carbon number of generally from 1 to 30, preferably from 1 to 20.

Each of $R_{201}$ to $R_{203}$ independently represents preferably an alkyl group, a cycloalkyl group, an allyl group or a vinyl group, more preferably a linear or branched 2-oxoalkyl group, a 2-oxocycloalkyl group or an alkoxycarbonylmethyl group, still more preferably a linear or branched 2-oxoalkyl group.

The alkyl group and cycloalkyl group of $R_{201}$ to $R_{203}$ are preferably a linear or branched alkyl group having a carbon number of 1 to 10 (e.g., methyl, ethyl, propyl, butyl, pentyl) and a cycloalkyl group having a carbon number of 3 to 10 (e.g., cyclopentyl, cyclohexyl, norbornyl). The alkyl group is more preferably a 2-oxoalkyl group or an alkoxycarbonylmethyl group. The cycloalkyl group is more preferably a 2-oxocycloalkyl group.

The 2-oxoalkyl group may be either linear or branched and is preferably a group having $>C=O$ at the 2-position of the above-described alkyl group.

The 2-oxocycloalkyl group is preferably a group having $>C=O$ at the 2-position of the above-described cycloalkyl group.

The alkoxy group in the alkoxycarbonylmethyl group is preferably an alkoxy group having a carbon number of 1 to 5 (e.g., methoxy, ethoxy, propoxy, butoxy, pentoxy).

Each of $R_{201}$ to $R_{203}$ may be further substituted by a halogen atom, an alkoxy group (for example, having a carbon number of 1 to 5), a hydroxyl group, a cyano group or a nitro group.

The compound (ZI-3) is a compound represented by the following formula (ZI-3), and this is a compound having a phenacylsulfonium salt structure.

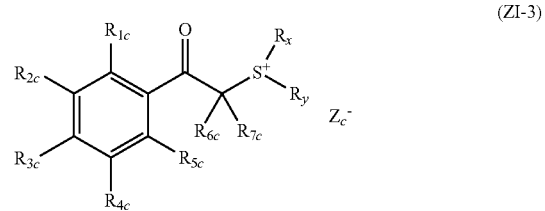

(ZI-3)

In formula (ZI-3), each of $R_{1c}$ to $R_{5c}$ independently represents a hydrogen atom, an alkyl group, a cycloalkyl group, an alkoxy group or a halogen atom.

Each of $R_{6c}$ and $R_{7c}$ independently represents a hydrogen atom, an alkyl group or a cycloalkyl group.

Each of $R_x$ and $R_y$ independently represents an alkyl group, a cycloalkyl group, an allyl group or a vinyl group.

Any two or more members out of $R_{1c}$ to $R_{5c}$, a pair of $R_{6c}$ and $R_{7c}$, or a pair of $R_x$ and $R_y$ may combine together to form a ring structure. This ring structure may contain an oxygen atom, a sulfur atom, an ester bond or an amide bond. Examples of the group formed by combining any two or more members out of $R_{1c}$ to $R_{5c}$, a pair of $R_{6c}$ and $R_{7c}$, or a pair of $R_x$ and $R_y$ include a butylene group and a pentylene group.

$Zc^-$ represents a non-nucleophilic anion, and examples thereof are the same as those of the non-nucleophilic anion of $Z^-$ in formula (ZI).

The alkyl group as $R_{1c}$ to $R_{7c}$ may be either linear or branched and is, for example, an alkyl group having a carbon number of 1 to 20, preferably a linear or branched alkyl group having a carbon number of 1 to 12 (e.g., methyl, ethyl, linear or branched propyl, linear or branched butyl, linear or branched pentyl). The cycloalkyl group is, for example, a cycloalkyl group having a carbon number of 3 to 8 (e.g., cyclopentyl, cyclohexyl).

The alkoxy group as $R_{1c}$ to $R_{5c}$ may be linear, branched or cyclic and is, for example, an alkoxy group having a carbon number of 1 to 10, preferably a linear or branched alkoxy group having a carbon number of 1 to 5 (e.g., methoxy, ethoxy, linear or branched propoxy, linear or branched butoxy, linear or branched pentoxy) or a cyclic alkoxy group having a carbon number of 3 to 8 (e.g., cyclopentyloxy, cyclohexyloxy).

A compound where any one of $R_{1c}$ to $R_{5c}$ is a linear or branched alkyl group, a cycloalkyl group or a linear, branched or cyclic alkoxy group is preferred, and a compound where the sum of carbon numbers of $R_{1c}$ to $R_{5c}$ is from 2 to 15 is more preferred. Thanks to such a compound, the solvent solubility is more enhanced and production of particles during storage can be suppressed.

Examples of the alkyl group and cycloalkyl group as $R_x$ and $R_y$ include the same alkyl groups and cycloalkyl groups as in $R_{1c}$ to $R_{7c}$. Among these, a 2-oxoalkyl group, a 2-oxocycloalkyl group and an alkoxycarbonylmethyl group are preferred.

Examples of the 2-oxoalkyl group and 2-oxocycloalkyl group include a group having >C=O at the 2-position of the alkyl group or cycloalkyl group as $R_{1c}$ to $R_{7c}$.

Examples of the alkoxy group in the alkoxycarbonylmethyl group include the same alkoxy groups as in $R_{1c}$ to $R_{5c}$.

Each of $R_x$ and $R_y$ is preferably an alkyl or cycloalkyl group having a carbon number of 4 or more, more preferably 6 or more, still more preferably 8 or more.

In formulae (ZII) and (ZIII), each of $R_{204}$ to $R_{207}$ independently represents an aryl group, an alkyl group or a cycloalkyl group.

The aryl group of $R_{204}$ to $R_{207}$ is preferably a phenyl group or a naphthyl group, more preferably a phenyl group. The aryl group of $R_{204}$ to $R_{207}$ may be an aryl group having a heterocyclic structure containing an oxygen atom, a nitrogen atom, a sulfur atom or the like. Examples of the aryl group having a heterocyclic structure include a pyrrole residue (a group formed by removing one hydrogen atom from a pyrrole), a furan residue (a group formed by removing one hydrogen atom from a furan), a thiophene residue (a group formed by removing one hydrogen atom from a thiophene), an indole residue (a group formed by removing one hydrogen atom from an indole), a benzofuran residue (a group formed by removing one hydrogen atom from a benzofuran) and a benzothiophene residue (a group formed by removing one hydrogen atom from a benzothiophene).

The alkyl group and cycloalkyl group in $R_{204}$ to $R_{207}$ are preferably a linear or branched alkyl group having a carbon number of 1 to 10 (e.g., methyl, ethyl, propyl, butyl, pentyl) and a cycloalkyl group having a carbon number of 3 to 10 (e.g., cyclopentyl, cyclohexyl, norbornyl).

The aryl group, alkyl group and cycloalkyl group of $R_{204}$ to $R_{207}$ may have a substituent. Examples of the substituent which the aryl group, alkyl group and cycloalkyl group of $R_{204}$ to $R_{207}$ may have include an alkyl group (for example, having a carbon number of 1 to 15), a cycloalkyl group (for example, having a carbon number of 3 to 15), an aryl group (for example, having a carbon number of 6 to 15), an alkoxy group (for example, having a carbon number of 1 to 15), a halogen atom, a hydroxyl group and a phenylthio group.

$Z^-$ represents a non-nucleophilic anion, and examples thereof are the same as those of the non-nucleophilic anion of $Z^-$ in formula (ZI).

Other examples of the acid generator include compounds represented by the following formulae (ZIV), (ZV) and (ZVI):

ZIV

ZV

ZVI

In formulae (ZIV) to (ZVI), each of $Ar_3$ and $Ar_4$ independently represents an aryl group.

Each of $R_{208}$, $R_{209}$ and $R_{210}$ independently represents an alkyl group, a cycloalkyl group or an aryl group.

A represents an alkylene group, an alkenylene group or an arylene group.

Among the acid generators, more preferred are the compounds represented by formulae (ZI) to (ZIII).

The acid generator is preferably a compound capable of generating an acid having one sulfonic acid group or imide group, more preferably a compound capable of generating a monovalent perfluoroalkanesulfonic acid, a compound capable of generating an aromatic sulfonic acid substituted by a monovalent fluorine atom or a fluorine atom-containing group, or a compound capable of generating an imide acid substituted by a monovalent fluorine atom or a fluorine atom-containing group, still more preferably a sulfonium salt of fluoro-substituted alkanesulfonic acid, fluorine-substituted benzenesulfonic acid, fluorine-substituted imide acid or fluorine-substituted methide acid. In the acid generator which can be used, the acid generated is preferably a fluoro-substituted alkanesulfonic acid, fluoro-substituted benzenesulfonic acid or fluoro-substituted imide acid having a pKa of −1 or less, and in this case, the sensitivity can be enhanced.

Out of the acid generators, particularly preferred examples are set forth below.

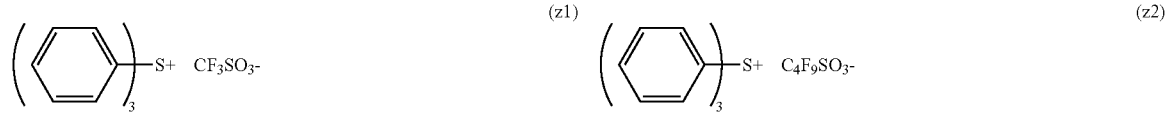

-continued
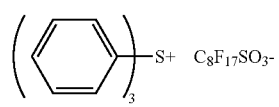
(z3)
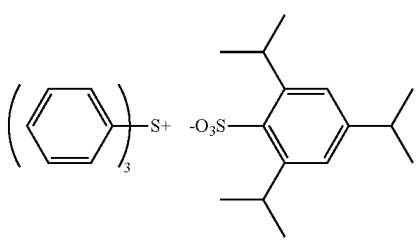
(z4)
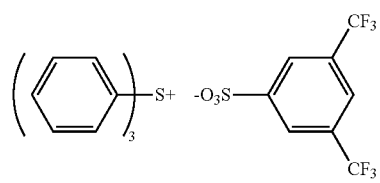
(z5)
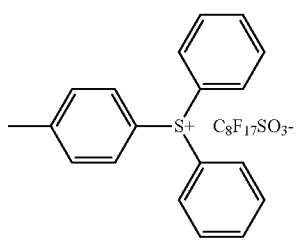
(z6)
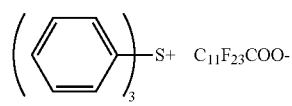
(z7)
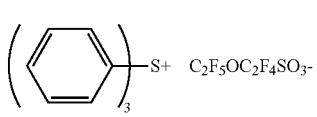
(z8)
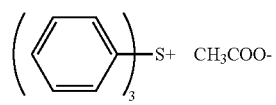
(z9)
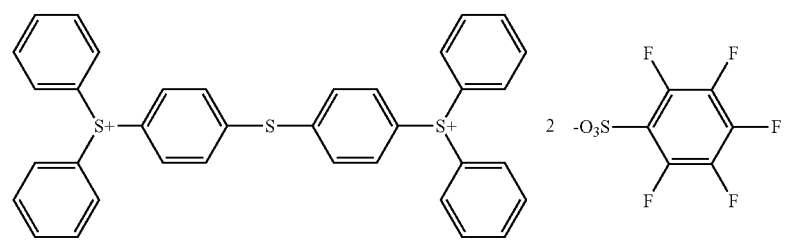
(z10)
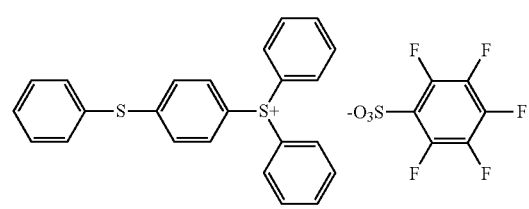
(z11)
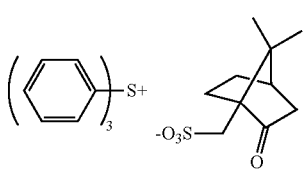
(z12)
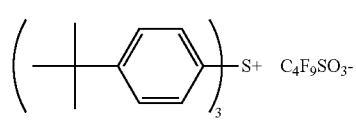
(z13)
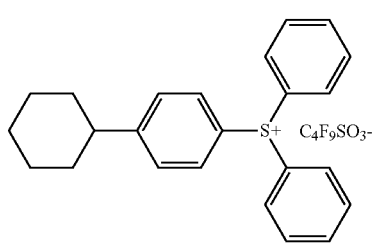
(z14)

-continued
(z15) 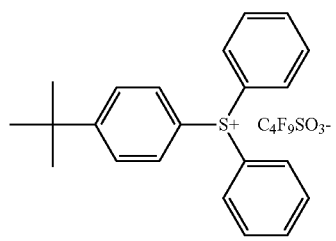
(z16) 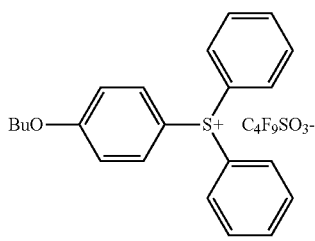
(z17) 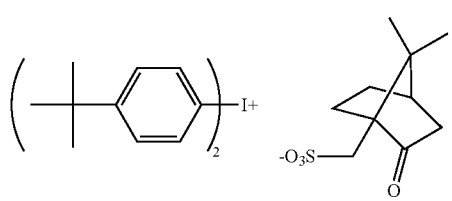
(z18) 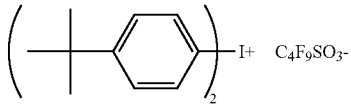
(z19) 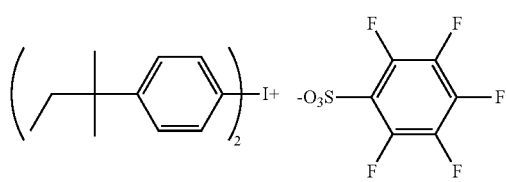
(z20) 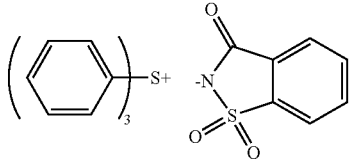
(z21) 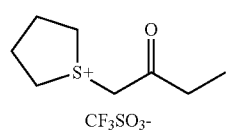
(z22) 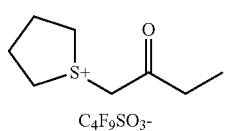
(z23) 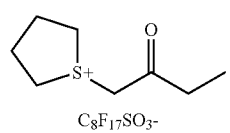
(z24) 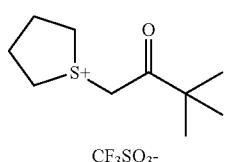
(z25) 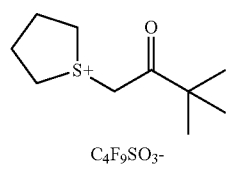
(z26) 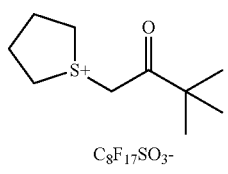
(z27) 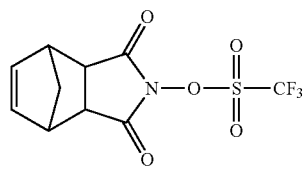
(z28) 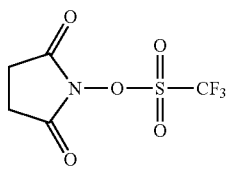
(z29) 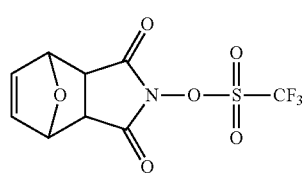
(z30) 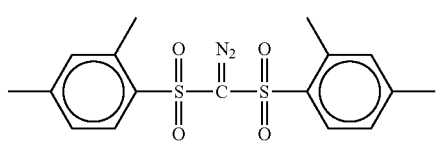
(z31) 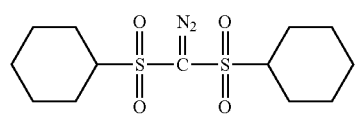
(z32) 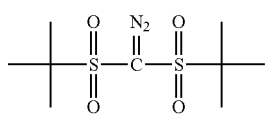

-continued
(z33)
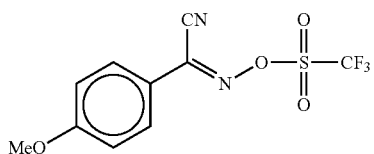
(z34)
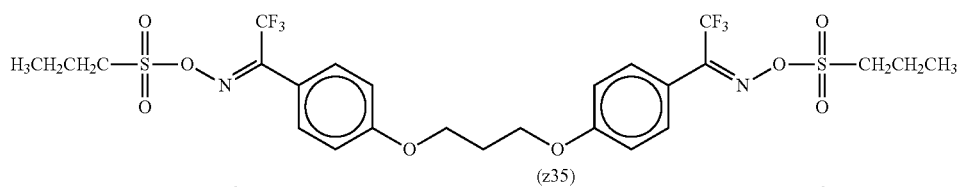
(z35)
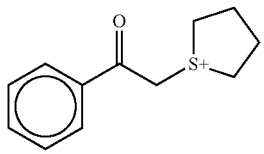
(z36)
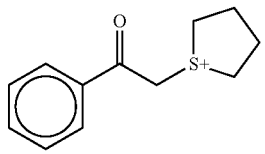
(z37)
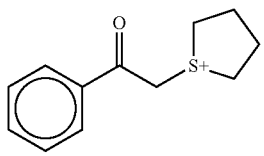
(z38)
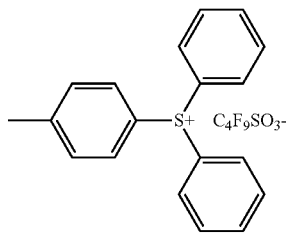
(z39)
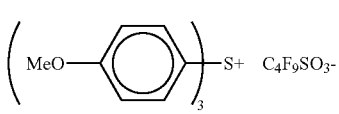
(z40)
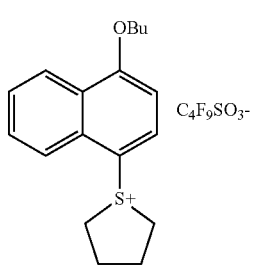
(z41)
(z42)
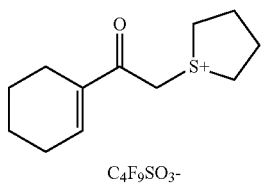
(z43)
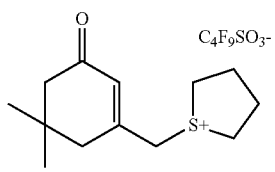
(z44)
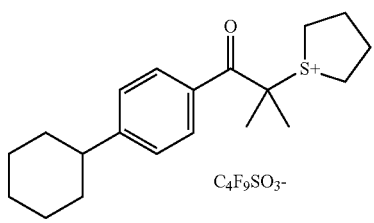
(z45)
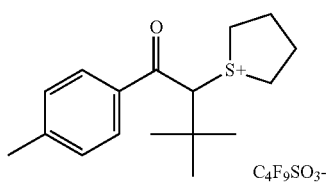
(z46)

-continued
(z47) 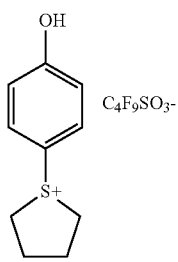
(z48) 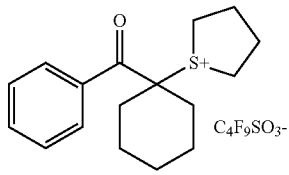
(z49) 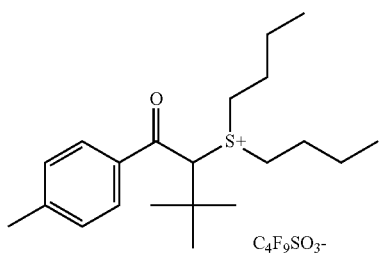
(z50) 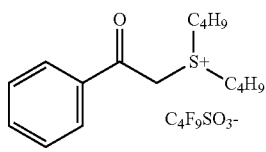
(z51) 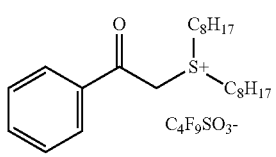
(z52) 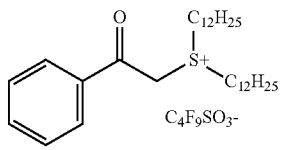
(z53) 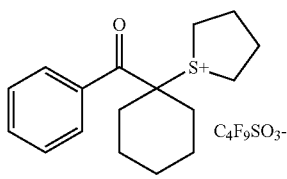
(z54) 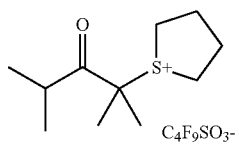
(z55) 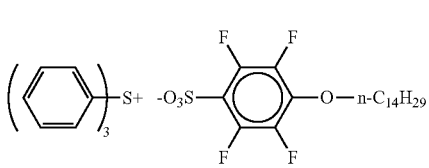
(z56) 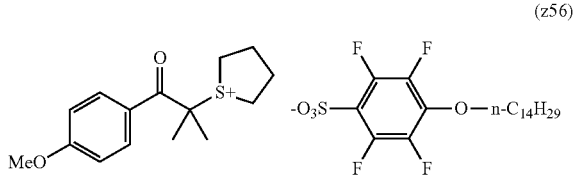
(z57) 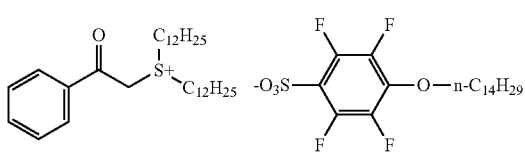
(z58) 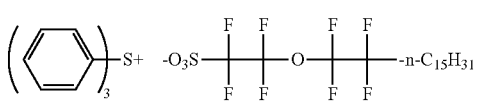
(z59) 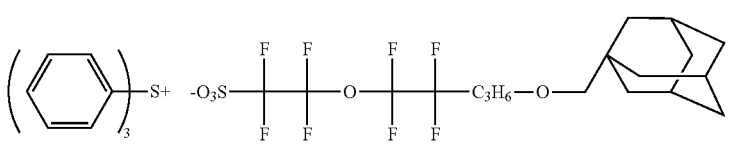
(z60) 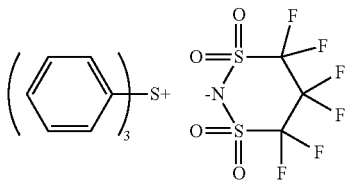
(z61) 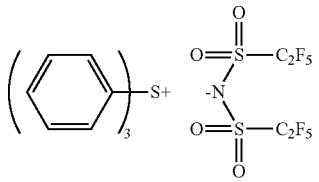

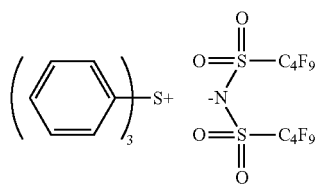
(z62)
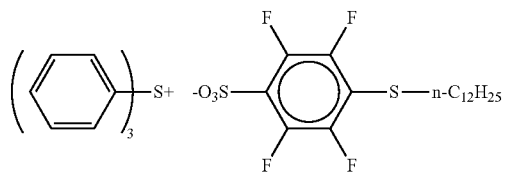
(z63)
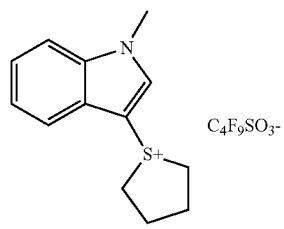
(z64)
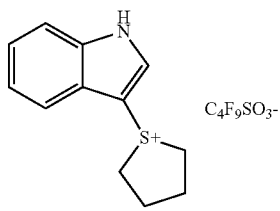
(z65)
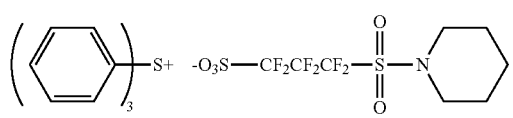
(z66)
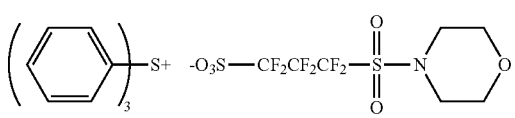
(z67)
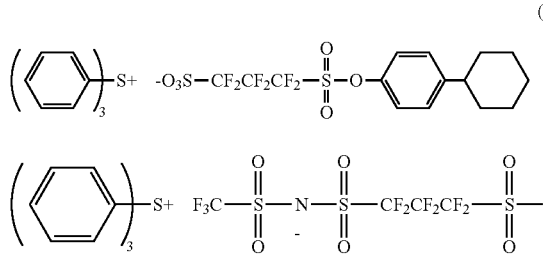
(z68)
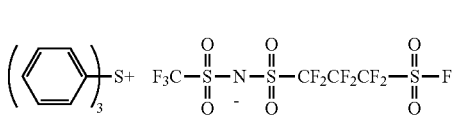
(z69)
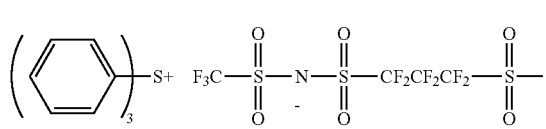
(z70)
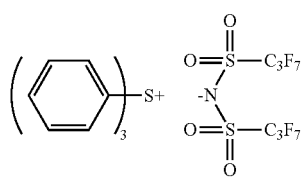
(z71)
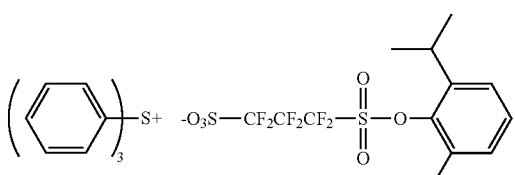
(z72)
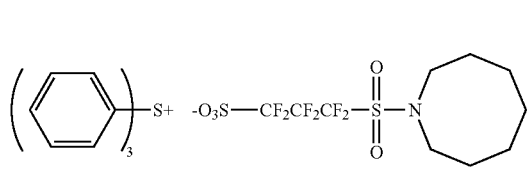
(z73)
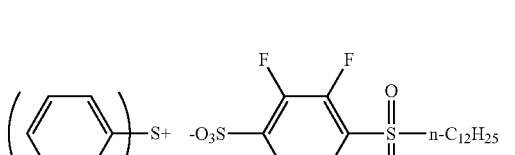
(z74)
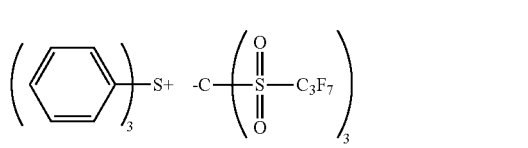
(z75)
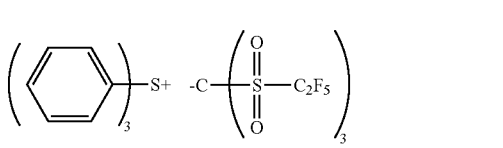
(z76)
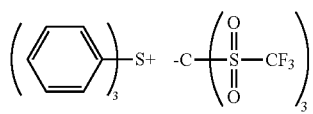
(z77)
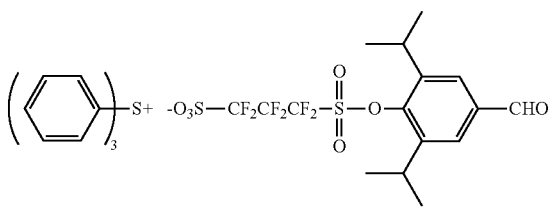
(z78)

-continued
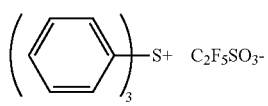 (z79)
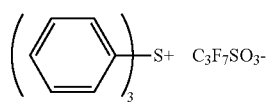 (z80)
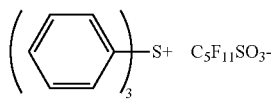 (z81)
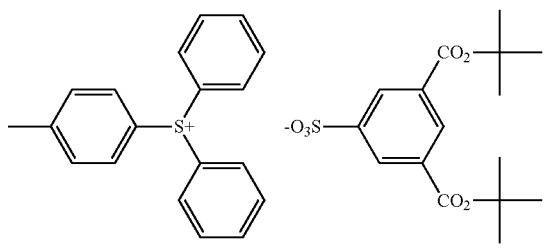 (z82)
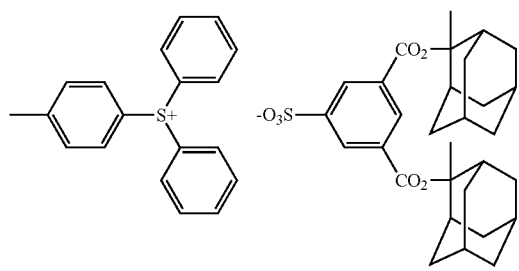 (z83)
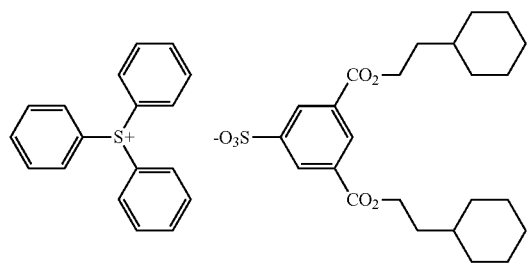 (z84)
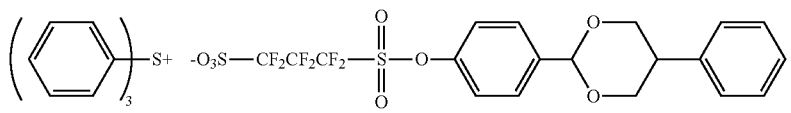 (z85)
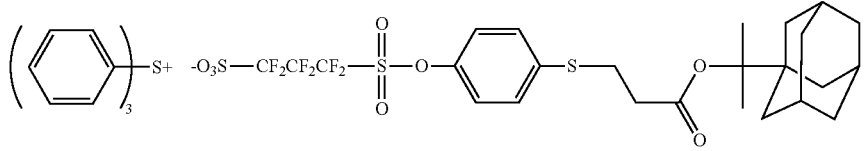 (z86)
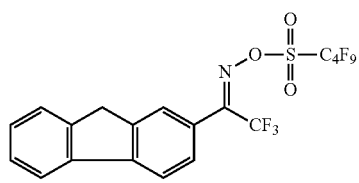 (z87)
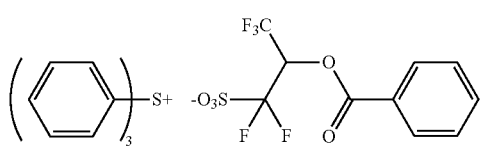 (z88)
(z89)
(z90)
(z91)

In the case of exposing the composition of the present invention to electron beam, X-ray or EUV light, a compound represented by the following formula (A1) is particularly preferred as the acid generator.

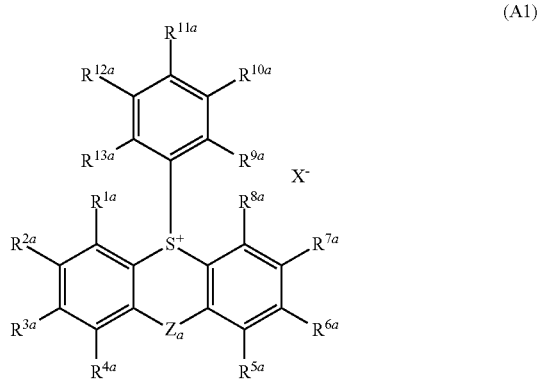

(A1)

In formula (A1), each of $R^{1a}$ to $R^{13a}$ independently represents a hydrogen atom or a substituent, and at least one of $R^{1a}$ to $R^{13a}$ is a substituent containing an alcoholic hydroxyl group.

Za represents a single bond or a divalent linking group.

$X^-$ represents a counter anion.

The alcoholic hydroxyl group as used in the present invention indicates a hydroxyl group bonded to a carbon atom of an alkyl group.

In the case where $R^{1a}$ to $R^{13a}$ are a substituent containing an alcoholic hydroxyl group, each of $R^{1a}$ to $R^{13a}$ is represented by —W—Y, wherein Y is an alkyl group substituted by a hydroxyl group and W is a single bond or a divalent linking group.

Examples of the alkyl group of Y include a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbornyl group and a boronyl group. Among these, preferred are an ethyl group, a propyl group, an isopropyl group, an n-butyl group, an isobutyl group and a sec-butyl group, and more preferred are an ethyl group, a propyl group and an isopropyl group. In particular, Y preferably contains a structure of —CH$_2$CH$_2$OH.

The divalent linking group represented by W is not particularly limited but includes, for example, a divalent group formed by substituting a single bond for an arbitrary hydrogen atom of a monovalent group such as alkoxyl group, acyloxy group, carbamoyloxy group, alkoxycarbonyloxy group, aryloxycarbonyloxy group, acylamino group, aminocarbonylamino group, alkoxycarbonylamino group, aryloxycarbonylamino group, sulfamoylamino group, alkyl- or aryl-sulfonylamino group, alkylthio group, arylthio group, sulfamoyl group, alkyl- or aryl-sulfinyl group, alkyl- or aryl-sulfonyl group, acyl group, aryloxycarbonyl group, alkoxycarbonyl group and carbamoyl group.

W is preferably a single bond or a divalent group formed by substituting a single bond for an arbitrary hydrogen atom of an alkoxyl group, an acyloxy group, an acylamino group, an alkyl- or aryl-sulfonylamino group, an alkylthio group, an alkylsulfonyl group, an acyl group, an alkoxycarbonyl group or a carbamoyl group, more preferably a single bond or a divalent group formed by substituting a single bond for an arbitrary hydrogen atom of an acyloxy group, an alkylsulfonyl group, an acyl group or an alkoxycarbonyl group.

In the case where $R^{1a}$ to $R^{13a}$ are a substituent containing an alcoholic hydroxyl group, the number of carbon atoms contained in the substituent is preferably from 2 to 10, more preferably from 2 to 6, still more preferably from 2 to 4.

The alcoholic hydroxyl group-containing substituent as $R^{1a}$ to $R^{13a}$ may have two or more alcoholic hydroxyl groups. The number of alcoholic hydroxyl groups in the alcoholic hydroxyl group-containing substituent as $R^{1a}$ to $R^{13a}$ is from 1 to 6, preferably from 1 to 3, more preferably 1.

The number of alcoholic hydroxyl groups in the compound represented by formula (A1) is, in total of all of $R^{1a}$ to $R^{13a}$, from 1 to 10, preferably from 1 to 6, more preferably from 1 to 3.

In the case where $R^{1a}$ to $R^{13a}$ are free of an alcoholic hydroxyl group, each of $R^{1a}$ to $R^{13a}$ is independently a hydrogen atom or a substituent, and the substituent may be any substituent and is not particularly limited, but examples thereof include a halogen atom, an alkyl group (including a cycloalkyl group, a bicycloalkyl group and a tricycloalkyl group), an alkenyl group (including a cycloalkenyl group and a bicycloalkenyl group), an alkynyl group, an aryl group, a heterocyclic group (may be called a hetero ring group), a cyano group, a nitro group, a carboxyl group, an alkoxyl group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonio group, an acylamino group; an aminocarbonylamino group, an alkoxycarbonylamino group, an aryloxycarbonylamino group, a sulfamoylamino group, an alkyl- or aryl-sulfonylamino group, a mercapto group, an alkylthio group, an arylthio group, a heterocyclic thio group, a sulfamoyl group, a sulfo group, an alkyl- or aryl-sulfinyl group, an alkyl- or aryl-sulfonyl group, an acyl group, an aryloxycarbonyl group, an alkoxycarbonyl group, a carbamoyl group, an aryl- or heterocyclic-azo group, an imido group, a phosphino group, a phosphinyl group, a phosphinyloxy group, a phosphinylamino group, a phosphono group, a silyl group, a hydrazino group, a ureido group, a boronic acid group (—B(OH)$_2$), a phosphato group (—OPO(OH)$_2$), a sulfato group (—OSO$_3$H), and other known substituents.

Two adjacent members out of $R^{1a}$ to $R^{13a}$ may form a ring (an aromatic or non-aromatic hydrocarbon ring or a heterocycle, and the rings may further combine to form a polycyclic condensed ring; examples of the ring include a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a quinolizine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiin ring, a phenothiazine ring and phenazine ring) in cooperation.

In the case where $R^{1a}$ to $R^{13a}$ are free of an alcoholic hydroxyl group, each of $R^{1a}$ to $R^{13a}$ is preferably a hydrogen atom, a halogen atom, an alkyl group (including a cycloalkyl group, a bicycloalkyl group and a tricycloalkyl group), an alkenyl group (including a cycloalkenyl group and a bicycloalkenyl group), an alkynyl group, an aryl group, a cyano group, a carboxyl group, an alkoxy group, an aryloxy group, an acyloxy group, a carbamoyloxy group, an acylamino group, an aminocarbonylamino group, an alkoxycarbonylamino group, an aryloxycarbonylamino group, a sulfamoylamino group, an alkyl- or aryl-sulfonylamino group, an alkylthio group, an arylthio group, a sulfamoyl group, an alkyl- or aryl-sulfonyl group, an aryloxycarbonyl group, an alkoxycarbonyl group, a carbamoyl group, an imido group, a silyl group, or a ureido group.

In the case where $R^{1a}$ to $R^{13a}$ are free of an alcoholic hydroxyl group, each of $R^{1a}$ to $R^{13a}$ is more preferably a hydrogen atom, a halogen atom, an alkyl group (including a cycloalkyl group, a bicycloalkyl group and a tricycloalkyl group), a cyano group, an alkoxy group, an acyloxy group, an acylamino group, an aminocarbonylamino group, an alkoxycarbonylamino group, an alkyl- or aryl-sulfonylamino group, an alkylthio group, a sulfamoyl group, an alkyl- or aryl-sulfonyl group, an alkoxycarbonyl group, or a carbamoyl group.

In the case where $R^{1a}$ to $R^{13a}$ are free of an alcoholic hydroxyl group, each of $R^{1a}$ to $R^{13a}$ is still more preferably a hydrogen atom, an alkyl group (including a cycloalkyl group, a bicycloalkyl group and a tricycloalkyl group), a halogen atom, or an alkoxy group.

In formula (A1), at least one of $R^{1a}$ to $R^{13a}$ contains an alcoholic hydroxyl group, and preferably, at least one of $R^9$ to $R^{13}$ contains an alcoholic hydroxyl group.

Za represents a single bond or a divalent linking group. Examples of the divalent linking group include an alkylene group, an arylene group, a carbonyl group, a sulfonyl group, a carbonyloxy group, a carbonylamino group, a sulfonylamido group, an ether group, a thioether group, an amino group, a disulfide group, an acyl group, an alkylsulfonyl group, —CH═CH—, —C≡C—, an aminocarbonylamino group, and an aminosulfonylamino group, and these groups may have a substituent. Examples of the substituent thereof are the same as those of the substituent described for $R^{11}$ to $R^{13a}$. Za is preferably a single bond or a non-electron-withdrawing substituent such as alkylene group, arylene group, ether group, thioether group, amino group, —CH═CH—, —C≡C—, aminocarbonylamino group and aminosulfonylamino group, more preferably a single bond, an ether group or a thioether group, still more preferably a single bond.

The compound represented by formula (A1) has a counter anion $X^-$. The anion is preferably an organic anion. The organic anion indicates an anion containing at least one carbon atom. Furthermore, the organic anion is preferably a non-nucleophilic anion. The non-nucleophilic anion is an anion having an extremely low ability of causing a nucleophilic reaction, and this anion can suppress decomposition with aging due to an intramolecular nucleophilic reaction.

Examples of the non-nucleophilic anion include sulfonate anion, carboxylate anion, sulfonylimide anion, bis(alkylsulfonyl)imide anion and tris(alkylsulfonyl)methyl anion.

Examples of the non-nucleophilic sulfonate anion include an alkylsulfonate anion, an arylsulfonate anion and a camphorsulfonate, anion. Examples of the non-nucleophilic carboxylate anion include an alkylcarboxylate anion, an arylcarboxylate anion and an aralkylcarboxylate anion.

The alkyl moiety in the alkylsulfonate anion may be an alkyl group or a cycloalkyl group and is preferably an alkyl group having a carbon number of 1 to 30 or a cycloalkyl group having a carbon number of 3 to 30, and examples thereof include a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbornyl group and a boronyl group.

The aryl group in the arylsulfonate anion is preferably an aryl group having a carbon number of 6 to 14, such as phenyl group, tolyl group and naphthyl group.

Examples of the substituent of the alkyl group, cycloalkyl group and aryl group in the alkylsulfonate anion and arylsulfonate anion include a nitro group, a halogen atom (fluorine, chlorine, bromine, iodine), a carboxyl group, a hydroxyl group, an amino group, a cyano group, an alkoxyl group (preferably having a carbon number of 1 to 5), a cycloalkyl group (preferably having a carbon number of 3 to 15), an aryl group (preferably having a carbon number of 6 to 14), an alkoxycarbonyl group (preferably having a carbon number of 2 to 7), an acyl group (preferably having a carbon number of 2 to 12), and an alkoxycarbonyloxy group (preferably having a carbon number of 2 to 7). As for the aryl group or ring structure of each group, examples of the substituent further include an alkyl group (preferably having a carbon number of 1 to 15).

Examples of the alkyl moiety in the alkylcarboxylate anion include the same alkyl groups and cycloalkyl groups as in the alkylsulfonate anion. Examples of the aryl group in the arylcarboxylate anion include the same aryl groups as in the arylsulfonate anion. The aralkyl group in the aralkylcarboxylate anion is preferably an aralkyl group having a carbon number of 6 to 12, and examples thereof include a benzyl group, a phenethyl group, a naphthylmethyl group, a naphthylethyl group and a naphthylmethyl group.

Examples of the substituent of the alkyl group, cycloalkyl group, aryl group and aralkyl group in the alkylcarboxylate anion, arylcarboxylate anion and aralkylcarboxylate anion include the same halogen atoms, alkyl groups, cycloalkyl groups, alkoxyl groups and alkylthio groups as in the arylsulfonate anion. Examples of the sulfonylimide anion include saccharin anion.

The alkyl group in the bis(alkylsulfonyl)imide anion and tris(alkylsulfonyl)methyl anion is preferably an alkyl group having a carbon number of 1 to 5, and examples thereof include a methyl group, an ethyl group, a propyl group, an isopropyl group, an n-butyl group, an isobutyl group, a sec-butyl group, a pentyl group and a neopentyl group. Examples of the substituent of such an alkyl group include a halogen atom, a halogen atom-substituted alkyl group, an alkoxy group and an alkylthio group.

Other examples of the non-nucleophilic anion include fluorinated phosphorus, fluorinated boron and fluorinated antimony.

The counter anion $X^-$ of the compound represented by formula (A1) is preferably a sulfonate anion, more preferably an arylsulfonate anion.

Specific examples of the counter anion include methanesulfonate anion, trifluoromethanesulfonate anion, pentafluoroethanesulfonate anion, heptafluoropropanesulfonate anion, perfluorobutanesulfonate anion, peril uorohexanesulfonate anion, perfluorooctanesulfonate anion, pentafluorobenzenesulfonate anion, 3,5-bistrifluoromethylbenzenesulfonate anion, 2,4,6-triisopropylbenzenesulfonate anion, perfluoroethoxyethanesulfonate anion, 2,3,5,6-tetrafluoro-4-dodecyloxybenzenesulfonate anion, p-toluenesulfonate anion and 2,4,6-trimethylbenzenesulfonate anion.

The amount added of the compound represented by formula (A1) is, in terms of the total amount, preferably from 0.1 to 20 mass %, more preferably from 0.5 to 10 mass %, still more preferably from 3 to 8 mass %, based on the entire solid content of the resist composition.

The molecular weight of the compound represented by formula (A1) is preferably, from 200 to 2,000, more preferably from 400 to 1,000.

The compound represented by formula (A1) can be synthesized, for example, by a method of condensing a cyclic sulfoxide compound with a benzene derivative containing, as the substituent, a hydroxyl group protected by a protective group, thereby forming a sulfonium salt, and deprotecting the protective group of the hydroxyl group.

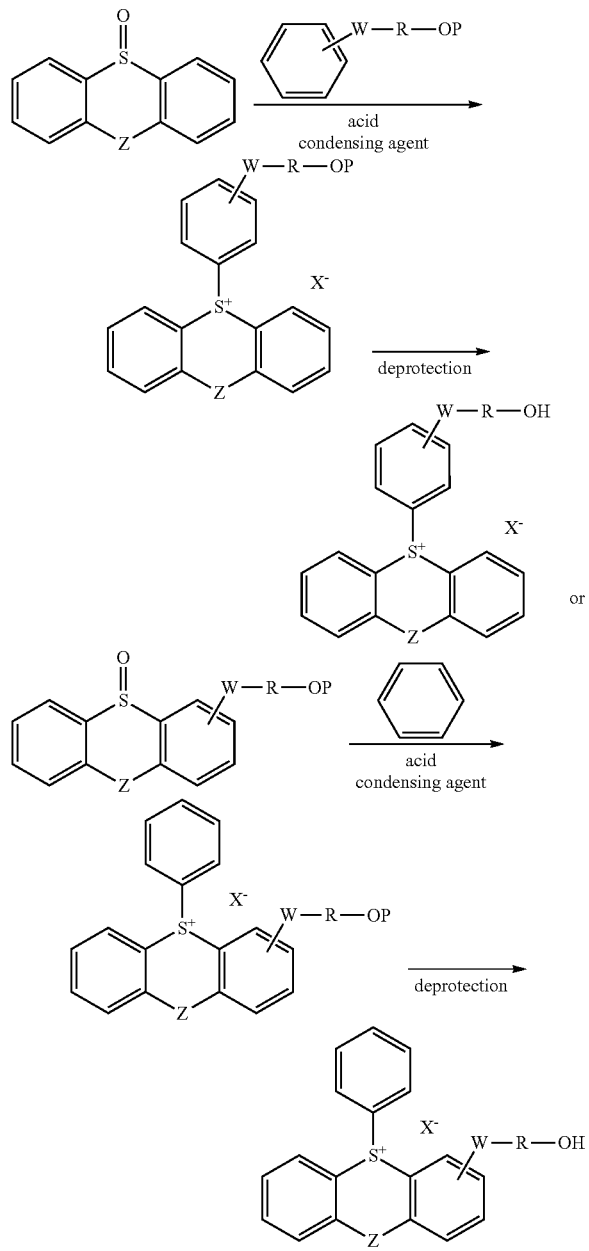

(In the FIGURE above, W is a divalent linking group, R is an alkylene group, and P is a protective group.)

Examples of the acid used for the reaction of sulfonium formation include a methanesulfonic acid, an ethanesulfonic acid, a propanesulfonic acid, a butanesulfonic acid, a pentanesulfonic acid, a trifluoromethanesulfonic acid, a benzenesulfonic kid, a p-toluenesulfonic acid, a p-ethylbenzenesulfonic acid and a nonafluorobutanesulfonic acid, and the conjugate base of the acid used becomes the anion of sulfonium. The condensing agent used in the reaction of sulfonium formation includes, for example, an acid anhydride, and examples thereof include an anhydride of strong acid, such as trifluoroacetic anhydride, polyphosphoric acid, methanesulfonic anhydride, trifluoromethanesulfonic anhydride, p-toluenesulfonic anhydride, nonafluorobutanesulfonic anhydride, tetrafluorosuccinic anhydride, hexafluoroglutaric anhydride, chlorodifluoroacetic anhydride, pentafluoropropionic anhydride and heptafluorobutanoic anhydride.

The protective group P of the hydroxyl group includes, for example, an ether and an ester, and examples thereof include a methyl ether, an aryl ether, a benzyl ether, an acetic acid ester, a benzoic acid ester and a carbonic acid ester.

The counter anion K can be converted into a desired anion by adding a conjugate acid of the objective anion through an ion exchange resin.

Specific examples of the compound represented by formula (A1) are set forth below, but the present invention is not limited thereto.

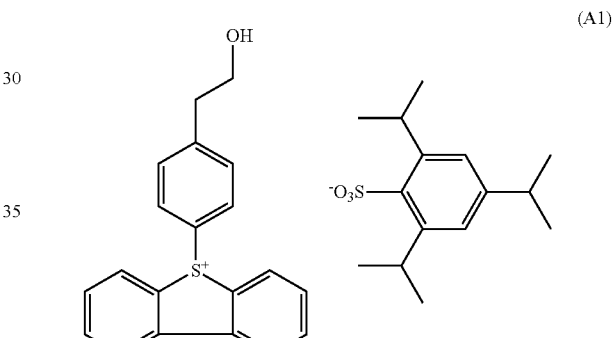
(A1)

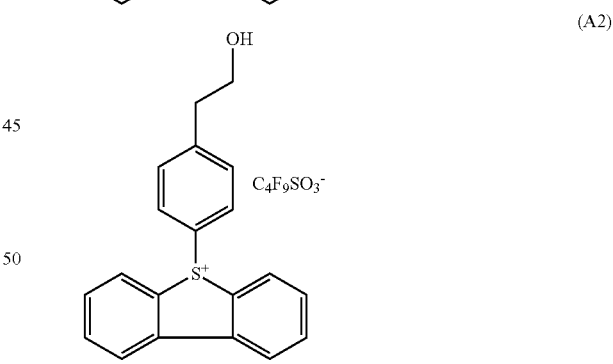
(A2)

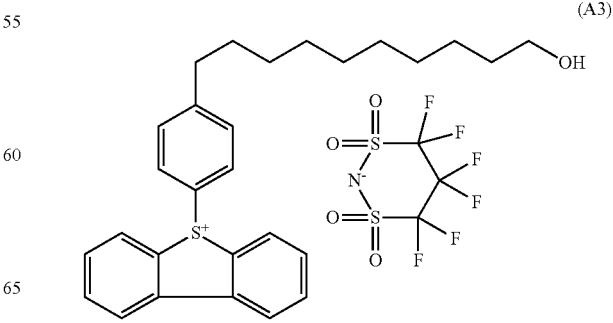
(A3)

(A4)
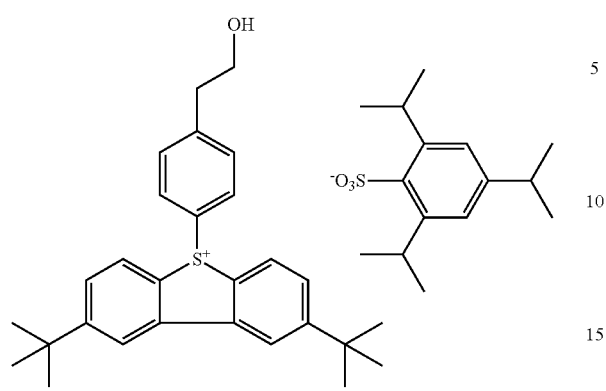
(A5)
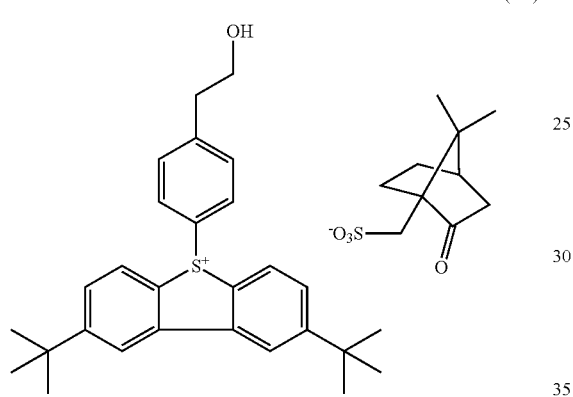
(A6)
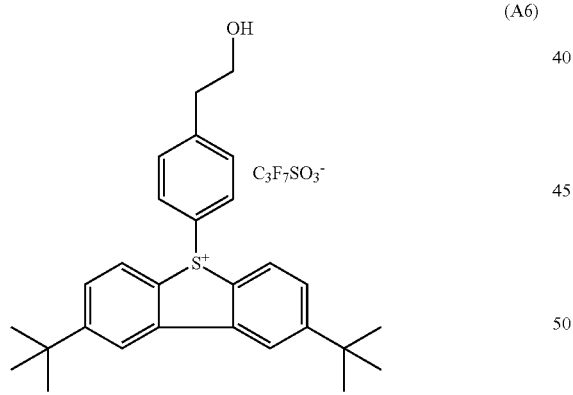
(A7)
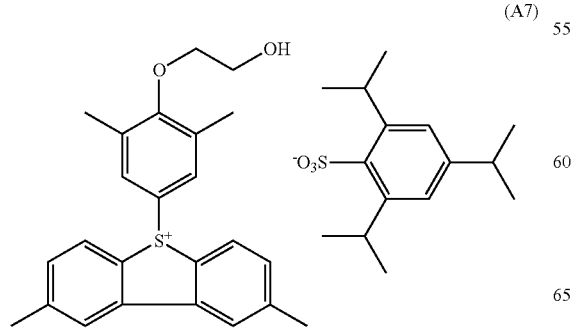
(A8)
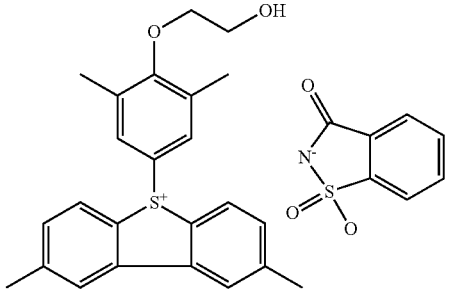
(A9)
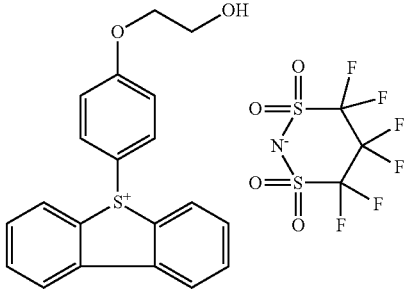
(A10)
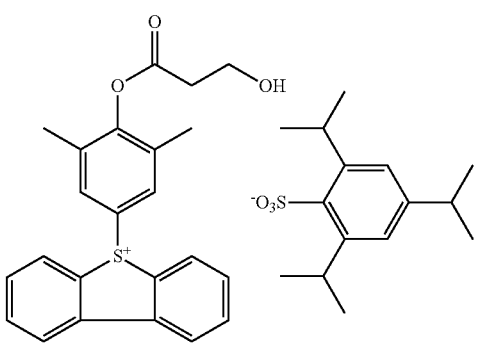
(A11)
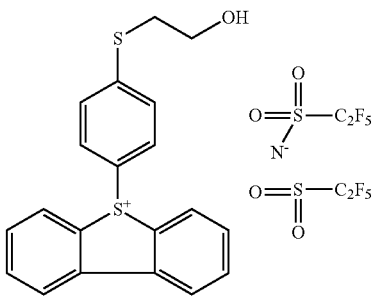
(A12)
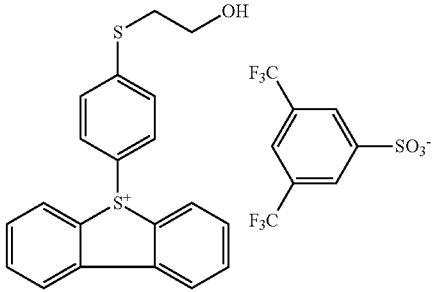

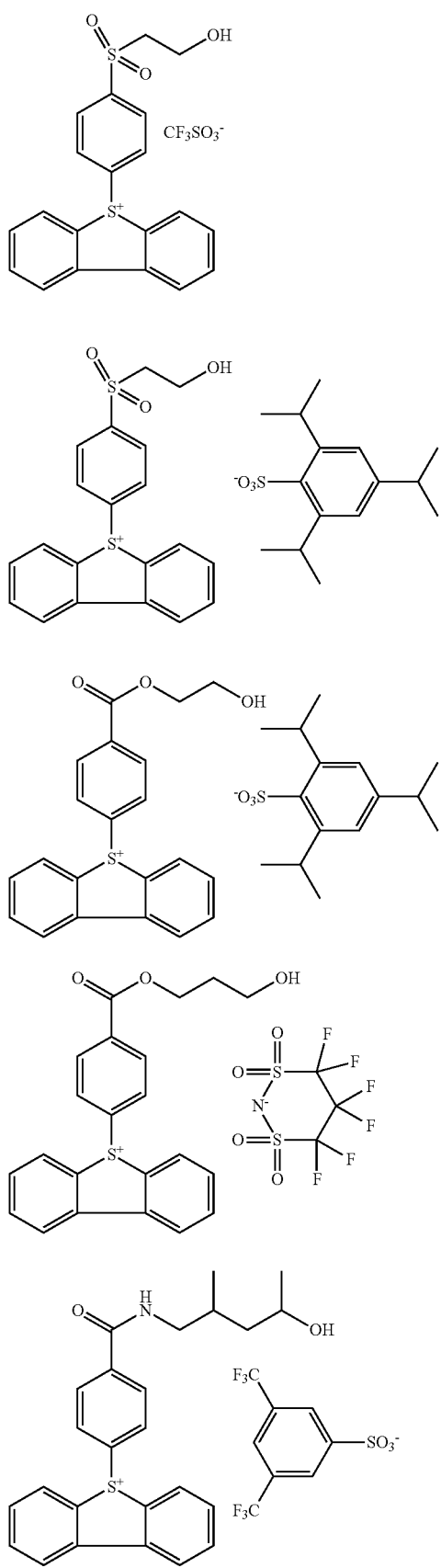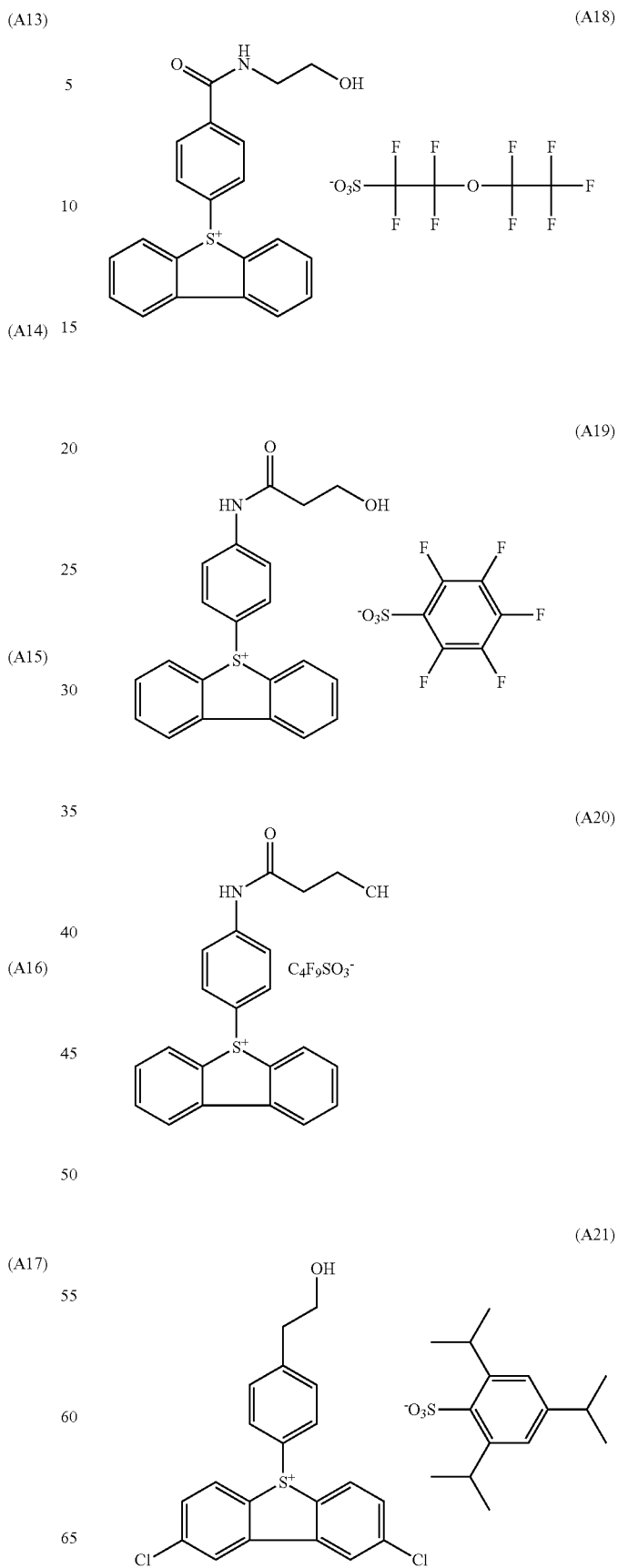

-continued
(A22)
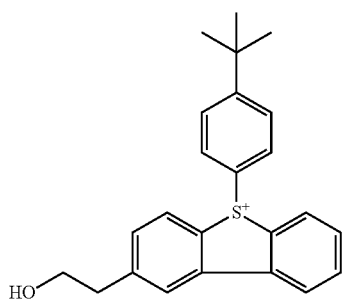 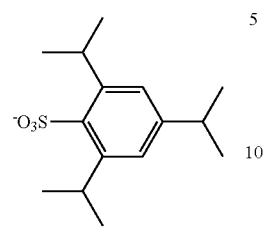
(A23)
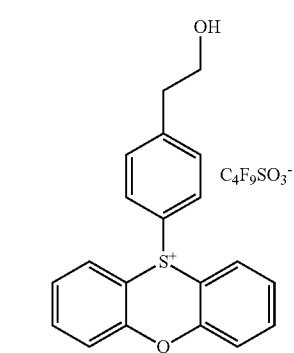
(A24)
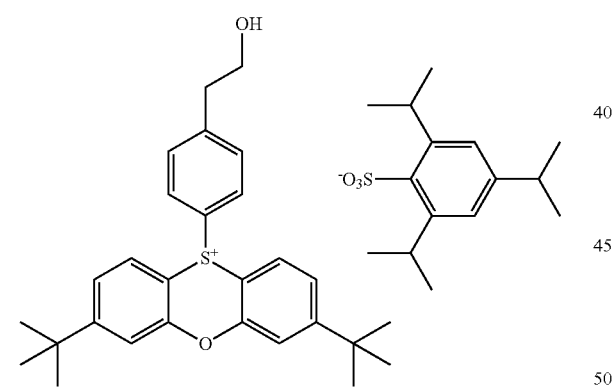
(A25)
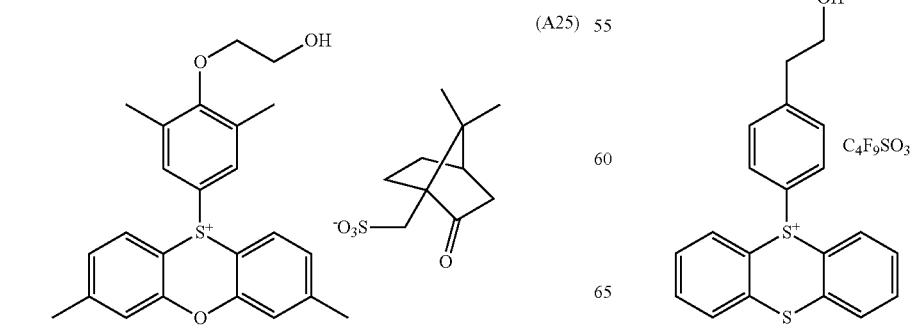
(A26)
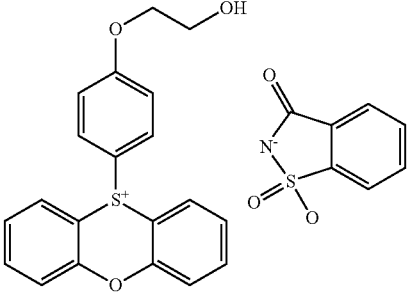
(A27)
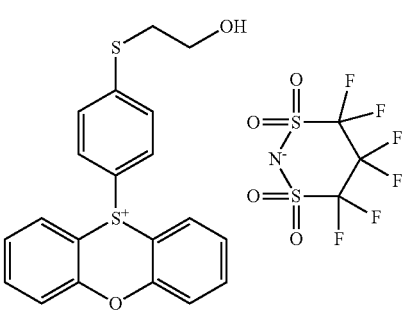
(A28)
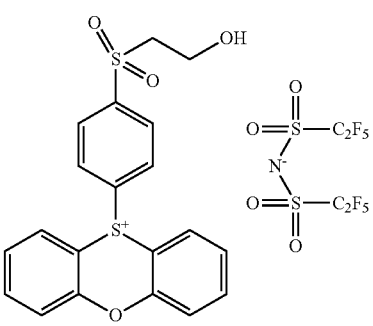
(A29)
(A30)
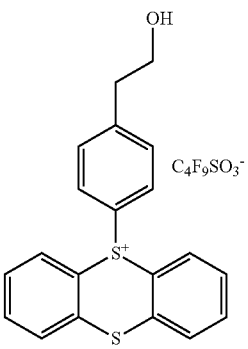

-continued (A31) 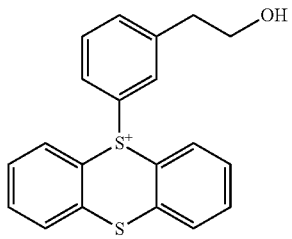 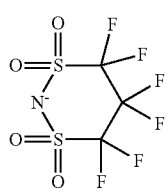

(A32) 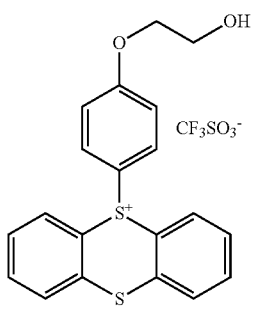

(A33) 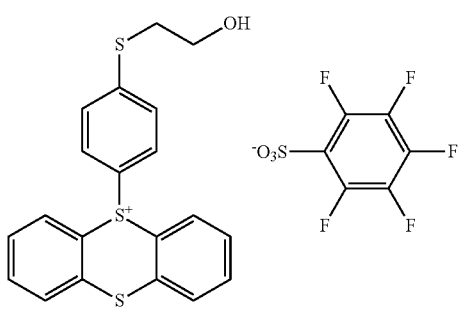

(A34) 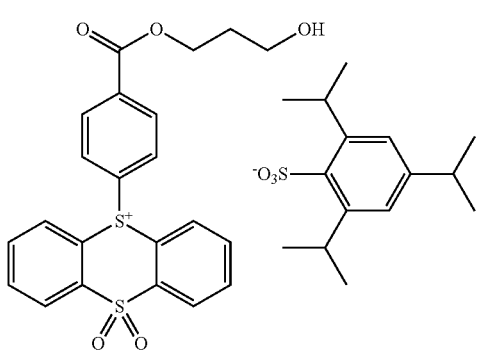

(A35) 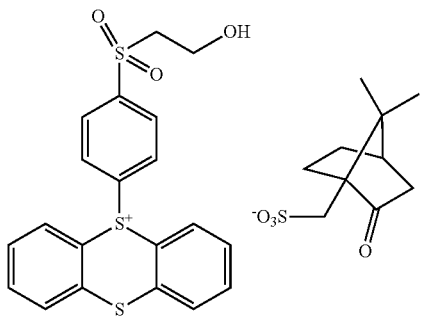

-continued (A36) 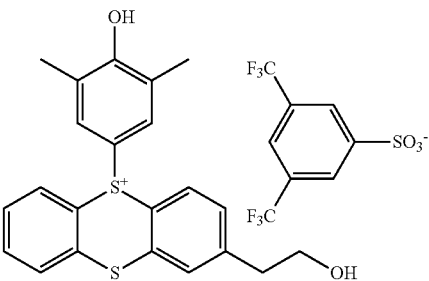

One kind of an acid generator may be used alone, or two or more kinds of acid generators may be used in combination.

The content of the acid generator in the positive resist composition is preferably from 0.1 to 20 mass %, more preferably from 0.5 to 10 mass %, still more preferably from 1 to 7 mass %, based on the entire solid content of the positive resist composition.

(B) Resin Capable of Increasing the Solubility in an Alkali Developer by the Action of an Acid The resin of the component (B) is a resin capable of increasing the solubility in an alkali developer by the action of an acid, and this is a resin having a group capable of decomposing by the action of an acid to produce an alkali-soluble group (hereinafter sometimes referred to as "an acid-decomposable group"), on either one or both of the main chain and the side chain of the resin.

Examples of the alkali-soluble group include a phenolic hydroxyl group, a carboxyl group, a fluorinated alcohol group, a sulfonic acid group, a sulfonamide group, a sulfonylimide group, an (alkylsulfonyl)(alkylcarbonyl)methylene group, an (alkylsulfonyl)(alkylcarbonyl)imide group, a bis(alkylcarbonyl)methylene group, a bis(alkylcarbonyl)imide group, a his(alkylsulfonyl)methylene group, a bis(alkylsulfonyl)imide group, a tris(alkylcarbonyl)methylene group and a tris(alkylsulfonyl)methylene group.

The alkali-soluble group is preferably a carboxyl group, a fluorinated alcohol group (preferably hexafluoroisopropanol) or a sulfonic acid group.

The acid-decomposable group is preferably a group formed by substituting a group capable of leaving by the action of an acid for a hydrogen atom of the alkali-soluble group above.

Examples of the group capable of leaving by the action of an acid include —C($R_{36}$)($R_{37}$)($R_{38}$), —C($R_{36}$)($R_{37}$)(O$R_{39}$) and —C($R_{01}$)($R_{02}$)(O$R_{39}$).

In the formulae, each of $R_{36}$ to $R_{39}$ independently represents an alkyl group, a cycloalkyl group, an aryl group, an aralkyl group or an alkenyl group. $R_{36}$ and $R_{37}$ may combine with each other to form a ring.

Each of $R_{01}$ and $R_{02}$ independently represents a hydrogen atom, an alkyl group, a cycloalkyl group, an aryl group, an aralkyl group or an alkenyl group.

The acid-decomposable group is, for example, preferably a cumyl ester group, an enol ester group, an acetal ester group or a tertiary alkyl ester group, more preferably a tertiary alkyl ester group.

The resin of the component (B) preferably contains a repeating unit having an acid-decomposable group. The repeating unit having an acid-decomposable group is preferably a repeating unit represented by the following formula (BI):

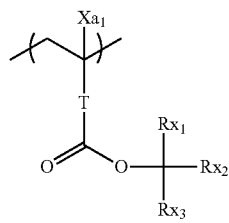

(BI)

In formula (B1), $Xa_1$ represents a hydrogen atom, a methyl group, a trifluoromethyl group or a hydroxymethyl group.

T represents a single bond or a divalent linking group.

Each of $Rx_1$ to $Rx_3$ independently represents an alkyl group (linear or branched) or a cycloalkyl group (monocyclic or polycyclic).

At least two members out of $Rx_1$ to $Rx_3$ may combine to form a cycloalkyl group (monocyclic or polycyclic).

Examples of the divalent linking group of T include an alkylene group, a —COO—Rt-group and a —O—Rt-group, wherein Rt represents an alkylene group or a cycloalkylene group.

T is preferably a single bond or a —COO—Rt-group. Rt is preferably an alkylene group having a carbon number of 1 to 5, more preferably a —$CH_2$— group or a —$(CH_2)_3$— group.

The alkyl group of $Rx_1$ to $Rx_3$ is preferably an alkyl group having a carbon number of 1 to 4, such as methyl group, ethyl group, n-propyl group, isopropyl group, n-butyl group, isobutyl group and tert-butyl group.

The cycloalkyl group of $Rx_1$ to $Rx_3$ is preferably a monocyclic cycloalkyl group such as cyclopentyl group and cyclohexyl group, or a polycyclic cycloalkyl group such as norbornyl group, tetracyclodecanyl group, tetracyclododecanyl group and adamantyl group.

The cycloalkyl group formed by combining at least two members out of $Rx_1$ to $Rx_3$ is preferably a monocyclic cycloalkyl group such as cyclopentyl group and cyclohexyl group, or a polycyclic cycloalkyl group such as norbornyl group, tetracyclodecanyl group, tetracyclododecanyl group and adamantyl group.

An embodiment where $Rx_1$ is a methyl group or an ethyl group and $Rx_2$ and $Rx_3$ are combined to form the above-described cycloalkyl group is preferred.

The content of the repeating unit having an acid-decomposable group is preferably from 20 to 50 mol %, more preferably from 25 to 45 mol %, based on all repeating units in the polymer.

Specific preferred examples of the repeating unit having an acid-decomposable group are set forth below, but the present invention is not limited thereto.

(In formulae, Rx represents H, $CH_3$, $CF_3$ or $CH_2OH$, and each of Rxa and Rxb represents an alkyl group having a carbon number of 1 to 4.)

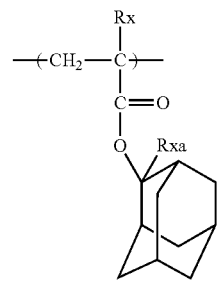

1

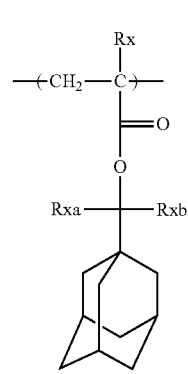

2

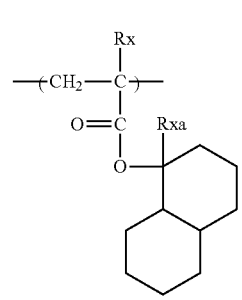

3

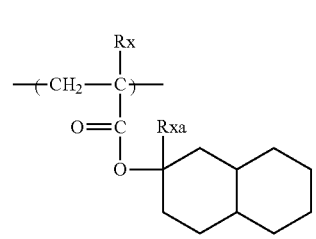

4

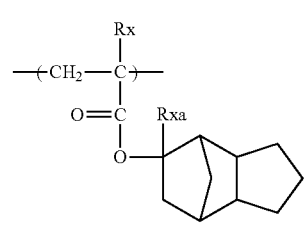

5

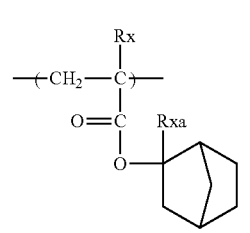

6

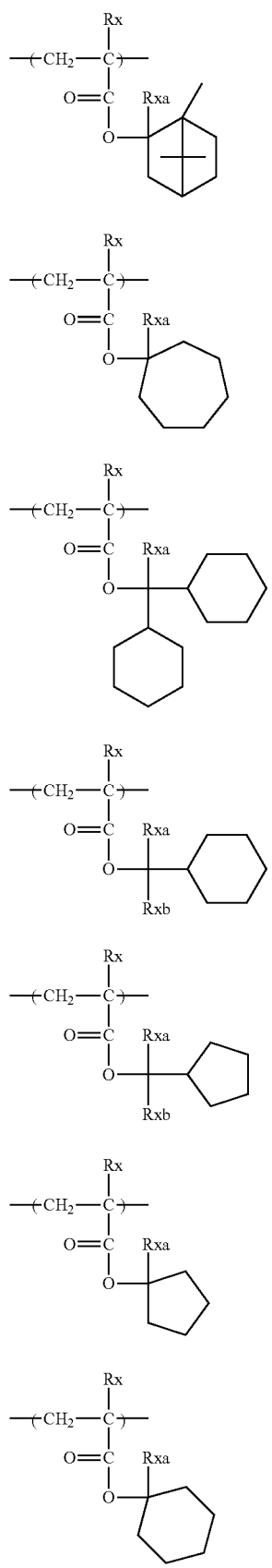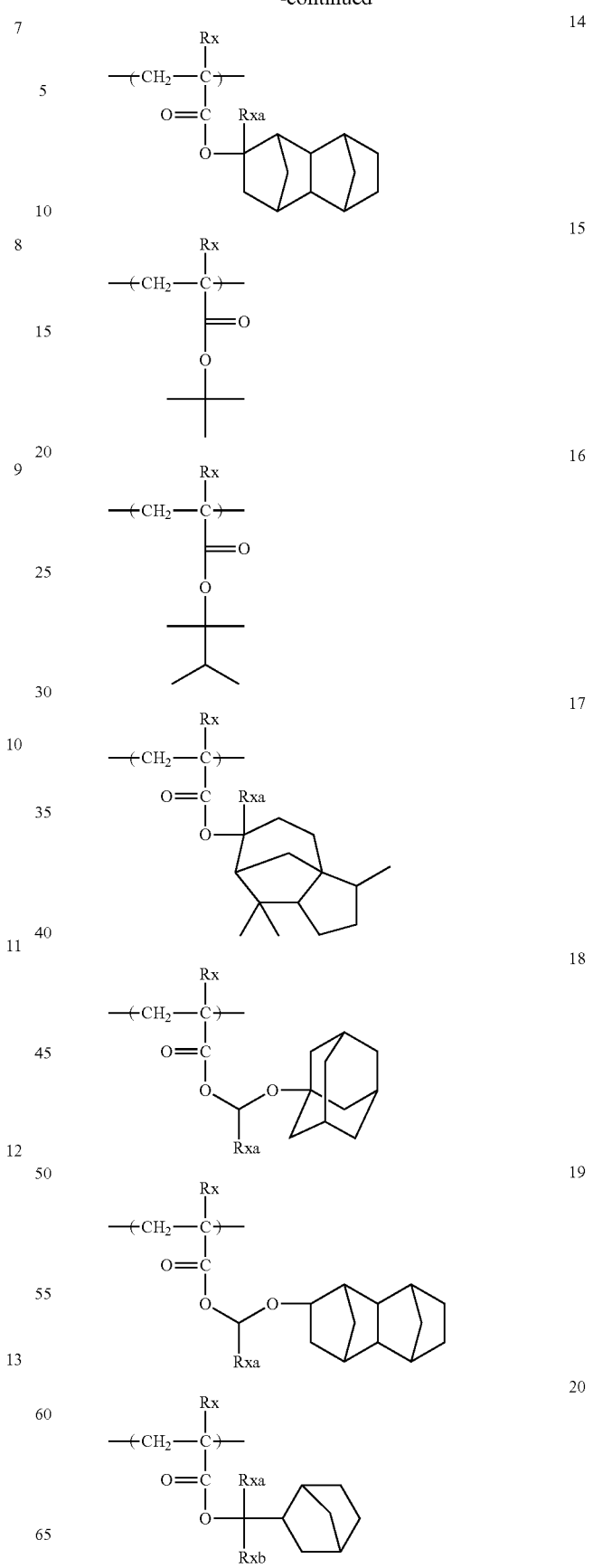

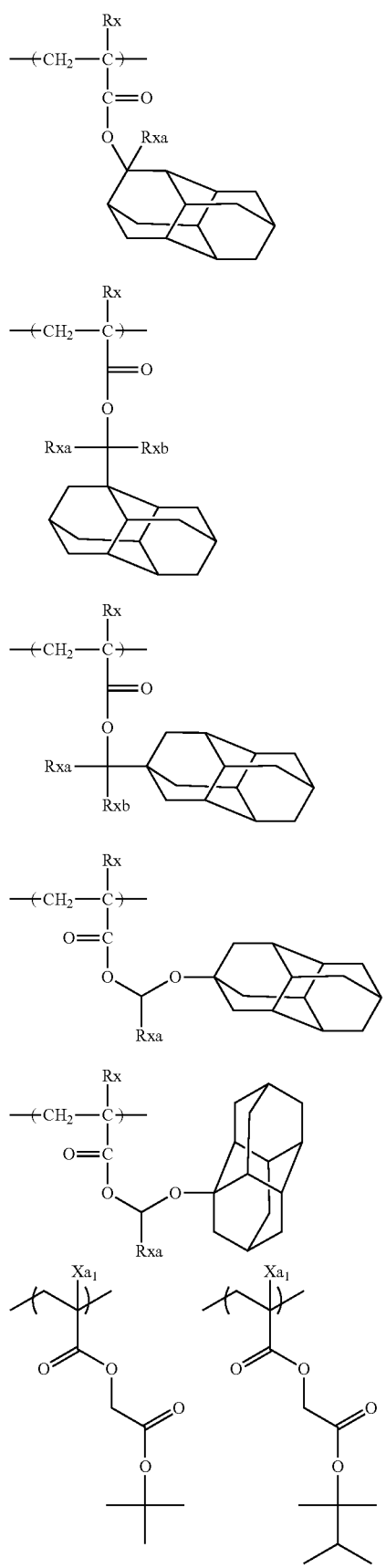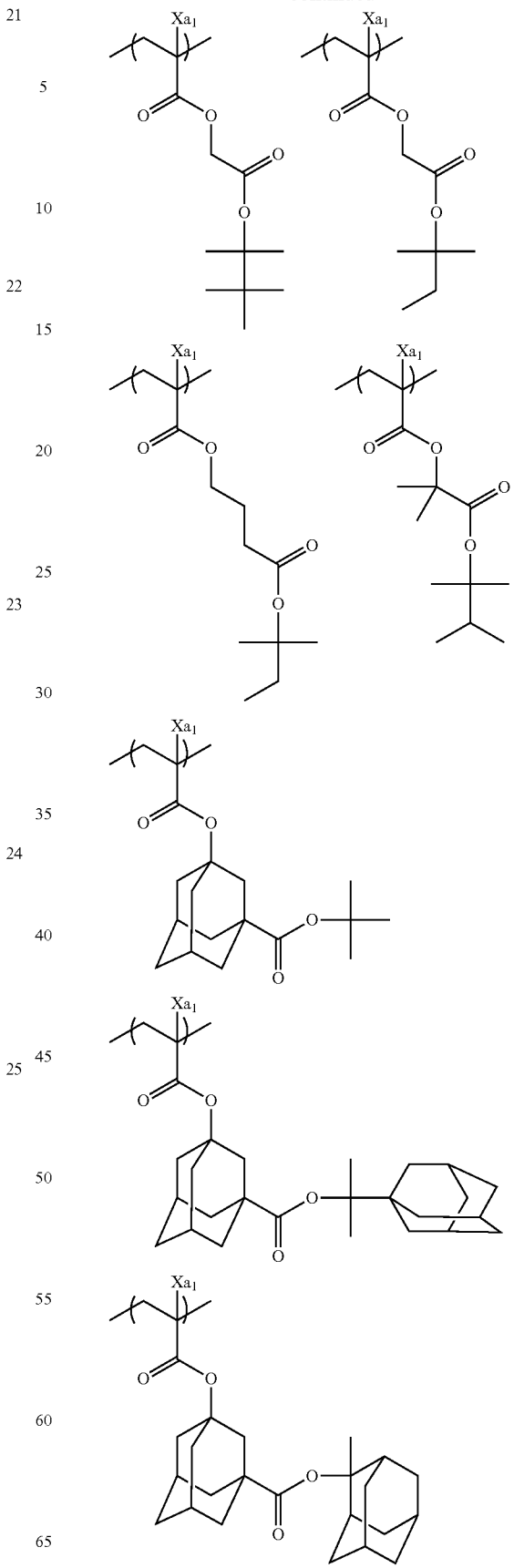

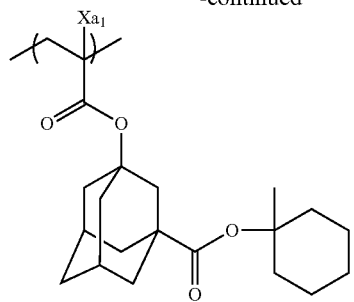
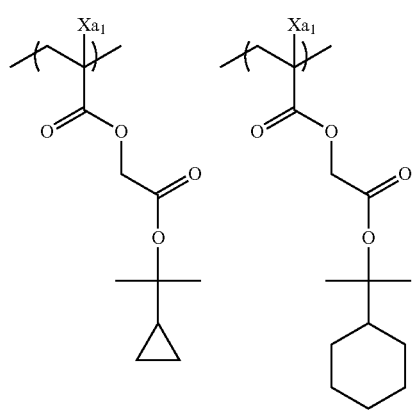
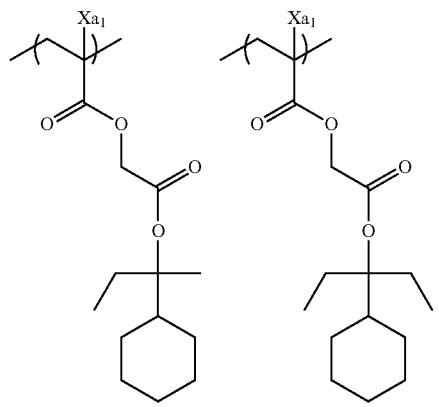
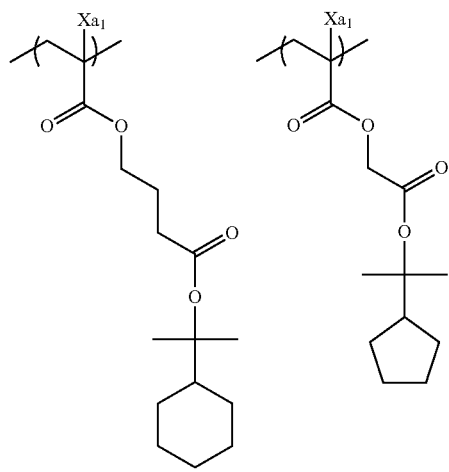
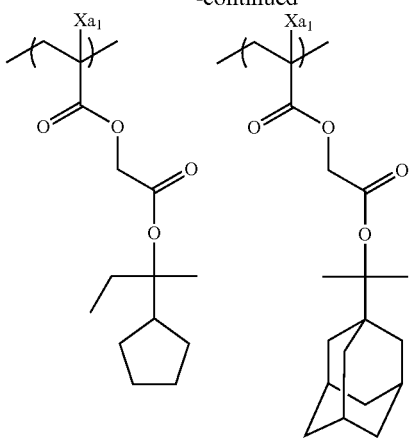
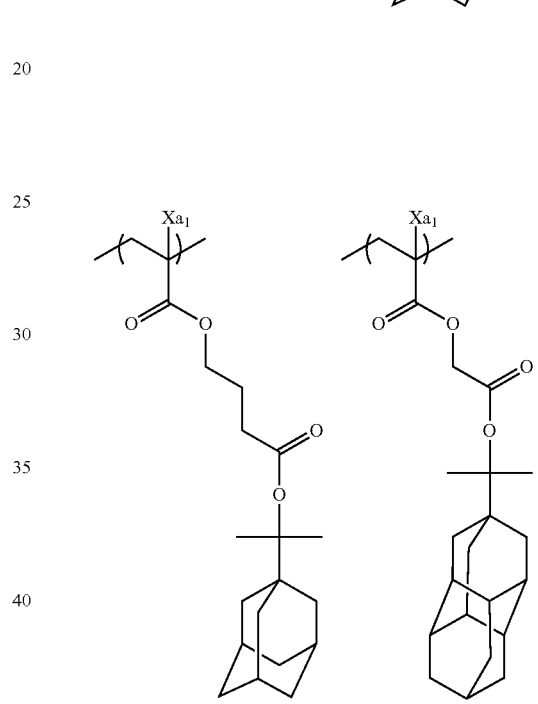
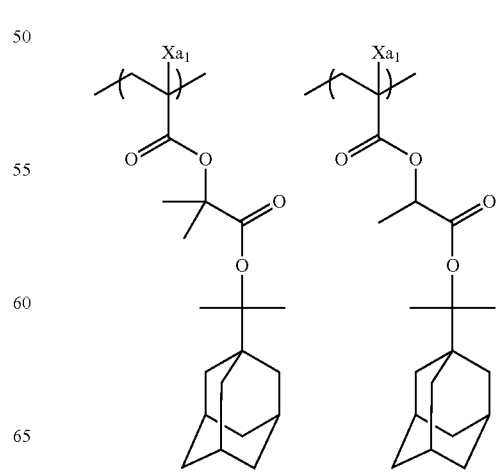

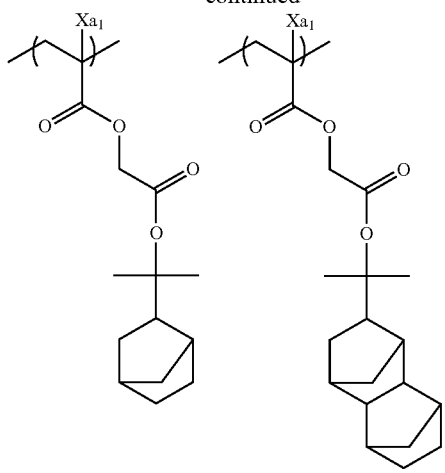
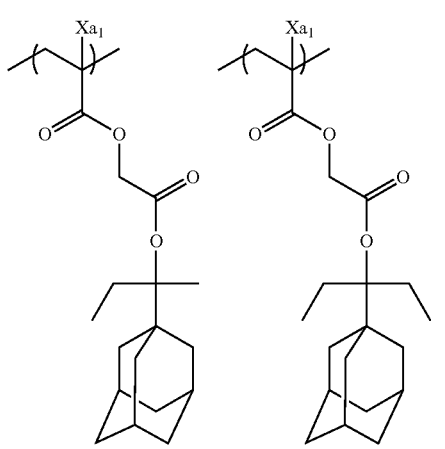
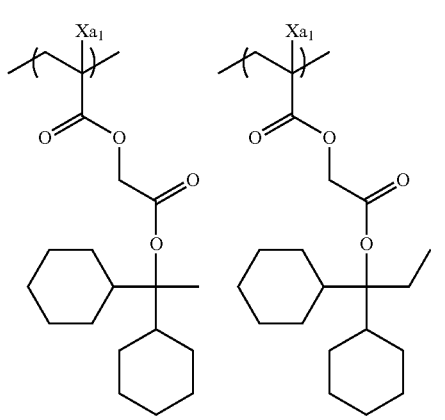
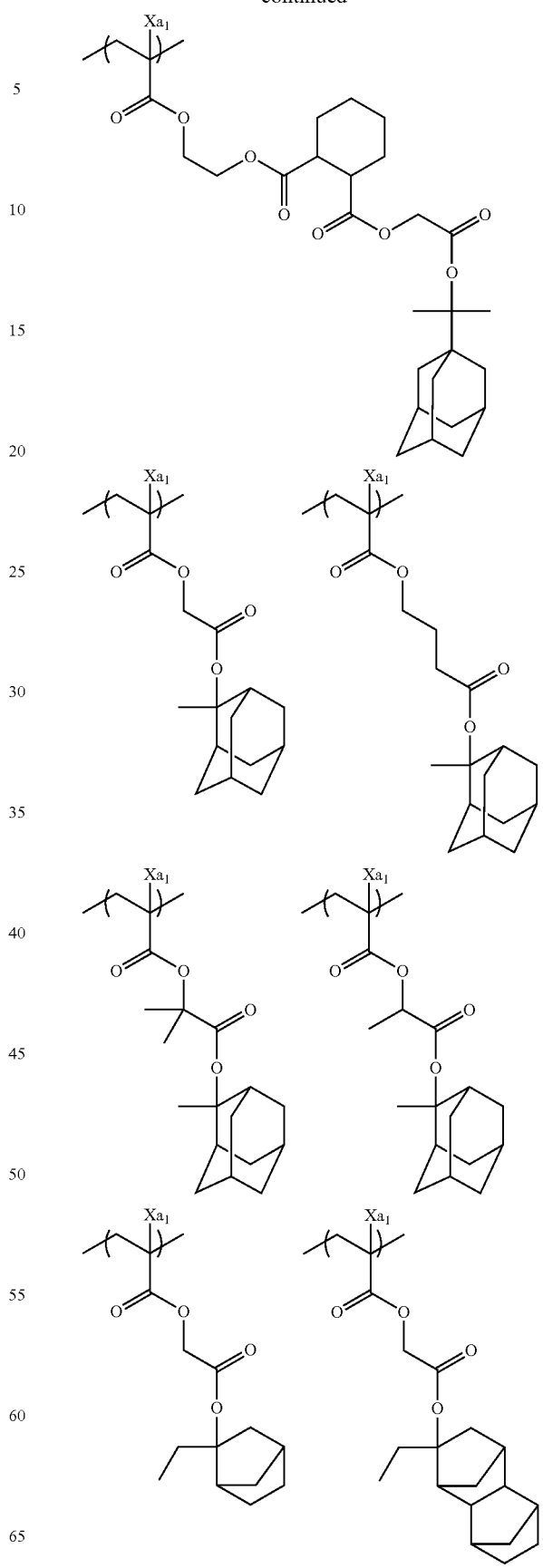

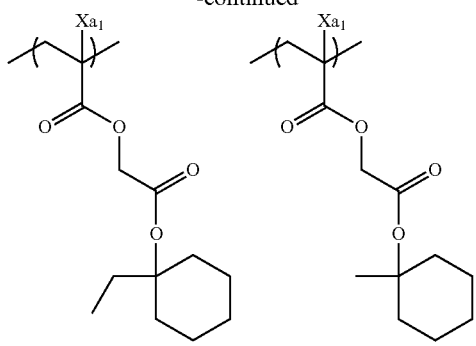
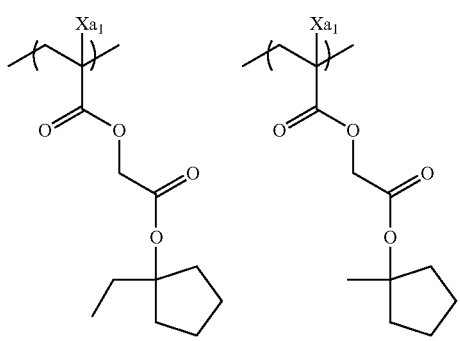
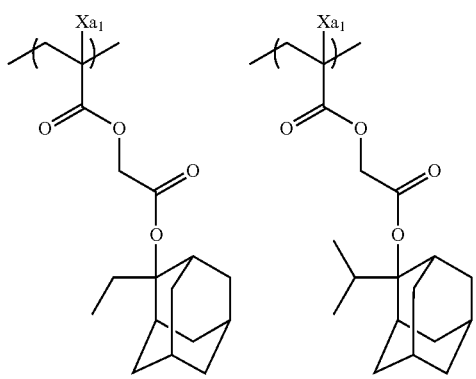

The resin of the component (B) preferably contains a repeating unit having at least one kind of a group selected from a lactone group, a hydroxyl group, a cyano group and an alkali-soluble group.

The resin of the component (B) preferably contains a repeating unit having a lactone group.

As for the lactone group, any group may be used as long as it has a lactone structure, but the lactone structure is preferably a 5- to 7-membered ring lactone structure, and a structure where another ring structure is condensed with a 5- to 7-membered ring lactone structure in the form of forming a bicyclo or Spiro structure is preferred. The resin more preferably contains a repeating unit having a lactone structure represented by any one of the following formulae (LC1-1) to (LC1-16). The lactone structure may be bonded directly to the main chain. Among these lactone structures, preferred are (LC1-1), (LC1-4), (LC1-5), (LC1-6), (LC1-13) and (LC1-14). By using a specific lactone structure, the line edge roughness and development defect are improved.

LC1-1
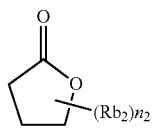

LC1-2
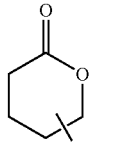

LC1-3
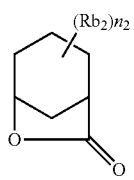

LC1-4
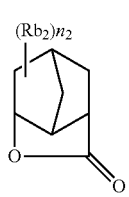

LC1-5
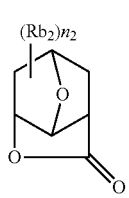

LC1-6
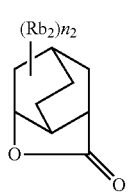

LC1-7
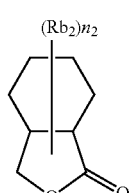

LC1-8
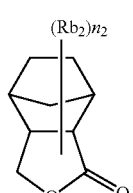

LC1-9
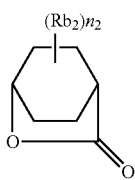

LC1-10
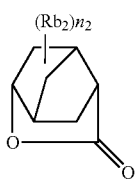

LC1-11
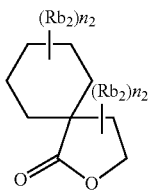

LC1-12
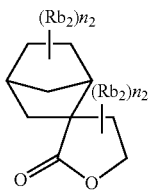

LC1-13
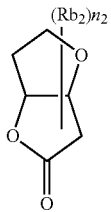

LC1-14
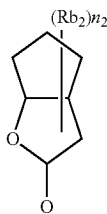

LC1-15
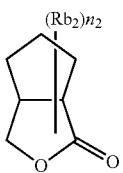

LC1-16

The lactone structure moiety may or may not have a substituent (Rb$_2$). Preferred examples of the substituent (Rb$_2$) include an alkyl group having a carbon number of 1 to 8, a cycloalkyl group having a carbon number of 4 to 7, an alkoxy group having a carbon number of 1 to 8, an alkoxycarbonyl group having a carbon number of 1 to 8, a carboxyl group, a halogen atom, a hydroxyl group, a cyano group and an acid-decomposable group. Among these, an alkyl group having a carbon number of 1 to 4, a cyano group and an acid-decomposable group are more preferred. n$_2$ represents an integer of 0 to 4. When n$_2$ is an integer of 2 or more, each substituent (Rb$_2$) may be the same as or different from every other substituent (Rb$_2$) and also, the plurality of substituents (Rb$_2$) may combine with each other to form a ring.

The repeating unit having a lactone structure represented by any one of formulae (LC1-1) to (LC1-16) includes a repeating unit represented by the following formula (AI):

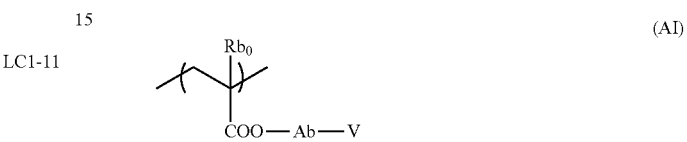

(AI)

In formula (AI), Rb$_0$ represents a hydrogen atom, a halogen atom or an alkyl group having a carbon number of 1 to 4. Preferred examples of the substituent which the alkyl group of Rb$_0$ may have include a hydroxyl group and a halogen atom. The halogen atom of Rb$_0$ includes a fluorine atom, a chlorine atom, a bromine atom and an iodine atom. Rb$_0$ is preferably a hydrogen atom or a methyl group.

Ab represents a single bond, an alkylene group, a divalent linking group having a monocyclic or polycyclic alicyclic hydrocarbon structure, an ether group, an ester group, a carbonyl group, or a divalent group comprising a combination thereof, and is preferably a single bond or a divalent linking group represented by -Ab$_1$-CO$_2$—. Ab$_1$ represents a linear or branched alkylene group or a monocyclic or polycyclic cycloalkylene group and is preferably a methylene group, an ethylene group, a cyclohexylene group, an adainantylene group or a norbornylene group.

V represents a group having a structure represented by any one of formulae (LC1-1) to (LC1-16).

The repeating unit having a lactone group usually has an optical isomer, but any optical isomer may be used. One optical isomer may be used alone, or a plurality of optical isomers may be mixed and used. In the case of mainly using one optical isomer, the optical purity (cc) thereof is preferably 90 or more, more preferably 95 or more.

The content of the repeating unit having a lactone group is preferably from 15 to 60 mol %, more preferably from 20 to 50 mol %, still more preferably from 30 to 50 mol %, based on all repeating units in the polymer.

Specific examples of the repeating unit containing a lactone group are set forth below, but the present invention is not limited thereto.

(In the formulae, Rx is H, CH$_3$, CH$_2$OH or CF$_3$.)

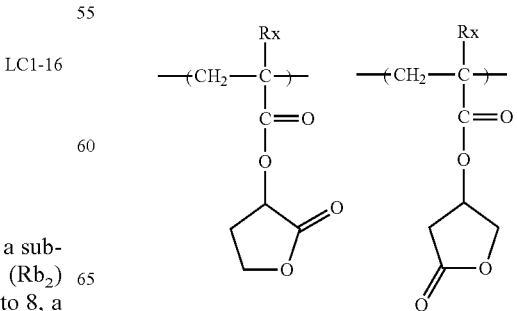

-continued
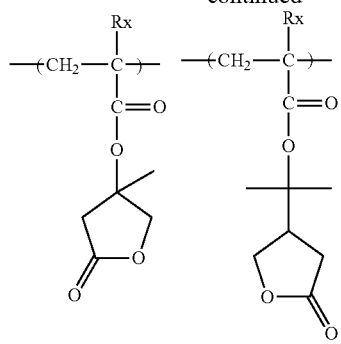
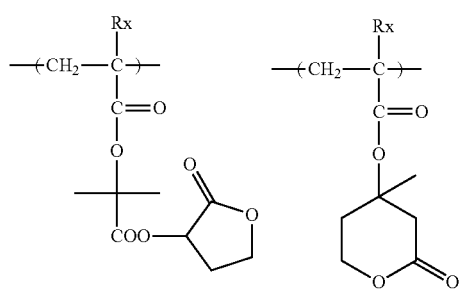
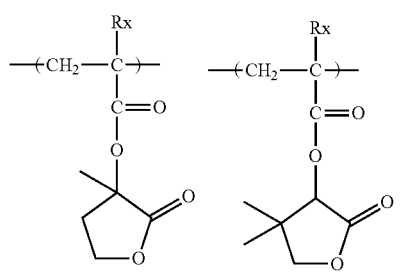
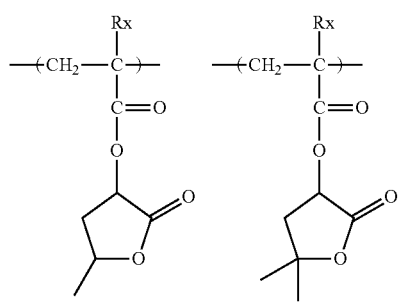
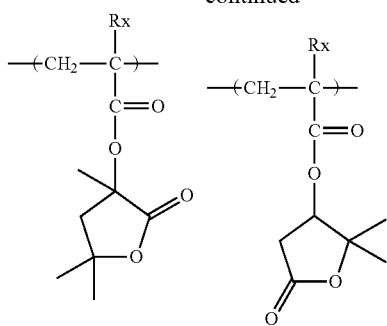
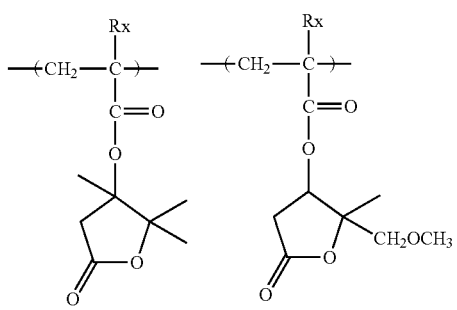
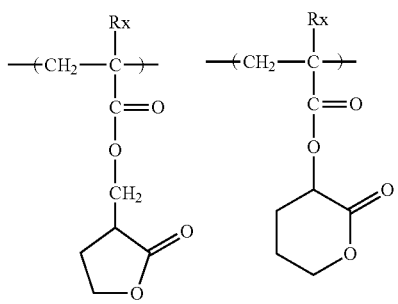
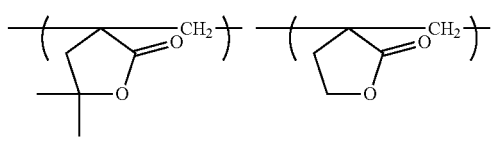
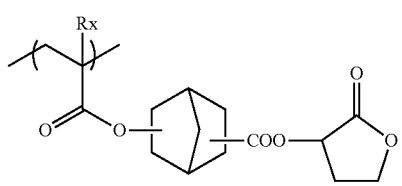
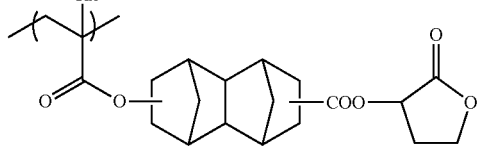

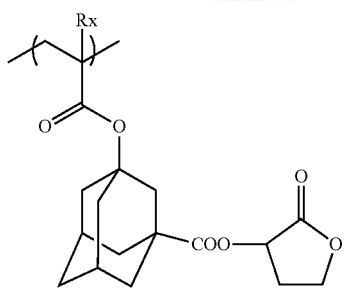
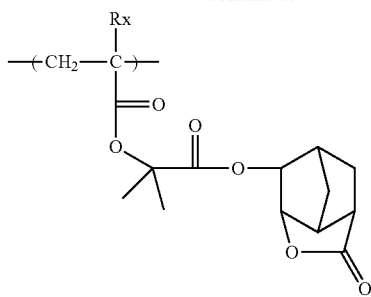
(In the formulae, Rx is H, CH₃, CH₂OH or CF₃.)
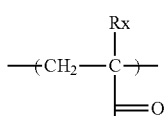 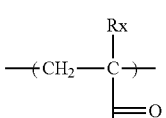
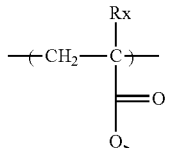
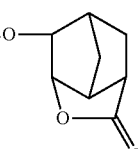
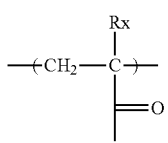 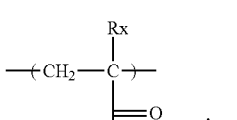
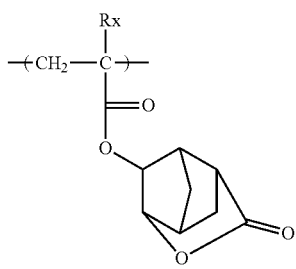
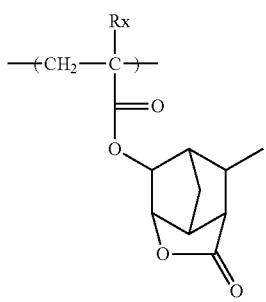 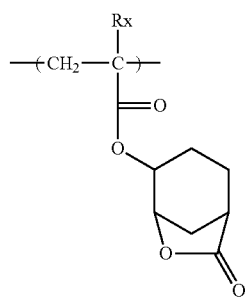
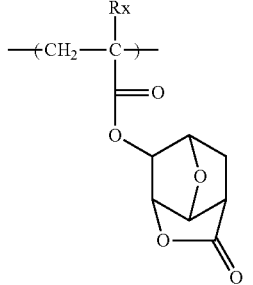
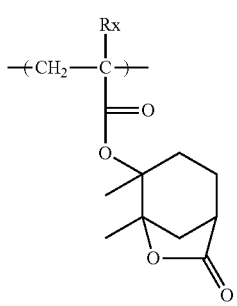 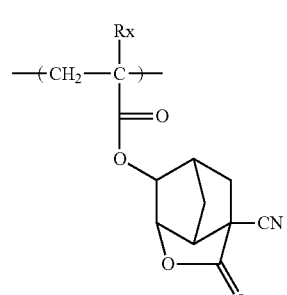
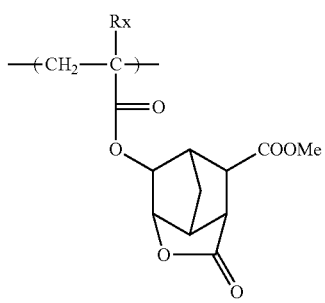

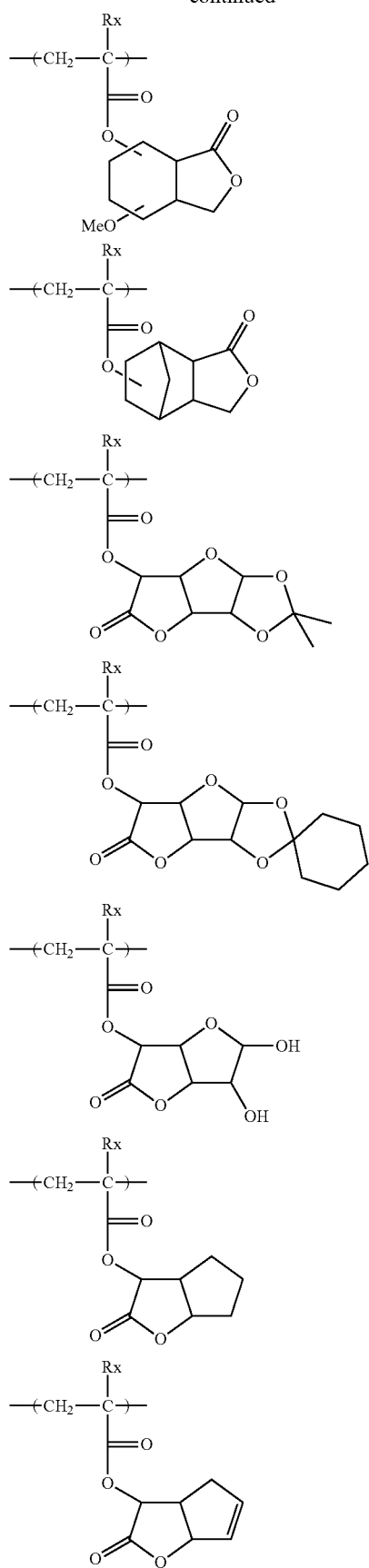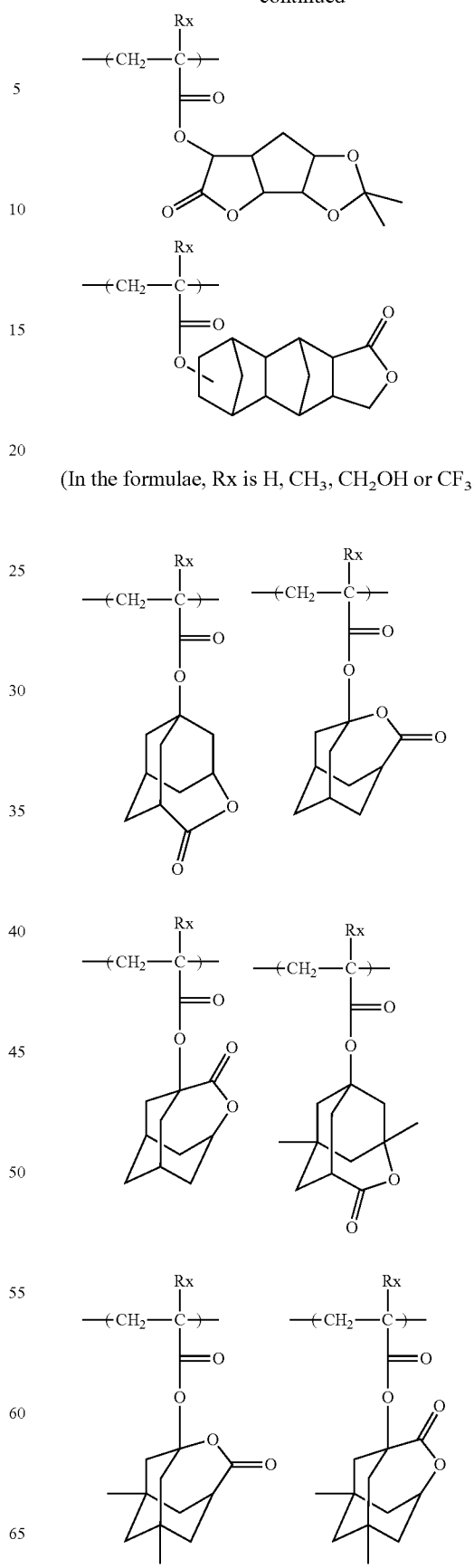
(In the formulae, Rx is H, CH₃, CH₂OH or CF₃.)

-continued
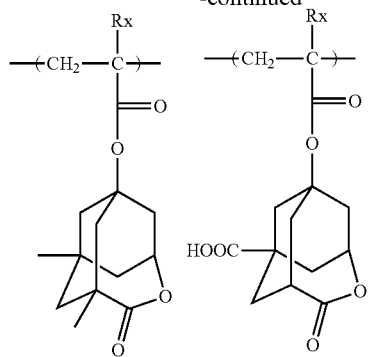
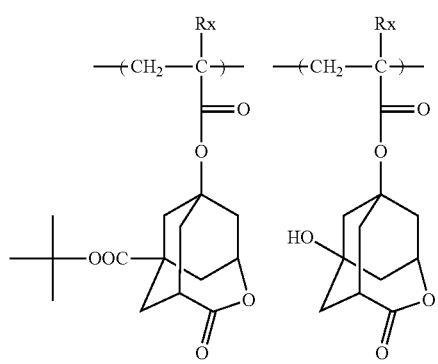
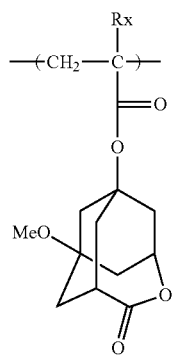
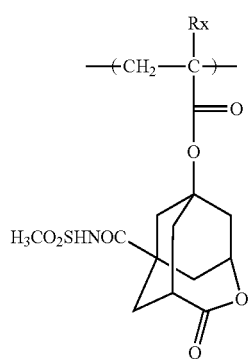
The repeating unit having a particularly preferred lactone group includes the repeating units shown below. By selecting an optimal lactone group, the pattern profile and the iso/dense bias are improved.
(In the formulae, Rx is H, $CH_3$, $CH_2OH$ or $CF_3$.)
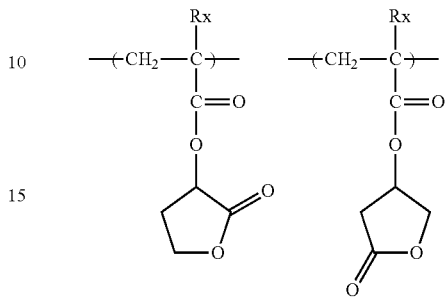
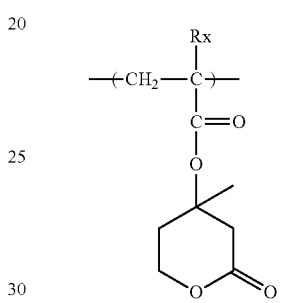
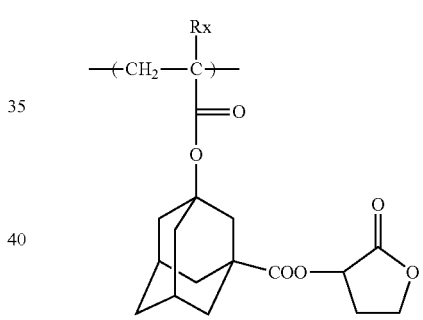
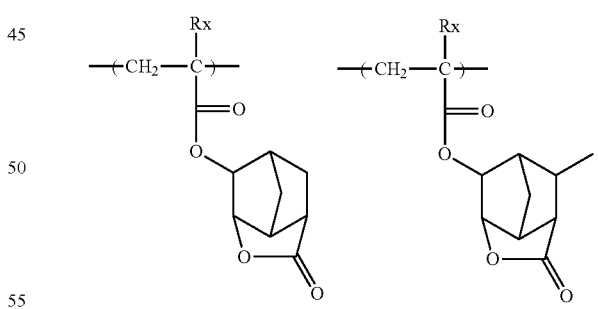
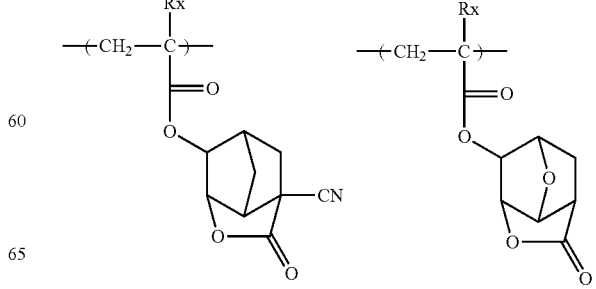

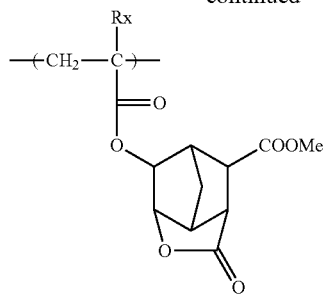
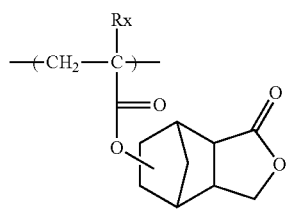
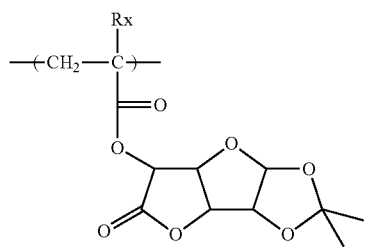
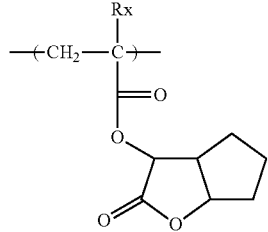

The resin of the component (B) preferably contains a repeating unit having a hydroxyl group or a cyano group. Thanks to this repeating unit, the adherence to substrate and the affinity for developer are enhanced. The repeating unit having a hydroxyl group or a cyano group is preferably a repeating unit having an alicyclic hydrocarbon structure substituted by a hydroxyl group or a cyano group. The alicyclic hydrocarbon structure in the alicyclic hydrocarbon structure substituted by a hydroxyl group or a cyano group is preferably an adamantyl group, a diamantyl group or a norbornane group. The alicyclic hydrocarbon structure substituted by a hydroxyl group or a cyano group is preferably a partial structure represented by the following formulae (VIIa) to (VIId):

(VIIa)
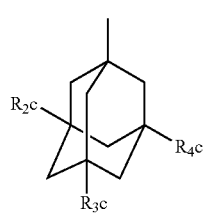

(VIIb)
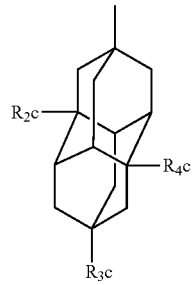

(VIIc)
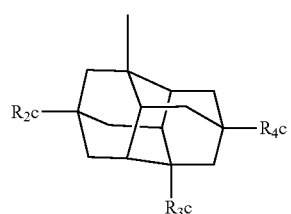

(VIId)
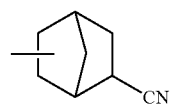

In formulae (VIIa) to (VIIe), each of $R_2c$ to $R_4c$ independently represents a hydrogen atom, a hydroxyl group or a cyano group; provided that at least one of $R_2c$ to $R_1c$ represents a hydroxyl group or a cyano group. A structure where one or two members out of $R_2c$ to $R_4c$ are a hydroxyl group with the remaining being a hydrogen atom is preferred. In formula (VIIa), it is more preferred that two members out of $R_2c$ to $R_4c$ are a hydroxyl group and the remaining is a hydrogen atom.

The repeating unit having a partial structure represented by formulae (VIIa) to (VIId) includes repeating units represented by the following formulae (AIIa) to (AIId):

(AIIa)
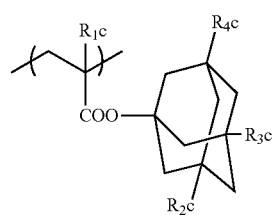

(AIIb)
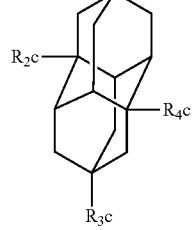

(AIIc)

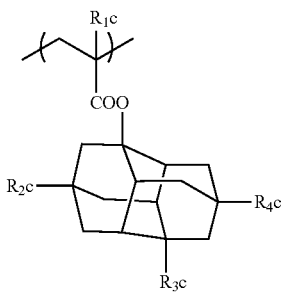

(AIId)

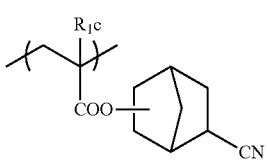

In formulae (AIIa) to (AIId), $R_1c$ represents a hydrogen atom, a methyl group, a trifluoromethyl group or a hydroxymethyl group.

$R_2c$ to $R_4c$ have the same meanings as $R_2c$ to $R_4c$ in formulae (VIIa) to (VIIe).

The content of the repeating unit having an alicyclic hydrocarbon structure substituted by a hydroxyl group or a cyano group is preferably from 5 to 40 mol %, more preferably from 5 to 30 mol %, still more preferably from 10 to 25 mol %, based on all repeating units in the polymer.

Specific examples of the repeating unit having a hydroxyl group or a cyano group are set forth below, but the present invention is not limited thereto.

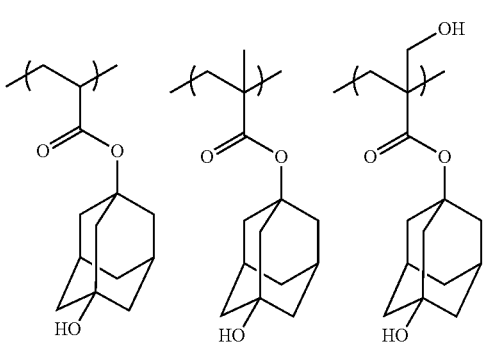

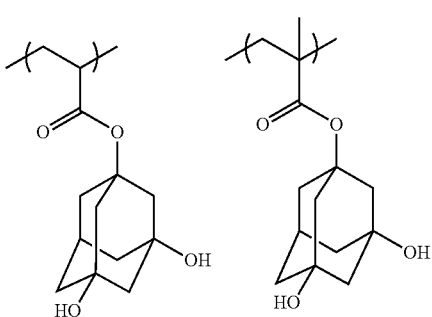

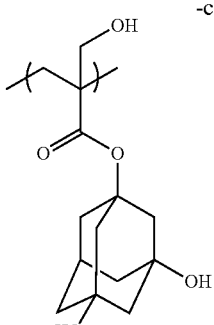

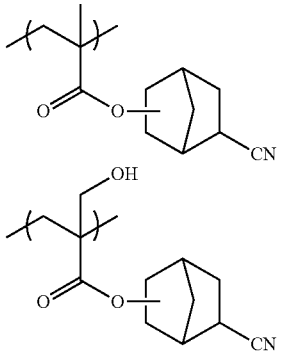

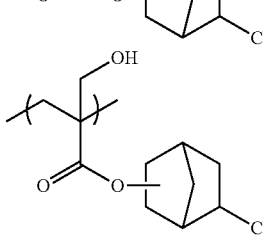

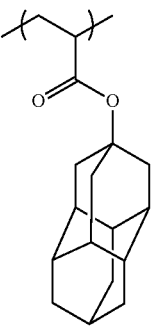

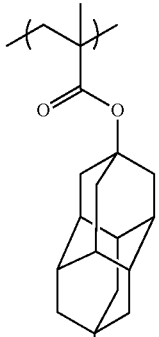

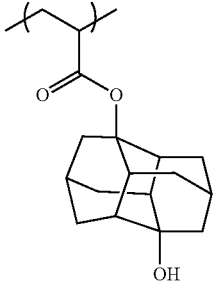

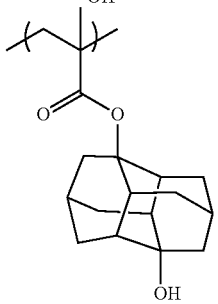

The resin of the component (B) preferably contains a repeating unit having an alkali-soluble group. The alkali-soluble group includes a carboxyl group, a sulfonamide group, a sulfonylimide group, a bisulfonylimide group, and an aliphatic alcohol with the α-position being substituted by an electron-withdrawing group, such as hexafluoroisopropanol group. It is more preferred to contain a repeating unit having a carboxyl group. By virtue of containing a repeating unit having an alkali-soluble group, the resolution increases in the usage of forming contact holes. As for the repeating unit having an alkali-soluble group, all of a repeating unit where an alkali-soluble group is directly bonded to the resin main chain, such as repeating unit by an acrylic acid or a methacrylic acid, a repeating unit where an alkali-soluble group is bonded to the resin main chain through a linking group, and a repeating unit where an alkali-soluble group is introduced into the polymer chain terminal by using an alkali-soluble group-containing polymerization initiator or chain transfer agent at the polymerization, are preferred. The linking group may have a monocyclic or polycyclic hydrocarbon structure. Above all, a repeating unit by an acrylic acid or a methacrylic acid is preferred.

The content of the repeating unit having an alkali-soluble group is preferably from 0 to 20 mol %, more preferably from 3 to 15 mol %, still more preferably from 5 to 10 mol %, based on all repeating units in the polymer.

Specific examples of the repeating unit having an alkali-soluble group are set forth below, but the present invention is not limited Hereto.

(In the formulae, Rx is H, $CH_3$, $CF_3$ or $CH_2OH$.)

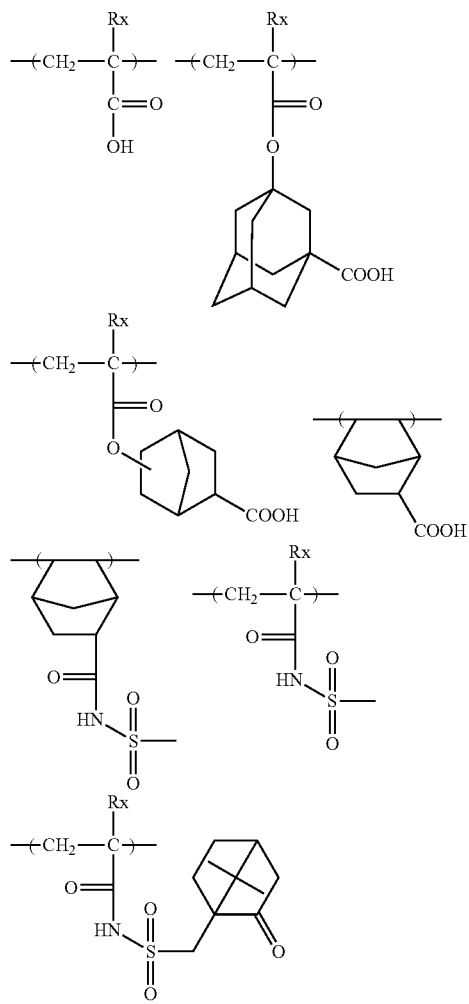

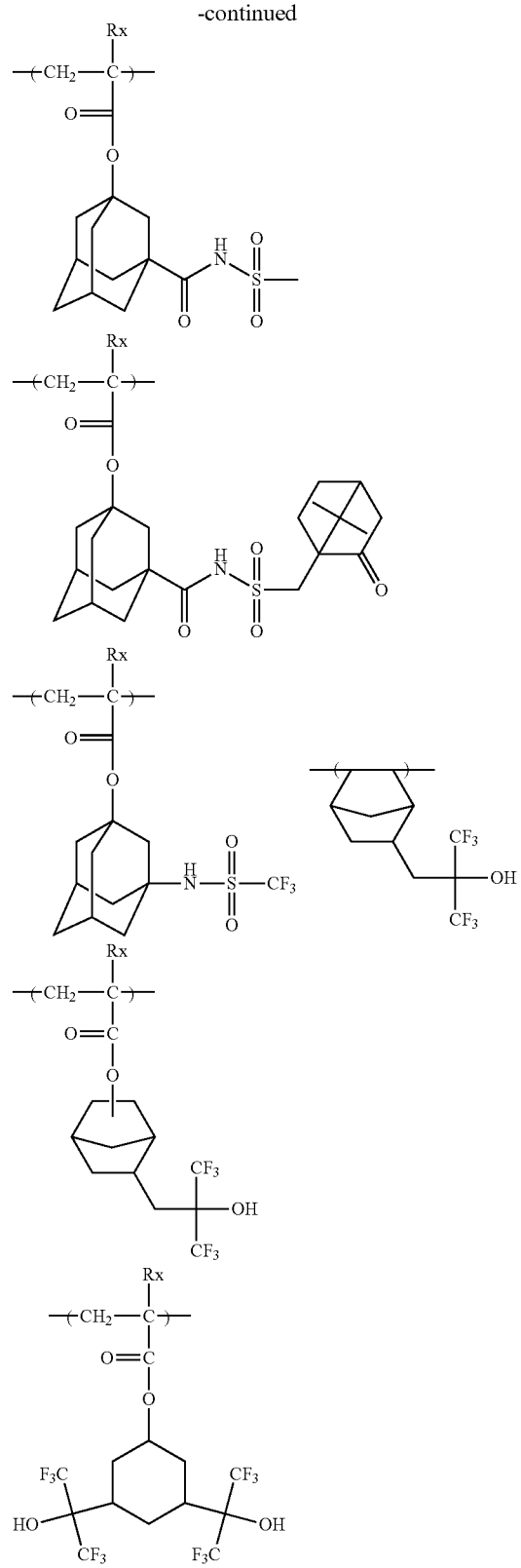

The repeating unit having at least one kind of a group selected from a lactone group, a hydroxyl group, a cyano group and an alkali-soluble group is preferably a repeating unit having at least two members selected from a lactone group, a hydroxyl group, a cyano group and an alkali-soluble group, more preferably a repeating unit having a cyano group and a lactone group. Above all, a repeating unit having a structure where a cyano group is substituted on the lactone structure of (LC1-4) is preferred.

The resin of the component (B) may further contain a repeating unit having an alicyclic hydrocarbon structure and not exhibiting acid decomposability. Thanks to such a repeating unit, the dissolving out of low molecular components from the resist film to the immersion liquid at the immersion exposure can be reduced. Examples of this repeating unit include a repeating unit composed of 1-adamantyl(meth) acrylate, diamantyl(meth)acrylate, tricyclodecanyl(meth) acrylate or cyclohexyl(meth)acrylate.

The resin of the component (B) may contain, in addition to the above-described repeating structural units, various repeating structural units for the purpose of controlling dry etching resistance, suitability for standard developer, adherence to substrate, resist profile and properties generally required of the resist, such as resolution, heat resistance and sensitivity.

Examples of such a repeating structural unit include, but are not limited to, repeating structural units corresponding to the monomers described below.

Thanks to such a repeating structural unit, the performance required of the resin of the component (B), particularly, (1) solubility in coating solvent,
(2) film-forming property (glass transition point),
(3) alkali developability,
(4) film loss (selection of hydrophilic, hydrophobic or alkali-soluble group),
(5) adherence of unexposed area to substrate,
(6) dry etching resistance and the like, can be subtly controlled.

Examples of the monomer include a compound having one addition-polymerizable unsaturated bond selected from acrylic acid esters, methacrylic acid esters, acrylamides, methacrylamides, allyl compounds, vinyl ethers and vinyl esters.

Other than these, an addition-polymerizable unsaturated compound copolymerizable with the monomers corresponding to the above-described various repeating structural units may be copolymerized.

In the resin of the component (B), the molar ratio of respective repeating structural units contained is appropriately determined to control dry etching resistance of resist, suitability for standard developer, adherence to substrate, resist profile and performances generally required of the resist, such as resolution, heat resistance and sensitivity.

In the case where the positive resist composition of the present invention is used for ArF exposure, the resin of the component (B) preferably has no aromatic group in view of transparency to ArF light.

The resin of the component (B) is preferably a resin where all repeating units are composed of a (meth)acrylate-based repeating unit. In this case, all repeating units may be a methacrylate-based repeating unit, all repeating units may be an acrylate-based repeating unit, or all repeating unit may be composed of a methacrylate-based repeating unit and an acrylate-based repeating unit, but the content of the acrylate-based repeating unit is preferably 50 mol % or less based on all repeating units. The resin is more preferably a copolymerized polymer containing from 20 to 50 mol % of an acid decomposable group-containing (meth)acrylate-based repeating unit represented by formula (A1), from 20 to 50 mol % of a lactone group-containing (meth)acrylate-based repeating unit, from 5 to 30 mol % of a (meth)acrylate-based repeating unit having an alicyclic hydrocarbon structure substituted by a hydroxyl group or a cyano group, and from 0 to 20 mol % of other (meth)acrylate-based repeating units.

In the case where the positive resist composition of the present invention is irradiated with KrF excimer laser light, electron beam, X-ray or high-energy beam at a wavelength of 50 nm or less (e.g., EUV), the resin of the component (B) preferably contains a hydroxystyrene-based repeating unit, more preferably a hydroxystyrene-based repeating unit and an acid-decomposable repeating unit such as a hydroxystyrene-based repeating unit protected by an acid-decomposable group and a tertiary alkyl (meth)acrylate.

Preferred examples of the repeating unit having an acid-decomposable group include a repeating unit composed of a tert-butoxycarbonyloxystyrene, a 1-alkoxyethoxystyrene or a tertiary alkyl(meth)acrylate. A repeating unit composed of a 2-alkyl-2-adamantyl(meth)acrylate or a dialkyl(1-adamantyl)methyl(meth)acrylate is more preferred.

The resin of the component (B) containing a hydroxystyrene-based repeating unit (hereinafter sometimes referred to as a "hydroxystyrene-based resin") is a resin having a group capable of decomposing by the action of an acid to produce an alkali-soluble group (acid-decomposable group), in either one or both of the main and side chains of the resin. Of these, a resin having an acid-decomposable group on the side chain is preferred.

The hydroxystyrene-based resin for use in the present invention resin can be obtained, as disclosed in European Patent 254853, JP-A-2-25850, JP-A-3-223860, JP-A-4-251259 and the like, by reacting an alkali-soluble resin with a precursor of a group capable of decomposing by the action of an acid or copolymerizing various monomers with an alkali-soluble resin monomer having bonded thereto a group capable of decomposing by the action of an acid.

The acid-decomposable group is preferably, for example, a group formed by substituting a group capable of leaving by the action of an acid for a hydrogen atom of an alkali-soluble group such as —COOH group and —OH group.

Examples of the group capable of leaving by the action of an acid include —C($R_{36}$)($R_{37}$)($R_{38}$), —C($R_{36}$)($R_{37}$)(O$R_{39}$), —C(=O)—O—C($R_{36}$)($R_{37}$)($R_{38}$), —C($R_{01}$)($R_{02}$)(O$R_{39}$), —C($R_{01}$)($R_{02}$)—C(=O)—O—C($R_{36}$)($R_{37}$)($R_{38}$) and —CH($R_{36}$)(Ar).

In the formulae, each of $R_{36}$ to $R_{39}$ independently represents an alkyl group, a cycloalkyl group, an aryl group, an aralkyl group or an alkenyl group. $R_{36}$ and $R_{37}$ may combine with each other to form a ring.

Each of $R_{01}$ and $R_{02}$ independently represents a hydrogen atom, an alkyl group, a cycloalkyl group, an aryl group, an aralkyl group or an alkenyl group.

Ar represents an aryl group.

The alkyl group of $R_{36}$ to $R_{39}$, $R_{01}$ and $R_{02}$ is preferably an alkyl group having a carbon number of 1 to 8, and examples thereof include a methyl group, an ethyl group, a propyl group, an n-butyl group, a sec-butyl group, a hexyl group and an octyl group.

The cycloalkyl group of $R_{36}$ to $R_{39}$, $R_{0l}$ and $R_{02}$ may be either monocyclic or polycyclic. The monocyclic cycloalkyl group is preferably a cycloalkyl group having a carbon number of 3 to 8, and examples thereof include a cyclopropyl group, a cyclobutyl group, a cyclopentyl group, a cyclohexyl group and a cyclooctyl group. The polycyclic cycloalkyl group is preferably a cycloalkyl group having a carbon number of 6 to 20, and examples thereof include an adamantyl group, a norbornyl group, an isobornyl group, a camphanyl group, a dicyclopentyl group, an α-pinel group, a tricyclodecanyl group, a tetracyclododecyl group and an androstanyl group. Incidentally, a part of carbon atoms in the cycloalkyl group may be substituted by a heteroatom such as oxygen atom.

The aryl group of $R_{36}$ to $R_{39}$, $R_{01}$, $R_{02}$ and Ar is preferably an aryl group having a carbon number of 6 to 10, and examples thereof include a phenyl group, a naphthyl group and an anthryl group.

The aralkyl group of $R_{36}$ to $R_{39}$, $R_{01}$ and $R_{02}$ is preferably an aralkyl group having a carbon number of 7 to 12, and examples thereof include a benzyl group, a phenethyl group and a naphthylmethyl group.

The alkenyl group of $R_{36}$ to $R_{39}$, $R_{01}$ and $R_{02}$ is preferably an alkenyl group having a carbon number of 2 to 8, and examples thereof include a vinyl group, an allyl group, a butenyl group and a cyclohexenyl group.

The ring formed by combining $R_{36}$ and $R_{37}$ with each other may be monocyclic or polycyclic. The monocyclic ring is preferably a cycloalkane structure having a carbon number of 3 to 8, and examples thereof include a cyclopropane structure, a cyclobutane structure, a cyclopentane structure, a cyclohexane structure, a cycloheptane structure and a cyclooctane structure. The polycyclic ring is preferably a cycloalkane structure having a carbon number of 6 to 20, and examples thereof include an adamantane structure, a norbornane structure, a dicyclopentane structure, a tricyclodecane structure and a tetracyclododecane structure. Incidentally, a part of carbon atoms in the cycloalkane may be substituted by a heteroatom such as oxygen atom.

$R_{36}$ to $R_{39}$, $R_{01}$, $R_{02}$ and Ar may have a substituent. Examples of the substituent which $R_{36}$ to $R_{39}$, $R_{01}$, $R_{02}$ and Ar may have include an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group and a nitro group.

The alkali-soluble resin is not particularly limited, but examples thereof include an alkali-soluble resin having a hydroxystyrene structure unit, such as poly(o-hydroxystyrene), poly(m-hydroxystyrene), poly(p-hydroxystyrene), copolymers thereof, hydrogenated poly(hydroxystyrene), poly(hydroxystyrenes) represented by the following structures, styrene-hydroxystyrene copolymer, α-methylstyrene-hydroxystyrene copolymer and hydrogenated novolak resin, and an alkali-soluble resin containing a repeating unit having a carboxyl group, such as (meth)acrylic acid and norbornenecarboxylic acid.

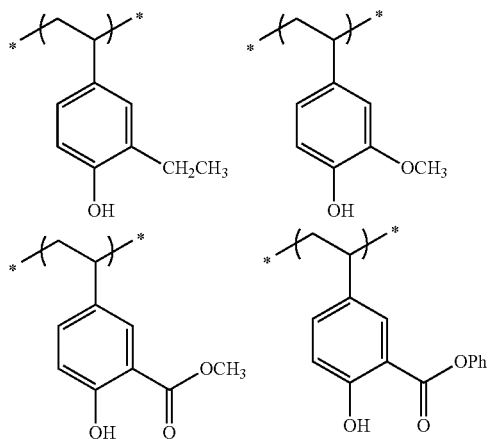

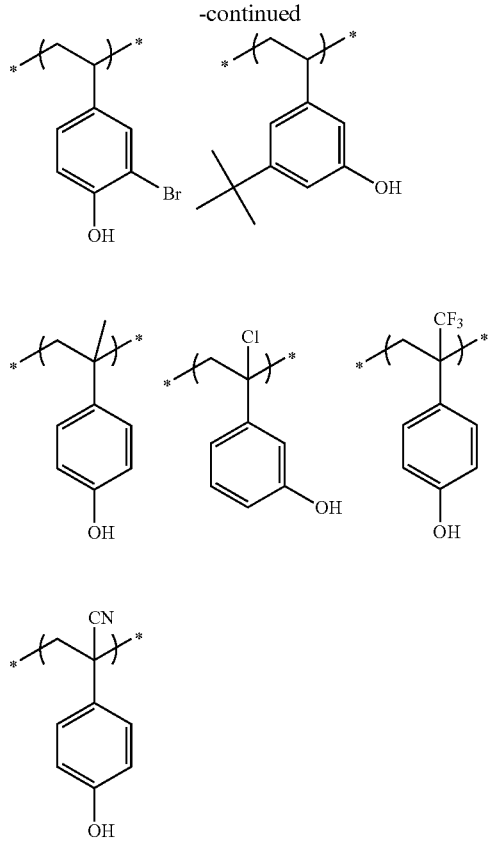

The alkali dissolution rate of the alkali-soluble resin is preferably 170 Å/sec or more, more preferably 330 Å/sec or more, as measured (at 23° C.) in 0.261 N tetramethylammonium hydroxide (TMAH).

The alkali-soluble resin monomer is not particularly limited, but examples thereof include an alkylcarbonyloxystyrene (e.g., tert-butoxycarbonyloxystyrene), an alkoxystyrene (e.g., 1-alkoxyethoxystyrene, tert-butoxystyrene) and a tertiary alkyl (meth)acrylate (e.g., tert-butyl (meth)acrylate, 2-alkyl-2-adamantyl (meth)acrylate, dialkyl(1-adamantyl) methyl (meth)acrylate).

The content of the group capable of decomposing by the action of an acid is expressed by B/(B+S) using the number (B) of repeating units having a group capable of decomposing by the action of an acid and the number (S) of repeating units having an alkali-soluble group not protected by a group capable of leaving by the action of an acid, in the resin. The content is preferably from 0.01 to 0.7, more preferably from 0.05 to 0.50, still more preferably from 0.05 to 0.40.

The hydroxystyrene-based resin for use in the present invention is not particularly limited but preferably contains a repeating unit having an aromatic group and is more preferably an acid-decomposable resin containing hydroxystyrene as a repeating unit (for example, a poly(hydroxystyrene/hydroxystyrene protected by an acid-decomposable group) and a poly(hydroxystyrene/(meth)acrylic acid protected by an acid-decomposable group)).

In particular, the hydroxystyrene-based resin for use in the present invention is preferably a resin containing a repeating unit represented by the following formula (III) and a repeating unit represented by formula (IV):

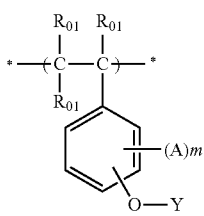
(III)

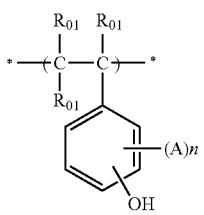
(IV)

In formulae (III) and (VI), each $R_{01}$ independently represents a hydrogen atom, an alkyl group, a cycloalkyl group, a halogen atom, a cyano group or an alkoxycarbonyl group.

Y represents a group capable of leaving by the action of an acid.

A represents a halogen atom, a cyano group, an acyl group, an alkyl group, an alkoxy group, an acyloxy group or an alkoxycarbonyl group.

m represents an integer of 0 to 4.

n represents an integer of 0 to 4.

The group capable of leaving by the action of an acid of Y is more preferably a structure represented by the following formula:

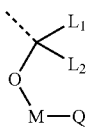

Each of $L_1$ and $L_2$, which may be the same or different, represents a hydrogen atom, an alkyl group, a cycloalkyl group, an aryl group or an aralkyl group.

M represents a single bond or a divalent linking group.

Q represents an alkyl group, a cycloalkyl group, an alicyclic group that may contain a heteroatom, an aromatic ring group that may contain a heteroatom, an amino group, an ammonium group, a mercapto group, a cyano group or an aldehyde group.

At least two members of Q, M and $L_1$ may combine to form a 5- or 6-membered ring.

Also, the hydroxystyrene-based resin may be a resin containing a repeating unit represented by formula (III), a repeating unit represented by formula (IV), and a repeating unit represented by the following formula (V):

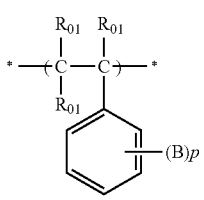
(V)

In formula (V), each $R_{01}$ independently represents a hydrogen atom, an alkyl group, a cycloalkyl group, a halogen atom, a cyano group or an alkoxycarbonyl group.

B represents a halogen atom, a cyano group, an acyl group, an alkyl group, a cycloalkyl group, a cycloalkyloxy group, an alkoxy group (excluding an —O-tertiary alkyl), an alkoxycarbonyl group, an alkenyl group, an alkenyloxy group, an aryl group, an aryloxy group, an alkylcarbonyloxy group, an alkylamidomethyloxy group, an alkylamide group, an arylamidomethyl group or an arylamide group.

p represents an integer of 0 to 5.

The substituent (—OY) on the benzene ring in the repeating unit represented by formula (III) is a group (acid-decomposable group) capable of decomposing by the action of an acid to produce a hydroxyl group (alkali-soluble group) and decomposes by the action of an acid to produce a hydroxystyrene unit and convert the resin into a resin whose solubility in an alkali developer is increased.

In formulae (III) to (V), each $R_{01}$ independently represents a hydrogen atom, an alkyl group, a cycloalkyl group, a halogen atom, a cyano group or an alkoxycarbonyl group and preferably has a carbon number or 20 or less.

The alkyl group and cycloalkyl group in $R_{01}$ preferably have a carbon number of 20 or less, and examples thereof include a methyl group, an ethyl group, a propyl group, an isopropyl group, an n-butyl group, an isobutyl group, a tert-butyl group, a pentyl group, a cyclopentyl group, a hexyl group, a cyclohexyl group, an octyl group and a dodecyl group. These groups each may have a substituent, and examples of the substituent include an alkoxy group, an alkoxycarbonyl group, a hydroxyl group, a halogen atom, a nitro group, an acyl group, an acyloxy group, an acylamino group, a sulfonylamino group, an alkylthio group, an arylthio group, an aralkylthio group, a thiophenecarbonyloxy group, a thiophenemethylcarbonyloxy group and a heterocyclic residue such as pyrrolidone residue. A substituent having a carbon number of 8 or less is preferred. The alkyl group in $R_{01}$ is more preferably a methyl group, a $CF_3$ group, an alkoxycarbonylmethyl group, an alkylcarbonyloxymethyl group, a hydroxymethyl group or an alkoxymethyl group.

The halogen atom in $R_{01}$ includes a fluorine atom, a chlorine atom, a bromine atom and an iodine atom and is preferably a fluorine atom.

As for the alkyl group contained in the alkoxycarbonyl group of $R_{01}$, the same as those described above for the alkyl group $R_{01}$ are preferred.

The alkyl group as $L_1$ and $L_2$ is, for example, an alkyl group having a carbon number of 1 to 8, and specific preferred examples thereof include a methyl group, an ethyl group, a propyl group, an n-butyl group, a sec-butyl group, a hexyl group and an octyl group.

The cycloalkyl group as $L_1$ and $L_2$ is, for example, a cycloalkyl group having a carbon number of 3 to 15, and specific preferred examples thereof include a cyclopentyl group, a cyclohexyl group, a norbornyl group and an adamantyl group.

The aryl group as $L_1$ and $L_2$ is, for example, an aryl group having a carbon number of 6 to 15, and specific preferred example thereof include a phenyl group, a tolyl group, a naphthyl group and an anthryl group.

The aralkyl group as $L_1$ and $L_2$ is, for example, an aralkyl group having a carbon number of 6 to 20, and examples thereof include a benzyl group and a phenethyl group.

The divalent linking group as M is, for example, an alkylene group, a cycloalkylene group, an alkenylene group, an arylene group, —O—, —CO—, —$SO_2$—, —N($R_0$)— or a divalent linking group formed by combining a plurality of these members. R₀ is a hydrogen atom or an alkyl group.

The alkyl group and cycloalkyl group of Q are the same as respective groups of L₁ and L₂.

The alicyclic group and aromatic ring group in the alicyclic group that may contain a heteroatom and the aromatic ring group that may contain a heteroatom of Q include, for example, the cycloalkyl group and aryl group as L₁ and L₂, and the carbon number thereof is preferably from 3 to 15.

Examples of the heteroatom-containing alicyclic group and heteroatom-containing aromatic ring group include a group having a heterocyclic structure, such as thiirane, cyclothiolane, thiophene, furan, pyrrole, benzothiophene, benzofuran, benzopyrrole, triazine, imidazole, benzimidazole, triazole, thiadiazole, thiazole and pyrrolidone, but the group is not limited thereto as long as it has a structure generally called a heterocycle (a ring formed by carbon and heteroatom or a ring formed by heteroatom).

As for the 5- or 6-membered ring that may be formed by combining at least two members of Q, M and L₁, there is included a case where at least two members of Q, M and L₁ are combined to form, for example, a propylene group or a butylene group, thereby forming an oxygen atom-containing 5- or 6-membered ring.

The group represented by -M-Q preferably has a carbon number of 1 to 30, more preferably from 5 to 20.

The acyl group as A is preferably an acyl group having a carbon number of 2 to 8, and specific preferred examples thereof include a formyl group, an acetyl group, a propanoyl group, a butanoyl group, a pivaloyl group and a benzoyl group.

The alkyl group as A is preferably an alkyl group having a carbon number of 1 to 8, and specific preferred examples thereof include a methyl group, an ethyl group, a propyl group, an n-butyl group, a sec-butyl group, a hexyl group and an octyl group.

The alkoxy group as A is preferably the above-described alkoxy group having a carbon number of 1 to 8, and examples thereof include a methoxy group, an ethoxy group, a propoxy group, a butoxy group, a pentyloxy group, a hexyloxy group and a cyclohexyloxy group.

Examples of the acyl group in the acyloxy group as A include groups corresponding to the above-described acyl group.

Examples of the alkoxy group in the alkoxycarbonyl group as A include groups corresponding to the above-described alkoxy group.

Each of these groups may have a substituent, and preferred examples of the substituent include a hydroxyl group, a carboxyl group, a halogen atom (fluorine, chlorine, bromine, iodine) and an alkoxy group (e.g., methoxy, ethoxy, propoxy, butoxy). As for the cyclic structure, examples of the substituent further include an alkyl group (preferably having a carbon number of 1 to 8).

Each of m and n independently represents an integer of 0 to 4. Each of m and n is preferably an integer of 0 to 2, more preferably 0 or 1.

Specific examples of the repeating unit represented by formula (III) are set forth below, but the present invention is not limited thereto.

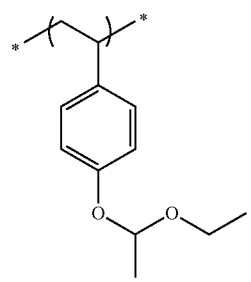

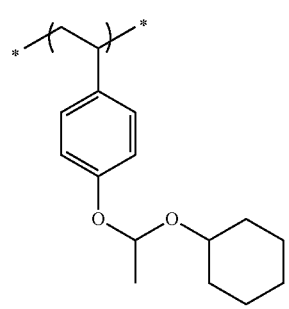

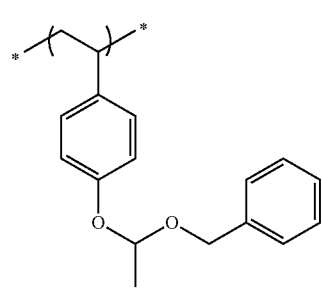

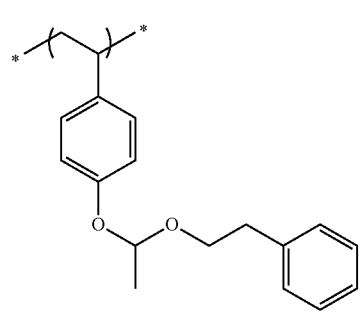

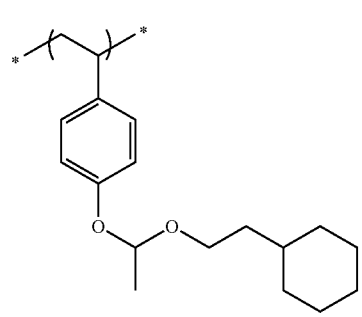

79
-continued
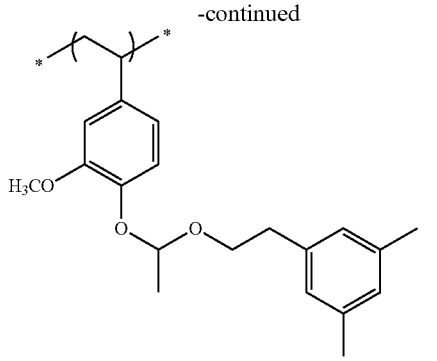
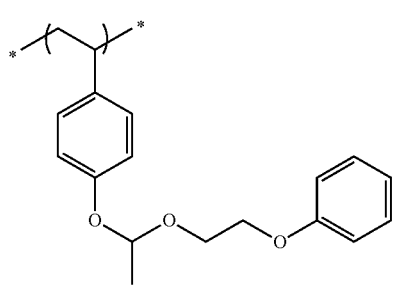
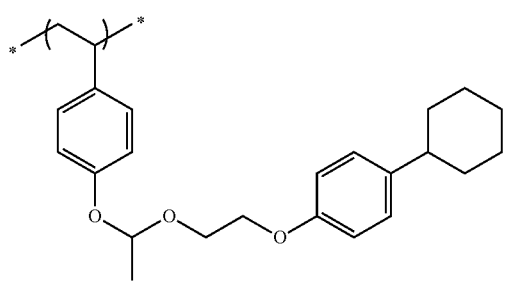
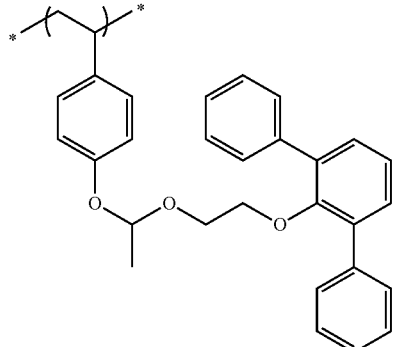
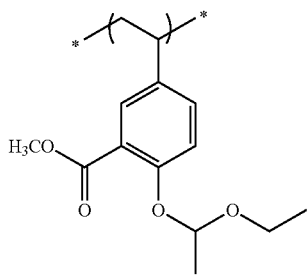
80
-continued
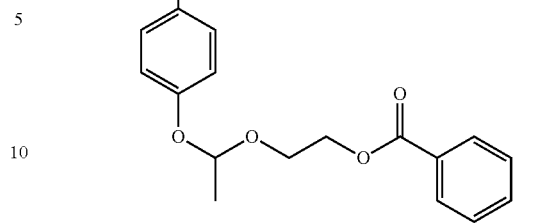
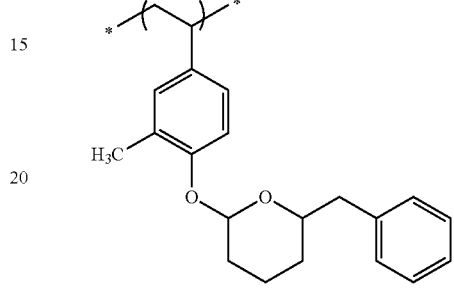
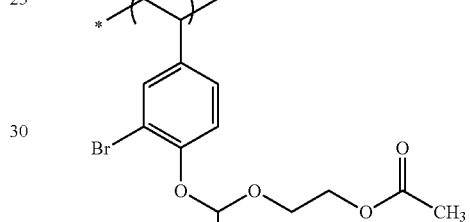
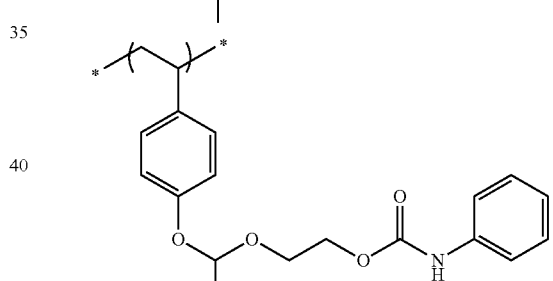
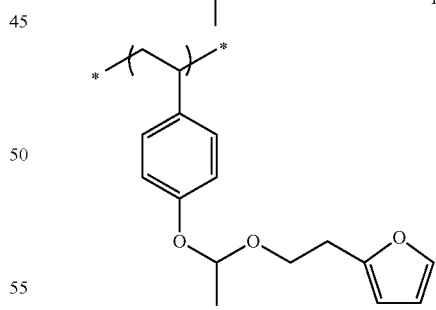
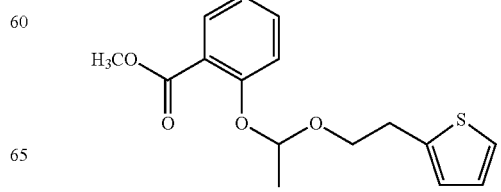

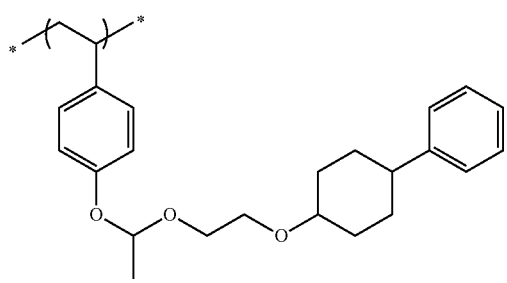

Specific examples of the repeating unit represented by formula (IV) are set forth below, but the present invention is not limited thereto.

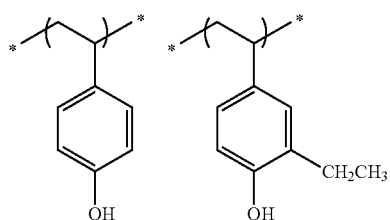

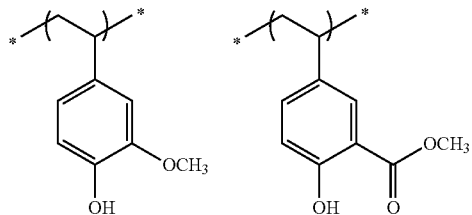

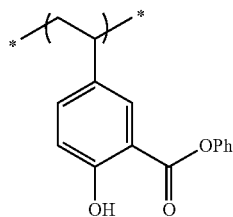

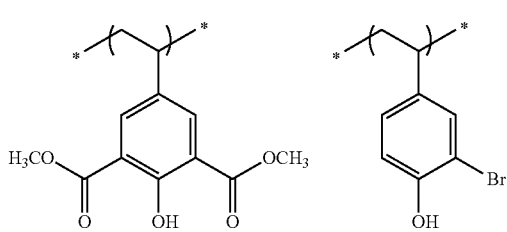

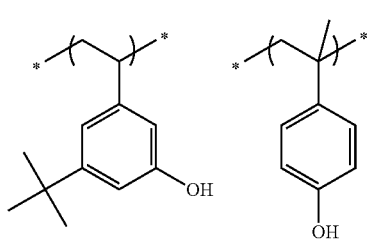

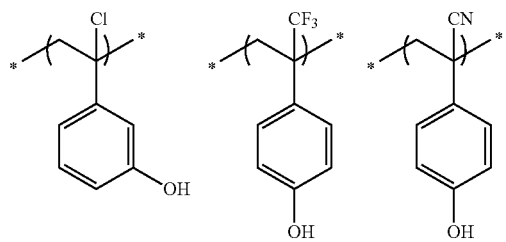

Each $R_{01}$ in formula (V) independently represents a hydrogen atom, an alkyl group, a cycloalkyl group, a halogen atom, a cyano group or an alkoxycarbonyl group and preferably has a carbon number of 20 or less, and examples thereof are the same as those of $R_{01}$ in formula (III) or (IV).

The acyl group, alkyl group, alkoxy group, acyloxy group and alkoxycarbonyl group as B in formula (V) are the same as respective groups of A in formula (III).

p represents an integer of 0 to 5 and is preferably an integer of 0 to 2, more preferably 1.

Specific examples of the repeating unit represented by formula (V) are set forth below, but the present invention is not limited thereto.

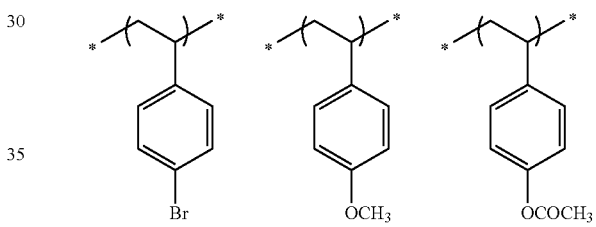

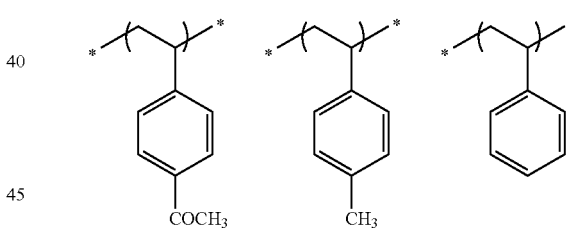

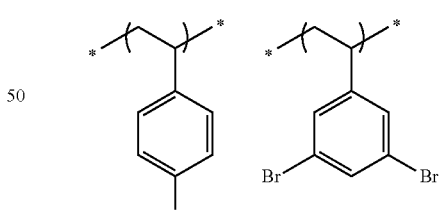

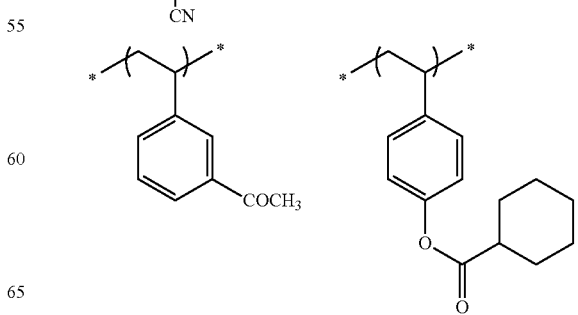

-continued

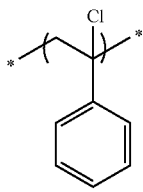

The hydroxystyrene-based resin for use in the present invention may contain a repeating unit represented by the following formula (VI):

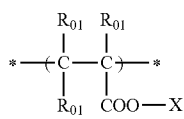

(VI)

In formula (VI), each $R_{01}$ independently represents a hydrogen atom, a fluorine atom, a chlorine atom, a cyano group or an alkyl group.

X represents a hydrogen atom or an organic group.

The alkyl group as $R_{01}$ in formula (V) is preferably an alkyl group having a carbon number of 1 to 5, and examples thereof include a methyl group, an ethyl group and a propyl group.

The organic group as X preferably has a carbon number of 1 to 40 and may be a group capable of leaving by the action of an acid (hereinafter, sometimes referred to as an "acid-leaving group") or a group incapable of leaving by the action of an acid (hereinafter, sometimes referred to as a "non-acid-leaving group").

Examples of the non-acid-leaving group include an alkyl group, a cycloalkyl group, an alkenyl group and an aryl group, which cannot leave by the action of an acid.

In the non-acid-leaving group, the alkyl group is preferably an alkyl group having a carbon number of 1 to 4, such as methyl group, ethyl group, propyl group, n-butyl group and sec-butyl group; the cycloalkyl group is preferably a cycloalkyl group having a carbon number of 3 to 10, such as cyclopropyl group, cyclobutyl group, cyclohexyl group and adamantyl group; the alkenyl group is preferably an alkenyl group having a carbon number of 2 to 4, such as vinyl group, propenyl group, allyl group and butenyl group; and the aryl group is preferably an aryl group having a carbon number of 6 to 14, such as phenyl group, xylyl group, toluoyl group, cumenyl group, naphthyl group and anthracenyl group.

Examples of the organic group as the acid-leaving group of X include —C($R_{11a}$)($R_{12a}$)($R_{13a}$), —C($R_{14a}$)($R_{15a}$)(O$R_{16a}$), —CH($R_{17a}$)(Ar) and —CO—OC($R_{11a}$)($R_{12a}$)($R_{13a}$).

Each of $R_{11a}$ to $R_{13a}$ independently represents an alkyl group, a cycloalkyl group, an alkenyl group, an aralkyl group or an aryl group. Each of $R_{14a}$ and $R_{15a}$ independently represents a hydrogen atom or an alkyl group. $R_{16a}$ represents an alkyl group, a cycloalkyl group, an alkenyl group, an aralkyl group or an aryl group. $R_{17a}$ represents an alkyl group, a cycloalkyl group, an aryl group or an alkoxy group. Ar represents an aryl group. Two members out of $R_{11a}$, $R_{12a}$ and $R_{13a}$, or two members out of $R_{14a}$, $R_{15a}$ and $R_{16a}$ may combine to form a ring.

Incidentally, a group having an acid-decomposable group may be introduced into X by modification. X having introduced thereinto an acid-decomposable group is, for example, represented by the following formula:

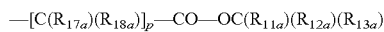

wherein each of $R_{17a}$ and $R_{18a}$ independently represents a hydrogen atom or an alkyl group, and p represents an integer of 1 to 4.

The organic group as X is preferably an acid-leaving group having at least one cyclic structure selected from an alicyclic structure, an aromatic cyclic structure and a crosslinked alicyclic structure, and the structure is preferably a structure containing an aromatic group (particularly phenyl group) or a structure containing an alicyclic or crosslinked alicyclic structure represented by the following formulae (pI) to (pVI):

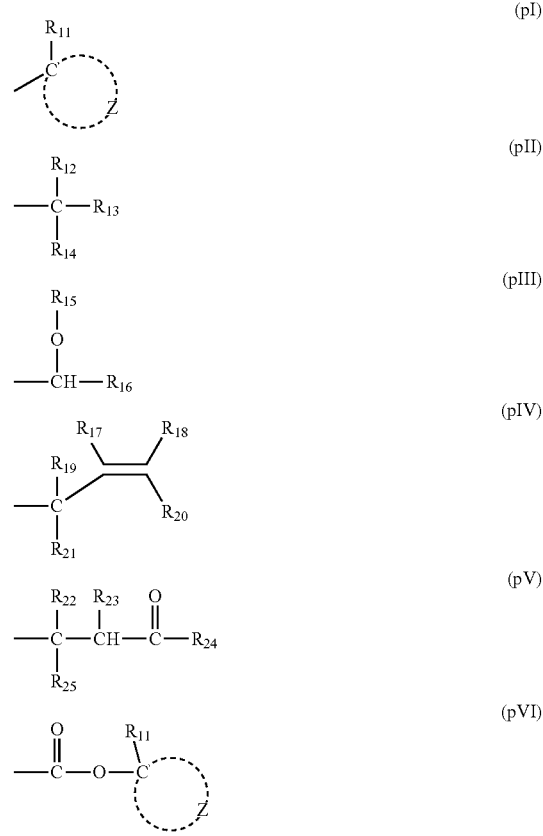

In the formulae, $R_{11}$ represents a methyl group, an ethyl group, an n-propyl group, an isopropyl group, an n-butyl group, an isobutyl group or a sec-butyl group, and Z represents an atomic group necessary for forming an alicyclic hydrocarbon group together with the carbon atom.

Each of $R_{12}$ to $R_{16}$ independently represents a linear or branched alkyl group having a carbon number of 1 to 4 or an alicyclic hydrocarbon group, provided that at least one of $R_{12}$ to $R_{14}$ or either one of $R_{15}$ and $R_{16}$ represents an alicyclic hydrocarbon group.

Each of $R_{17}$ to $R_{21}$ independently represents a hydrogen atom, a linear or branched alkyl group having a carbon number of 1 to 4 or an alicyclic hydrocarbon group, provided that at least one of $R_{17}$ to $R_{21}$ represents an alicyclic hydrocarbon group and that either one of $R_{19}$ and $R_{21}$ represents a linear or branched alkyl group having a carbon number of 1 to 4 or an alicyclic hydrocarbon group.

Each of $R_{22}$ to $R_{25}$ independently represents a hydrogen atom, a linear or branched alkyl group having a carbon number of 1 to 4 or an alicyclic hydrocarbon group, provided that at least one of $R_{22}$ to $R_{25}$ represents an alicyclic hydrocarbon group, and $R_{23}$ and $R_{24}$ may combine together to form a ring.

In formulae (pI) to (pVI), the alkyl group of $R_{12}$ to $R_{25}$ is a linear or branched alkyl group having a carbon number of 1 to 4, which may be substituted or unsubstituted, and examples of the alkyl group include a methyl group, an ethyl group, an n-propyl group, an isopropyl group, an n-butyl group, an isobutyl group, a sec-butyl group and a tert-butyl group.

Examples of the substituent which the alkyl group above may further have include an alkoxy group having a carbon number of 1 to 4, a halogen atom (fluorine, chlorine, bromine, iodine), an acyl group, an acyloxy group, a cyano group, a hydroxyl group, a carboxy group, an alkoxycarbonyl group and a nitro group.

The alicyclic hydrocarbon group of $R_{12}$ to $R_{25}$ and the alicyclic hydrocarbon group formed by Z together with the carbon atom may be monocyclic or polycyclic. Specific examples thereof include a group having a monocyclo, bicyclo, tricyclo or tetracyclo structure with a carbon number of 5 or more. The carbon number thereof is preferably from 6 to 30, more preferably from 7 to 25. These alicyclic hydrocarbon groups may have a substituent.

Examples of the structure of the alicyclic moiety in the alicyclic hydrocarbon group are set forth below.

(1)

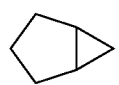
(2)

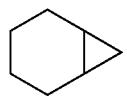
(3)

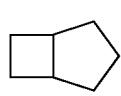
(4)

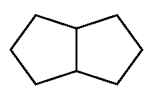
(5)

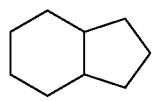
(6)

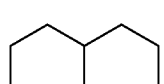
(7)

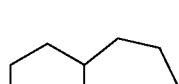
(8)

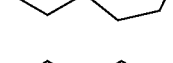
(9)

-continued

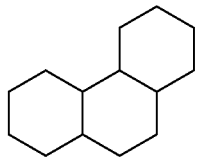
(10)

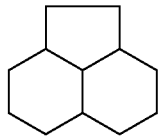
(11)

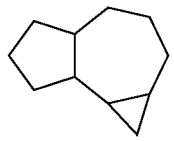
(12)

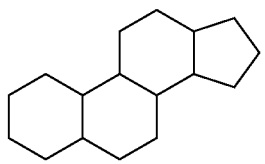
(13)

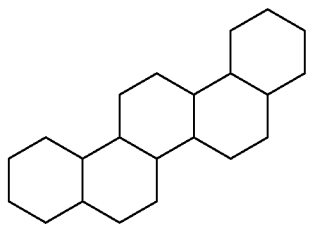
(14)

(15)

(16)

(17)

(18)

(19)

(20)

-continued
(21)
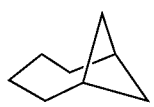
(22)
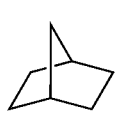
(23)
(24)
(25)
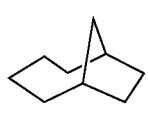
(26)
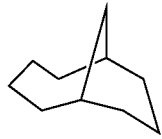
(27)
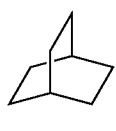
(28)
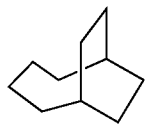
(29)
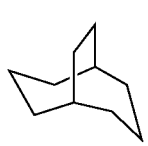
(30)
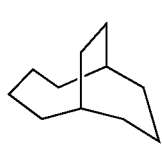
(31)
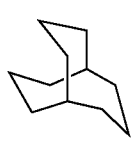
(32)
-continued
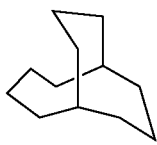
(33)
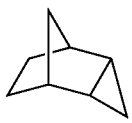
(34)
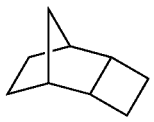
(35)
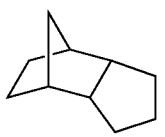
(36)
(37)
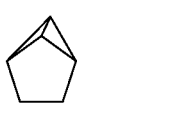
(38)
(39)
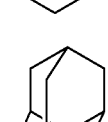
(40)
(41)
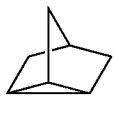
(42)
(43)
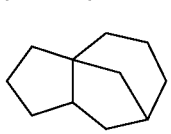
(44)

 (45)

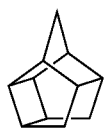 (46)

 (47)

 (48)

 (49)

 (50)

In the present invention, preferred examples of the alicyclic moiety include an adamantyl group, a noradamantyl group, a decalin residue, a tricyclodecanyl group, a tetracyclododecanyl group, a norbornyl group, a cedrol group, a cyclohexyl group, a cycloheptyl group, a cyclooctyl group, a cyclodecanyl group and a cyclododecanyl group. Among these, more preferred are an adamantyl group, a decalin residue, a norbornyl group, a cedrol group, a cyclohexyl group, a cycloheptyl group, a cyclooctyl group, a cyclodecanyl group and a cyclododecanyl group.

Examples of the substituent which the alicyclic hydrocarbon group may have include an alkyl group, a halogen atom, a hydroxyl group, an alkoxy group, a carboxyl group and an alkoxycarbonyl group. The alkyl group is preferably a lower alkyl group such as methyl group, ethyl group, propyl group, isopropyl group and butyl group, and the substituent is more preferably a substituent selected from the group consisting of a methyl group, an ethyl group, a propyl group and an isopropyl group. Examples of the alkoxy group include an alkoxy group having a carbon number of 1 to 4, such as methoxy group, ethoxy group, propoxy group and butoxy group.

The alkyl group, alkoxy group and alkoxycarbonyl group may further have a substituent, and examples of the substituent include an alkoxy group having a carbon number of 1 to 4 (e.g., methoxy, ethoxy, butoxy), a hydroxy group, an oxo group, an alkylcarbonyl group (preferably having a carbon number of 2 to 5), an alkylcarbonyloxy group (preferably having a carbon number of 2 to 5), an alkyloxycarbonyl group (preferably having a carbon number of 2 to 5) and a halogen atom (e.g., chlorine, bromine, fluorine).

In the hydroxystyrene-based resin for use in the present invention, in order to maintain good developability with an alkali developer, another appropriate polymerizable monomer may be copolymerized so that an alkali-soluble group such as phenolic hydroxyl group, carboxyl group, sulfonic acid group and hexafluoroisopropanol group ($—C(CF_3)_2OH$) can be introduced, or for enhancing the film quality, another hydrophobic polymerizable monomer such as alkyl acrylate and alkyl methacrylate may be copolymerized.

Also, in the hydroxystyrene-based resin for use in the present invention, a monomer having a lactone structure and a monomer having an alicyclic hydrocarbon structure substituted by a hydroxyl group or a cyano group may be copolymerized.

The content of the repeating unit represented by formula (III) is preferably from 5 to 60 mol %, more preferably from 10 to 50 mol %, still more preferably from 10 to 40 mol %, based on all repeating units constituting the resin.

The content of the repeating unit represented by formula (IV) is preferably from 40 to 90 mol %, more preferably from 45 to 80 mol %, still more preferably from 50 to 75 mol %, based on all repeating units constituting the resin.

The content of the repeating unit represented by formula (V) is preferably from 5 to 50 mol %, more preferably from 10 to 40 mol %, still more preferably from 15 to 30 mol %, based on all repeating units constituting the resin.

The content of the repeating unit represented by formula (VI) is preferably from 0 to 30 mol %, more preferably from 0 to 20 mol %, still more preferably from 0 to 10 mol %, based on all repeating units constituting the resin.

The content of the repeating unit having an alkali-soluble group such as hydroxyl group, carboxy group and sulfonic acid group is preferably from 1 to 99 mmol %, more preferably from 3 to 95 mol %, still more preferably from 5 to 90 mol %, based on all repeating units constituting the resin.

The content of the repeating unit having an acid-decomposable group is preferably from 3 to 95 mol %, more preferably from 5 to 90 mol %, still more preferably from 10 to 85 mol %, based on all repeating units constituting the resin.

The hydroxystyrene-based resin may be synthesized by a known synthesis method as described in European Patent 254853, JP-A-2-258500, JP-A-3-223860 and JP-A-4-251259, for example, a method of reacting a precursor of a group capable of decomposing by the action of an acid wish an alkali-soluble resin or a method of copolymerizing a monomer having a group capable of decomposing by the action of an acid with various monomers.

The weight average molecular weight of the hydroxystyrene-based resin for use in the present invention is, as a polystyrene-equivalent value by the GPC method, preferably 50,000 or less, more preferably from 1,000 to 20,000, still more preferably from 1,000 to 10,000.

The polydispersity (Mw/Mn) of the acid-decomposable resin for use in the present invention is preferably from 1.0 to 3.0, more preferably from 1.05 to 2.0, still more preferably from 1.1 to 1.7.

Two or more kinds of hydroxystyrene-based resins for use in the present invention may be used in combination.

Specific preferred examples of the hydroxystyrene-based resin for use in the present invention are set forth below, but the present invention is not limited thereto.

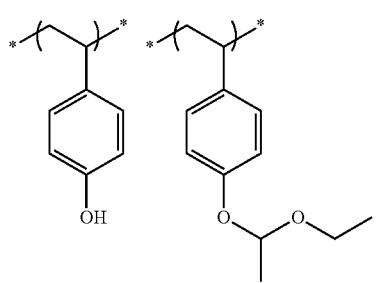
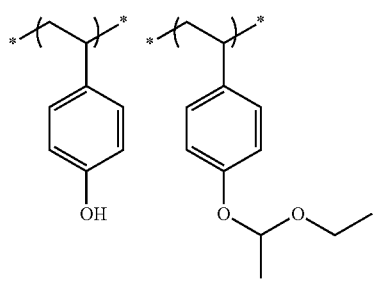
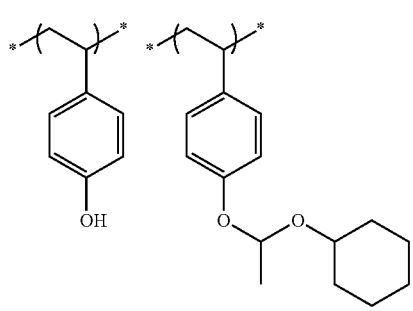
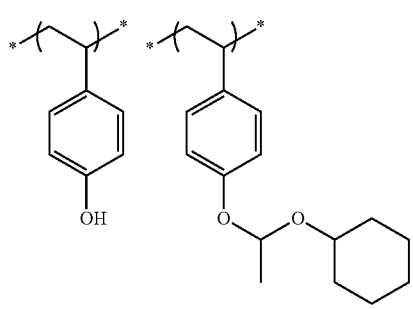
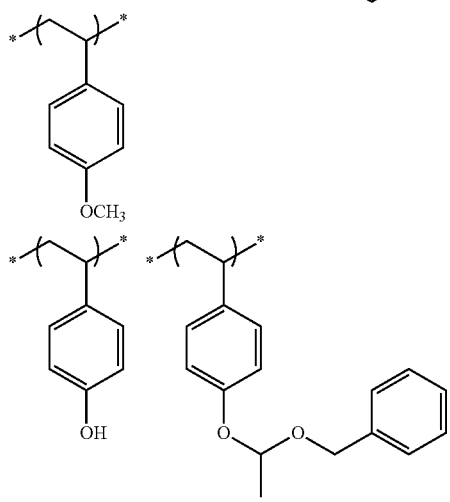
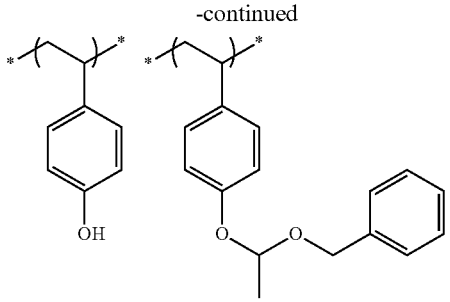
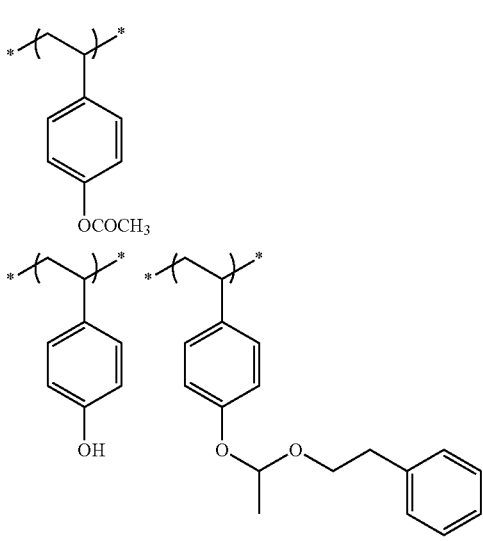
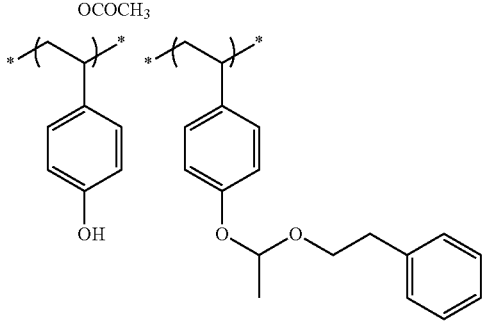
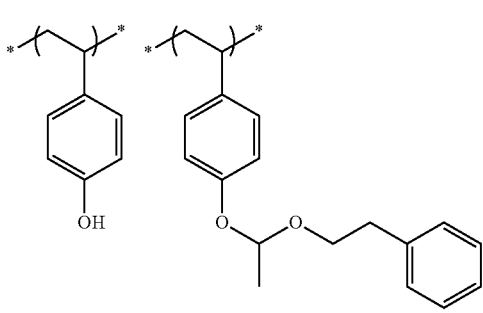
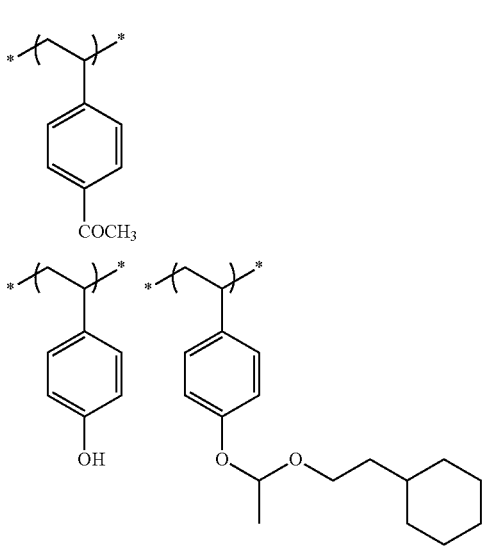

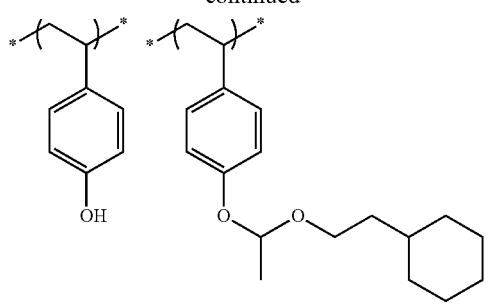
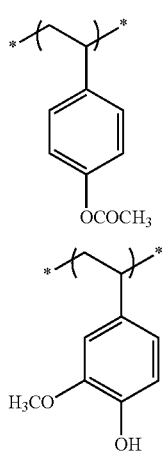
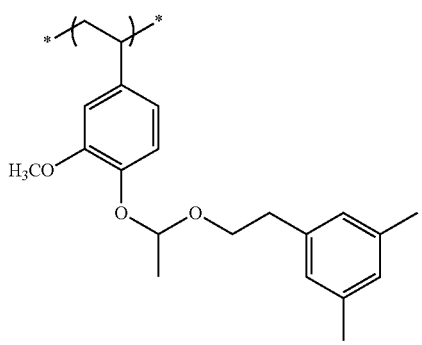
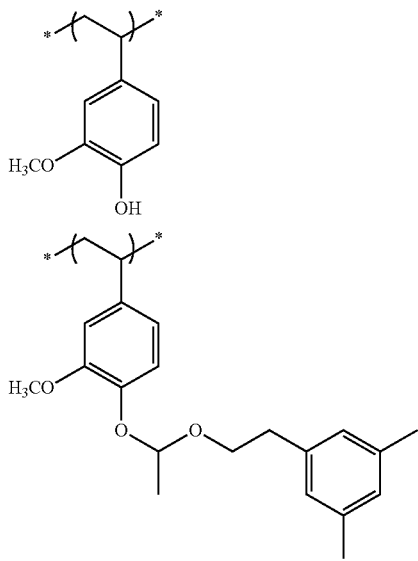
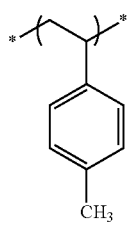
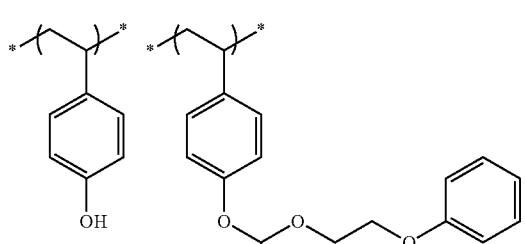
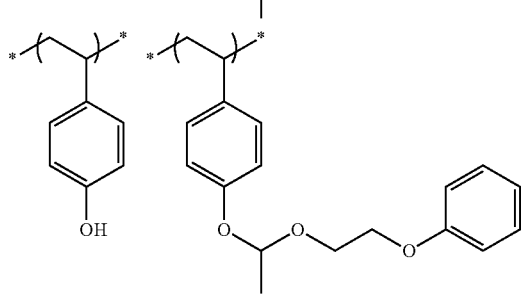
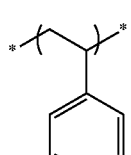
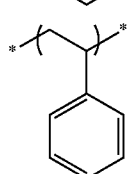
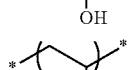
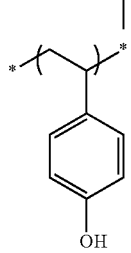

95
-continued
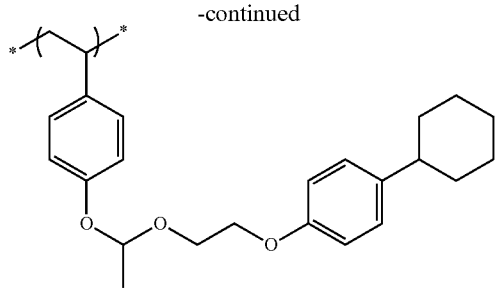
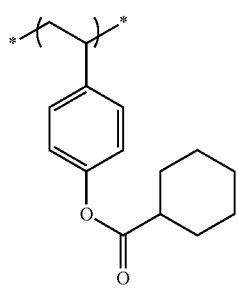
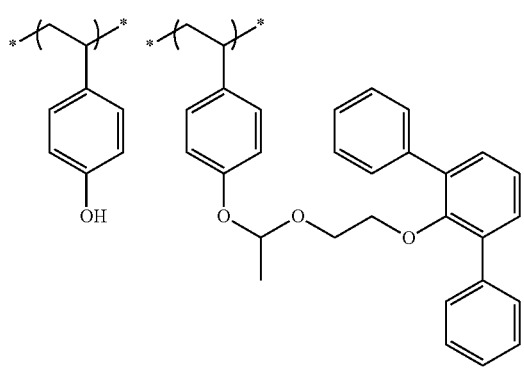
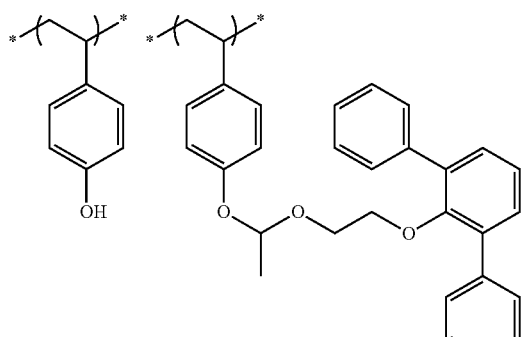
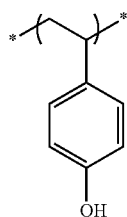
96
-continued
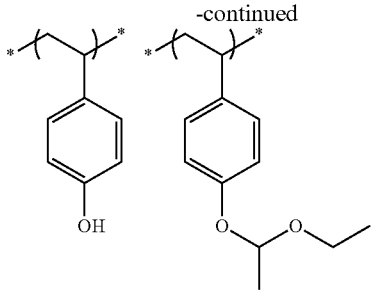
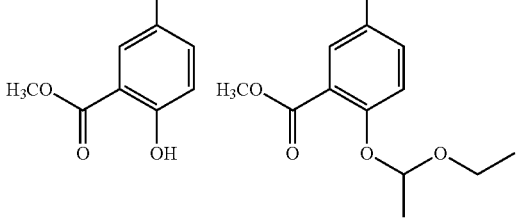
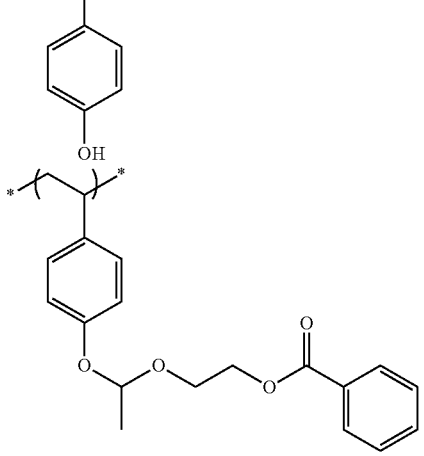
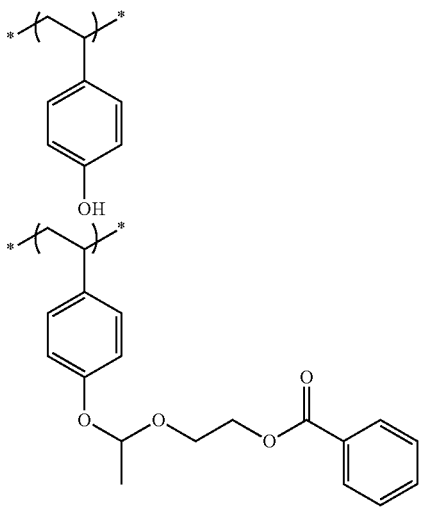
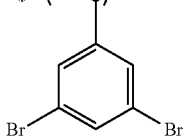

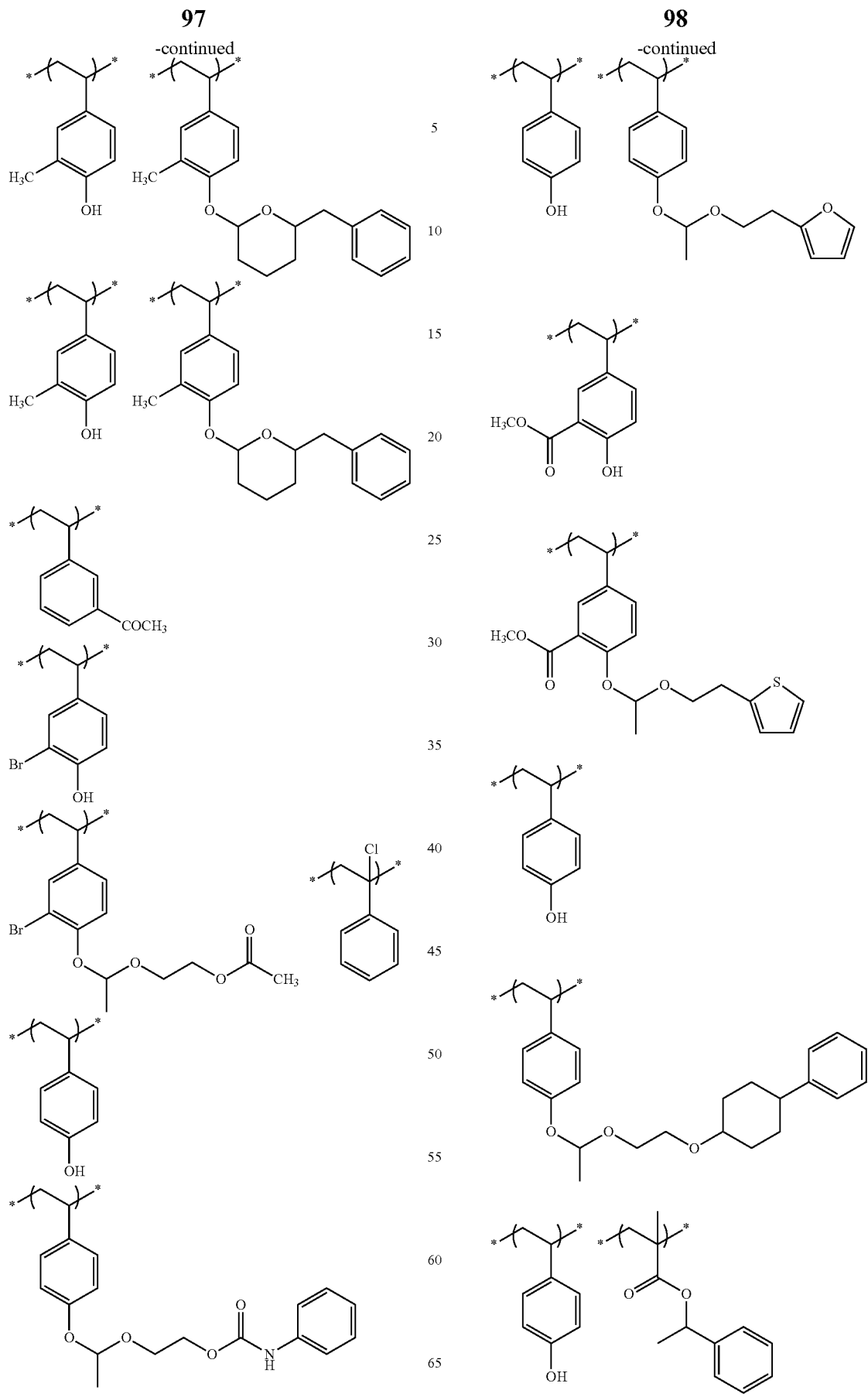

-continued

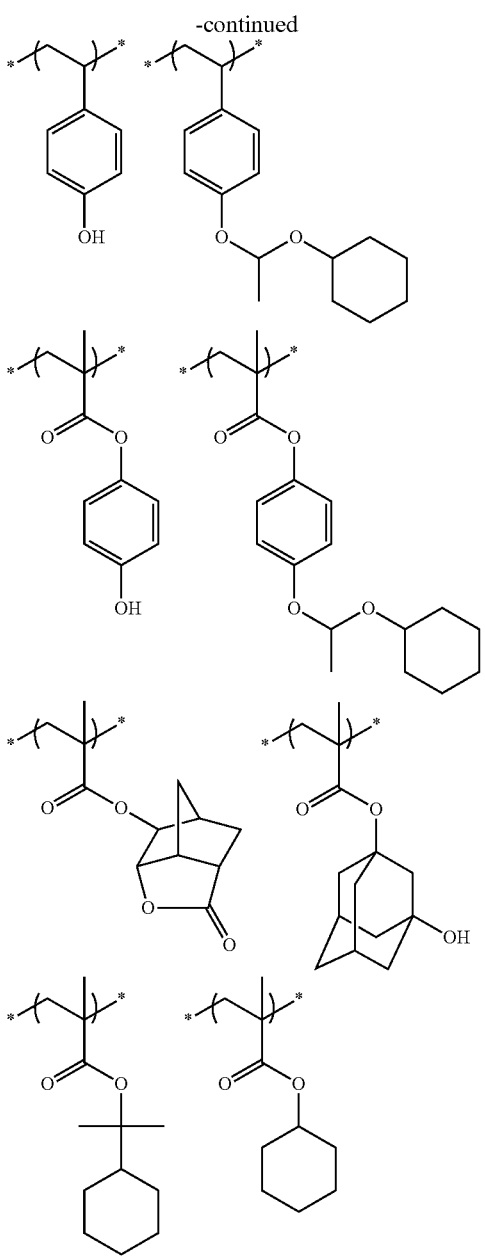

The resin of the component (B) can be synthesized by an ordinary method (for example, radical polymerization). Examples of the general synthesis method include a batch polymerization method of dissolving monomer species and an initiator in a solvent and heating the solution, thereby effecting the polymerization, and a dropping polymerization method of adding dropwise a solution containing monomer species and an initiator to a heated solvent over 1 to 10 hours. A dropping polymerization method is preferred. Examples of the reaction solvent include ethers such as tetrahydrofuran, 1,4-dioxane and diisopropyl ether, ketones such as methyl ethyl ketone and methyl isobutyl ketone, an ester solvent such as ethyl acetate, an amide solvent such as dimethylformamide and dimethylacetamide, and the later-described solvent capable of dissolving the composition of the present invention, such as propylene glycol monomethyl ether acetate, propylene glycol monomethyl ether and cyclohexanone. The polymerization is more preferably performed using the same solvent as the solvent used in the positive resist composition of the present invention. By the use of this solvent, production of particles during storage can be suppressed.

The polymerization reaction is preferably performed in an inert gas atmosphere such as nitrogen and argon. As for the polymerization initiator, the polymerization is started using a commercially available radical initiator (e.g., azo-based initiator, peroxide). The radical initiator is preferably an azo-based initiator, and an azo-based initiator having an ester group, a cyano group or a carboxyl group is preferred. Preferred examples of the initiator include azobisisobutyronitrile, azobisdimethylvaleronitrile and dimethyl 2,2'-azobis(2-methylpropionate). The initiator is added additionally or in parts, if desired. After the completion of reaction, the reaction product is charged into a solvent, and the desired polymer is collected by a method such as powder or solid recovery. The reaction concentration is from 5 to 50 mass %, preferably from 10 to 30 mass %, and the reaction temperature is usually from 10 to 150° C., preferably from 30 to 120° C., more preferably from 60 to 100° C.

The weight average molecular weight of the resin of the component (B) is, as a polystyrene-equivalent value by the GPC method, preferably from 1,000 to 200,000, more preferably from 2,000 to 20,000, still more preferably from 3,000 to 15,000, yet still more preferably from 3,000 to 10,000. When the weight average molecular weight is from 1,000 to 200,000, deterioration in the heat resistance, dry etching resistance and developability can be prevented and the film-forming property can be prevented from deteriorating due to increase in the viscosity.

The polydispersity (molecular weight distribution) is usually from 1 to 3, preferably from 1 to 2.6, more preferably from 1 to 2, still more preferably from 1.4 to 1.7. As the molecular weight distribution is smaller, the resolution and resist profile are more excellent, the side wall of the resist pattern is smoother, and the roughness is more improved.

In the positive resist composition of the present invention, the amount of the resin of the component (B) blended in the entire composition is preferably from 50 to 99.99 mass %, more preferably from 60 to 99.0 mass %, based on the entire solid content.

As regards the resin of the component (B) for use in the present invention, one kind may be used, or a plurality of kinds may be used in combination.

(C) Compound Represented by Formula (I), Which Decomposes by the Action of an Acid to Generate an Acid The positive resist composition of the present invention contains a compound represented by the following formula (I), which decomposes by the action of an acid to generate an acid (hereinafter sometimes referred to as an "acid-increasing agent").

(I)

In formula (I), $R_1$ represents an alkyl group, a cycloalkyl group, an alkoxy group, an aryl group or an aryloxy group.

$R_2$ represents an alkyl group or a cycloalkyl group.

$R_1$ and $R_2$ may combine with each other to form a monocyclic or polycyclic hydrocarbon structure.

Each of $R_3$ and $R_4$ independently represents a hydrogen atom or an alkyl group.

$R_5$ represents a group capable of leaving by the action of an acid.

X represents $-SO_2-$, $-SO-$ or $-CO-$.

Z represents a residue of an organic acid represented by

In formula (I), the alkyl group of $R_1$, $R_2$, $R_3$ and $R_4$ is preferably an alkyl group having a carbon number of 1 to 8, and specific examples thereof include a methyl group, an ethyl group, a propyl group, an isopropyl group, a butyl group and an octyl group.

The cycloalkyl group of $R_1$ and $R_2$ is preferably a cycloalkyl group having a carbon number of 4 to 10, and specific examples thereof include a cyclopropyl group, a cyclopentyl group, a cyclohexyl group, a cycloheptyl group, an adamantyl group, a boronyl group, an isoboronyl group, a tricyclodecanyl group, a dicyclopentenyl group, a norbornane epoxy group, a menthyl group, an isomenthyl group, a neomenthyl group and a tetracyclododecanyl group.

The alkoxy group of $R_1$ is preferably a linear or branched alkoxy group having a carbon number of 1 to 30, and examples thereof include a methoxy group, an ethoxy group, a propoxy group, an isopropoxy group, an n-butoxy group, an isobutoxy group, a sec-butoxy group, a tert-butoxy group, a hexyloxy group, a heptyloxy group, an octyloxy group, a nonyloxy group, a decyloxy group, an undecyloxy group and a dodecyloxy group.

The aryl group of $R_1$ is preferably an aryl group having a carbon number of 6 to 14, and examples thereof include a phenyl group and a naphthyl group.

The aryloxy group of $R_1$ is preferably an aryloxy group having a carbon number of 6 to 20, and examples thereof include a phenoxy group.

The monocyclic or polycyclic hydrocarbon structure formed by combining $R_1$ and $R_2$ is preferably a cyclic hydrocarbon structure having a carbon number of 3 to 15, and examples thereof include a cyclic hydrocarbon structure having an oxo group, such as cyclopentanone structure, cyclohexanone structure, norbornanone structure and adamantanone structure.

Each of these groups may have a substituent. Examples of the substituent which each of these groups may have include a halogen atom, a hydroxyl group, a nitro group, a cyano group, a carboxyl group, a cycloalkyl group (preferably having a carbon number of 3 to 20), an aryl group (preferably having a carbon number of 6 to 14), an alkoxy group (preferably having a carbon number of 1 to 20), an acyl group (preferably having a carbon number of 2 to 20) and an acyloxy group (preferably having a carbon number of 2 to 20). As for the group having a cyclic structure, such as cycloalkyl group and aryl group, examples of the substituent further include an alkyl group (preferably having a carbon number of 1 to 20).

Examples of the group capable of leaving by the action of an acid of $R_5$ include $-C(R_{36})(R_{37})(R_{38})$, $-C(R_{36})(R_{37})(OR_{39})$, $-C(R_{01})(R_{02})(OR_{39})$ and $-CH(R_{40})(R_{41})$.

In the formulae, each of $R_{36}$ to $R_{39}$ independently represents an alkyl group, a cycloalkyl group, an aryl group, an aralkyl group or an alkenyl group, and $R_{36}$ and $R_{37}$ may combine with each other to form a ring.

$R_{40}$ represents a hydrogen atom, an alkyl group, a cycloalkyl group, an alkoxy group, an aryl group or an alkylene group bonded to $R_{41}$.

$R_{41}$ represents an aryl group.

Each of $R_{01}$ and $R_{02}$ independently represents a hydrogen atom, an alkyl group, a cycloalkyl group, an aryl group, an aralkyl group, an alkenyl group or an alkylene group bonded to $R_{39}$.

Examples of the group capable of leaving by the action of an acid of $R_5$ include groups represented by the following formulae (pI) to (pV), and a group having a monocyclic or polycyclic alicyclic hydrocarbon structure is preferred.

(pI)

(pII)

(pIII)

(pIV)

(pV)

In formulae (pI) to (pV), $R_{11}$ represents an alkyl group.

Z represents an atomic group necessary for forming a cycloalkyl group together with the carbon atom.

Each of $R_{12}$ to $R_{14}$ independently represents an alkyl group or a cycloalkyl group. At least one of $R_{12}$ to $R_{14}$ is preferably a cycloalkyl group.

Each of $R_{15}$ and $R_{16}$ independently represents an alkyl group or a cycloalkyl group. At least either one of $R_{15}$ and $R_{16}$ is preferably A cycloalkyl group.

Each of $R_{17}$ to $R_{21}$ independently represents a hydrogen atom, an alkyl group or a cycloalkyl group, provided that any one of $R_{19}$ and $R_{21}$ represents an alkyl group or a cycloalkyl group. At least one of $R_{17}$ to $R_{21}$ is preferably a cycloalkyl group.

Each of $R_{22}$ to $R_{25}$ independently represents a hydrogen atom, an alkyl group or a cycloalkyl group. $R_{23}$ and $R_{24}$ may combine with each other to form a ring. At least one of $R_{22}$ to $R_{25}$ is preferably a cycloalkyl group.

In formulae (pI) to (pV), the alkyl group of $R_{11}$ to $R_{25}$ is preferably a linear or branched alkyl group having a carbon number of 1 to 4, and examples thereof include a methyl group, an ethyl group, an n-propyl group, an isopropyl group, an n-butyl group, an isobutyl group and a sec-butyl group.

The cycloalkyl group of $R_{12}$ to $R_{25}$ and the cycloalkyl group formed by Z together with the carbon atom may be monocyclic or polycyclic. Specific examples thereof include a group having a monocyclo, bicyclo, tricyclo or tetracyclo structure with a carbon number of 5 or more. The carbon number thereof is preferably from 6 to 30, more preferably from 7 to 25.

Preferred examples of the cycloalkyl group include an adamantyl group, a noradamantyl group, a decalin residue, a tricyclodecanyl group, a tetracyclododecanyl group, a norbornyl group, a cedrol group, a cyclopentyl group, a cyclohexyl group, a cycloheptyl group, a cyclooctyl group, a cyclodecanyl group and a cyclododecanyl group. Among these, more preferred are an adamantyl group, a norbornyl group, a cyclohexyl group, a cyclopentyl group, a tetracyclododecanyl group and a tricyclodecanyl group.

These alkyl and cycloalkyl groups may further have a substituent. Examples of the substituent which these alkyl and cycloalkyl groups may further have include an alkyl group (having a carbon number of 1 to 4), a halogen atom, a hydroxyl group, an alkoxy group (having a carbon number of 1 to 4), a carboxyl group and an alkoxycarbonyl group (having a carbon number of 2 to 6). Examples of the substituent which the above-described alkyl, alkoxy and alkoxycarbonyl group's may further have include a hydroxyl group, a halogen atom and an alkoxy group.

The organic acid of is preferably a sulfonic acid, a carboxylic acid, an imide acid or a methide acid.

Z is preferably a group represented by the following structural formulae:

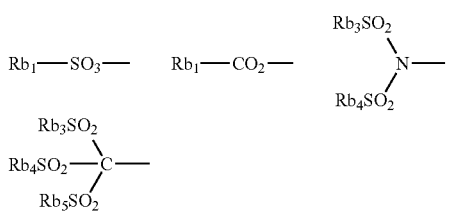

In the structural formulae above, $Rb_1$ represents an organic group. The organic group of $Rb_1$ is preferably an organic group having a carbon number of 1 to 30, and examples thereof include an alkyl group, a cycloalkyl group, an aryl group, and a group where a plurality of these groups are connected through a single bond or a linking group such as —O—, —$CO_2$—, —S—, —$SO_3$— and —$SO_2N(Rc_1)$-. In the formula, $Rc_1$ represents a hydrogen atom or an alkyl group.

Each of $Rb_3$, $Rb_4$ and $Rb_5$ independently represents an organic group. Examples of the organic group of $Rb_3$, $Rb_4$ and $Rb_5$ are the same as those of the organic group of $Rb_1$. Above all, a perfluoroalkyl group having a carbon number of 1 to 4 is preferred.

$Rb_3$ and $Rb_4$ may combine to form a ring. The group formed by combining $Rb_3$ and $Rb_4$ includes an alkylene group and an arylene group, and a perfluoroalkylene group having a carbon number of 2 to 4 is preferred.

The organic group of $Rb_1$ and $Rb_3$ to $Rb_5$ is preferably an alkyl group with the 1-position being substituted by a fluorine atom or a fluoroalkyl group, or a phenyl group substituted by a fluorine atom or a fluoroalkyl group. By virtue of having a fluorine atom or a fluoroalkyl group, the acidity of the acid generated upon irradiation with light rises and the sensitivity is enhanced.

Formula (I) is preferably the following formula (Ia) or (Ib):

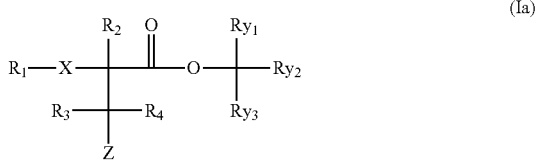

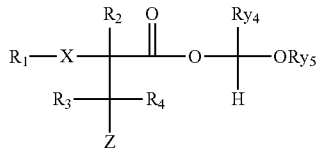

In formulae (Ia) and (Ib), $R_1$ represents an alkyl group, a cycloalkyl group, an alkoxy group, an aryl group or an aryloxy group.

$R_2$ represents an alkyl group or a cycloalkyl group.

$R_1$ and $R_2$ may combine with each other to form a monocyclic or polycyclic hydrocarbon structure.

Each of $R_3$ and $R_4$ independently represents a hydrogen atom or an alkyl group.

X represents —$SO_2$—, —SO— or —CO—.

Z represents a residue of an organic acid represented by ZH.

Each of $Ry_1$ to $Ry_3$ independently represents an alkyl group or a cycloalkyl group, and at least two members out of $Ry_1$ to $Ry_3$ may combine with each other to form a monocyclic or polycyclic hydrocarbon structure, provided that at least one of $Ry_1$ to $Ry_3$ represents a cycloalkyl group or at least two members out of $Ry_1$ to $Ry_3$ are combined to form a monocyclic or polycyclic hydrocarbon structure.

$Ry_4$ represents a hydrogen atom, an alkyl group or a cycloalkyl group.

$Ry_5$ represents a cycloalkyl group.

$Ry_4$ and $Ry_5$ may combine with each other to form a monocyclic or polycyclic hydrocarbon structure.

In formulae (Ia) and (Ib), $R_1$ to $R_4$, X and Z have the same meanings as $R_1$ to $R_4$, X and Z in formula (I).

The alkyl group of $Ry_1$ to $Ry_4$ may be either a linear alkyl group or a branched alkyl group and may have a substituent. The linear or branched alkyl group is preferably a linear or branched alkyl group having a carbon number of 1 to 8, more preferably from 1 to 4, and examples thereof include a methyl group, an ethyl group, a propyl group, an isopropyl group, a butyl group, an isobutyl group and a tert-butyl group, with a methyl group and an ethyl group being preferred.

The cycloalkyl group of $Ry_1$ to $Ry_5$ includes, for example, a monocyclic cycloalkyl group having a carbon number of 3 to 8 and a polycyclic cycloalkyl group having a carbon number of 7 to 14 and may have a substituent. Preferred examples of the monocyclic cycloalkyl group include a cyclopentyl group, a cyclohexyl group and a cyclopropyl group, and preferred examples of the polycyclic cycloalkyl group include an adamantyl group, a norbornane group, a tetracyclododecanyl group, a tricyclodecanyl group and a diamantyl group.

The monocyclic hydrocarbon structure formed by combining at least two members out of $Ry_1$ to $Ry_3$ is preferably a cyclopentyl group or a cyclohexyl group. The polycyclic hydrocarbon structure formed by combining at least two members out of $Ry_1$ to $Ry_3$ is preferably an adamantane group, a norbornane group or a tetracyclododecane group.

Examples of the monocyclic or polycyclic hydrocarbon structure formed by combining $Ry_4$ and $Ry_5$ include a tetramethylene oxide ring structure, a pentamethylene oxide ring structure and a hexamethylene oxide ring structure.

Each of these groups may have a substituent. Examples of the substituent which each of these group may have include a halogen atom, a hydroxyl group, a nitro group, a cyano group, a carboxyl group, a cycloalkyl group (preferably having a carbon number of 3 to 20), an aryl group (preferably having a carbon number of 6 to 14), an alkoxy group (preferably having a carbon number of 1 to 20), an acyl group (preferably having a carbon number of 2 to 20) and an acyloxy group (preferably having a carbon number of 2 to 20). As for the group having a cyclic structure, such as cycloalkyl group and aryl group, examples of the substituent further include an alkyl group (preferably having a carbon number of 1 to 20).

The compound represented by formula (I), which decomposes by the action of an acid to generate an acid, is a novel compound.

The compound represented by formula (I), which decomposes by the action of an acid to generate an acid, can be synthesized as follows. An a-substituted acetic acid ester that is an active methylene compound is first synthesized by a method of condensing an ester compound under base conditions, a method of reacting alcohol and diketene (described in Synthesis, 387-388 (1989)), or a method of reacting acetoacetate and chloromethyl ether and after sequentially performing monoalkylation of the active methylene and hydroxymethylation of the active methylene by the method described in J. Am. Chem. Soc., 120, 37-45 (1998), the hydroxymethylated product is finally reacted with sulfonic acid chloride in the presence of a base.

Specific examples of the acid-increasing agent are set forth below, but the present invention is not limited thereto.

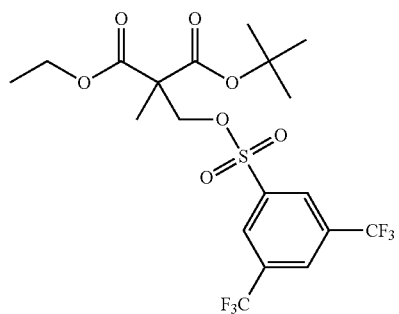
(I-1)

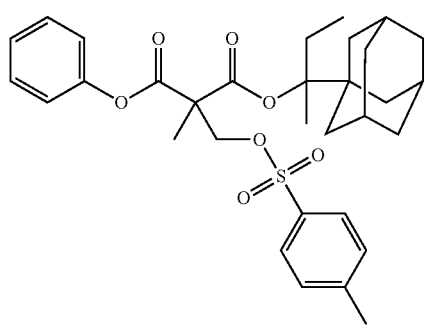
(I-2)

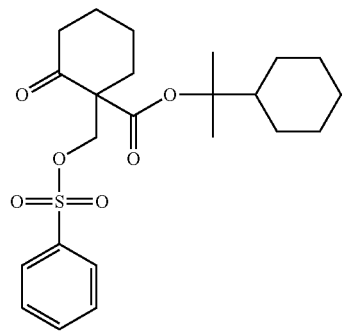
(I-3)

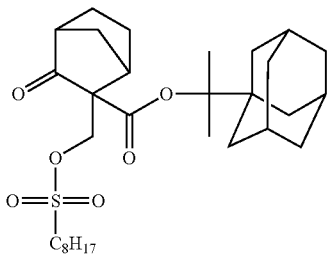
(I-4)

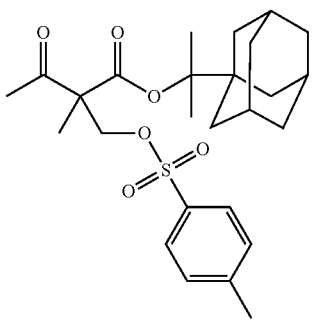
(I-5)

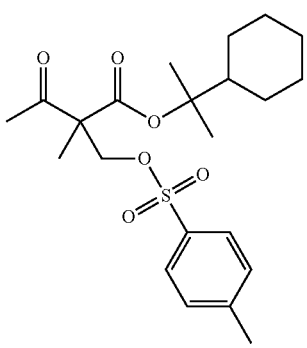
(I-6)

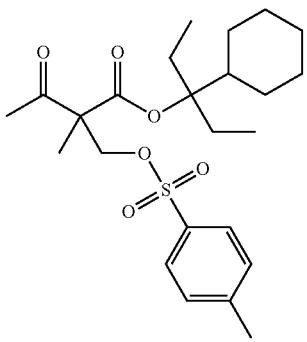
(I-7)

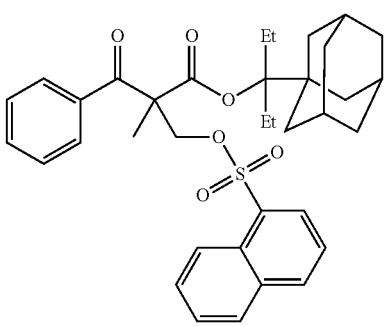
(I-8)

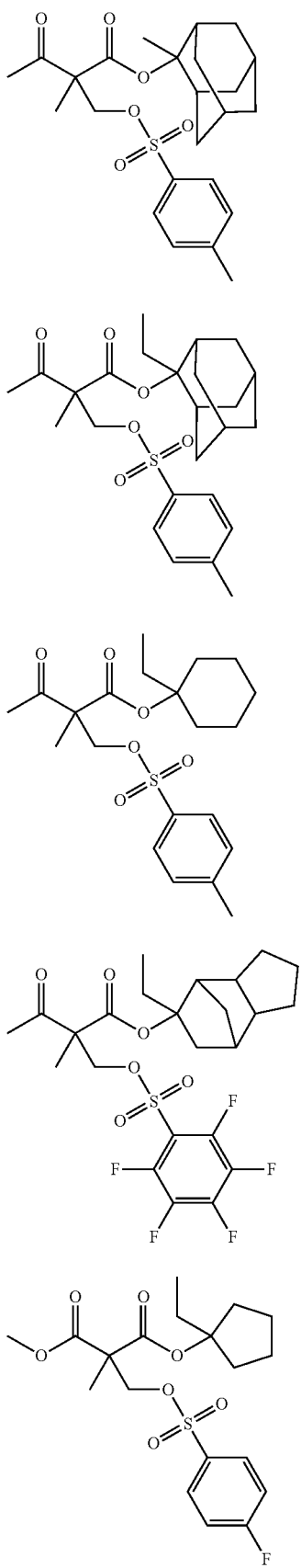
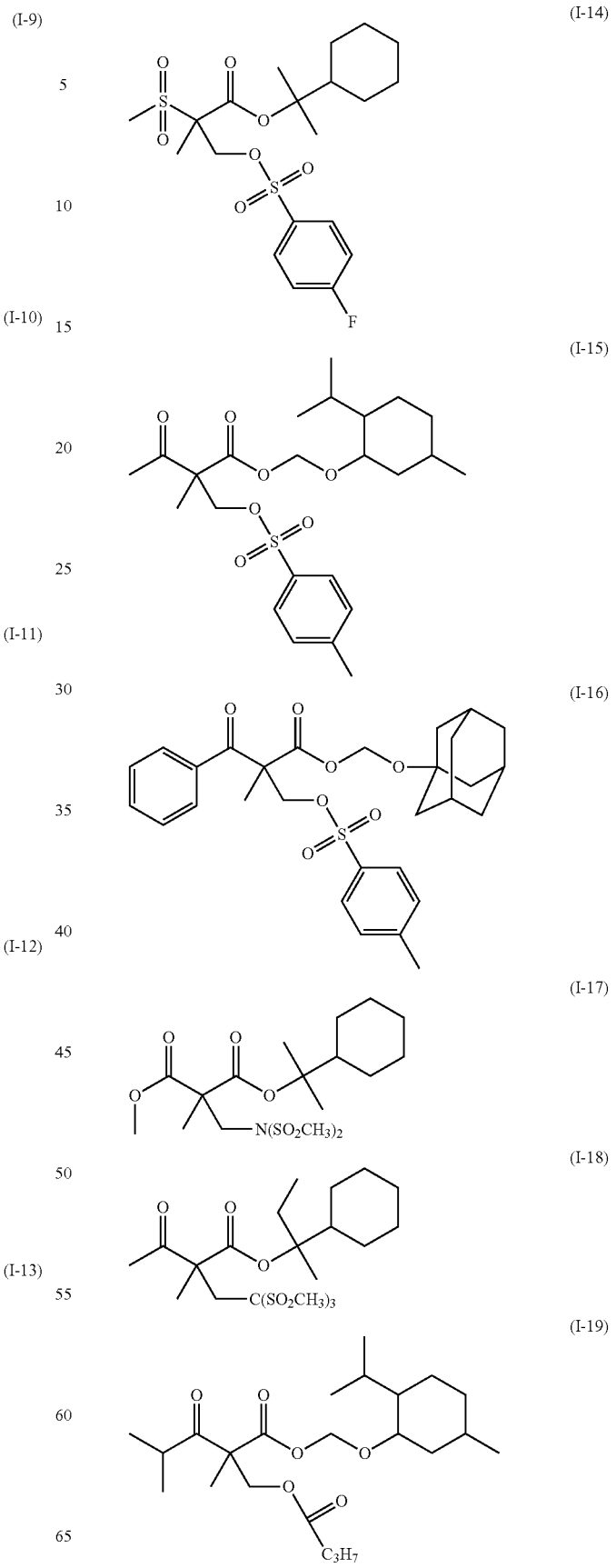

-continued
(I-20)
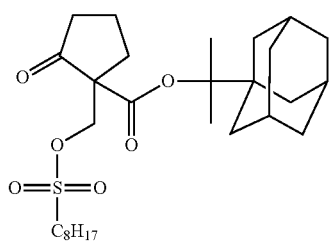
(I-21)
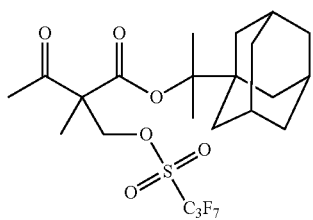
(I-22)
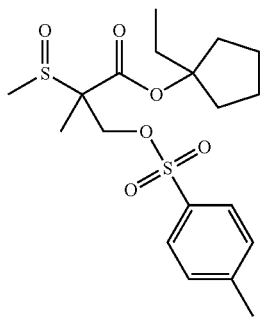
(I-23)
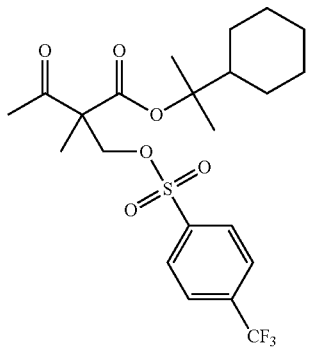
(I-24)
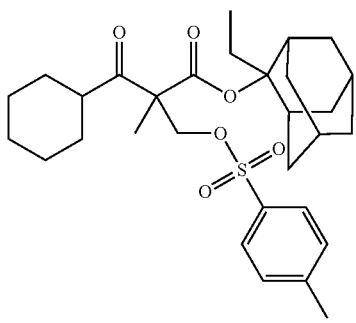
-continued
(I-25)
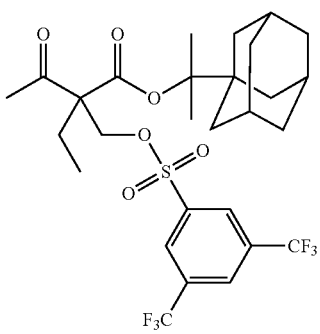
(I-26)
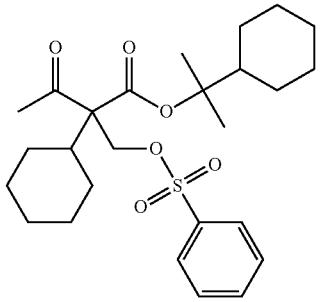
(I-27)
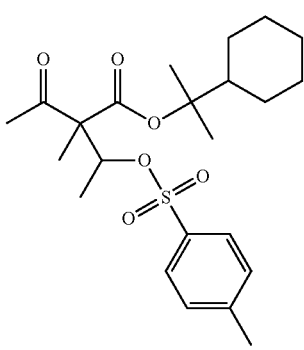
(I-28)
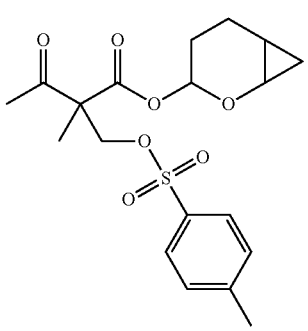
(I-29)
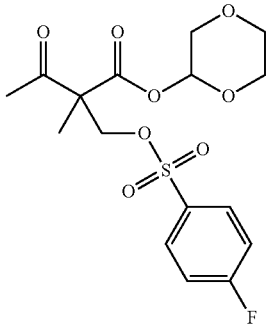

-continued (I-30)
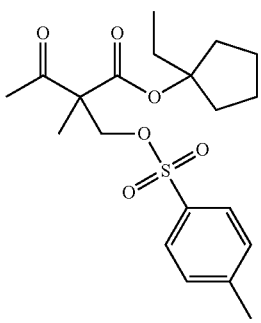

(I-31)
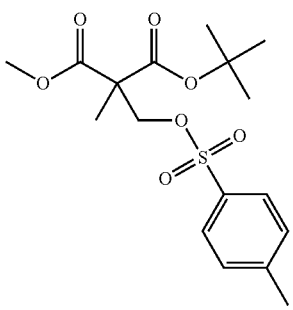

(I-32)
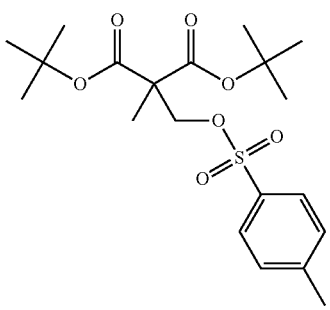

(I-33)
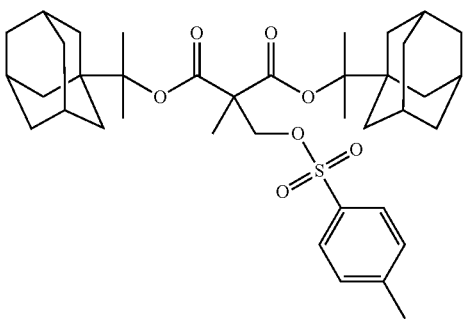

(I-34)
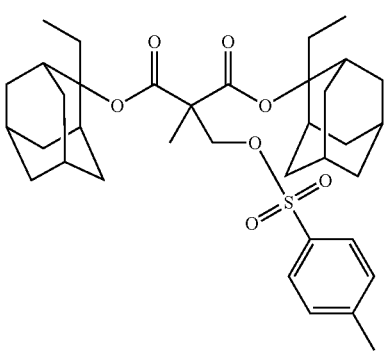

A compound represented by the following formula (U) is also preferred as the compound represented by formula (I).

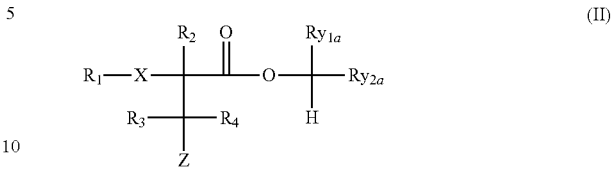

(II)

In formula (II), $R_1$ represents an alkyl group, a cycloalkyl group, an alkoxy group, an aryl group or an aryloxy group.

$R_2$ represents an alkyl group or a cycloalkyl group.

$R_1$ and $R_2$ may combine with each other to form a monocyclic or polycyclic hydrocarbon structure.

Each of $R_3$ and $R_4$ independently represents a hydrogen atom or an alkyl group.

$Ry_{1a}$ represents a hydrogen atom, an alkyl group, a cycloalkyl group, an alkoxy group, an aryl group, or an alkylene group bonded to $Ry_{2a}$.

$Ry_{2a}$ represents an aryl group or an aryloxy group.

X represents —$SO_2$—, —SO— or —CO—.

Z represents a residue of an organic acid represented by ZH.

In formula (II), the alkyl group of $R_1$, $R_2$, $R_3$, $R_4$ and $Ry_{1a}$ is preferably an alkyl group having a carbon number of 1 to 8, and specific examples thereof include a methyl group, an ethyl group, a propyl group, an isopropyl group, a butyl group and an octyl group.

The cycloalkyl group of $R_1$, $R_2$ and $Ry_{1a}$ is preferably a cycloalkyl group having a carbon number of 4 to 10, and specific examples thereof include a cyclopropyl group, a cyclopentyl group, a cyclohexyl group, a cycloheptyl group, an adamantyl group, a boronyl group, an isoboronyl group, a tricyclodecanyl group, a dicyclopentenyl group, a norbornane epoxy group, a menthyl group, an isomenthyl group, a neomenthyl group and a tetracyclododecanyl group.

The alkoxy group of $R_1$ and $Ry_{1a}$ is preferably a linear or branched alkoxy group having a carbon number of 1 to 30, and examples thereof include a methoxy group, an ethoxy group, a propoxy group, an isopropoxy group, an n-butoxy group, an isobutoxy group, a sec-butoxy group, a tert-butoxy group, a hexyloxy group, a heptyloxy group, an octyloxy group, a nonyloxy group, a decyloxy group, an undecyloxy group and a dodecyloxy group.

The aryl group of $R_1$, $Ry_{1a}$ and $Ry_{2a}$ is preferably an aryl group having a carbon number of 6 to 14, and examples thereof include a phenyl group and a naphthyl group.

The aryloxy group or $R_1$ and $Ry_{2a}$ is preferably an aryloxy group having a carbon number of 6 to 20, and examples thereof include a phenoxy group and a naphthoxy group.

The monocyclic or polycyclic hydrocarbon structure formed by combining $R_1$ and $R_2$ is preferably a cyclic hydrocarbon structure having a carbon number of 3 to 15, and examples thereof include a cyclic hydrocarbon structure having an oxo group, such as cyclopentanone structure, cyclohexanone structure, norbornanone structure and adamantanone structure.

The alkylene group of $Ry_{1a}$, which is bonded to $Ry_{2a}$, is preferably an alkylene group having a carbon number of 1 to 5, and examples thereof include a methylene group, an ethylene group, a propylene group and a butylene group.

Each of these groups may have a substituent. Examples of the substituent which each of these groups may have include a halogen atom, a hydroxyl group, a nitro group, a cyano group, a carboxyl group, a cycloalkyl group (preferably having a carbon number of 3 to 20), an aryl group (preferably having a carbon number of 6 to 14), an alkoxy group (preferably having a carbon number of 1 to 20), an acyl group (preferably having a carbon number of 2 to 20) and an acyloxy group (preferably having a carbon number of 2 to 20). As for the group having a cyclic structure, such as cycloalkyl group and aryl group, examples of the substituent further include an alkyl group (preferably having a carbon number of 1 to 20).

The organic acid of ZH is preferably a sulfonic acid, a carboxylic acid, an imide acid or a methide acid.

Z is preferably a group represented by the following structural formulae:

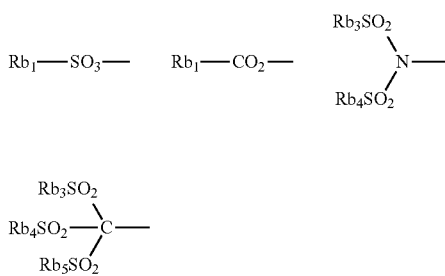

In the structural formulae above, $Rb_1$ represents an organic group. The organic group of $Rb_1$ is preferably an organic group having a carbon number of 1 to 30, and examples thereof include an alkyl group, a cycloalkyl group, an aryl group, and a group where a plurality of these groups are connected through a single bond or a linking group such as —O—, —$CO_2$—, —S—, —$SO_3$— and —$SO_2N(Rc_1)$-. In the formula, $Rc_1$ represents a hydrogen atom or an alkyl group.

Each of $Rb_3$, $Rb_4$ and $Rb_5$ independently represents an organic group. Examples of the organic group of $Rb_3$, $Rb_4$ and $Rb_5$ are the same as those of the organic group of $Rb_1$. Above all, a perfluoroalkyl group having a carbon number of 1 to 4 is preferred.

$Rb_3$ and $Rb_4$ may combine to form a ring. The group formed by combining $Rb_3$ and $Rb_4$ includes an alkylene group and an arylene group, and a perfluoroalkylene group having a carbon number of 2 to 4 is preferred.

The organic group of $Rb_1$ and $Rb_3$ to $Rb_5$ is preferably an alkyl group with the 1-position being substituted by a fluorine atom or a fluoroalkyl group, or a phenyl group substituted by a fluorine atom or a fluoroalkyl group. By virtue of having a fluorine atom or a fluoroalkyl group, the acidity of the acid generated upon irradiation with light rises and the sensitivity is enhanced.

Formula (II) is preferably represented by the following formula (IIa) or (IIb):

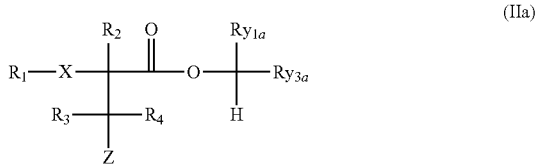

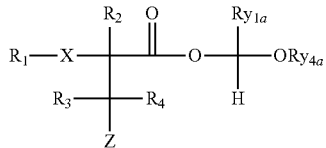

In formulae (IIa) and (IIb), $R_1$ represents an alkyl group, a cycloalkyl group, an alkoxy group, an aryl group or an aryloxy group.

$R_2$ represents an alkyl group or a cycloalkyl group.

$R_1$ and $R_2$ may combine with each other to form a monocyclic or polycyclic hydrocarbon structure.

Each of $R_3$ and $R_4$ independently represents a hydrogen atom or an alkyl group.

$Ry_{1a}$ represents a hydrogen atom, an alkyl group, a cycloalkyl group, an alkoxy group, an aryl group, or an alkylene group bonded to $Ry_{3a}$ or $Ry_{4a}$.

$Ry_{3a}$ represents an aryl group.

$Ry_{4a}$ represents an aryl group.

X represents —$SO_2$—, —SO— or —CO—.

Z represents a residue of an organic add represented by ZH.

In formulae (IIa) and (IIb), $R_1$ to $R_4$, $Ry_{1a}$, X and Z have the same meanings as $R_1$ to $R_4$, $Ry_{1a}$, X and Z in formula (II).

Examples of the aryl group of $Ry_{3a}$ and $Ry_{4a}$ are the same as those of the aryl group in $Ry_{2a}$.

The alkylene group of $Ry_{1a}$, which is bonded to $Ry_{3a}$ or $Ry_{4a}$, is preferably an alkylene group having a carbon number of 1 to 5, and examples thereof include a methylene group, an ethylene group, a propylene group and a butylene group.

Each of these groups may have a substituent. Examples of the substituent which each of these groups may have include a halogen atom, a hydroxyl group, a nitro group, a cyano group, a carboxyl group, a cycloalkyl group (preferably having a carbon number of 3 to 20), an aryl group (preferably having a carbon number of 6 to 14), an alkoxy group (preferably having a carbon number of 1 to 20), an acyl group (preferably having a carbon number of 2 to 20) and an acyloxy group (preferably having a carbon number of 2 to 20). As for the group having a cyclic structure, such as cycloalkyl group and aryl group, examples of the substituent further include an alkyl group (preferably having a carbon number of 1 to 20).

The compound represented by formula (II), which decomposes by the action of an acid to generate an acid, is a novel compound.

The compound represented by formula (II), which decomposes by the action of an acid to generate an acid, can be synthesized as follows. An a-substituted acetic acid ester that is an active methylene compound is first synthesized by a method of condensing an ester compound under base conditions, a method of reacting alcohol and diketone (described in Synthesis, 387-388 (1989)), or a method of reacting acetoacetate and chloromethyl ether and after sequentially performing monoalkylation of the active methylene and hydroxymethylation of the active methylene by the method described in J. Am. Chem. Soc., 120, 37-45 (1998), the hydroxymethylated product is finally reacted with sulfonic acid chloride in the presence of a base.

Specific examples of the acid-increasing agent are set forth below, but the present invention is not limited thereto.

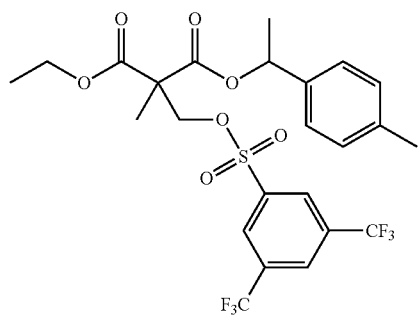 (II-1)
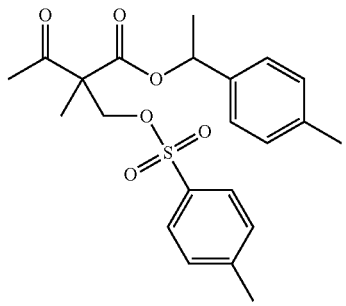 (II-6)
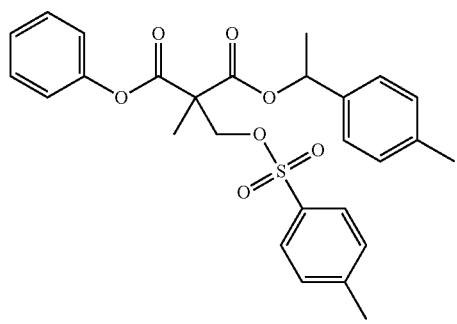 (II-2)
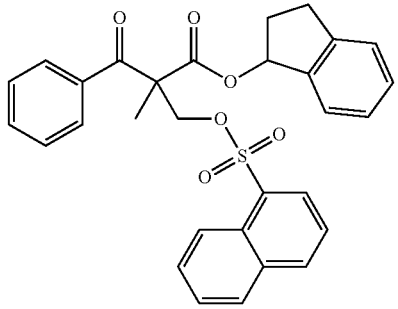 (II-7)
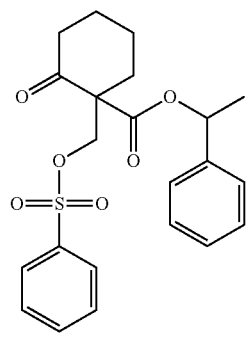 (II-3)
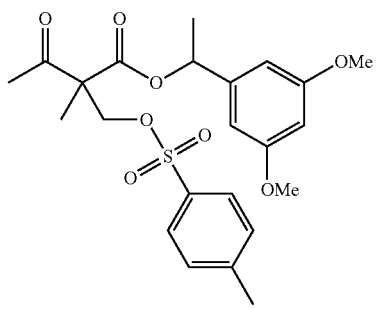 (II-8)
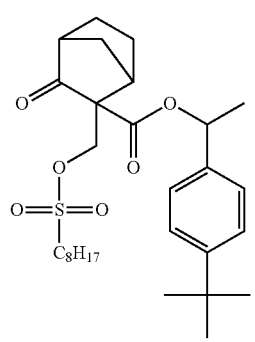 (II-4)
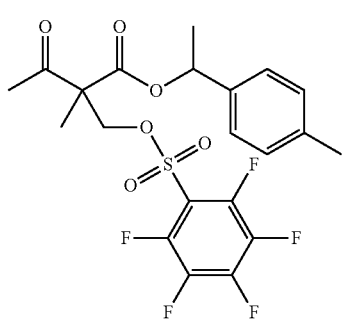 (II-9)
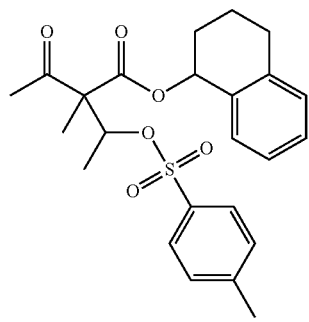 (II-5)
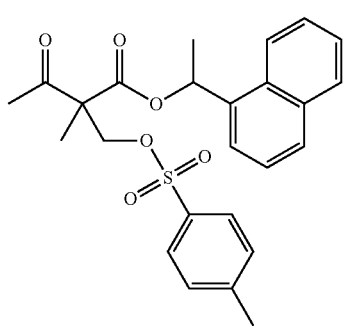 (II-10)

117
-continued
(II-11)
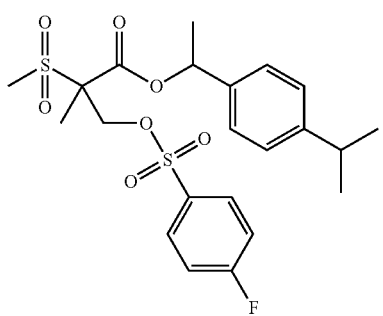
(II-12)
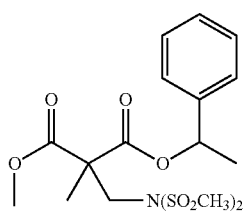
(II-13)
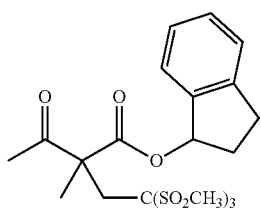
(II-14)
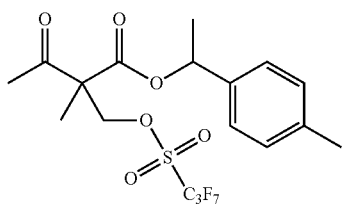
(II-15)
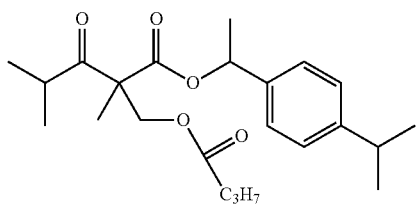
(II-16)
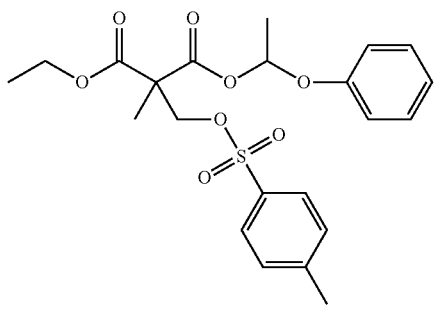
118
-continued
(II-17)
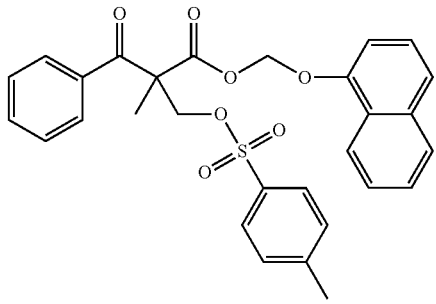
(II-18)
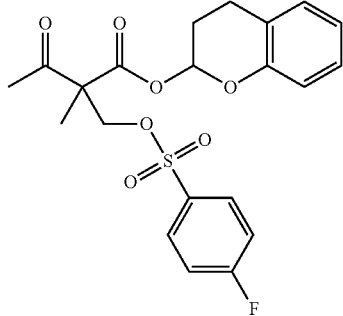
(II-19)
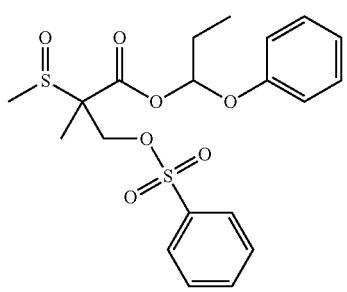
(II-20)
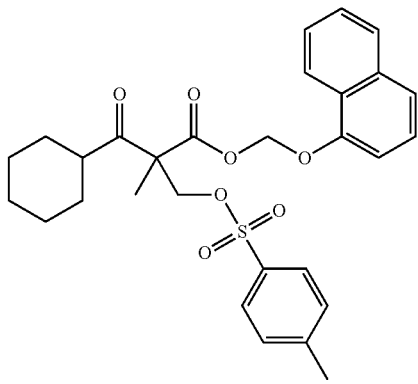
(II-21)
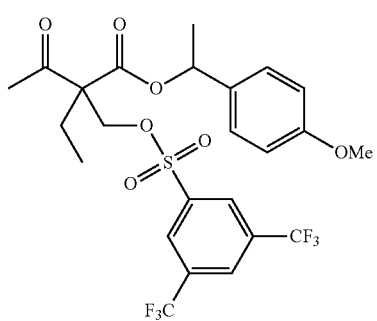

(II-22)
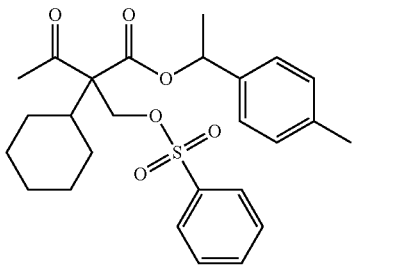

(II-23)
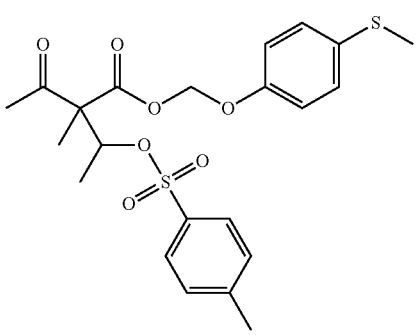

(II-24)
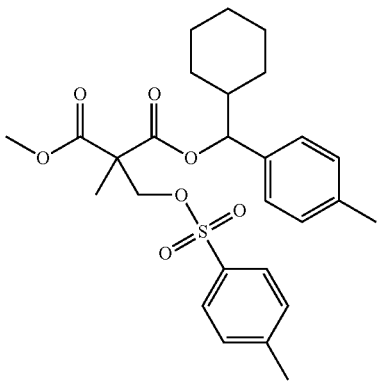

(II-25)
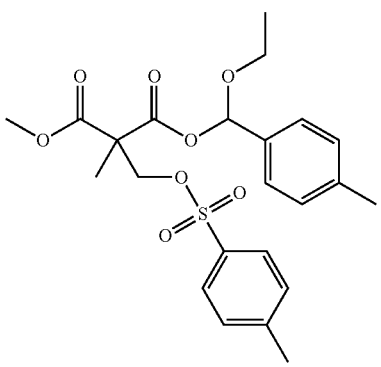

(II-26)
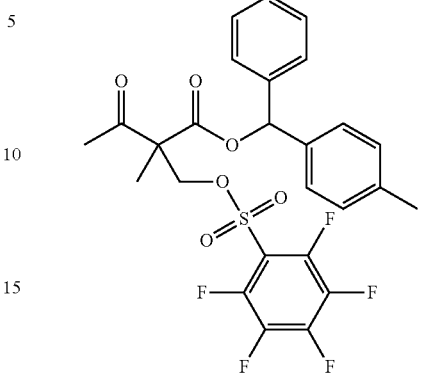

The content of the acid-increasing agent in the positive resist composition of the present invention is preferably from 0.1 to 20.0 mass %, more preferably from 0.1 to 10.0 mass %, based on the solid content of the composition.

Solvent:

Examples of the solvent which can be used at the time of preparing the positive resist composition by dissolving the above-described components include an organic solvent such as alkylene glycol monoalkyl ether carboxylate, alkylene glycol monoalkyl ether, alkyl lactate, alkyl alkoxypropionate, cyclic lactone (preferably having a carbon number of 4 to 10), monoketone compound (preferably having a carbon number of 4 to 10) which may contain a ring, alkylene carbonate, alkyl alkoxyacetate and alkyl pyruvate.

Preferred examples of the alkylene glycol monoalkyl ether carboxylate include propylene glycol monomethyl ether acetate, propylene glycol monoethyl ether acetate, propylene glycol monopropyl ether acetate, propylene glycol monobutyl ether acetate, propylene glycol monomethyl ether propionate, propylene glycol monoethyl ether propionate, ethylene glycol monomethyl ether acetate and ethylene glycol monoethyl ether acetate.

Preferred examples of the alkylene glycol monoalkyl ether include propylene glycol monomethyl ether, propylene glycol monoethyl ether, propylene glycol monopropyl ether, propylene glycol monobutyl ether, ethylene glycol monomethyl ether and ethylene glycol monoethyl ether.

Preferred examples of the alkyl lactate include methyl lactate, ethyl lactate, propyl lactate and butyl lactate.

Preferred examples of the alkyl alkoxypropionate include ethyl 3-ethoxypropionate, methyl 3-methoxypropionate, methyl 3-ethoxypropionate and ethyl 3-methoxypropionate.

Preferred examples of the cyclic lactone include β-propiolactone, β-butyrolactone, γ-butyrolactone, α-methyl-γ-butyrolactone, β-methyl-γ-butyrolactone, γ-valerolactone, γ-caprolactone, γ-octanoic lactone and α-hydroxy-γ-butyrolactone.

Preferred examples of the monoketone compound that may contain a ring include 2-butanone, 3-methylbutanone, pinacolone, 2-pentanone, 3-pentanone, 3-methyl-2-pentanone, 4-methyl-2-pentanone, 2-methyl-3-pentanone, 4,4-dimethyl-2-pentanone, 2,4-dimethyl-3-pentanone, 2,2,4,4-tetramethyl-3-pentanone, 2-hexanone, 3-hexanone, 5-methyl-3-hexanone, 2-heptanone, 3-heptanone, 4-heptanone, 2-methyl-3-heptanone, 5-methyl-3-heptanone, 2,6-dimethyl-4-heptanone, 2-octanone, 3-octanone, 2-nonanone, 3-nonanone, 5-nonanone, 2-decanone, 3-decanone, 4-decanone, 5-hexen-2-one, 3-penten-2-one, cyclopentanone, 2-methylcyclopentanone, 3-methylcyclopentanone, 2,2-dimethylcyclopentanone, 2,4,4-trimethylcyclopentanone, cyclohexanone, 3-methylcyclohexanone, 4-methylcyclohexanone, 4-ethylcyclohexanone, 2,2-dimethylcyclohexanone, 2,6-dimethylcyclohexanone, 2,2,6-trimethylcyclohexanone, cycloheptanone, 2-methylcycloheptanone and 2-methylcycloheptanone.

Preferred examples of the alkylene carbonate include propylene carbonate, vinylene carbonate, ethylene carbonate and butylene carbonate.

Preferred examples of the alkyl alkoxyacetate include 2-methoxyethyl acetate, 2-ethoxyethyl acetate, 2-(2-ethoxyethoxy)ethyl acetate, 3-methoxy-3-methylbutyl acetate and 1-methoxy-2-propyl acetate.

Preferred examples of the alkyl pyruvate include methyl pyruvate, ethyl pyruvate and propyl pyruvate.

The solvent which can be preferably used includes a solvent having a boiling point of 130° C. or more at ordinary temperature under atmospheric pressure, and specific examples thereof include cyclopentanone, γ-butyrolactone, cyclohexanone, ethyl lactate, ethylene glycol monoethyl ether acetate, propylene glycol monomethyl ether acetate, ethyl 3-ethoxypropionate, ethyl pyruvate, 2-ethoxyethyl acetate, 2-(2-ethoxyethoxy)ethyl acetate and propylene carbonate.

In the present invention, one of these solvents may be used alone, or two or more kinds thereof may be used in combination.

In the present invention, a mixed solvent prepared by mixing a solvent containing a hydroxyl group in the structure and a solvent containing no hydroxyl group may be used as the organic solvent.

Examples of the solvent containing a hydroxyl group include ethylene glycol, ethylene glycol monomethyl ether, ethylene glycol monoethyl ether, propylene glycol, propylene glycol monomethyl ether, propylene glycol monoethyl ether and ethyl lactate. Among these, propylene glycol monomethyl ether and ethyl lactate are preferred.

Examples of the solvent containing no hydroxyl group include propylene glycol monomethyl ether acetate, ethyl ethoxypropionate, 2-heptanone, γ-butyrolactone, cyclohexanone, butyl acetate, N-methylpyrrolidone, N,N-dimethylacetamide and dimethylsulfoxide. Among these, propylene glycol monomethyl ether acetate, ethyl ethoxypropionate, 2-heptanone, γ-butyrolactone, cyclohexanone and butyl acetate are preferred, and propylene glycol monomethyl ether acetate, ethyl ethoxypropionate and 2-heptanone are most preferred.

The mixing ratio (by mass) of the solvent containing a hydroxyl group and the solvent containing no hydroxyl group is from 1/99 to 99/1, preferably from 10/90 to 90/10, more preferably from 20/80 to 60/40. A mixed solvent in which the solvent containing no hydroxyl group is contained in an amount of 50 mass % or more is preferred in view of coating uniformity.

The solvent is preferably a mixed solvent of two or more kinds of solvents including propylene glycol monomethyl ether acetate.

Basic Compound:

The positive resist composition of the present invention preferably contains a basic compound so as to reduce the change of performance with aging from exposure to heating.

Preferred basic compounds include a compound having a structure represented by the following formulae (A) to (E):

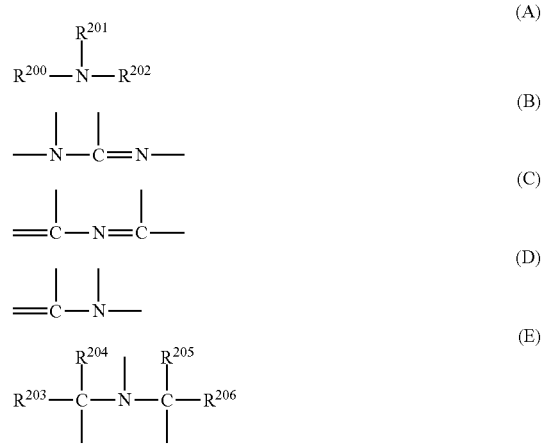

In formulae (A) to (E), each of $R^{200}$, $R^{201}$ and $R^{202}$, which may be the same or different, represents a hydrogen atom, an alkyl group (preferably having a carbon number of 1 to 20), a cycloalkyl group (preferably having a carbon number of 3 to 20) or an aryl group (having a carbon number of 6 to 20), and $R^{201}$ and $R^{202}$ may combine together to form a ring.

As for the alkyl group, the alkyl group having a substituent is preferably an aminoalkyl group having a carbon number of 1 to 20, a hydroxyalkyl group having a carbon number of 1 to 20, or a cyanoalkyl group having a carbon number of 1 to 20.

Each of $R^{203}$, $R^{204}$, $R^{205}$ and $R^{206}$, which may be the same or different, represents an alkyl group having a carbon number of 1 to 20.

The alkyl group in these formulae (A) to (E) is more preferably unsubstituted.

Preferred examples of the compound include guanidine, aminopyrrolidine, pyrazole, pyrazoline, piperazine, aminomorpholine, aminoalkylmorpholine and piperidine. More preferred examples of the compound include a compound having an imidazole structure, a diazabicyclo structure, an onium hydroxide structure, an onium carboxylate structure, a trialkylamine structure, an aniline structure or a pyridine structure; an alkylamine derivative having a hydroxyl group and/or an ether bond; and an aniline derivative having a hydroxyl group and/or an ether bond.

Examples of the compound having an imidazole structure include imidazole, 2,4,5-triphenylimidazole, benzimidazole and 2-phenylbenzimidazole. Examples of the compound having a diazabicyclo structure include 1,4-diazabicyclo[2,2,2]octane, 1,5-diazabicyclo[4,3,0]non-5-ene and 1,8-diazabicyclo[5,4,0]undec-7-ene. Examples of the compound having an onium hydroxide structure include tetrabutylammonium hydroxide, triarylsulfonium hydroxide, phenacylsulfonium hydroxide, and sulfonium hydroxide having a 2-oxoalkyl group, specifically, triphenylsulfonium hydroxide, tris(tert-butylphenyl)sulfonium hydroxide, bis(tert-butylphenyl)iodonium hydroxide, phenacylthiophenium hydroxide and 2-oxopropylthiophenium hydroxide. Examples of the compound having an onium carboxylate structure include a compound where the anion moiety of the compound having an onium hydroxide structure becomes a carboxylate, such as acetate, adamantane-1-carboxylate and perfluoroalkyl carboxylate. Examples of the compound having a trialkylamine structure include tri(n-butyl)amine and tri(n-octyl)amine. Examples of the aniline compound include 2,6-diisopropylaniline, N,N-dimethylaniline, N,N-dibutylaniline and N,N-dihexylaniline. Examples of the alkylamine derivative having a hydroxyl group and/or an ether bond include ethanolamine, diethanolamine, triethanolamine, N-phenyldiethanolamine and tris(methoxyethoxyethyl)amine. Examples of the aniline derivative having a hydroxyl group and/or an ether bond include N,N-bis(hydroxyethyl)aniline.

Other preferred basic compounds include a phenoxy group-containing amine compound, a phenoxy group-containing ammonium salt compound, a sulfonic acid ester group-containing amine compound and a sulfonic acid ester group-containing ammonium salt compound.

As for the amine compound, a primary, secondary or tertiary amine compound can be used, and an amine compound where at least one alkyl group is bonded to the nitrogen atom is preferred. The amine compound is more preferably a tertiary amine compound. In the amine compound, as long as at least one alkyl group (preferably having a carbon number of 1 to 20) is bonded to the nitrogen atom, a cycloalkyl group (preferably having a carbon number of 3 to 20) or an aryl group (preferably having a carbon number of 6 to 12) may be bonded to the nitrogen atom, in addition to the alkyl group. The amine compound preferably has an oxygen atom in the alkyl chain to form an oxyalkylene group. The number of oxyalkylene groups within the molecule is 1 or more, preferably from 3 to 9, more preferably from 4 to 6. Among oxyalkylene groups, an oxyethylene group (—CH$_2$CH$_2$O—) and an oxypropylene group (—CH(CH$_3$)CH$_2$O— or —CH$_2$CH$_2$CH$_2$O—) are preferred, and an oxyethylene group is more preferred.

As for the ammonium salt compound, a primary, secondary, tertiary or quaternary ammonium salt compound can be used, and an ammonium salt compound where at least one alkyl group is bonded to the nitrogen atom is preferred. In the ammonium salt compound, as long as at least one alkyl group (preferably having a carbon number of 1 to 20) is bonded to the nitrogen atom, a cycloalkyl group (preferably having a carbon number of 3 to 20) or an aryl group (preferably having a carbon number of 6 to 12) may be bonded to the nitrogen atom, in addition to the alkyl group. The ammonium salt compound preferably has an oxygen atom in the alkyl chain to form an oxyalkylene group. The number of oxyalkylene groups within the molecule is 1 or more, preferably from 3 to 9, more preferably from 4 to 6. Among oxyalkylene groups, an oxyethylene group (—CH$_2$CH$_2$O—) and an oxypropylene group (—CH(CH$_3$)CH$_2$O— or —CH$_2$CH$_2$CH$_2$O—) are preferred, and an oxyethylene group is more preferred. Examples of the anion of the ammonium salt compound include a halogen atom, a sulfonate, a borate and a phosphate, with a halogen atom and a sulfonate being preferred. The halogen atom is preferably chloride, bromide or iodide, and the sulfonate is preferably an organic sulfonate having a carbon number of 1 to 20. The organic sulfonate includes an alkylsulfonate having a carbon number of 1 to 20 and an arylsulfonate. The alkyl group of the alkylsulfonate may have a substituent, and examples of the substituent include fluorine, chlorine, bromine, an alkoxy group, an acyl group and an aryl group. Specific examples of the alkylsulfonate include methanesulfonate, ethanesulfonate, butanesulfonate, hexanesulfonate, octanesulfonate, benzylsulfonate, trifluoromethanesulfonate, pentafluoroethanesulfonate and nonafluorobutanesulfonate. The aryl group of the arylsulfonate includes a benzene ring, a naphthalene ring and an anthracene ring. The benzene ring, naphthalene ring and anthracene ring may have a substituent, and the substituent is preferably a linear or branched alkyl group having a carbon number of 1 to 6, or a cycloalkyl group having a carbon number of 3 to 6. Specific examples of the linear or branched alkyl group and cycloalkyl group include methyl, ethyl, n-propyl, isopropyl, n-butyl, i-butyl, tert-butyl, n-hexyl and cyclohexyl. Other examples of the substituent include an alkoxy group having a carbon number of 1 to 6, a halogen atom, cyano, nitro, an acyl group and an acyloxy group.

The phenoxy group-containing amine compound and the phenoxy group-containing ammonium salt compound are a compound where the alkyl group of an amine compound or ammonium salt compound has a phenoxy group at the terminal opposite the nitrogen atom. The phenoxy group may have a substituent. Examples of the substituent of the phenoxy group include an alkyl group, an alkoxy group, a halogen atom, a cyano group, a nitro group, a carboxyl group, a carboxylic acid ester group, a sulfonic acid ester group, an aryl group, an aralkyl group, an acyloxy group and an aryloxy group. The substitution site of the substituent may be any of 2- to 6-positions, and the number of substituents may be any in the range from 1 to 5.

The compound preferably has at least one oxyalkylene group between the phenoxy group and the nitrogen atom. The number of oxyalkylene groups within the molecule is 1 or more, preferably from 3 to 9, more preferably from 4 to 6. Among oxyalkylene groups, an oxyethylene group (—CH$_2$CH$_2$O—) and an oxypropylene group (—CH(CH$_3$)CH$_2$O— or —CH$_2$CH$_2$CH$_2$O—) are preferred, and an oxyethylene group is more preferred.

The sulfonic acid ester group in the sulfonic acid ester group-containing amine compound and sulfonic acid ester group-containing ammonium salt compound may be any of an alkylsulfonic acid ester, a cycloalkylsulfonic acid ester and an arylsulfonic acid ester. In the case of an alkylsulfonic acid ester, the alkyl group preferably has a carbon number of 1 to 20; in the case of a cycloalkylsulfonic acid ester, the cycloalkyl group preferably has a carbon number of 3 to 20; and in the case of an arylsulfonic acid ester, the aryl group preferably has a carbon number of 6 to 12. The alkylsulfonic acid ester, cycloalkylsulfonic acid ester and arylsulfonic acid ester may have a substituent, and the substituent is preferably a halogen atom, a cyano group, a nitro group, a carboxyl group, a carboxylic acid ester group or a sulfonic acid ester group.

The compound preferably has at least one oxyalkylene group between the sulfonic acid ester group and the nitrogen atom. The number of oxyalkylene groups within the molecule is 1 or more, preferably from 3 to 9, more preferably from 4 to 6. Among oxyalkylene groups, an oxyethylene group (—CH$_2$CH$_2$O—) and an oxypropylene group (—CH(CH$_3$)CH$_2$O— or —CH$_2$CH$_2$CH$_2$O—) are preferred, and an oxyethylene group is more preferred.

One of these basic compounds may be used alone, or two or more kinds thereof may be used in combination.

The amount of the basic compound used is usually from 0.001 to 10 mass %, preferably from 0.01 to 5 mass %, based on the solid content of the positive resist composition.

The ratio of acid generator and basic compound used in the composition is preferably acid generator/basic compound (by mol)=from 2.5 to 300. That is, the molar ratio is preferably 2.5 or more in view of sensitivity and resolution and preferably 300 or less from the standpoint of suppressing the reduction in resolution due to thickening of the resist pattern with aging after exposure until heat treatment. The acid generator/basic compound (by mol) is more preferably from 5.0 to 200, still more preferably from 7.0 to 150.

Surfactant:

The positive resist composition of the present invention preferably further contains a surfactant, more preferably any one of fluorine-containing and/or silicon-containing surfactants (a fluorine-containing surfactant, a silicon-containing surfactant and a surfactant containing both a fluorine atom and a silicon atom), or two or more kinds thereof.

By incorporating the above-described surfactant into the positive resist composition of the present invention, a resist pattern with good performance in terms of sensitivity, resolution and adherence as well as less development defect can be provided when an exposure light source of 250 nm or less, particularly 220 nm or less, is used.

Examples of the fluorine-containing and/or silicon-containing surfactants include surfactants described in JP-A-62-36663, JP-A-61-226746, JP-A-61-226745, JP-A-62-170950, JP-A-63-34540, JP-A-7-230165, JP-A-8-62834, JP-A-9-54432, JP-A-9-5988, JP-A-2002-277862 and U.S. Pat. Nos. 5,405,720, 5,360,692, 5,529,881, 5,296,330, 5,436,098, 5,576,143, 5,294,511 and 5,824,451. The following commercially available surfactants each may also be used as it is.

Examples of the commercially available surfactant which can be used include a fluorine-containing surfactant and a silicon-containing surfactant, such as EFtop EF301 and EF303 (produced by Shin-Akita Kasei K.K.); Florad FC430, 431 and 4430 (produced by Sumitomo 3M Inc.); Megaface F171, F173, F176, F189, F113, F110, F177, F120 and R08 (produced by Dainippon Ink & Chemicals, Inc.); Surflon S-382, SC101, 102, 103, 104, 105 and 106 (produced by Asahi Glass Co., Ltd.); Troysol S-366 (produced by Troy Chemical); GF-300 and OF-150 (produced by Toagosei Chemical Industry Co., Ltd.); Surflon S-393 (produced by Seimi Chemical Co., Ltd.); EFtop EF121, EF122A, FF122B, RF122C, EF125M, EF135M, EF351, 352, EF801, EF802 and EF601 (produced by JEMCO Inc.); PF636, PF656, PF6320 and PF6520 (produced by OMNOVA); and FTX-204G, 208G, 218G, 230G, 204D, 208D, 212D, 218D and 222D (produced by NEOS Co., Ltd.). In addition, polysiloxane polymer KP-341 (produced by Shin-Etsu Chemical Co., Ltd.) may also be used as a silicon-containing surfactant.

Other than these known surfactants, a surfactant using a polymer having a fluoro-aliphatic group derived from a fluoro-aliphatic compound that is produced by a telomerization process (also called a telomer process) or an oligomerization process (also called an oligomer process), may be used. The fluoro-aliphatic compound can be synthesized by the method described in JP-A-2302-90991.

The polymer having a fluoro-aliphatic group is preferably a copolymer of a fluoro-aliphatic group-containing monomer with a (poly(oxyalkylene)) acrylate and/or a (poly(oxyalkylene)) methacrylate, and the polymer may have an irregular distribution or may be a block copolymer. Examples of the poly(oxyalkylene) group include a poly(oxyethylene) group, a poly(oxypropylene) group and a poly(oxybutylene) group. This group may also be a unit having alkylenes differing in the chain length within the same chain, such as block-linked poly(oxyethylene, oxypropylene and oxyethylene) and block-linked poly(oxyethylene and oxypropylene). Furthermore, the copolymer of a fluoro-aliphatic group-containing monomer and a (poly(oxyalkylene)) acrylate (or methacrylate) is not limited only to a binary copolymer but may also be a ternary or greater copolymer obtained by simultaneously copolymerizing two or more different fluoro-aliphatic group-containing monomers or two or more different (poly(oxyalkylene)) acrylates (or methacrylates).

Examples thereof include, as the commercially available surfactant, Megaface F178, F-470, F-473, F-475, F-476 and F-472 (produced by Dainippon Ink & Chemicals, Inc.) and further include a copolymer of a $C_6F_{13}$ group-containing acrylate (or methacrylate) with a (poly(oxyalkylene))acrylate (or methacrylate), and a copolymer of a $C_3F_7$ group-containing acrylate (or methacrylate) with a (poly(oxyethylene)) acrylate (or methacrylate) and a (poly(oxypropylene))acrylate (or methacrylate).

In the present invention, a surfactant other than the fluorine-containing and/or silicon-containing surfactants may also be used. Specific examples thereof include a nonionic surfactant such as polyoxyethylene alkyl ethers (e.g., polyoxyethylene lauryl ether, polyoxyethylene stearyl ether, polyoxyethylene cetyl ether, polyoxyethylene oleyl ether), polyoxyethylene alkylallyl ethers (e.g., polyoxyethylene octylphenol ether, polyoxyethylene nonylphenol ether), polyoxyethylene polyoxypropylene block copolymers, sorbitan fatty acid esters (e.g., sorbitan monolaurate, sorbitan monopalmitate, sorbitan monostearate, sorbitan monooleate, sorbitan trioleate, sorbitan tristearate), and polyoxyethylene sorbitan fatty acid esters (e.g., polyoxyethylene sorbitan monolaurate, polyoxyethylene sorbitan monopalmitate, polyoxyethylene sorbitan monostearate, polyoxyethylene sorbitan trioleate, polyoxyethylene sorbitan tristearate).

One of such surfactants may be used alone, or some of them may be used in combination.

The amount of the surfactant used is preferably from 0.01 to 10 mass %, more preferably from 0.1 to 5 mass %, based on the entire amount of the positive resist composition (excluding the solvent).

Onium Carboxylate:

The positive resist composition of the present invention may contain an onium carboxylate. Examples of the onium carboxylate include sulfonium carboxylate, iodonium carboxylate and ammonium carboxylate. In particular, the onium carboxylate is preferably an iodonium salt or a sulfonium salt. Furthermore, the carboxylate residue of the onium carboxylate for use in the present invention preferably contains no aromatic group and no carbon-carbon double bond. The anion moiety is preferably a linear or branched, monocyclic or polycyclic alkylcarboxylate anion having a carbon number of 1 to 30, more preferably the carboxylate anion above with the alkyl group being partially or entirely fluorine-substituted. The alkyl chain may contain an oxygen atom. By virtue of such a construction, transparency to light at 220 nm or less is ensured, the sensitivity and resolution are enhanced, and the iso/dense bias and exposure margin are improved.

Examples of the fluorine-substituted carboxylate anion include fluoroacetate, difluoroacetate, trifluoroacetate, pentafluoropropionate, heptafluorobutyrate, nonafluoropentanoate, perfluorododecanoate, perfluorotridecanoate, perfluorocyclohexanecarboxylate and 2,2-bistrifluoromethylpropionate anions.

These onium carboxylates can be synthesized by reacting a sulfonium, iodonium or ammonium hydroxide and a carboxylic acid with silver oxide in an appropriate solvent.

The content of the onium carboxylate in the composition is generally from 0.1 to 20 mass %, preferably from 0.5 to 10 mass %, more preferably from 1 to 7 mass %, based on the entire solid content of the composition.

Dissolution inhibiting compound having a molecular weight of 3,000 or less and being capable of decomposing by the action of an acid to increase the solubility in an alkali developer:

The dissolution inhibiting compound having a molecular weight of 3,000 or less and being capable of decomposing by the action of an acid to increase the solubility in an alkali developer (hereinafter, sometimes referred to as a "dissolution inhibiting compound") is preferably an alicyclic or aliphatic compound containing an acid-decomposable group, such as acid-decomposable group-containing cholic acid derivative described in Proceeding of SPIE, 2724, 355

(1996), so as not to reduce the transparency to light at 220 nm or less. Examples of the acid-decomposable group and alicyclic structure are the same as those described above with respect to the resin as the component (B).

In the case where the positive resist composition of the present invention is exposed to KrF excimer laser or irradiated with electron beam, the composition preferably contains a structure where the phenolic hydroxyl group of a phenol compound is substituted by an acid-decomposable group. The phenol compound is preferably a compound containing from 1 to 9 phenol skeletons, more preferably from 2 to 6 phenol skeletons.

The molecular weight of the dissolution inhibiting compound for use in the present invention is 3,000 or less, preferably from 300 to 3,000, more preferably from 500 to 2,500.

The amount of the dissolution inhibiting compound added is preferably from 3 to 50 mass %, more preferably from 5 to 40 mass %, based on the solid content of the positive resist composition.

Specific examples of the dissolution inhibiting compound are set forth below, but the present invention is not limited thereto.

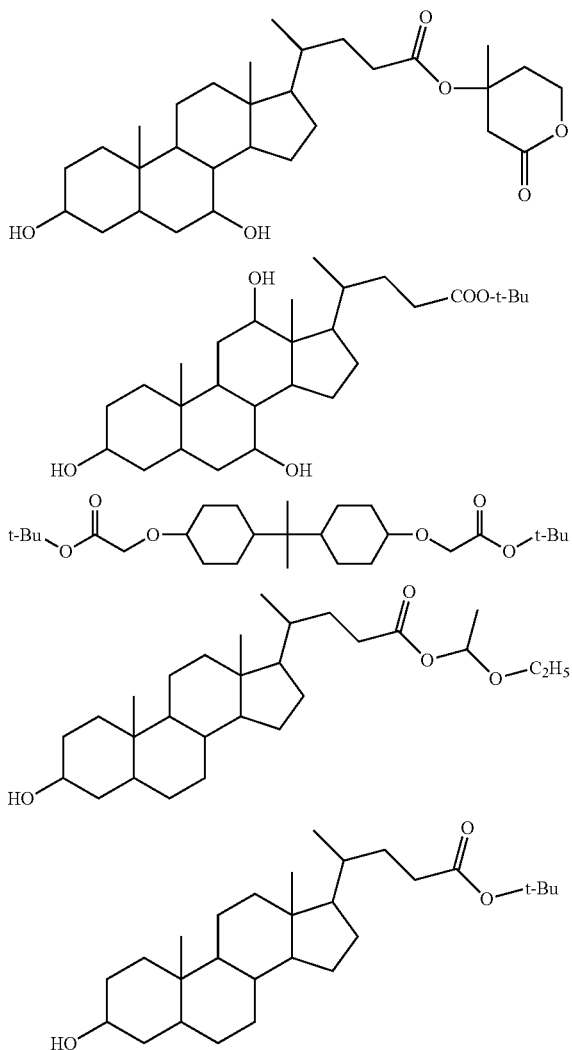

-continued

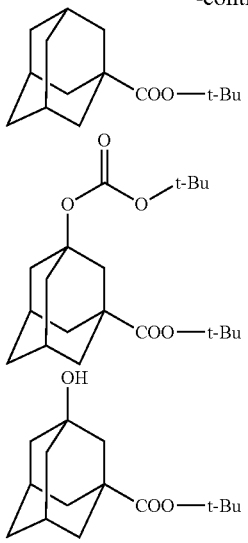

Other Additives:

The positive resist composition of the present invention may further contain, for example, a dye, a plasticizer, a photosensitizer, a light absorber and a compound for accelerating dissolution in a developer (for example, a phenol compound having a molecular weight of 1,000 or less, or a carboxyl group-containing alicyclic or aliphatic compound), if desired.

The phenol compound having a molecular weight of 1,000 or less can be easily synthesized by one skilled in the art by referring to the methods described, for example, in JP-A-4-122938, JP-A-2-28531, U.S. Pat. No. 4,916,210 and European Patent 219294.

Specific examples of the carboxyl group-containing alicyclic or aliphatic compound include, but are not limited to, a carboxylic acid derivative having a steroid structure, such as cholic acid, deoxycholic acid and lithocholic acid, an adamantanecarboxylic acid derivative, an adamantanedicarboxylic acid, a cyclohexanecarboxylic acid and a cyclohexanedicarboxylic acid.

Pattern Forming Method:

The positive resist composition of the present invention is preferably used in a film thickness of 30 to 250 nm, more preferably from 30 to 200 nm, from the standpoint of enhancing the resolution. Such a film thickness can be obtained by setting the solid content concentration in the positive resist composition to an appropriate range, thereby imparting an appropriate viscosity and enhancing the coatability and film-forming property.

The entire solid content concentration in the positive resist composition is generally from 1 to 10 mass %, preferably from 1 to 8.0 mass %, more preferably from 1.0 to 6.0 mass %.

The positive resist composition of the present invention is used by dissolving the components above in a predetermined organic solvent, preferably in the above-described mixed solvent, filtering the solution, and applying it on a predetermined support as follows. The filter used for filtering is preferably a polytetrafluoroethylene-, polyethylene- or nylon-made filter having a pore size of 0.1 μm or less, more preferably 0.05 μm or less, still more preferably 0.03 μm or less.

For example, the positive resist composition is applied on such a substrate (e.g., silicon/silicon dioxide-coated substrate) as used in the production of a precision integrated circuit device, by an appropriate coating method such as spinner or coater and dried to form a resist film.

The resist film is irradiated with an actinic ray or radiation through a predetermined mask, preferably heated (baked) and then subjected to development and rinsing, whereby a good pattern can be obtained.

Examples of the actinic ray or radiation include infrared light, visible light, ultraviolet light, far ultraviolet light, X-ray and electron beam, but the radiation is preferably far ultraviolet light at a wavelength of 250 nm or less, more preferably 220 nm or less, still more preferably from 1 to 200 nm. Specific examples thereof include KrF excimer laser (248 nm), ArF excimer laser (193 nm), $F_2$ excimer laser (157 nm), X-ray and electron beam, with ArF excimer laser, $F_2$ excimer laser, EUV (13 nm) and electron beam being preferred.

Before forming the resist film, an antireflection film may be previously provided by coating on the substrate.

The antireflection film used may be ether an inorganic film type such as titanium, titanium dioxide, titanium nitride, chromium oxide, carbon and amorphous silicon, or an organic film type composed of a light absorber and a polymer material. Also, a commercially available organic antireflection film such as DUV30 Series and DUV-40 Series produced by Brewer Science, Inc., and AR-2, AR-3 and AR-5 produced by Shipley Co., Ltd. can be used as the organic antireflection film.

In the development step, an alkali developer is used as follows. The alkali developer which can be used for the positive resist composition is an alkaline aqueous solution of, for example, inorganic alkalis such as sodium hydroxide, potassium hydroxide, sodium carbonate, sodium silicate, sodium metasilicate and aqueous ammonia, primary amines such as ethylamine and n-propylamine, secondary amines such as diethylamine and di-n-butylamine, tertiary amines such as triethylamine and methyldiethylamine, alcohol amines such as dimethylethanolamine and triethanolamine, quaternary ammonium salts such as tetramethylammonium hydroxide and tetraethylammonium hydroxide, or cyclic amines such as pyrrole and piperidine.

Furthermore, this alkali developer may be used after adding thereto alcohols and a surfactant each in an appropriate amount.

The alkali concentration of the alkali developer is usually from 0.1 to 20 mass %.

The pH of the alkali developer is usually from 10.0 to 15.0.

Also, the above-described alkaline aqueous solution may be used after adding thereto alcohols and a surfactant each in an appropriate amount.

As for the rinsing solution, pure water is used, and the pure water may be used after adding thereto a surfactant in an appropriate amount.

After the development or rinsing, the developer or rinsing solution adhering on the pattern may removed by a supercritical fluid.

The exposure may also be performed by filling a liquid (immersion medium) having a refractive index higher than that of air between the resist film and a lens at the irradiation with an actinic ray or radiation (immersion exposure). By this exposure, the resolution can be enhanced. The immersion medium used may be any liquid as long as it has a refractive index higher than that of air, but pure water is preferred.

The immersion liquid used in the immersion exposure is described below.

The immersion liquid is preferably a liquid being transparent to light at the exposure wavelength and having as small a temperature coefficient of refractive index as possible so as to minimize the distortion of an optical image projected on the resist film. Particularly, when the exposure light source is an ArF excimer laser (wavelength: 193 nm), water is preferably used in view of easy availability and easy handleability, in addition to the above-described aspects.

Furthermore, a medium having a refractive index of 1.5 or more can also be used from the standpoint that the refractive index can be more enhanced. This medium may be either an aqueous solution or an organic solvent.

In the case of using water as the immersion liquid, for decreasing the surface tension of water and increasing the surface activity, an additive (liquid) which does not dissolve the resist film on a wafer and at the same time, gives only a negligible effect on the optical coat at the undersurface of the lens element, may be added in a small ratio. The additive is preferably an aliphatic alcohol having a refractive index nearly equal to that of water, and specific examples thereof include methyl alcohol, ethyl alcohol and isopropyl alcohol. By virtue of adding an alcohol having a refractive index nearly equal to that of water, even when the alcohol component in water is evaporated and its content concentration is changed, the change in the refractive index of the entire liquid can be advantageously made very small. On the other hand, if a substance opaque to light at 193 nm or an impurity greatly differing in the refractive index from water is mingled, this incurs distortion of the optical image projected on the resist film. Therefore, the water used is preferably distilled water. Pure water obtained by further filtering the distilled water through an ion exchange filter or the like may also be used.

The electrical resistance of water is preferably 18.3 MΩcm or more, and TOC (total organic carbon) is preferably 20 ppb or less. The water is preferably subjected to a deaeration treatment.

Also, the lithography performance can be enhanced by increasing the refractive index of the immersion liquid. From such a standpoint, an additive for increasing the refractive index may be added to water, or deuterated water ($D_2O$) may be used in place of water.

In the case where the resist film formed of the positive resist composition of the present invention is exposed through an immersion medium, a hydrophobic resin (HR) (sometimes referred to as a "surface hydrophobizing resin") may be further added, if desired. The hydrophobic resin (FIR) when added is unevenly distributed to the surface layer of the resist film and in the case of using water as the immersion medium, the resist film formed can be enhanced in the receding contact angle on the resist film surface for water as well as in the followability of the immersion liquid. The hydrophobic resin (HR) may be any resin as long as the receding contact angle on the surface can be enhanced by its addition, but a resin having at least either one of a fluorine atom and a silicon atom is preferred. The receding contact angle of the resist film is preferably from 60 to 90°, more preferably 70° or more. The amount of the hydrophobic resin added may be appropriately adjusted to give a resist film having a receding contact angle in the range above but is preferably from 0.1 to 10 mass %, more preferably from 0.1 to 5 mass %, based on the entire solid content of the positive resist composition. The hydrophobic resin (HR) is, as described above, unevenly distributed to the interface but unlike a surfactant, need not have necessarily a hydrophilic group in the molecule and may not contribute to uniform mixing of polar/nonpolar substances.

The receding contact angle is a contact angle measured when a contact line recedes on the liquid droplet-substrate interface, and this contact angle is generally known to be useful in simulating the mobility of a liquid droplet in a dynamic state. In a simple manner, the receding contact angle can be defined as a contact angle at the time of the liquid droplet interface receding when a liquid droplet ejected from a needle tip is landed on a substrate and then the liquid droplet is again suctioned into the needle. In general, the receding contact angle can be measured by a contact angle measuring method called an expansion/contraction method.

In the immersion exposure step, the immersion liquid needs to move on a wafer following the movement of an exposure head that is scanning the wafer at a high speed and forming an exposure pattern. Therefore, the contact angle of the immersion liquid with the resist film in a dynamic state is important, and a performance of allowing a liquid droplet to follow the high-speed scanning of an exposure head with no remaining is required of the resist.

The fluorine atom or silicon atom in the hydrophobic resin (HR) may be present in the main chain of the resin or may be substituted on the side chain.

The hydrophobic resin (HR) is preferably a resin having a fluorine atom-containing alkyl group, a fluorine atom-containing cycloalkyl group or a fluorine atom-containing aryl group, as a fluorine atom-containing partial structure.

The fluorine atom-containing alkyl group (preferably having a carbon number of 1 to 10, more preferably from 1 to 4) is a linear or branched alkyl group with at least one hydrogen atom being replaced by a fluorine atom and may further have other substituents.

The fluorine atom-containing cycloalkyl group is a monocyclic or polycyclic cycloalkyl group with at least one hydrogen atom being replaced by a fluorine atom and may further have other substituents.

The fluorine atom-containing aryl group is an aryl group (e.g., phenyl, naphthyl) with at least one hydrogen atom being replaced by a fluorine atom and may further have other substituents.

Preferred examples of the fluorine atom-containing alkyl group, fluorine atom-containing cycloalkyl group and fluorine atom-containing aryl group include the groups represented by the following formulae (F2) to (F4), but the present invention is not limited thereto.

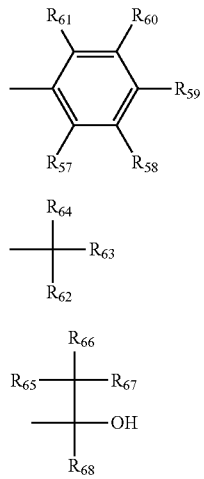

In formulae (F2) to (F4), each of $R_{57}$ to $R_{68}$ independently represents a hydrogen atom, a fluorine atom or an alkyl group, provided that at least one of $R_{57}$ to $R_{61}$, at least one of $R_{62}$ to $R_{64}$ and at least one of $R_{65}$ to $R_{68}$ are a fluorine atom or an alkyl group (preferably having a carbon number of 1 to 4) with at least one hydrogen atom being replaced by a fluorine atom. It is preferred that $R_{57}$ to $R_{61}$ and $R_{65}$ to $R_{67}$ all are a fluorine atom. Each of $R_{62}$, $R_{63}$ and $R_{68}$ is preferably an alkyl group (preferably having a carbon number of 1 to 4) with at least one hydrogen atom being replaced by a fluorine atom, more preferably a perfluoroalkyl group having a carbon number of 1 to 4. $R_{62}$ and $R_{63}$ may combine together to form a ring.

Specific examples of the group represented by formula (F2) include p-fluorophenyl group, pentafluorophenyl group and 3,5-di(trifluoromethyl)phenyl group.

Specific examples of the group represented by formula (F3) include trifluoromethyl group, pentafluoropropyl group, pentafluoroethyl group, heptafluorobutyl group, hexafluoroisopropyl group, heptafluoroisopropyl group, hexafluoro(2-methyl)isopropyl group, nonafluorobutyl group, octafluoroisobutyl group, nonafluorohexyl group, nonafluoro-tort-butyl group, perfluoroisopentyl group, perfluorooctyl group, perfluoro(trimethyl)hexyl group, 2,2,3,3-tetrafluorocyclobutyl group and perfluorocyclohexyl group. Among these, hexafluoroisopropyl group, heptafluoroisopropyl group, hexafluoro(2-methyl)isopropyl group, octafluoroisobutyl group, nonafluoro-tert-butyl group and perfluoroisopentyl group are preferred, and hexafluoroisopropyl group and heptafluoroisopropyl group are more preferred.

Specific examples of the group represented by formula (F4) include —C(CF$_3$)$_2$OH, —C(C$_2$F$_5$)$_2$OH, —C(CF$_3$)(CH$_3$)OH and —CH(CF$_3$)OH, with —C(CF$_3$)$_2$OH being preferred.

Specific examples of the repeating unit having a fluorine atom are set forth below, but the present invention is not limited thereto.

In specific examples, $X_1$ represents a hydrogen atom, —CH$_3$, —F or —CF$_3$.

$X_2$ represents —F or —CF$_3$.

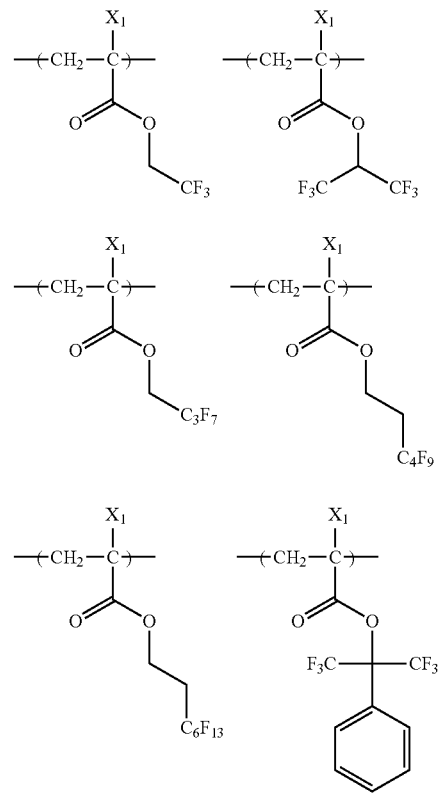

-continued
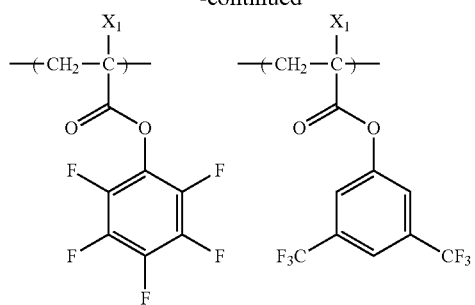
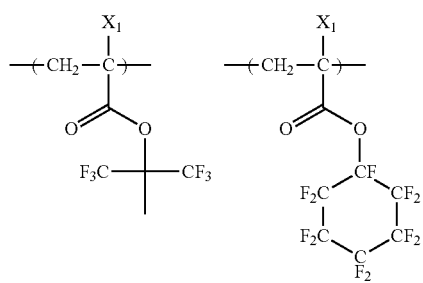
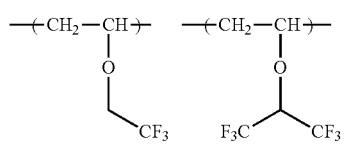
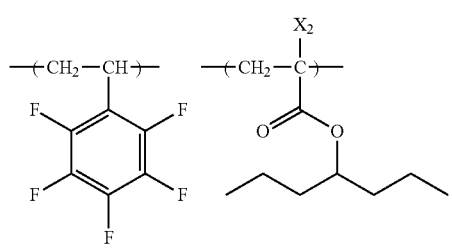
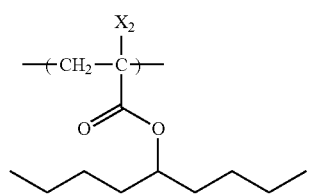
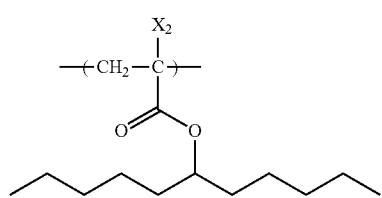
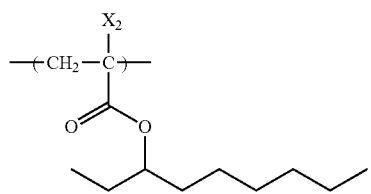
-continued
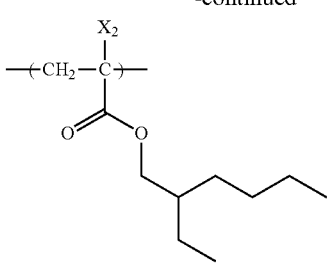
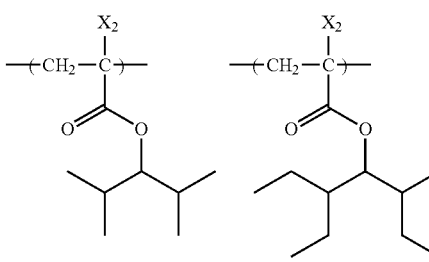
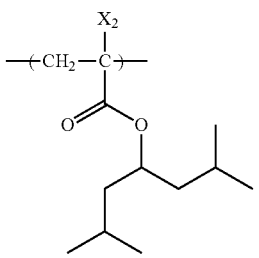
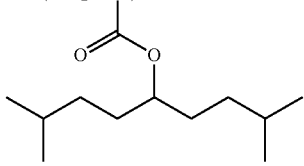
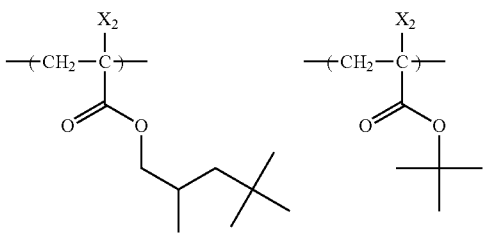
The hydrophobic resin (HR) is preferably a resin having an alkylsilyl structure (preferably a trialkylsilyl group) or a cyclic siloxane structure, as a silicon atom-containing partial structure.
Specific examples of the alkylsilyl structure and cyclic siloxane structure include groups represented by the following formulae (CS-1) to (CS-3):
(CS-1)
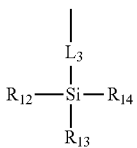

-continued (CS-2)

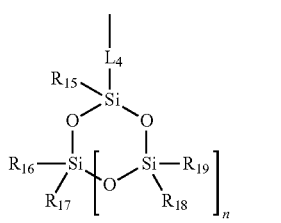

(CS-3)

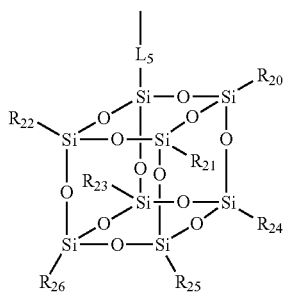

In formulae (CS-1) to (CS-3), each of $R_{12}$ to $R_{26}$ independently represents a linear or branched alkyl group (preferably having a carbon number of 1 to 20) or a cycloalkyl group (preferably having a carbon number of 3 to 20).

Each of $L_3$ to $L_5$ represents a single bond or a divalent linking group. Examples of the divalent linking group include a single group and a combination of two or more groups, selected from the group consisting of an alkylene group, a phenyl group, an ether group, a thioether group, a carbonyl group, an ester group, an amide group, a urethane group and a urea group.

n represents an integer of 1 to 5.

Specific examples of the repeating unit having a silicon atom are set forth below, but the present invention is not limited thereto.

In specific examples, $X_1$ represents a hydrogen atom, —$CH_3$, —F or —$CF_3$.

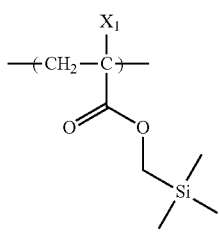

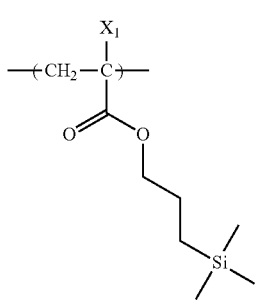

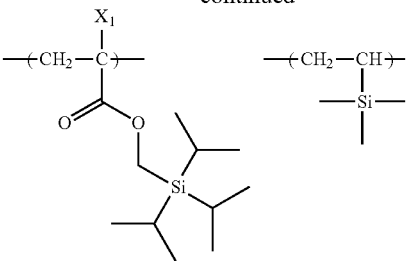

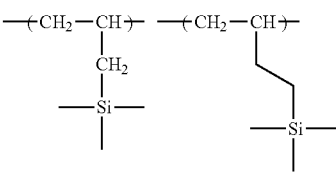

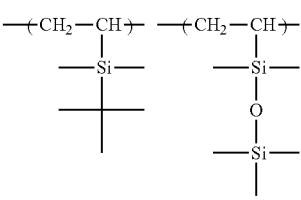

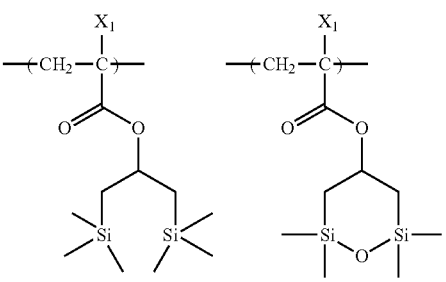

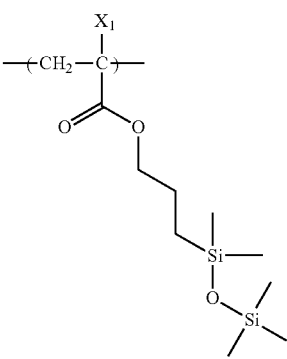

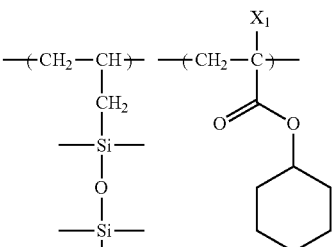

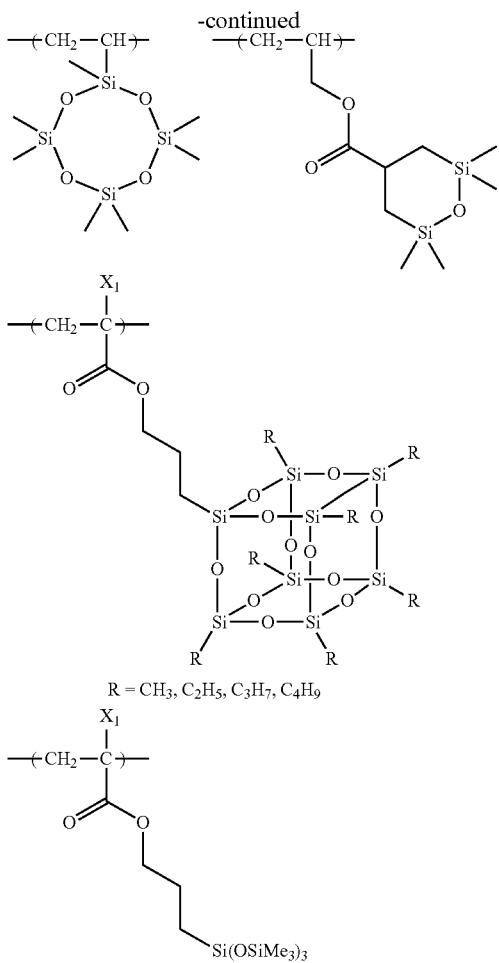

Furthermore, the hydrophobic resin (HR) may contain at least one group selected from the group consisting of the following (x) to (z):

(x) an alkali-soluble group,
(y) a group capable of decomposing by the action of an alkali developer to increase the solubility in an alkali developer, and
(z) a group capable of decomposing by the action of an acid.

Examples of the (x) alkali-soluble group include a group having a phenolic hydroxyl group, a carboxylic acid group, a fluorinated alcohol group, a sulfonic acid group, a sulfonamide group, a sulfonylimide group, an (alkylsulfonyl)(alkylcarbonyl)methylene group, an (alkylsulfonyl)(alkylcarbonyl)imide group, a bis(alkylcarbonyl)methylene group, a bis(alkylcarbonyl)imide group, a bis(alkylsulfonyl)methylene group, a bis(alkylsulfonyl)imide group, a tris(alkylcarbonyl)methylene group or a tris(alkylsulfonyl)methylene group.

Preferred alkali-soluble groups include a fluorinated alcohol group (preferably hexafluoroisopropanol), a sulfonimide group and a bis(carbonyl)methylene group.

As for the repeating unit having (x) an alkali-soluble group, all of a repeating unit where an alkali-soluble group is directly bonded to the resin main chain, such as repeating unit by an acrylic acid or a methacrylic acid, a repeating unit where an alkali-soluble group is bonded to the resin main chain through a linking group, and a repeating unit where an alkali-soluble group is introduced into the polymer chain terminal by using an alkali-soluble group-containing polymerization initiator or chain transfer agent at the polymerization, are preferred.

The content of the repeating unit having (x) an alkali-soluble group is preferably from 1 to 50 mol %, more preferably from 3 to 35 mol %, still more preferably from 5 to 20 mol %, based on all repeating units in the polymer.

Specific examples of the repeating unit having (x) an alkali-soluble group are set forth below, but the present invention is not limited thereto.

In the formulae, Rx represents H, CH$_3$, CF$_3$ or CH$_2$OH.

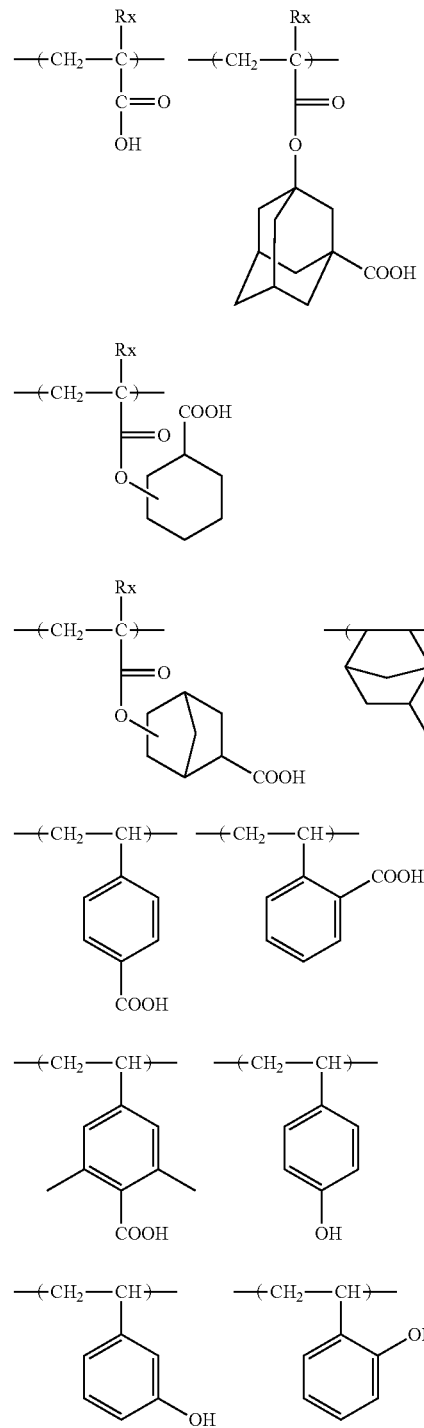

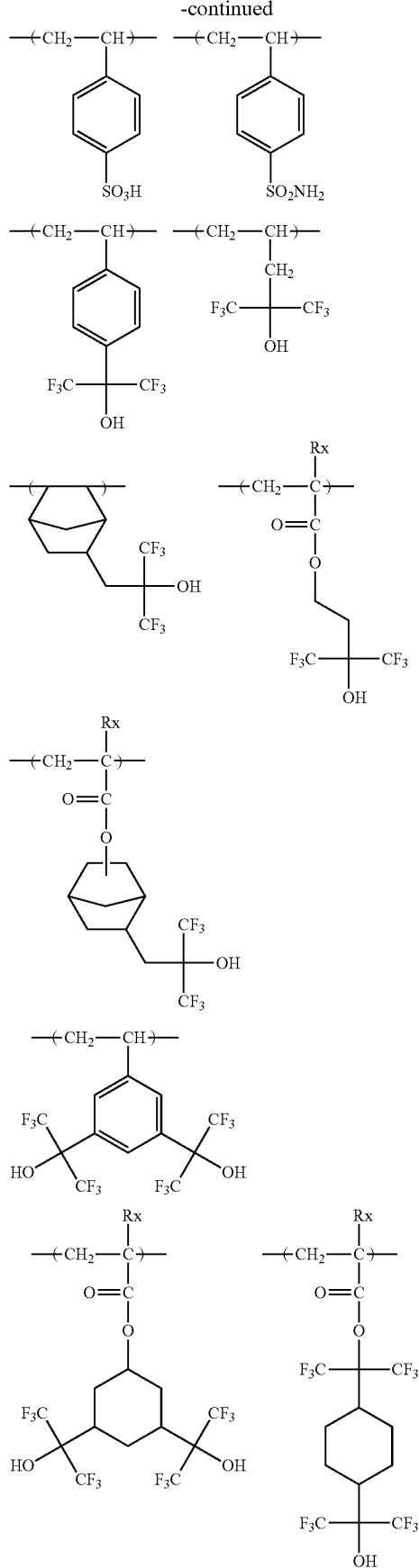
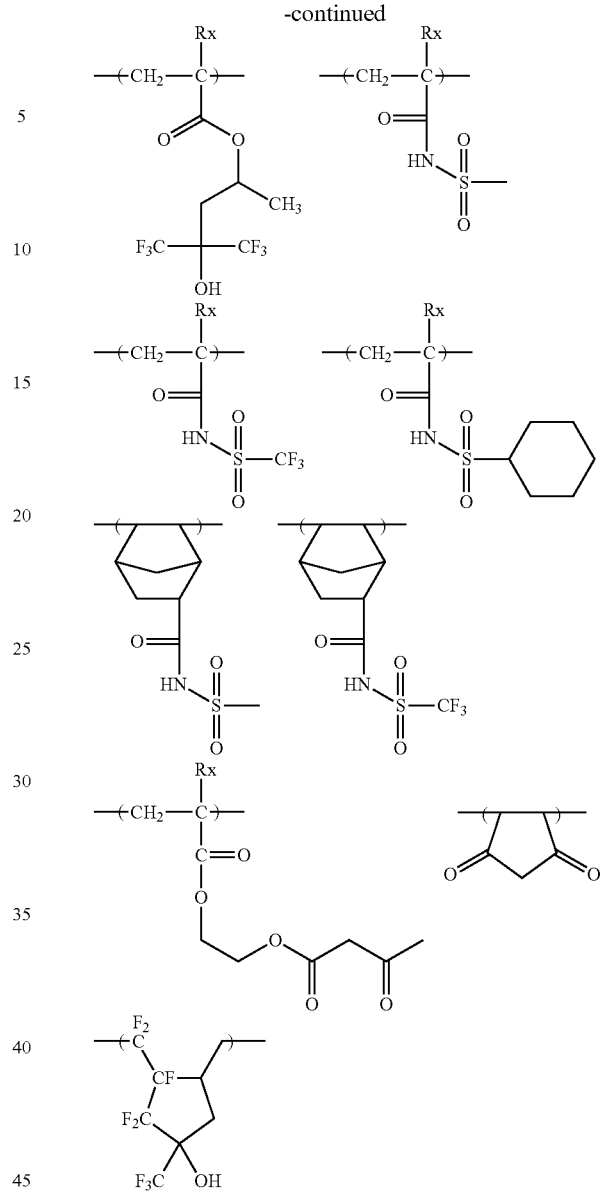

Examples of the (y) group capable of decomposing by the action of an alkali developer to increase the solubility in an alkali developer include a lactone structure-containing group, an acid anhydride group and an acid imide group, with a lactone group being preferred.

As for the repeating unit having (y) a group capable of decomposing by the action of an alkali developer to increase the solubility in an alkali developer, both a repeating unit where (y) a group capable of decomposing by the action of an alkali developer to increase the solubility in an alkali developer is bonded to the main chain of the resin, such as repeating unit by an acrylic acid ester or a methacrylic acid ester, and a repeating unit where (y) a group capable of increasing the solubility in an alkali developer is introduced into the polymer chain terminal by using a polymerization initiator or chain transfer agent containing the group (y) at the polymerization, are preferred.

The content of the repeating unit having (y) a group capable of increasing the solubility in an alkali developer is preferably from 1 to 40 mol %, more preferably from 3 to 30 mol %, still more preferably from 5 to 15 mol %, based on all repeating units in the polymer.

Specific examples of the repeating unit having (y) a group capable of increasing the solubility in an alkali developer are the same as those of the repeating unit having a lactone structure described for the resin as the component (B).

Examples of the repeating unit having (z) a group capable of decomposing by the action of an acid, contained in the hydrophobic resin (FIR), are the same as those of the repeating unit having an acid-decomposable group described for the resin as the component (B). In the hydrophobic resin (HR), the content of the repeating unit having (z) a group capable of decomposing by the action of an acid is preferably from 1 to 80 mol %, more preferably from 10 to 80 mol %, still more preferably from 20 to 60 mol %, based on all repeating units in the polymer.

The hydrophobic resin (HR) may further contain a repeating unit represented by the following formula (III):

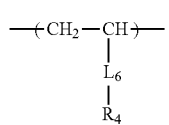

(III)

In formula (III), $R_4$ represents a group having an alkyl group, a cycloalkyl group, an alkenyl group or a cycloalkenyl group.

$L_6$ represents a single bond or a divalent linking group.

In formula (III), the alkyl group of $R_4$ is preferably a linear or branched alkyl group having a carbon number of 3 to 20.

The cycloalkyl group is preferably a cycloalkyl group having a carbon number of 3 to 20.

The alkenyl group is preferably an alkenyl group having a carbon number of 3 to 20.

The cycloalkenyl group is preferably cycloalkenyl group having a carbon number of 3 to 20.

The divalent linking group of $L_6$ is preferably an alkylene group (preferably having a carbon number of 1 to 5) or an oxy group.

In the case where the hydrophobic resin (FIR) contains a fluorine atom, the fluorine atom content is preferably from 5 to 80 mass %, more preferably from 10 to 80 mass %, based on the molecular weight of the hydrophobic resin (FIR). Also, the fluorine atom-containing repeating unit preferably occupies from 10 to 100 mass %, more preferably from 30 to 100 mass %, in the hydrophobic resin (HR).

In the case where the hydrophobic resin (FIR) contains a silicon atom, the silicon atom content is preferably from 2 to 50 mass %, more preferably from 2 to 30 mass %, based on the molecular weight of the hydrophobic resin (FIR). Also, the silicon atom-containing repeating unit preferably occupies from 10 to 100 mass %, more preferably from 20 to 100 mass %, in the hydrophobic resin (HR).

The standard polystyrene-equivalent weight average molecular of the hydrophobic resin (HR) is preferably from 1,000 to 100,000, more preferably from 1,000 to 50,000, still more preferably from 2,000 to 15,000.

In the hydrophobic resin (HR), similarly to the resin of the component (B), as well as little impurities such as metal, the content of the residual monomer or oligomer component is preferably from 0 to 10 mass %, more preferably from 0 to 5 mass %, still more preferably from 0 to 1 mass %. When these conditions are satisfied, a resist free of in-liquid foreign matters and sensitivity change with aging can be obtained. Also, in view of resolution, resist profile, side wall of resist pattern, roughness and the like, the molecular weight distribution (Mw/Mn, also called polydispersity) is preferably from 1 to 5, more preferably from 1 to 3, still more preferably from 1 to 2.

As for the hydrophobic resin (HR), various commercial products may be used or the resin may be synthesized by an ordinary method (for example, radical polymerization). Examples of the general synthesis method include a batch polymerization method of dissolving monomer species and an initiator in a solvent and heating the solution, thereby effecting the polymerization, and a dropping polymerization method of adding dropwise a solution containing monomer species and an initiator to a heated solvent over 1 to 10 hours. A dropping polymerization method is preferred. Examples of the reaction solvent include ethers such as tetrahydrofuran, 1,4-dioxane and diisopropyl ether, ketones such as methyl ethyl ketone and methyl isobutyl ketone, an ester solvent such as ethyl acetate, an amide solvent such as dimethylformamide and dimethylacetamide, and the later-described solvent capable of dissolving the composition of the present invention, such as propylene glycol monomethyl ether acetate, propylene glycol monomethyl ether and cyclohexanone. The polymerization is more preferably performed using the same solvent as the solvent used in the positive resist composition of the present invention. By the use of the same solvent, production of particles during storage can be suppressed.

The polymerization reaction is preferably performed in an inert gas atmosphere such as nitrogen or argon. As for the polymerization initiator, the polymerization is started using a commercially available radical initiator (e.g., azo-based initiator, peroxide). The radical initiator is preferably an azo-based initiator, and an azo-based initiator having an ester group, a cyano group or a carboxyl group is preferred. Preferred examples of the initiator include azobisisobutyronitrile, azobisdimethylvaleronitrile and dimethyl 2,2'-azobis(2-methylpropionate). The reaction concentration is from 5 to 50 mass %, preferably from 30 to 50 mass %, and the reaction temperature is usually from 10 to 150° C., preferably from 30 to 120° C., more preferably from 60 to 100° C.

After the completion of reaction, the reaction solution is allowed to cool to room temperature and purified. The purification may be performed by a normal method, for example, a liquid-liquid extraction method of combining water washing and an appropriate solvent to remove residual monomers or oligomer components; a purification method in a solution sate, such as ultrafiltration of removing by extraction only those having a molecular weight not more than a specific value; a reprecipitation method of adding dropwise the resin solution in a poor solvent to solidify the resin in the poor solvent and thereby remove residual monomers or the like; and a purification method in a solid state, such as washing of a resin slurry separated by filtration with a poor solvent. For example, the resin is precipitated as a solid by contacting the reaction solution with a solvent in which the resin is sparingly soluble or insoluble (poor solvent) and which is in a volumetric amount of 10 times or less, preferably from 10 to 5 times, the reaction solution.

The solvent used at the operation of precipitation or reprecipitation from the polymer solution (precipitation or reprecipitation solvent) may be sufficient if it is a poor solvent to the polymer, and the solvent may be appropriately selected, for example, from a hydrocarbon, a halogenated hydrocarbon, a nitro compound, an ether, a ketone, an ester, a carbonate, an alcohol, a carboxylic acid, water, and a mixed solvent containing such a solvent, according to the kind of the polymer. Among these solvents, a solvent containing at least an alcohol (particularly, methanol or the like) or water is preferred as the precipitation or reprecipitation solvent.

The amount of the precipitation or reprecipitation solvent used may be appropriately selected by taking into consideration the efficiency, yield and the like, but in general, the amount used is from 100 to 10,000 parts by mass, preferably from 200 to 2,000 parts by mass, more preferably from 300 to 1,000 parts by mass, per 100 parts by mass of the polymer solution.

The temperature at the precipitation or reprecipitation may be appropriately selected by taking into consideration the efficiency or operability but is usually on the order of 0 to 50° C., preferably in the vicinity of room temperature (for example, approximately from 20 to 35° C.). The precipitation or reprecipitation operation may be performed using a commonly employed mixing vessel such as stirring tank, by a known method such as batch system and continuous system.

The precipitated or reprecipitated polymer is usually subjected to commonly employed solid-liquid separation such as filtration and centrifugation, then dried and used. The filtration is performed using a solvent-resistant filter element preferably under pressure. The drying is performed under atmospheric pressure or reduced pressure (preferably under reduced pressure) at a temperature of approximately from 30 to 100° C., preferably on the order of 30 to 50° C.

Incidentally, after the resin is once precipitated and separated, the resin may be again dissolved in a solvent and then put into contact with a solvent in which the resin is sparingly soluble or insoluble. That is, there may be used a method comprising, after the completion of radical polymerization reaction, bringing the polymer into contact with a solvent in which the polymer is sparingly soluble or insoluble, to precipitate a resin (step a), separating the resin from the solution (step b), anew dissolving the resin in a solvent to prepare a resin solution A (step c), bringing the resin solution A into contact with a solvent in which the resin is sparingly soluble or insoluble and which is in a volumetric amount of less than 10 times (preferably 5 times or less) the resin solution A, to precipitate a resin solid (step d), and separating the precipitated resin (step e).

Specific examples of the hydrophobia resin (HR) are set forth below. Also, the molar ratio of repeating units (corresponding to repeating units from the left), weight average molecular weight and dispersity of each resin are shown in Table 1 below.

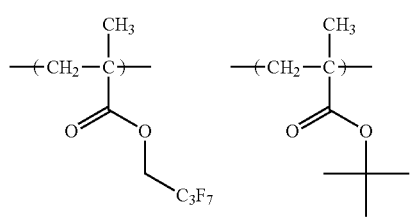

(HR-1)

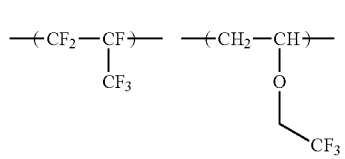

(HR-2)

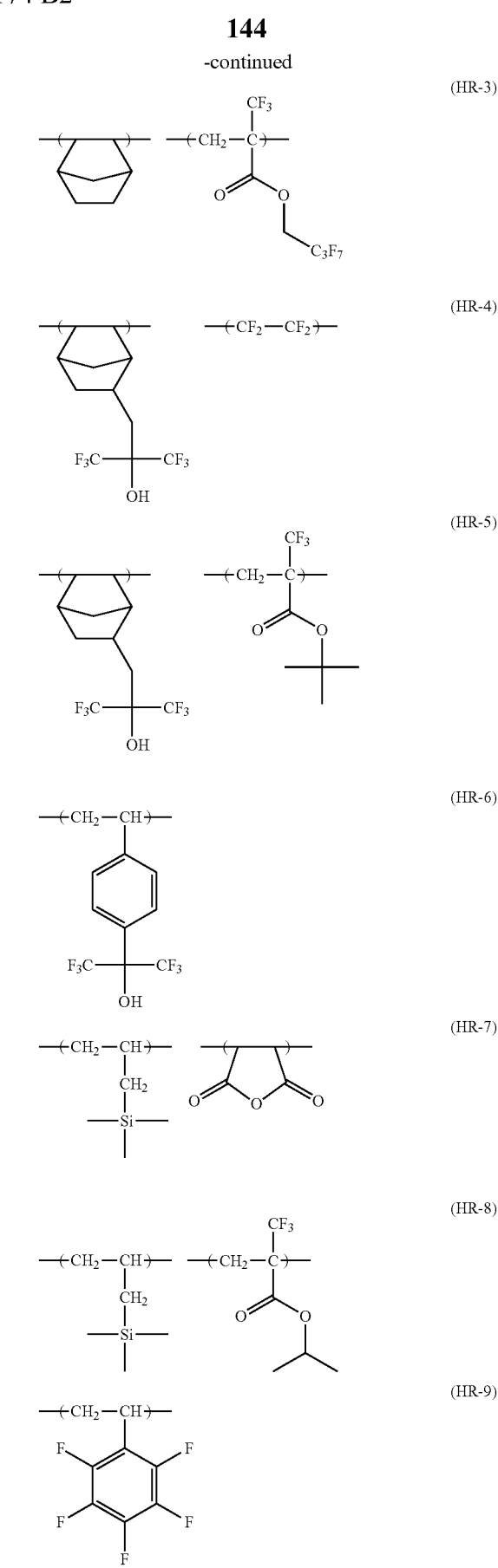

(HR-10)
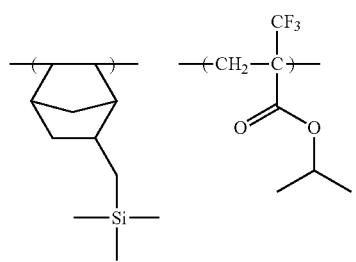
(HR-11)
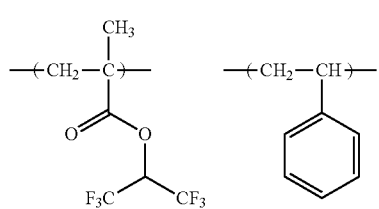
(HR-12)
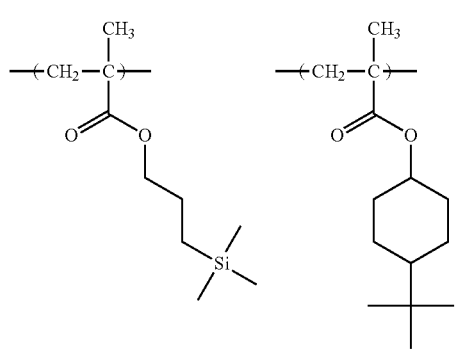
(HR-13)
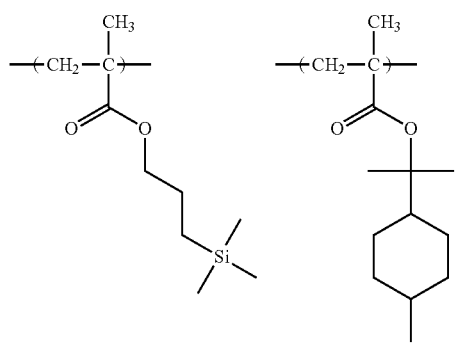
(HR-14)
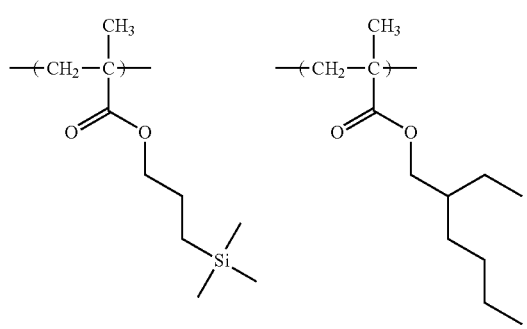
(HR-15)
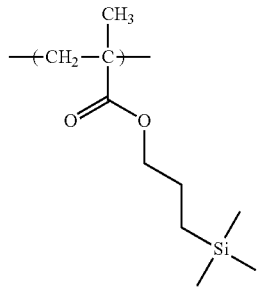
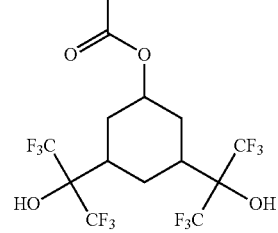
(HR-16)
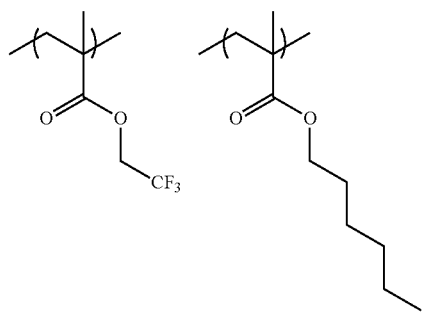
(HR-17)
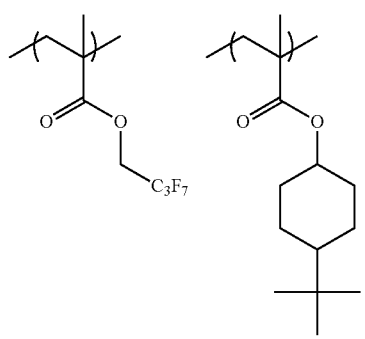
(HR-18)
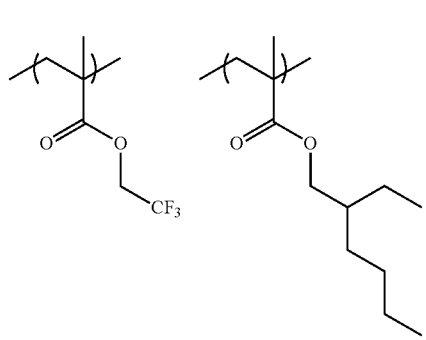

(HR-19) 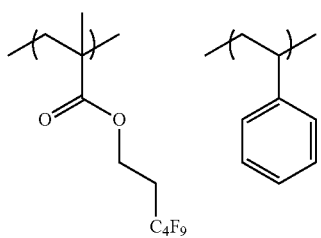
(HR-20) 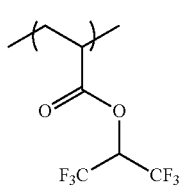
(HR-21) 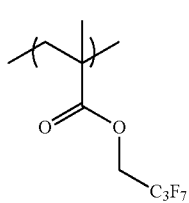
(HR-22) 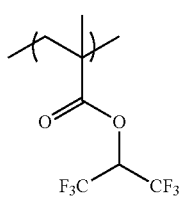
(HR-23) 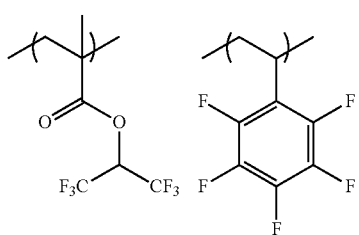
(HR-24) 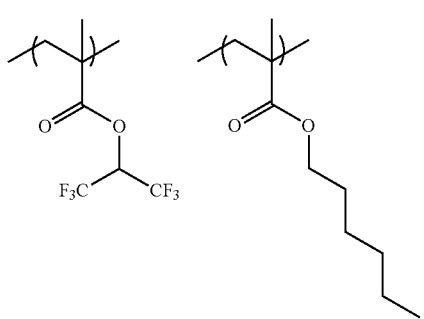
(HR-25) 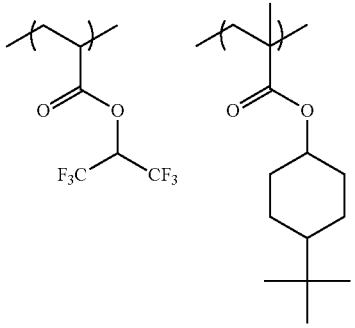
(HR-26) 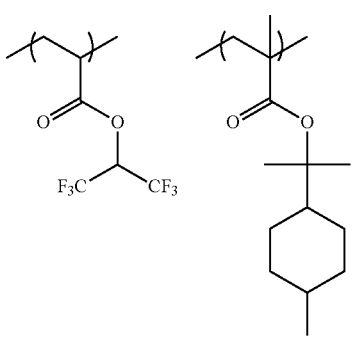
(HR-27) 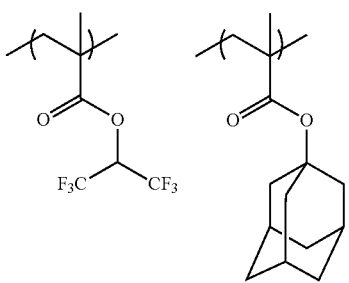
(HR-28) 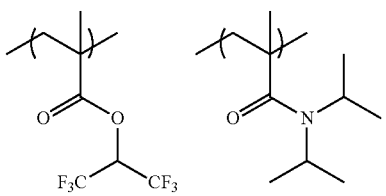
(HR-29) 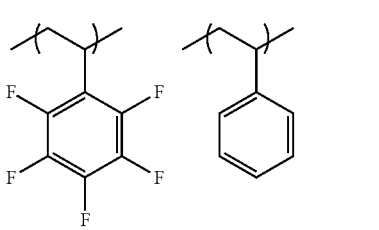
(HR-30) 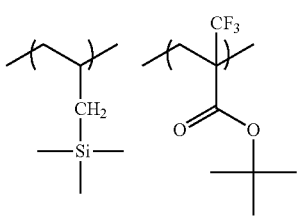

(HR-31)
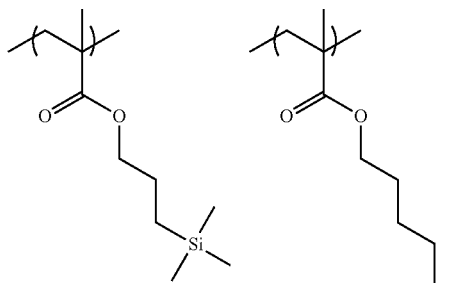
(HR-32)
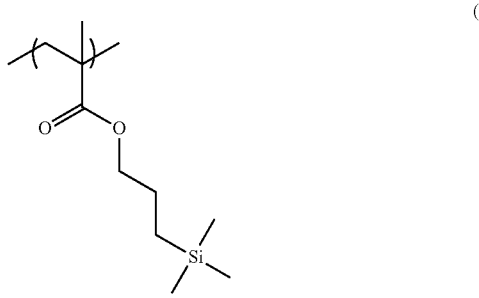
(HR-33)
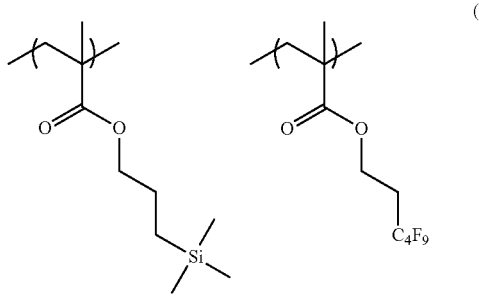
(HR-34)
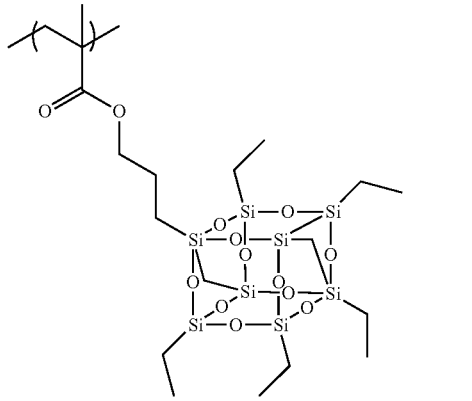
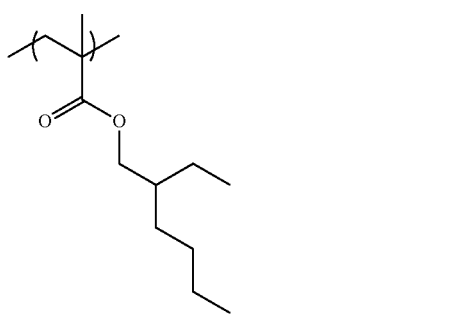
(HR-35)
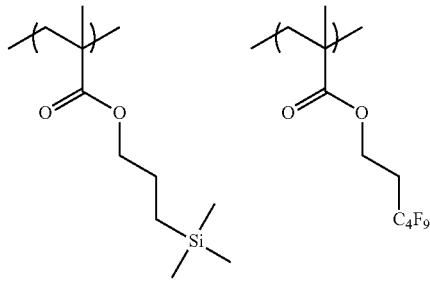
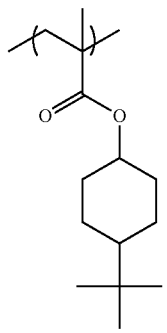
(HR-36)
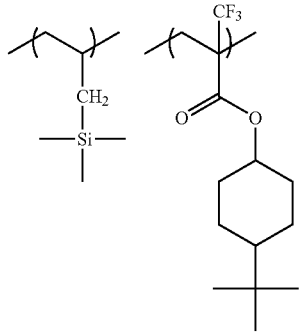
(HR-37)
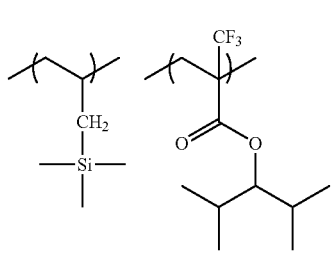
(HR-38)
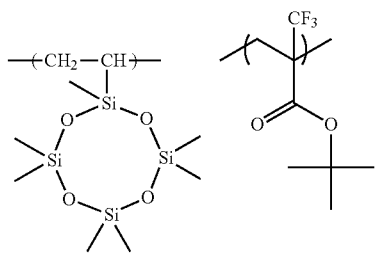

(HR-39) 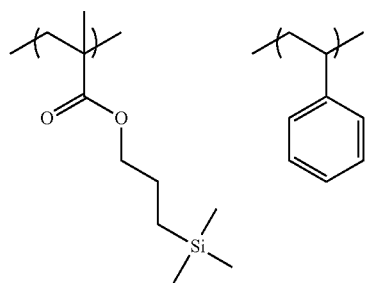
(HR-40) 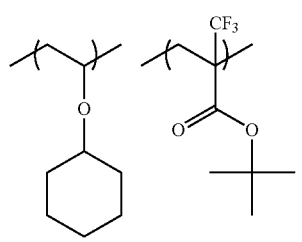
(HR-41) 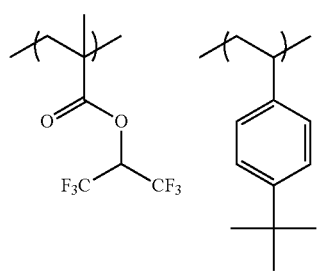
(HR-42) 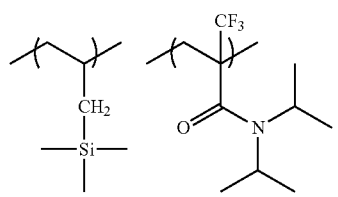
(HR-43) 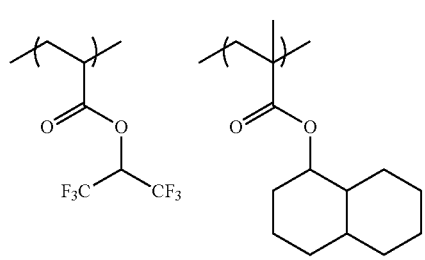
(HR-44) 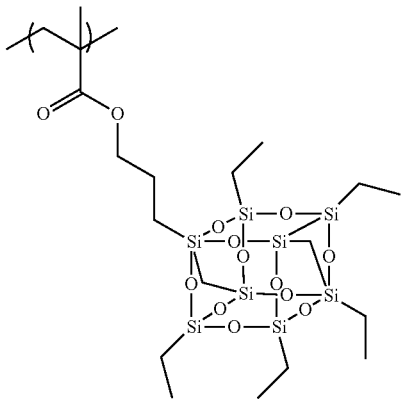
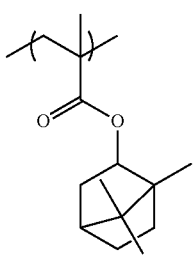
(HR-45) 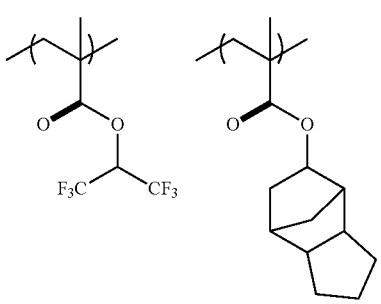
(HR-46) 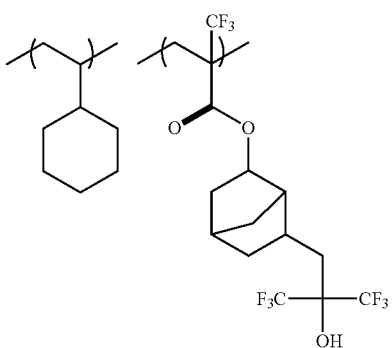
(HR-47)

(HR-48)
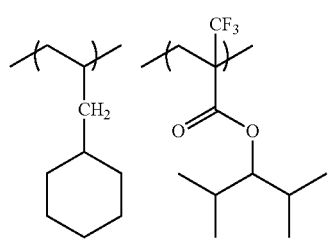
(HR-49)
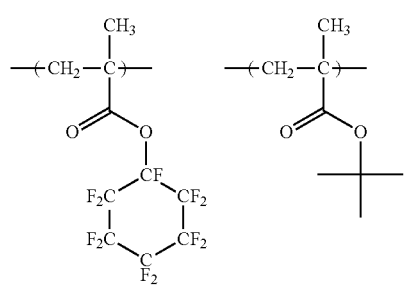
(HR-50)
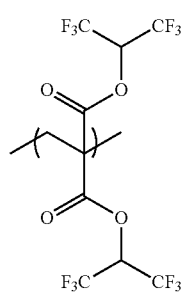
(HR-51)
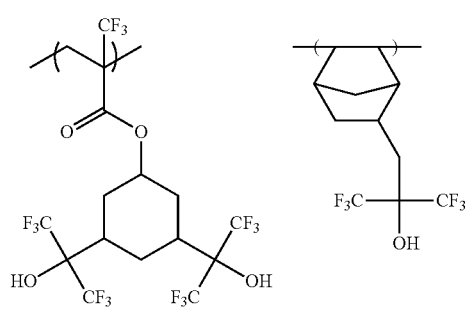
(HR-52)
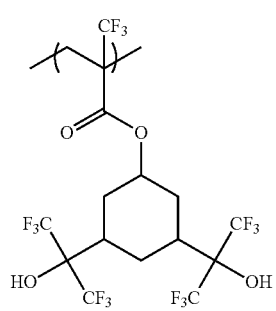
(HR-53)
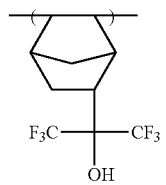
(HR-54)
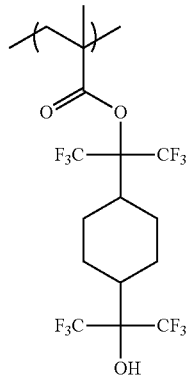
(HR-55)
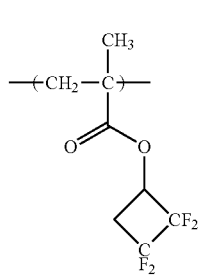
(HR-56)
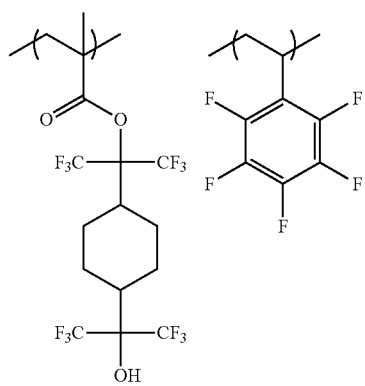
(HR-57)
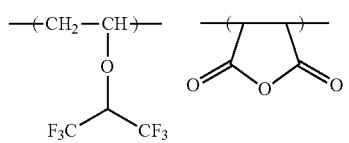
(HR-58)
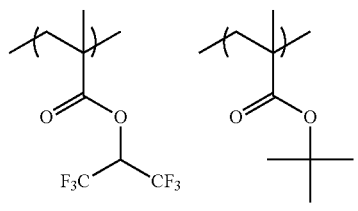

(HR-59)
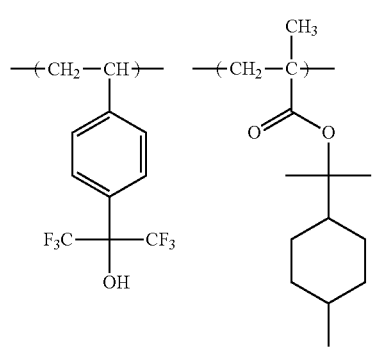
(HR-60)
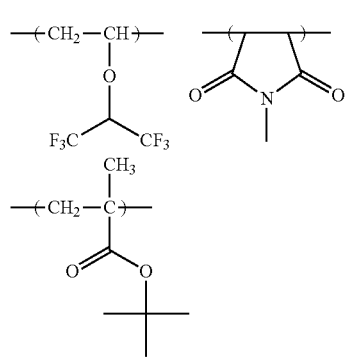
(HR-61)
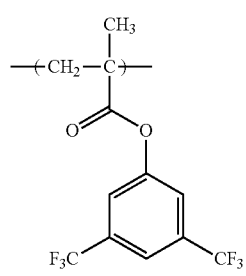
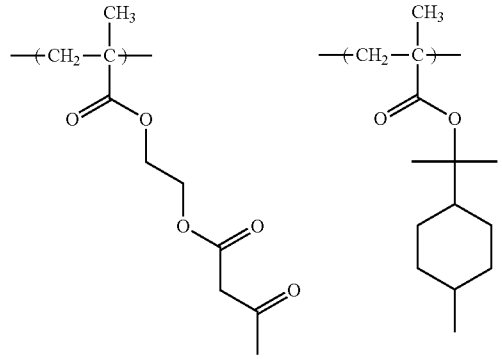
(HR-62)
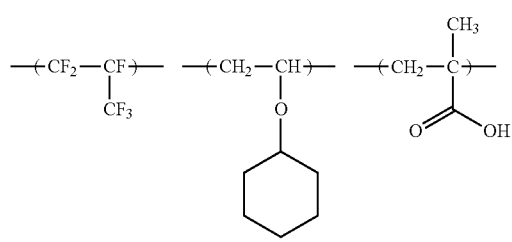
(HR-63)
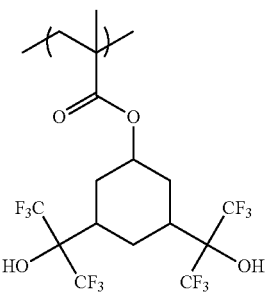
(HR-64)
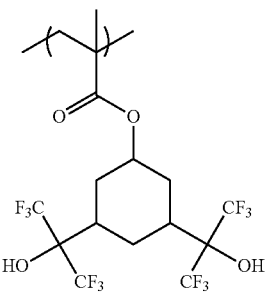
(HR-65)
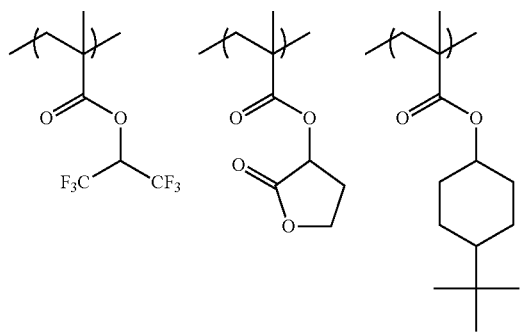
(HR-66)
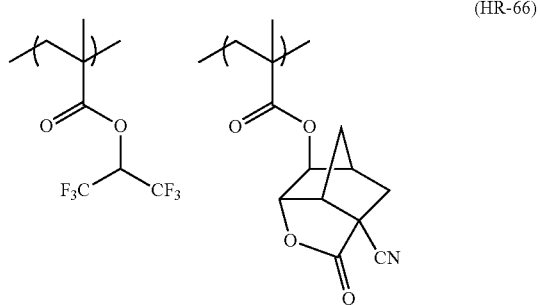
(HR-67)
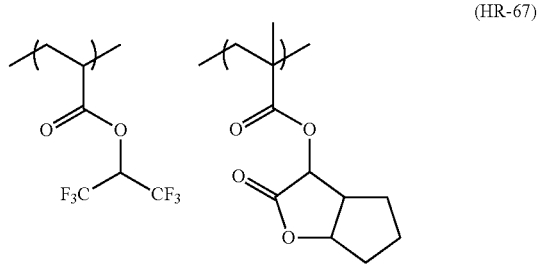

(HR-68)
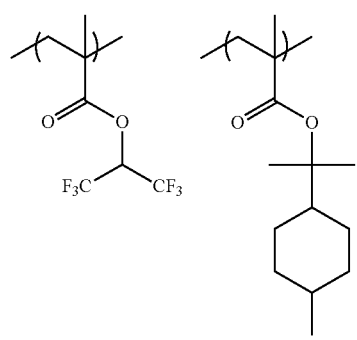
(HR-69)
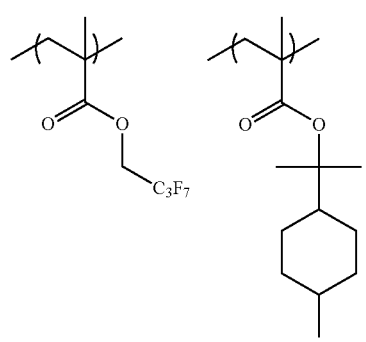
(HR-70)
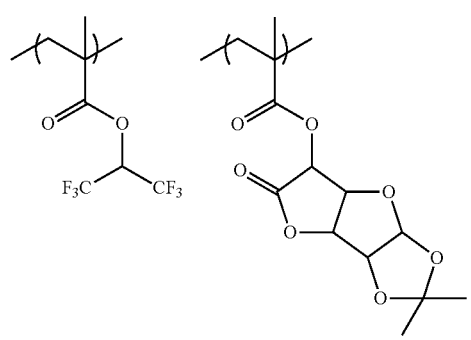
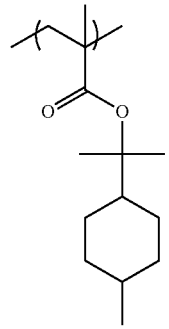
(HR-71)
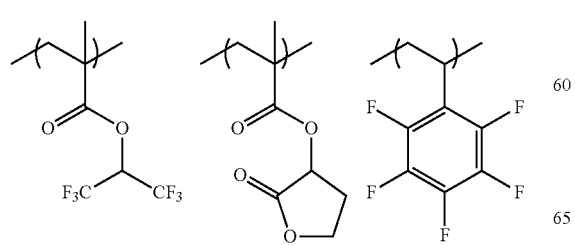
(HR-72)
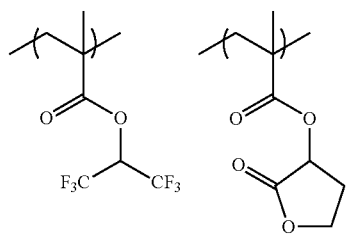
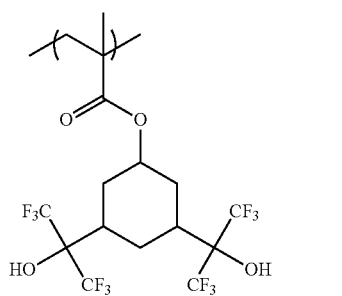
(HR-73)
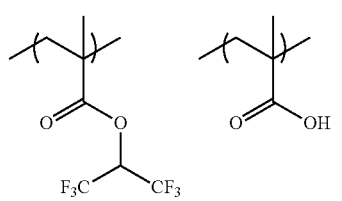
(HR-74)
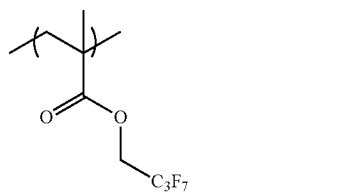
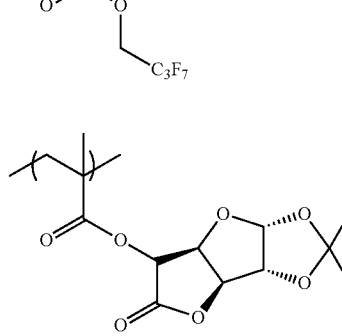
(HR-75)
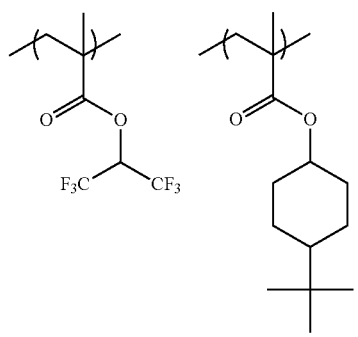

-continued
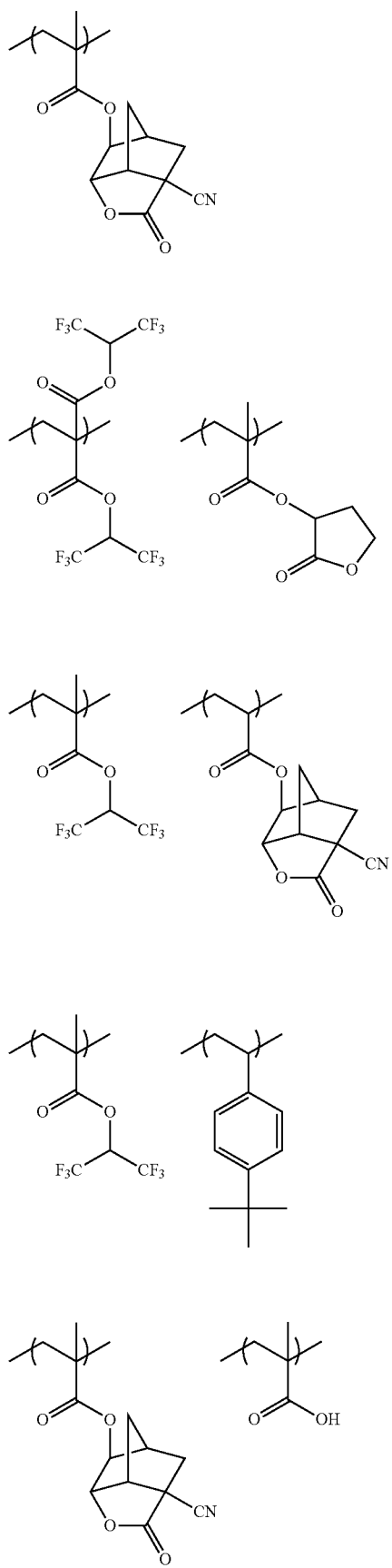
-continued
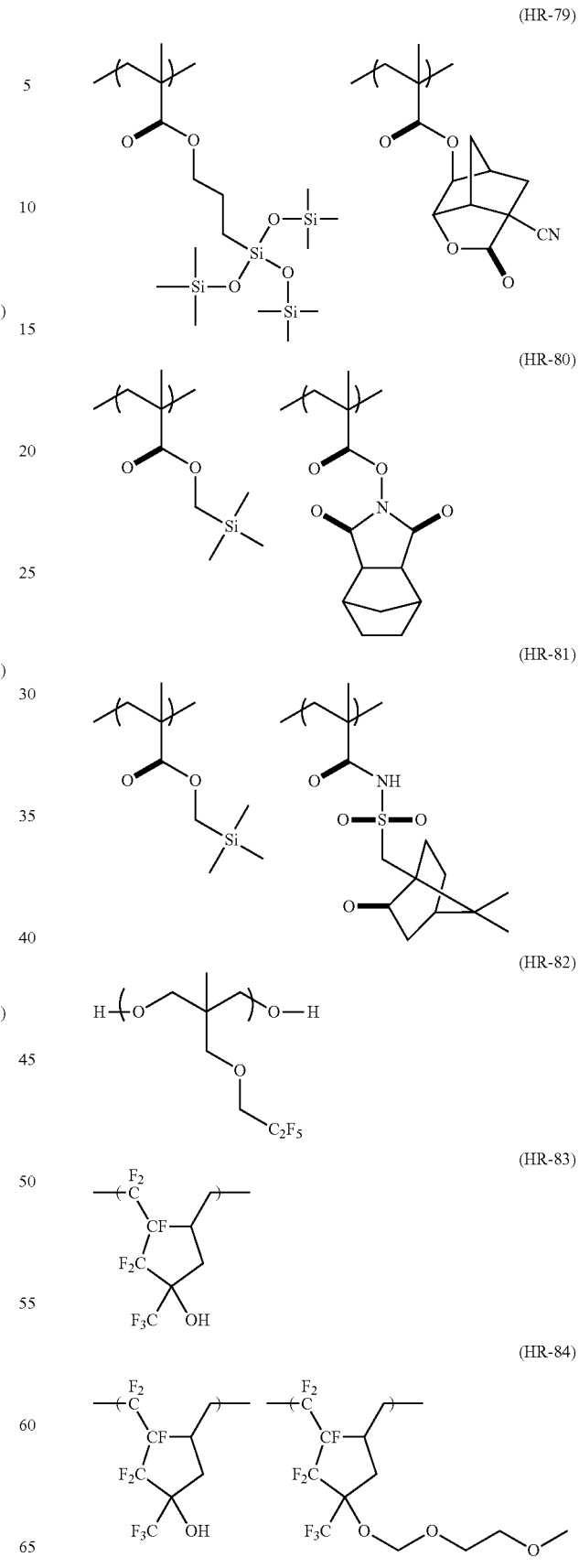

TABLE 1

| Resin | Composition | Mw | Mw/Mn |
|---|---|---|---|
| HR-1 | 50/50 | 8800 | 2.1 |
| HR-2 | 50/50 | 5200 | 1.8 |
| HR-3 | 50/50 | 4800 | 1.9 |
| HR-4 | 50/50 | 5300 | 1.9 |
| HR-5 | 50/50 | 6200 | 1.9 |
| HR-6 | 100 | 12000 | 2.0 |
| HR-7 | 50/50 | 5800 | 1.9 |
| HR-8 | 50/50 | 6300 | 1.9 |
| HR-9 | 100 | 5500 | 2.0 |
| HR-10 | 50/50 | 7500 | 1.9 |
| HR-11 | 70/30 | 10200 | 2.2 |
| HR-12 | 40/60 | 15000 | 2.2 |
| HR-13 | 40/60 | 13000 | 2.2 |
| HR-14 | 80/20 | 11000 | 2.2 |
| HR-15 | 60/40 | 9800 | 2.2 |
| HR-16 | 50/50 | 8000 | 2.2 |
| HR-17 | 50/50 | 7600 | 2.0 |
| HR-18 | 50/50 | 12000 | 2.0 |
| HR-19 | 20/80 | 6500 | 1.8 |
| HR-20 | 100 | 6500 | 1.2 |
| HR-21 | 100 | 6000 | 1.6 |
| HR-22 | 100 | 2000 | 1.6 |
| HR-23 | 50/50 | 6000 | 1.7 |
| HR-24 | 50/50 | 8800 | 1.9 |
| HR-25 | 50/50 | 7800 | 2.0 |
| HR-26 | 50/50 | 8000 | 2.0 |
| HR-27 | 80/20 | 8000 | 1.8 |
| HR-28 | 30/70 | 7000 | 1.7 |
| HR-29 | 50/50 | 6500 | 1.6 |
| HR-30 | 50/50 | 6500 | 1.6 |
| HR-31 | 50/50 | 9000 | 1.8 |
| HR-32 | 100 | 10000 | 1.6 |
| HR-33 | 70/30 | 8000 | 2.0 |
| HR-34 | 10/90 | 8000 | 1.8 |
| HR-35 | 30/30/40 | 9000 | 2.0 |
| HR-36 | 50/50 | 6000 | 1.4 |
| HR-37 | 50/50 | 5500 | 1.5 |
| HR-38 | 50/50 | 4800 | 1.8 |
| HR-39 | 60/40 | 5200 | 1.8 |
| HR-40 | 50/50 | 8000 | 1.5 |
| HR-41 | 20/80 | 7500 | 1.8 |
| HR-42 | 50/50 | 6200 | 1.6 |
| HR-43 | 60/40 | 16000 | 1.8 |
| HR-44 | 80/20 | 10200 | 1.8 |
| HR-45 | 50/50 | 12000 | 2.6 |
| HR-46 | 50/50 | 10900 | 1.9 |
| HR-47 | 50/50 | 6000 | 1.4 |
| HR-48 | 50/50 | 4500 | 1.4 |
| HR-49 | 50/50 | 6900 | 1.9 |
| HR-50 | 100 | 2300 | 2.6 |
| HR-51 | 60/40 | 8800 | 1.5 |
| HR-52 | 68/32 | 11000 | 1.7 |
| HR-53 | 100 | 8000 | 1.4 |
| HR-54 | 100 | 8500 | 1.4 |
| HR-55 | 80/20 | 13000 | 2.1 |
| HR-56 | 70/30 | 18000 | 2.3 |
| HR-57 | 50/50 | 5200 | 1.9 |
| HR-58 | 50/50 | 10200 | 2.2 |
| HR-59 | 60/40 | 7200 | 2.2 |
| HR-60 | 32/32/36 | 5600 | 2.0 |
| HR-61 | 30/30/40 | 9600 | 1.6 |
| HR-62 | 40/40/20 | 12000 | 2.0 |
| HR-63 | 100 | 6800 | 1.6 |
| HR-64 | 50/50 | 7900 | 1.9 |
| HR-65 | 40/30/30 | 5600 | 2.1 |
| HR-66 | 50/50 | 6800 | 1.7 |
| HR-67 | 50/50 | 5900 | 1.6 |
| HR-68 | 49/51 | 6200 | 1.8 |
| HR-69 | 50/50 | 8000 | 1.9 |
| HR-70 | 30/40/30 | 9600 | 2.3 |
| HR-71 | 30/40/30 | 9200 | 2.0 |
| HR-72 | 40/29/31 | 3200 | 2.1 |
| HR-73 | 90/10 | 6500 | 2.2 |
| HR-74 | 50/50 | 7900 | 1.9 |
| HR-75 | 20/30/50 | 10800 | 1.6 |
| HR-76 | 50/50 | 2200 | 1.9 |
| HR-77 | 50/50 | 5900 | 2.1 |
| HR-78 | 40/20/30/10 | 14000 | 2.2 |
| HR-79 | 50/50 | 5500 | 1.8 |
| HR-80 | 50/50 | 10600 | 1.9 |
| HR-81 | 50/50 | 8600 | 2.3 |
| HR-82 | 100 | 15000 | 2.1 |
| HR-83 | 100 | 6900 | 2.5 |
| HR-84 | 50/50 | 9900 | 2.3 |

In order to prevent the resist film from directly contacting with the immersion liquid, a film (hereinafter, sometimes referred to as a "topcoat") sparingly soluble in the immersion liquid may be provided between the resist film formed of the positive resist composition of the present invention and the immersion liquid. The functions required of the topcoat are suitability for coating as an overlayer of the resist, transparency to radiation particularly at 193 nm, and scarce solubility in the immersion liquid. The topcoat is preferably unmixable with the resist and capable of being uniformly applied as an overlayer of the resist.

In view of transparency to light at 193 nm, the topcoat is preferably a polymer not abundantly containing an aromatic, and specific examples thereof include a hydrocarbon polymer, an acrylic acid ester polymer, a polymethacrylic acid, a polyacrylic acid, a polyvinyl ether, a silicon-containing polymer and a fluorine-containing polymer. The above-described hydrophobic resin (HR) is suitable also as the topcoat. If impurities are dissolved out into the immersion liquid from the topcoat, the optical lens is contaminated. In this viewpoint, the amount of residual monomers of the polymer contained in the topcoat is preferably smaller.

On peeling off the topcoat, a developer may be used or a releasing agent may be separately used. The releasing agent is preferably a solvent less permeating into the resist film. From the standpoint that the peeling step can be performed simultaneously with the development step of the resist film, the topcoat is preferably peelable with an alkali developer and in terms of peeling with an alkali developer, the topcoat is preferably acidic, but in view of non-intermixing with the resist film, the topcoat may be neutral or alkaline.

With no difference in the refractive index between the topcoat and the immersion liquid, the resolution is enhanced. At the exposure with ArF excimer laser (wavelength: 193 nm), when water is used as the immersion liquid, the topcoat for ArF immersion exposure preferably has a refractive index close to the refractive index of the immersion liquid. From the standpoint of approximating the refractive index to that of the immersion liquid, the topcoat preferably contains a fluorine atom. Also, in view of transparency and refractive index, the topcoat is preferably a thin film.

The topcoat is preferably unmixable with the resist film and further unmixable with the immersion liquid. From this standpoint, when the immersion liquid is water, the topcoat solvent is preferably a medium that is sparingly soluble in the solvent used for the positive resist composition and insoluble in water. Furthermore, when the immersion liquid is an organic solvent, the topcoat may be either water-soluble or water-insoluble.

The double exposure process as used in the present invention is, as described in JP-A-2002-75857, a process of performing exposure two times on the same photoresist film, which is a method of dividing the pattern in the exposure field into two pattern groups and exposing respective divided pattern groups in twice. In a specific dividing method, as shown in FIG. 1, two masks having a 60-nm line 180-nm space pattern are used and exposure is performed in twice by displacing the masks by 120 nm to form a 60-nm 1:1 line-and-space pattern. In general, as the pitch of the pattern (in the 60-nm 1:1 line-and-space pattern, the pitch is 120 nm)

becomes narrow, the optical resolution decreases. However, in the double exposure, the divided respective patterns come to give a pitch of 2 times the pitch in the original pattern and the resolution is enhanced.

The positive resist composition of the present invention may be applied to a multilayer resist process (particularly, a three-layer resist process). The multilayer resist process comprises the following steps:

(a) forming a lower resist layer comprising an organic material on a to-be-processed substrate, (b) sequentially stacking on the lower resist layer an intermediate layer and an upper resist layer comprising an organic material capable of crosslinking or decomposing upon irradiation with radiation, and (c) forming a predetermined pattern on the upper resist layer and then sequentially etching the intermediate layer, the lower layer and the substrate.

An organopolysiloxane (silicone resin) or $SiO_2$ coating solution (SOG) is generally used for the intermediate layer. As for the lower layer resist, an appropriate organic polymer film is used, but various known photoresists may be used. Examples thereof include various series such as FH Series and FHi Series produced by Fujifilm Arch Co., Ltd., and PFI Series produced by Sumitomo Chemical Co., Ltd.

The film thickness of the lower resist layer is preferably from 0.1 to 4.0 μm, more preferably from 0.2 to 2.0 μm, still more preferably from 0.25 to 1.5 μm. The film thickness is preferably 0.1 μm or more in view of antireflection or dry etching resistance and preferably 4.0 μm or less in view of aspect ratio or pattern collapse of the fine pattern formed.

EXAMPLES

The present invention is described in greater detail below by referring to Examples, but the contents of the present invention should not be construed as being limited thereto.

Synthesis Example 1

Synthesis of Compound (I-5)

10.00 Gram (51.5 mmol) of 2-adamantyl-2-propanol and 503 mg (4.12 mmol) of N,N-dimethylaminopyridine were dissolved in 80 mL of tetrahydrofuran (THF), and the resulting solution was cooled to 0° C. under nitrogen flow. A solution prepared by dissolving 8.65 g (103 mmol) of diketene in 80 mL of THF was added dropwise to the solution above over 0.5 hours and then, the reaction was allowed to proceed at 0° C. for 1 hour. After adding 200 mL of ethyl acetate, the organic layer was washed, in order, twice with an aqueous saturated sodium hydrogencarbonate solution and twice with water, and dried over sodium sulfate. The solvent was concentrated, and the residue was purified by column chromatography ($SiO_2$, hexane/ethyl acetate=4/1) to obtain 13.5 g of 2-adamantylpropan-2-yl 3-oxobutanoate as a colorless transparent oil. Thereafter, 15.85 g (56.9 mmol) of the oil was dissolved in 40 mL of THF, and the resulting solution was added dropwise to a suspension containing 2.28 g (60 wt %, 56.9 mmol) of sodium hydride (NaH) and 80 mL of THF at 0° C. over 0.5 hours, followed by stirring for 0.5 hours. Furthermore, a solution containing 8.08 g (56.9 mmol) of methyl iodide (MeI) and 20 mL of THF was added dropwise over 0.5 hours, and the resulting mixture was stirred at 0° C. for 0.5 hours and further stirred at 25° C. for 5 hours. After adding 200 mL of ethyl acetate, the organic layer was washed, in order, twice with saturated brine and twice with water, and dried over sodium sulfate, and the solvent was concentrated to obtain 16.0 g of 2-adamantylpropan-2-yl 2-methyl-3-oxobutanoate as a colorless transparent oil. Subsequently, 48.5 g of an aqueous formalin solution was added to 17.48 g (59.8 mmol) of the oil. The resulting mixture was cooled to 0° C., and 8.26 g of potassium carbonate was added thereto. The obtained mixture was stirred at 0° C. for 1 hour and further stirred at 25° C. for 2 hours. After adding 200 mL of ethyl acetate, the organic layer was washed, in order, three times with an aqueous saturated sodium hydrogensulfite solution and twice with water, and dried over sodium sulfate. The solvent was concentrated, and the residue was recrystallized from hexane to obtain 15.40 g of 2-adamantylpropan-2-yl 2-(hydroxymethyl)-2-methyl-3-oxobutanoate) as a white solid. Thereafter, 6.0 g (18.6 mmol) of this solid was dissolved in 20 mL of pyridine, and the resulting solution was cooled to 0° C. Furthermore, 4 g of p-toluenesulfonyl chloride was added, and the mixture was stirred at 0° C. for 2 hours and then stirred at 80° C. for 6 hours. After adding 200 mL of ethyl acetate, the organic layer was washed, in order, three times with an aqueous saturated ammonium chloride solution and twice with water, and dried over sodium sulfate. The residue was purified by column chromatography ($SiO_2$, hexane/ethyl acetate=4/1) to obtain 3.54 g of the objective Compound (I-5) as a white solid.

$^1$H-NMR (400 MHz, $CDCl_3$) δ 1.40 (s, 3H), 1.41 (s, 3H), 1.43 (s, 3H), 1.52 (bs, 6H), 1.54-1.70 (m, 6H), 1.96 (bs, 3H), 2.13 (s, 3H), 2.45 (s, 3H), 4.29 (s, 2H), 7.34 (d, 2H), 7.77 (d, 2H).

Synthesis Example 2

Synthesis of Compound (I-6)

Compound (I-6) was obtained as a colorless transparent oil in the same manner.

$^1$H-NMR (400 MHz, $CDCl_3$) δ 0.88-1.25 (m, 5H), 1.37 (s, 3H), 1.39 (s, 3H), 1.40 (s, 3H), 1.62-1.76 (m, 6H), 2.14 (s, 3H), 2.45 (s, 3H), 4.28 (AB quartet, 2H), 7.35 (d, 2H), 7.77 (d, 2H).

Synthesis Example 3

Synthesis of Compound (I-7)

Compound (I-7) was obtained as a colorless transparent oil in the same manner.

$^1$H-NMR (400 MHz, $CDCl_3$) δ 0.86-1.130 (m, 6H), 1.03-1.27 (m, 5H), 1.43 (s, 3H), 1.64-1.91 (m, 10H), 2.17 (s, 3H), 2.45 (s, 3H), 4.30 (AB quartet, 2H), 7.34 (d, 2H), 7.77 (d, 2H).

Synthesis Example 4

Synthesis of Compound (I-9)

Compound (I-9) was obtained as a white solid in the same manner as Compound (I-5).

$^1$H-NMR (400 MHz, $CDCl_3$) δ 1.44 (s, 3H), 1.56 (s, 2H), 1.57 (s, 3H), 1.69-1.94 (m, 10H), 2.17 (s, 3H), 2.24 (bs, 2H), 2.45 (s, 3H), 4.33 (AB quartet, 2H), 7.34 (d, 2H), 7.76 (d, 2H).

Synthesis Example 5

Synthesis of Compound, I-10)

Compound (I-10) was obtained as a colorless transparent oil in the same manner as Compound (I-5).

$^1$H-NMR (400 MHz, $CDCl_3$) δ 0.77 (t, 3H), 1.54 (s, 3H), 1.70 (bs, 6H), 1.80-1.83 (m, 8H), 2.14 (q, 2H), 2.21 (s, 3H), 2.45 (s, 3H), 4.35 (AB quartet, 2H), 7.34 (d, 2H), 7.76 (d, 2H).

Synthesis Example 6

Synthesis of Compound (I-30)

Compound (I-30) was obtained as a colorless transparent oil in the same manner as Compound (I-5).

¹H-NMR (400 MHz, CDCl₃) δ 0.83 (s, 3H), 1.57 (s, 3H), 1.62 (m, 7H), 1.94-1.96 (m, 3H), 2.15 (s, 3H), 2.45 (s, 3H), 4.29 (s, 2H), 7.34 (d, 2H), 7.76 (d, 2H).

Synthesis Example 7

Synthesis of Compound (I-31)

9.91 Gram (95%, 56.9 mmol) of tert-butyl methyl malonate was dissolved in 120 mL of tetrahydrofuran (THF), and the resulting solution was added dropwise to a suspension containing 2.28 g (60 wt %, 56.9 mmol) of sodium hydride (NaH) and 120 mL of THF at 0° C. over 0.5 hours, followed by stirring for 0.5 hours. Thereafter, a solution containing 8.08 g (56.9 mmol) of methyl iodide (MeI) and 20 mL of TI-IF was added dropwise over 0.5 hours, and the resulting mixture was stirred at 0° C. for 0.5 hours and further stirred at 25° C. for 5 hours. After adding 200 of ethyl acetate, the organic layer was washed, in order, twice with saturated brine and twice with water, and dried over sodium sulfate, and the solvent was concentrated to obtain 13.0 g of 1-tert-butyl 3-methyl 2-methylmalonate as a colorless transparent oil. Subsequently, 45.9 g of an aqueous formalin solution was added to 13.0 g of the oil, and resulting mixture was cooled to 0° C. Furthermore, 7.81 g of potassium carbonate was added, and the mixture was stirred at 0° C. for 1 hour and further stirred at 25° C. for 3 hours. After adding 200 mL of ethyl acetate, the organic layer was washed, in order, three times with an aqueous saturated sodium hydrogensulfite solution and twice with water, and dried over sodium sulfate. The solvent was concentrated, and the residue was dissolved in 50 mL of pyridine. The resulting solution was cooled to 0° C., and 21.7 g of p-toluenesulfonyl chloride was added thereto. The obtained mixture was stirred at 0° C. for 2 hours and then stirred at 60° C. for 4 hours. After adding 200 mL of ethyl acetate, the organic layer was washed, in order, three times with an aqueous saturated ammonium chloride solution and twice with water, and dried over sodium sulfate. The residue was purified by column chromatography (SiO₂, hexane/ethyl acetate=4/1) to obtain 15.8 g of the objective Compound (I-31) as a colorless transparent oil.

¹H-NMR (400 MHz, CDCl₃) δ 1.40 (s, 9H), 1.43 (s, 3H), 2.45 (s, 3H), 3.67 (s, 3H), 4.30 (s, 2H), 7.36 (d, 2H), 7.77 (d, 2H).

Synthesis Example 8

Synthesis of Compound (I-32)

4.29 g (36.4 mmol) of 2-methylmalonic acid and 8.09 g (109 mmol) of tert-butyl alcohol were dissolved in 80 mL of acetonitrile and thereto, a solution prepared by dissolving 15.0 g (72.7 mmol) of dicyclohexylcarbodiimide in 70 mL of acetonitrile was added dropwise at 0° C. over 0.5 hours, followed by stirring for 0.5 hours. Furthermore, a solution containing 8.08 g (56.9 mmol) of methyl iodide (MeI) and 20 mL of THF was added dropwise over 0.5 hours, and the resulting mixture was stirred at 0° C. for 0.5 hours and further stirred at 25° C. for 3 hours. The precipitated solid was filtered, and the filtrate was concentrated. To the residue, 40 g of an aqueous formalin solution was added, and the resulting mixture was cooled to 0° C. Subsequently, 15 g of potassium carbonate was added, and the obtained mixture was stirred at 0° C. for 1 hour and further stirred at 50° C. for 2 hours. After adding 200 mL of ethyl acetate, the organic layer was washed, in order, three times with an aqueous saturated sodium hydrogensulfite solution and twice with water; and dried over sodium sulfate. The solvent was concentrated, and the residue was dissolved in 20 mL of pyridine. The resulting solution was cooled to 0° C., and 10.4 g of p-toluenesulfonyl chloride was added thereto. The obtained mixture was stirred at 0° C. for 2 hours and then stirred at 50° C. for 4 hours. After adding 200 mL of ethyl acetate, the organic layer was washed, in order, three times with an aqueous saturated ammonium chloride solution and twice with water, and dried over sodium sulfate. The residue was purified by column chromatography (SiO₂, hexane/ethyl acetate=4/1) to obtain 4.51 g of the objective Compound (I-32) as a white plate-like crystal.

¹H-NMR (400 MHz, CDCl₃) δ 1.37 (s, 3H), 1.41 (s, 18H), 2.45 (s, 3H), 4.26 (s, 2H), 7.36 (d, 2H), 7.77 (d, 2H).

Synthesis Example 9

Synthesis of Compound (I-33)

Compound (I-33) was obtained as a white needle-like crystal in the same manner as Compound (I-32).

¹H-NMR (400 MHz, CDCl₃) δ 1.40 (s, 3H), 1.41 (s, 12H), 1.55-1.70 (m, 2H), 1.97 (hs, 6H), 2.44 (s, 3H), 4.28 (s, 2H), 7.33 (d, 2H), 7.76 (d, 2H).

Synthesis Example 10

Synthesis of Compound (I-34)

Compound (I-34) was obtained as a white crystal in the same manner as Compound (I-32).

¹H-NMR (400 MHz, CDCl₃) δ 0.89 (t, 6H), 1.30 (s, 3H), 1.55 (q, 4H), 1.67-1.72 (m, 20H), 1.82-1.85 (m, 8H), 2.45 (s, 3H), 4.36 (s, 2H), 7.33 (d, 2H), 7.77 (d, 2H).

Other acid-increasing agents were synthesized in the same manner With respect to Resins (1) to (23) as the component (B) used in Examples, the monomers used for the synthesis, the compositional ratio, the weight average molecular weight and the polydispersity are shown in Tables 2 and 3 below.

TABLE 2

| No. | Monomer (1) | Monomer (2) | Monomer (3) | Monomer (4) | Compositional Ratio (by mol) | Mw | Mw/Mn |
|---|---|---|---|---|---|---|---|
| 1 | [structure] | [structure] | [structure] | [structure] | 35/15/35/15 | 10000 | 1.9 |

TABLE 2-continued

| No. | Monomer (1) | Monomer (2) | Monomer (3) | Monomer (4) | Compositional Ratio (by mol) | Mw | Mw/Mn |
|---|---|---|---|---|---|---|---|
| 2 | | | | | 40/5/45/10 | 8900 | 1.9 |
| 3 | | | | | 40/30/30 | 12000 | 1.8 |
| 4 | | | | | 40/20/40 | 8900 | 1.9 |
| 5 | | | | | 40/20/30/10 | 10200 | 2.3 |
| 6 | | | | | 40/10/40/10 | 8900 | 1.7 |

TABLE 2-continued

| No. | Monomer (1) | Monomer (2) | Monomer (3) | Monomer (4) | Compositional Ratio (by mol) | Mw | Mw/Mn |
|---|---|---|---|---|---|---|---|
| 7 | | | | | 20/20/50/10 | 7800 | 1.7 |
| 8 | | | | | 30/30/40 | 6800 | 1.9 |
| 9 | | | | | 40/20/30/10 | 9800 | 1.6 |
| 10 | | | | | 40/30/30 | 13000 | 1.8 |

TABLE 2-continued

| No. | Monomer (1) | Monomer (2) | Monomer (3) | Monomer (4) | Compositional Ratio (by mol) | Mw | Mw/Mn |
|---|---|---|---|---|---|---|---|
| 11 | | | | | 40/30/30 | 3600 | 1.4 |
| 12 | | | | | 40/20/30/10 | 7000 | 1.6 |

TABLE 3

| No. | Monomer (1) | Monomer (2) | Monomer (3) | Monomer (4) | Compositional Ratio (by mol) | Mw | Mw/Mn |
|---|---|---|---|---|---|---|---|
| 13 | | | | | 30/35/30/5 | 5500 | 1.9 |
| 14 | | | | | 40/30/30 | 9800 | 2.0 |

TABLE 3-continued
| No. | Monomer (1) | Monomer (2) | Monomer (3) | Monomer (4) | Compositional Ratio (by mol) | Mw | Mw/Mn |
|---|---|---|---|---|---|---|---|
| 15 | 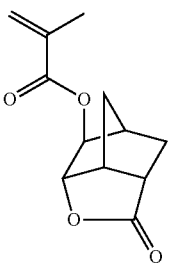 [SMILES: C=C(C)C(=O)OC1C2CC3C(=O)OC1C3C2] | 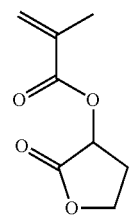 | 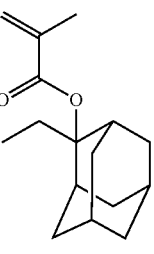 | | 40/20/40 | 7700 | 2.1 |
| 16 | 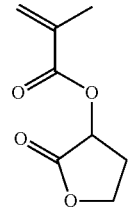 | 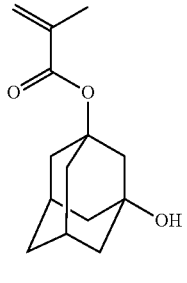 [SMILES: C=C(C)C(=O)OC12CC3CC(CC(O)(C3)C1)C2] | 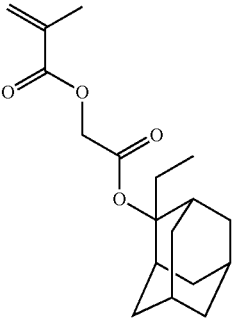 [SMILES: C=C(C)C(=O)OCC(=O)OC1(CC)C2CC3CC(C2)CC1C3] | | 30/30/40 | 8800 | 2.6 |
| 17 | 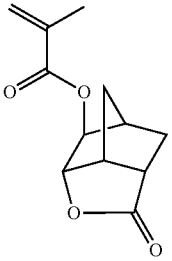 [SMILES: C=C(C)C(=O)OC1C2CC3C(=O)OC1C3C2] | 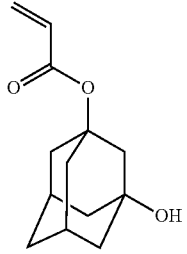 [SMILES: C=CC(=O)OC12CC3CC(CC(O)(C3)C1)C2] | 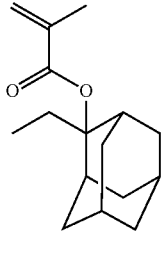 [SMILES: C=C(C)C(=O)OC1(CC)C2CC3CC(C2)CC1C3] | | 40/30/30 | 9000 | 2.1 |
| 18 | 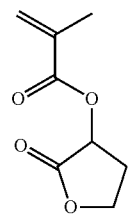 | 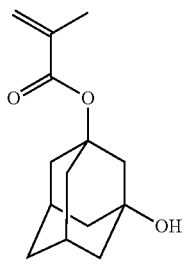 [SMILES: C=C(C)C(=O)OC12CC3CC(CC(O)(C3)C1)C2] | 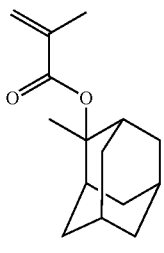 [SMILES: C=C(C)C(=O)OC1(C)C2CC3CC(C2)CC1C3] | 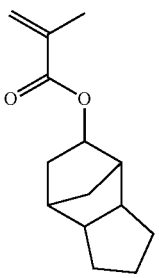 [SMILES: C=C(C)C(=O)OC1CC2CC1C1CCCC21] | 30/20/40/10 | 5800 | 2.2 |
| 19 | 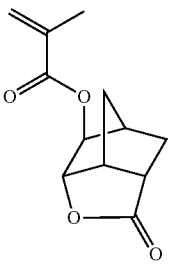 [SMILES: C=C(C)C(=O)OC1C2CC3C(=O)OC1C3C2] | 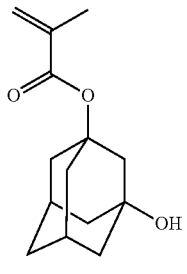 [SMILES: C=C(C)C(=O)OC12CC3CC(CC(O)(C3)C1)C2] | 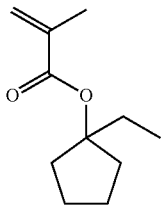 | | 30/30/40 | 9800 | 2.1 |

TABLE 3-continued

| No. | Monomer (1) | Monomer (2) | Monomer (3) | Monomer (4) | Compositional Ratio (by mol) | Mw | Mw/Mn |
|---|---|---|---|---|---|---|---|
| 20 | (structure) | (structure) | (structure) | | 35/35/30 | 9800 | 2.1 |
| 21 | (structure) | (structure) | (structure) | | 50/20/30 | 5100 | 1.6 |
| 22 | (structure) | (structure) | (structure) | (structure) | 30/25/25/20 | 8900 | 1.8 |
| 23 | (structure) | (structure) | (structure) | | 40/20/40 | 7500 | 1.6 |

Examples 1 to 31 and Comparative Examples 1 to 5

<Preparation of Resist>

The components shown in Table 4 below were dissolved in a solvent to prepare a solution having a solid content concentration of 5 mass %, and the obtained solution was filtered through a polyethylene filter having a pore size of 0.1 μm to prepare a positive resist composition. The positive resist compositions prepared were evaluated by the following methods, and the results are shown in Table 4. With respect to each component in the Table, the ratio when using a plurality of kinds is a ratio by mass.

Incidentally, in Table 4, when the positive resist composition contained a hydrophobic resin (HR), the mode of addition is denoted by "added", and when the positive resist composition did not contain a hydrophobic resin (HR) and after the formation of a resist film, a topcoat protective film containing a hydrophobic resin (HR) was formed as an overlayer of the resist film, the mode of addition is denoted by "TC".

Image Performance Test:

(Exposure Condition (I): Normal Dry Exposure)

An organic antireflection film, ARC29A (produced by Nissan Chemical Industries, Ltd.), was applied on a silicon wafer and baked at 205° C. for 60 seconds to form a 78 nm-thick antireflection film, and the positive resist composition prepared was applied thereon and baked at 130° C. for 60 seconds to form a 120 nm-thick resist film. The obtained wafer was exposed using an ArF excimer laser scanner (PAS5500/1100, manufactured by ASML, NA: 0.75) through a 6% halftone mask having a 65-nm 1:1 line-and-space pattern. Thereafter, the resist film was heated at 130° C. for 60 seconds, developed with an aqueous tetramethylammonium hydroxide solution (2.38 mass %) for 30 seconds, rinsed with pure water and spin-dried to obtain a resist pattern.

(Exposure Condition (2): Normal Immersion Exposure)

An organic antireflection film, ARC29A (produced by Nissan Chemical Industries, Ltd.), was applied on a silicon wafer and baked at 205° C. for 60 seconds to form a 78 nm-thick antireflection film, and the positive resist composition prepared was applied thereon and baked at 130° C. for 60 seconds to form a 120 nm-thick resist film. The obtained wafer was exposed using an ArF excimer laser immersion scanner (PAS5500/1250i, manufactured by ASML, NA: 0.85) through a 6% halftone mask having a 65-nm 1:1 line-and-space pattern. The immersion liquid used was ultrapure water. Thereafter, the resist film was heated at 130° C. for 60 seconds, developed with an aqueous tetramethylammonium hydroxide solution (2.38 mass %) for 30 seconds, rinsed with pure water and spin-dried to obtain a resist pattern.

(Exposure Condition (3): Dry Double Exposure)

An organic antireflection film, ARC29A (produced by Nissan Chemical Industries, Ltd.), was applied on a silicon wafer and baked at 205° C. for 60 seconds to form a 78 nm-thick antireflection film, and the positive resist composition prepared was applied thereon and baked at 130° C. for 60 seconds to form a 120 nm-thick resist film. The obtained wafer was subjected to first exposure by using an ArF excimer laser scanner (PAS5500/1100, manufactured by ASML, NA: 0.75) through a 6% halftone mask having a 60-nm space 180-nm line pattern and further to second exposure through a mask having the same pattern as in the first mask by displacing the mask by 120 nm so as to locate the space between a space and a space at the'first exposure. Thereafter, the resist film was heated at 130° C. for 60 seconds, developed with an aqueous tetramethylammonium hydroxide solution (2.38 mass %) for 30 seconds, rinsed with pure water and spin-dried to obtain a resist pattern.

(Exposure Condition (4): Immersion Double Exposure)

An organic antireflection film, ARC29A (produced by Nissan Chemical Industries, Ltd.), was applied on a silicon wafer and baked at 205° C. for 60 seconds to form a 78 nm-thick antireflection film, and the positive resist composition prepared was applied thereon and baked at 130° C. for 60 seconds to form a 120 nm-thick resist film. The obtained wafer was subjected to first exposure by using an ArF excimer laser immersion scanner (PAS5500/12501, manufactured by ASML, NA: 0.85) through a 6% halftone mask having a 50-nm space 150-nm line pattern and further to second exposure through a mask having the same pattern as in the first mask by displacing the mask by 100 nm so as to locate the space between a space and a space at the first exposure. The immersion liquid used was ultrapure water. Thereafter, the resist film was heated at 130° C. for 60 seconds, developed with an aqueous tetramethylammonium hydroxide solution (2.38 mass %) for 30 seconds, rinsed with pure water and spin-dried obtain a resist pattern.

When the addition mode of the hydrophobic resin (HR) is "TC", the following operation was performed after the formation of the resist film.

<Topcoat Forming Method>

The hydrophobic resin (HR) shown in Table 4 was dissolved in a solvent and applied by a spin coater on the resist film above, and the wafer was dried by heating at 115° C. for 60 seconds to form a 0.05 μm-thick topcoat layer. At this time, the topcoat was observed whether coating unevenness was present or not, and it was confirmed that the topcoat was uniformly applied without coating unevenness.

The abbreviations of the solvents are as follows.
SL-1: 2-ethylbutanol
SL-2: perfluorobutyltetrahydrofuran Pattern Profile:

The pattern profile was observed through a scanning microscope (S-4800, manufactured by Hitachi, Ltd.). A rectangular profile was rated A, and others were rated B.

LER:

With respect to the range of 5 μm edge in the longitudinal direction of a pattern, the distance from the reference line where the edge should be present was measured at 50 points by a Critical Dimension SEM (S-8840, manufactured by Hitachi Ltd.) and after determining the standard deviation, 3σ was computed. A smaller value indicates higher performance.

TABLE 4

| | Acid-Increasing Agent | (g) | Acid Generator | (g) | Resin (10 g) | Basic Compound | (g) | Surfactant (0.03 g) | Solvent | (ratio by mass) |
|---|---|---|---|---|---|---|---|---|---|---|
| Example | | | | | | | | | | |
| 1 | I-1 | (1.0) | z38 | (0.1) | 1 | PEA | (0.02) | W-4 | A1/B1 | (80/20) |
| 2 | I-3 | (1.0) | z78 | (0.2) | 2 | TOA | (0.005) | W-4 | A1/B1 | (60/40) |
| 3 | I-4 | (0.3) | z60, 38 | (0.1/0.05) | 3 | PEA | (0.01) | W-6 | A1/B1 | (80/20) |
| 4 | I-7 | (0.3) | z60 | (0.2) | 4 | PEA/DIA | (0.01/0.01) | W-4 | A1/B1 | (80/20) |
| 5 | I-8 | (0.5) | z64 | (0.3) | 5 | PEA | (0.02) | W-4 | A1/B2 | (60/40) |
| 6 | I-6 | (1.5) | z70 | (0.2) | 6 | TOA | (0.02) | W-1 | A1/A3 | (60/40) |
| 7 | I-5 | (1.0) | z72 | (0.4) | 7 | TBAH | (0.02) | W-4 | A1/B1 | (80/20) |
| 8 | I-9 | (0.3) | z38 | (0.3) | 8 | PEA | (0.02) | W-4 | A1/B2 | (60/40) |
| 9 | I-10 | (1.0) | z69 | (0.1) | 9 | PBI | (0.01) | W-6 | A1/B1 | (60/40) |
| 10 | I-11 | (0.5) | z66 | (0.2) | 10 | PEA | (0.02) | W-4 | A1 | (100) |
| 11 | I-12 | (2.0) | z60, 68 | (0.2/0.2) | 11 | PEA | (0.02) | W-2 | A1/B1 | (60/40) |
| 12 | I-13 | (1.0) | z68 | (0.4) | 12 | PEA | (0.01) | W-4 | A1/B1 | (80/20) |
| 13 | I-14 | (1.0) | z63 | (0.1) | 13 | PEA/DIA | (0.01/0.005) | W-6 | A1/B1 | (80/20) |
| 14 | I-15 | (2.0) | z78 | (0.3) | 14 | PEA | (0.01) | W-4 | A1/B1 | (80/20) |
| 15 | I-15 | (0.5) | z61 | (0.2) | 15 | PEA | (0.01) | W-4 | A1/B1 | (80/20) |

TABLE 4-continued

| | | | | | | | | | | |
|---|---|---|---|---|---|---|---|---|---|---|
| 16 | I-16 | (2.0) | z72 | (0.2) | 16 | TBAH | (0.02) | W-4 | A1 | (100) |
| 17 | I-7 | (1.5) | z38 | (0.2) | 17 | PEA | (0.02) | W-5 | A1 | (100) |
| 18 | I-18 | (2.0) | z69 | (0.2) | 18 | TMEA | (0.02) | W-4 | A1/B1 | (80/20) |
| 19 | I-19 | (0.6) | z60, 68 | (0.2/0.2) | 19 | PEA | (0.02) | W-6 | A1/B1 | (60/40) |
| 20 | I-20 | (2.0) | z60, 68 | (0.2/0.2) | 20 | PEA | (0.02) | W-4 | A1 | (100) |
| 21 | I-21 | (1.0) | z69 | (0.1) | 21 | TOA | (0.01) | W-4 | A1 | (100) |
| 22 | I-22 | (0.5) | z66 | (0.2) | 22 | PBI | (0.02) | W-2 | A1/B1 | (80/20) |
| 23 | I-23 | (2.0) | z50 | (0.2) | 23 | PEA | (0.02) | W-4 | A1 | (100) |
| 24 | I-9 | (2.0) | z38 | (0.3) | 5 | PEA/DIA | (0.01/0.005) | W-4 | A1/B1 | (60/40) |
| 25 | I-9 | (2.0) | z69 | (0.1) | 6 | PEA | (0.01) | W-4 | A1/B1 | (80/20) |
| 26 | I-10 | (2.0) | z66 | (0.2) | 7 | PEA | (0.01) | W-1 | A1/B1 | (80/20) |
| 27 | I-30 | (2.5) | z60, 68 | (0.2/0.2) | 8 | TBAH | (0.02) | W-4 | A1/A3 | (60/40) |
| 28 | I-31 | (2.0) | z68 | (0.4) | 9 | PEA | (0.01) | W-4 | A1/B1 | (80/20) |
| 29 | I-32 | (3.0) | z63 | (0.1) | 10 | PEA/DIA | (0.01/0.01) | W-6 | A1/B2 | (60/40) |
| 30 | I-33 | (2.0) | z78 | (0.3) | 6 | PEA | (0.02) | W-4 | A1/B1 | (60/40) |
| 31 | I-34 | (1.5) | z61 | (0.2) | 7 | PEA | (0.01) | W-4 | A1 | (100) |
| Comparative Example | | | | | | | | | | |
| 1 | — | (—) | z38 | (0.15) | 1 | PEA | (0.03) | W-4 | A1/B1 | (60/40) |
| 2 | — | (—) | z38 | (0.2) | 2 | PEA/DIA | (0.01/0.005) | W-2 | A1/B1 | (80/20) |
| 3 | — | (—) | z78 | (0.2) | 10 | DIA | (0.03) | W-4 | A1 | (100) |
| 4 | — | (—) | z60 | (0.4) | 5 | TBAH | (0.04) | W-6 | A1/A3 | (60/40) |
| 5 | — | (—) | z38 | (0.4) | 22 | PBI | (0.01) | W-4 | A1/A3 | (80/20) |

| | Dissolution Inhibiting Compound (g) | Hydrophobic Resin (HR) | Mode of Addition | (g) or (solvent) | Exposure Condition (1) | | Exposure Condition (2) | | Exposure Condition (3) | | Exposure Condition (4) | |
|---|---|---|---|---|---|---|---|---|---|---|---|---|
| | | | | | Pattern Profile | LER (nm) | Pattern Profile | LER (nm) | Pattern Profile | LER (nm) | Pattern Profile | LER (nm) |
| Example | | | | | | | | | | | | |
| 1 | | HR-22 | added | (0.1) | A | 4.5 | A | 5.9 | A | 6.7 | A | 5.2 |
| 2 | | HR-5 | added | (0.2) | A | 5.0 | A | 7.2 | A | 7.4 | A | 3.8 |
| 3 | | HR-11, 73 | added | (0.1/0.05) | A | 5.2 | A | 7.0 | A | 6.9 | A | 4.0 |
| 4 | | HR-15 | added | (0.2) | A | 5.3 | A | 7.2 | A | 6.0 | A | 4.4 |
| 5 | LCB(0.2) | HR-53 | TC | (SL-1) | A | 4.3 | A | 4.8 | A | 4.6 | A | 4.1 |
| 6 | | HR-20 | added | (0.2) | A | 4.5 | A | 6.5 | A | 5.9 | A | 6.4 |
| 7 | | HR-37 | added | (0.4) | A | 6.2 | A | 7.2 | A | 5.4 | A | 4.9 |
| 8 | | HR-30 | added | (0.3) | A | 6.9 | A | 6.7 | A | 6.2 | A | 6.2 |
| 9 | | HR-47 | added | (0.1) | A | 6.4 | A | 5.9 | A | 5.1 | A | 5.9 |
| 10 | | HR-51 | added | (0.2) | A | 5.6 | A | 4.6 | A | 5.3 | A | 6.6 |
| 11 | LCB(0.3) | HR-65 | added | (0.2) | A | 5.8 | A | 4.8 | A | 5.6 | A | 5.3 |
| 12 | | HR-66 | added | (0.4) | A | 4.8 | A | 6.1 | A | 6.0 | A | 6.1 |
| 13 | | HR-44 | added | (0.1) | A | 5.6 | A | 5.1 | A | 7.4 | A | 5.1 |
| 14 | | HR-63 | added | (0.3) | A | 6.9 | A | 5.3 | A | 4.8 | A | 4.6 |
| 15 | | HR-83 | TC | (SL-2) | A | 6.7 | A | 5.5 | A | 5.2 | A | 5.4 |
| 16 | | HR-80 | added | (0.2) | A | 6.9 | A | 5.6 | A | 4.9 | A | 4.3 |
| 17 | | HR-80 | added | (0.2) | A | 5.5 | A | 5.8 | A | 7.2 | A | 6.6 |
| 18 | | HR-80 | added | (0.2) | A | 6.5 | A | 5.4 | A | 7.4 | A | 4.5 |
| 19 | | HR-11, 73 | added | (0.1/0.05) | A | 4.9 | A | 6.2 | A | 4.8 | A | 4.8 |
| 20 | LCB(0.3) | HR-51 | added | (0.2) | A | 4.6 | A | 6.8 | A | 6.3 | A | 5.2 |
| 21 | | HR-83 | TC | (SL-2) | A | 5.7 | A | 5.2 | A | 7.0 | A | 6.6 |
| 22 | | HR-83 | TC | (SL-2) | A | 5.9 | A | 4.9 | A | 6.1 | A | 4.0 |
| 23 | | HR-80 | added | (0.2) | A | 5.1 | A | 6.0 | A | 5.7 | A | 5.5 |
| 24 | | HR-30 | added | (0.3) | A | 5.5 | A | 5.8 | A | 6.9 | A | 5.2 |
| 25 | | HR-47 | added | (0.1) | A | 6.0 | A | 6.0 | A | 8.0 | A | 5.8 |
| 26 | | HR-51 | added | (0.2) | A | 6.2 | A | 6.2 | A | 5.3 | A | 6.0 |
| 27 | | HR-44 | added | (0.1) | A | 5.8 | A | 6.8 | A | 4.8 | A | 6.2 |
| 28 | | HR-63 | added | (0.3) | A | 4.5 | A | 5.9 | A | 4.0 | A | 6.9 |
| 29 | | HR-83 | TC | (SL-2) | A | 6.9 | A | 5.5 | A | 6.4 | A | 5.1 |
| 30 | | HR-80 | added | (0.2) | A | 6.8 | A | 4.6 | A | 5.2 | A | 4.9 |
| 31 | | HR-80 | added | (0.2) | A | 5.5 | A | 4.3 | A | 5.1 | A | 6.0 |

TABLE 4-continued

| Comparative Example | | | | | | | | | | | | |
|---|---|---|---|---|---|---|---|---|---|---|---|---|
| 1 | | HR-22 | added | (0.15) | B | 12.2 | B | 10.1 | B | 10.9 | B | 12.5 |
| 2 | | HR-65 | added | (0.2) | B | 9.8 | B | 10.4 | B | 12.0 | B | 9.8 |
| 3 | | HR-66 | added | (0.4) | B | 10.1 | B | 11.4 | B | 13.0 | B | 10.1 |
| 4 | LCB(0.2) | HR-83 | TC | (SL-2) | B | 12.0 | B | 12.3 | B | 13.3 | B | 11.2 |
| 5 | | HR-47 | added | (0.4) | B | 11.1 | B | 12.5 | B | 10.6 | B | 12.2 |

The denotations in the Table are as follows.
[Basic Compound]
DIA: 2,6-diisopropylaniline
TBAH: tetrabutylammonium hydroxide
TMEA: tris(methoxyethoxyethyl)amine
PEA: N-phenyldiethanolamine
TOA: trioctylamine
PBI: 2-phenylbenzimidazole
[Surfactant]
W-1: Megaface F176 (produced by Dainippon Ink & Chemicals, Inc.) (fluorine-containing)
W-2: Megaface R08 (produced by Dainippon Ink & Chemicals, Inc.) (fluorine- and silicon-containing)
W-4: Troysol S-366 (produced by Troy Chemical)
W-5: PF656 (produced by OMNOVA, fluorine-containing)
W-6: PF6320 (produced by OMNOVA, fluorine-containing)
[Solvent]
A1: propylene glycol monomethyl ether acetate
A3: cyclohexanone
B1: propylene glycol monomethyl ether
B2: ethyl lactate
[Dissolution Inhibiting Compound]
LCB: tert-butyl lithocholate As seen from the results in Table 4, the positive resist composition of the present invention exhibits good performance in terms of pattern profile and LER not only in normal exposure (dry exposure) but also in immersion exposure and at the same time, exhibits good performance in terms of pattern profile and LER even in double exposure. Synthesis Example 11 (Synthesis of Compound (II-6)):

7.01 Gram (51.5 mmol) of 1-p-tolylethanol and 503 mg (4.12 mmol) of N,N-dimethylaminopyridine were dissolved in 80 mL of tetrahydrofuran (THF), and the resulting solution was cooled to 0° C. under nitrogen flow. A solution prepared by dissolving 8.65 g (103 mmol) of diketene in 80 mL of THF was added dropwise to the solution above over 0.5 hours and then, the reaction was allowed to proceed at 0° C. for 1 hour. After adding 200 mL of ethyl acetate, the organic layer was washed, in order, twice with an aqueous saturated sodium hydrogencarbonate solution and twice with water, and dried over sodium sulfate. The solvent was concentrated, and the residue was purified by column chromatography (SiO$_2$, hexane/ethyl acetate=4/1) to obtain 8.9 g of 1-p-tolylethyl 3-oxobutanoate as a colorless transparent oil. Thereafter, 12.4 g (56.3 mmol) of the oil was dissolved in 40 ml of THF, and the resulting solution was added dropwise to a suspension containing 2.25 g (60 wt %, 56.3 mmol) of NaH and 80 mL of TIFF at 0° C. over 0.5 hours, followed by stirring for 0.5 hours. Furthermore, a solution containing 7.99 g (56.3 mmol) of MeI and 20 mL of THF was added dropwise over 0.5 hours, and the resulting mixture was stirred at 0° C. for 0.5 hours and further stirred at 25° C. for 5 hours. After adding 200 ml., of ethyl acetate, the organic layer was washed, in order, twice with saturated brine and twice with water, and dried over sodium sulfate, and the solvent was concentrated to obtain 12.0 g of 1-p-tolylethyl 2-methyl-3-oxobutanoate as a colorless transparent oil. Subsequently, 45.9 g of an aqueous formalin solution was added to 13.23 g (56.5 mmol) of the oil. The resulting mixture was cooled to 0° C., and 7.81 g of potassium carbonate was added thereto. The obtained mixture was stirred at 0° C. for 1 hour and further stirred at 25° C. for 2 hours. After adding 200 mL of ethyl acetate, the organic layer was washed, in order, three times with an aqueous saturated sodium hydrogensulfite solution and twice with water, and dried over sodium sulfate. The solvent was concentrated to obtain 13.4 of 1-p-tolylethyl 2-(hydroxymethyl)-2-methyl-3-oxobutanoate as a colorless transparent oil, and 6.0 g (22.7 mmol) of the oil was dissolved in 20 mL of pyridine. The resulting solution was cooled to 0° C., and 13.0 g of p-toluenesulfonyl chloride was added thereto. The mixture was stirred at 0° C. for 2 hours and then stirred at 80° C. for 6 hours. After adding 200 mL of ethyl acetate, the organic layer was washed, in order, three times with an aqueous saturated ammonium chloride solution and twice with water, and dried over sodium sulfate. The residue was purified by column chromatography (SiO$_2$, hexane/ethyl acetate=4/1) to obtain 5.17 g of a diastereomer mixture, that is, the objective Compound (II-6), as a colorless transparent oily product.

$^1$H-NMR (400 MHz, CDCl$_3$) δ 1.40, 1.43 (s, 3H), 1.47, 1.51 (s, 3H), 2.04 (s, 3H), 2.33, 2.44 (s, 3H), 2.44, 2.45 (s, 3H), 4.26-4.39 (m, 2H), 5.86 (m, 1H), 7.13-7.18 (m, 4H), 7.28, 7.34 (b, 2H), 7.69, 7.75 (d, 2H).

Other acid-increasing agents were synthesized in the same manner.

With respect to Resins (1a) to (23a) as the component (B) used in Examples, the monomers used for the synthesis, the compositional ratio, the weight average molecular weight and the polydispersity are shown in Tables 5 and 6 below.

TABLE 5

| No. | Monomer (1) | Monomer (2) | Monomer (3) | Monomer (4) | Compositional Ratio (by mol) | Mw | Mw/Mn |
|---|---|---|---|---|---|---|---|
| 1a | | | | | 35/15/35/15 | 10000 | 1.9 |
| 2a | | | | | 40/5/45/10 | 8900 | 1.9 |
| 3a | | | | | 40/30/30 | 12000 | 1.8 |
| 4a | | | | | 40/20/40 | 8900 | 1.9 |
| 5a | | | | | 50/20/30 | 10200 | 2.3 |

TABLE 5-continued

| No. | Monomer (1) | Monomer (2) | Monomer (3) | Monomer (4) | Compositional Ratio (by mol) | Mw | Mw/Mn |
|---|---|---|---|---|---|---|---|
| 6a | (structure) | (structure) | (structure) | (structure) | 40/10/40/10 | 8900 | 1.7 |
| 7a | (structure) | (structure) | (structure) | (structure) | 20/20/50/10 | 7800 | 1.7 |
| 8a | (structure) | (structure) | (structure) | (structure) | 40/10/40/10 | 9800 | 1.8 |
| 9a | (structure) | (structure) | (structure) | (structure) | 40/20/30/10 | 9800 | 1.6 |
| 10a | (structure) | (structure) | (structure) |  | 40/30/30 | 13000 | 1.8 |

TABLE 5-continued

| No. | Monomer (1) | Monomer (2) | Monomer (3) | Monomer (4) | Compositional Ratio (by mol) | Mw | Mw/Mn |
|---|---|---|---|---|---|---|---|
| 11a | (structure with lactone and CN) | (structure with diethyl cyclohexyl ester) | (cyclohexyl acrylate) | | 40/30/30 | 3600 | 1.4 |
| 12a | (bicyclic lactone acetonide methacrylate) | (hydroxyadamantyl methacrylate) | (methyladamantyl methacrylate) | (methacrylic acid) | 40/20/30/10 | 7000 | 1.6 |

TABLE 6

| No. | Monomer (1) | Monomer (2) | Monomer (3) | Monomer (4) | Compositional Ratio (by mol) | Mw | Mw/Mn |
|---|---|---|---|---|---|---|---|
| 13a | (norbornane lactone methacrylate) | (hydroxyadamantyl methacrylate) | (ethyl tricyclic methacrylate) | (tricyclodecanyl methacrylate) | 30/35/30/5 | 5500 | 1.9 |
| 14a | (norbornane lactone methacrylate) | (hydroxyadamantyl methacrylate) | (ethyladamantyl methacrylate) | | 40/30/30 | 9800 | 2.0 |

TABLE 6-continued

| No. | Monomer (1) | Monomer (2) | Monomer (3) | Monomer (4) | Compositional Ratio (by mol) | Mw | Mw/Mn |
|---|---|---|---|---|---|---|---|
| 15a | | | | | 40/20/40 | 7700 | 2.1 |
| 16a | | | | | 30/30/40 | 8800 | 2.6 |
| 17a | | | | | 40/30/30 | 9000 | 2.1 |
| 18a | | | | | 30/20/40/10 | 5800 | 2.2 |
| 19a | | | | | 30/30/40 | 9800 | 2.1 |

TABLE 6-continued

| No. | Monomer (1) | Monomer (2) | Monomer (3) | Monomer (4) | Compositional Ratio (by mol) | Mw | Mw/Mn |
|---|---|---|---|---|---|---|---|
| 20a | | | | | 35/35/30 | 9800 | 2.1 |
| 21a | | | | | 50/20/30 | 5100 | 1.6 |
| 22a | | | | | 30/25/25/20 | 8900 | 1.8 |
| 23a | | | | | 40/20/40 | 7500 | 1.6 |

Examples 32 to 54 and Comparative Examples 6 to 10

<Preparation of Resist>

The components shown in Tables 7 and 8 below were dissolved in a solvent to prepare a solution having a solid content concentration of 5 mass %, and the obtained solution was filtered through a polyethylene filter having a pore size of 0.1 μm to prepare a positive resist composition. The positive resist compositions prepared were evaluated by the following methods, and the results are shown in Tables 7 and 8. With respect to each component in the Table, the ratio when using a plurality of kinds is a ratio by mass.

Incidentally, in Tables 7 and 8, when the positive resist composition contained a surface hydrophobizing resin (HR), the mode of addition is denoted by "added", and when the positive resist composition did not contain a surface hydrophobizing resin (HR) and after the formation of a resist film, a topcoat containing a surface hydrophobizing resin (HR) was formed as an overlayer of the resist film, the mode of addition is denoted by "TC".

Image Performance Test:
(Exposure Condition (1): Normal Dry Exposure)

An organic antireflection film, ARC29A (produced by Nissan Chemical Industries, Ltd.), was applied on a silicon wafer and baked at 205° C. for 60 seconds to form a 78 nm-thick antireflection film, and the positive resist composition prepared was applied thereon and baked at 130° C. for 60 seconds to form a 120 nm-thick resist film. The obtained wafer was exposed using an ArF excimer laser scanner (PAS5500/1100, manufactured by ASML, NA: 0.75) through a 6% halftone mask having a 65-nm 1:1 line-and-space pattern. Thereafter, the resist film was heated at 130° C. for 60 seconds, developed with an aqueous tetramethylammonium hydroxide solution (2.38 mass %) for 30 seconds, rinsed with pure water and spin-dried to obtain a resist pattern.

(Exposure Condition (2): Normal Immersion Exposure)

An organic antireflection film, ARC29A (produced by Nissan Chemical Industries, Ltd.), was applied on a silicon wafer and baked at 205° C. for 60 seconds to form a 78 nm-thick antireflection film, and the positive resist composition prepared was applied thereon and baked at 130° C. for 60 seconds to form a 120 nm-thick resist film. The obtained wafer was exposed using an ArF excimer laser immersion scanner (PAS5500/1250i, manufactured by ASML, NA: 0.85) through a 6% halftone mask having a 65-nm 1:1 line-and-space pattern. The immersion liquid used was ultrapure water. Thereafter, the resist film was heated at 130° C. for 60 seconds, developed with an aqueous tetramethylammonium hydroxide solution (2.38 mass %) for 30 seconds, rinsed with pure water and spin-dried to obtain a resist pattern.

(Exposure Condition (3): Dry Double Exposure)

An organic antireflection film, ARC29A (produced by Nissan Chemical Industries, Ltd.), was applied on a silicon wafer and baked at 205° C. for 60 seconds to form a 78 nm-thick antireflection film, and the positive resist composition prepared was applied thereon and baked at 130° C. for 60 seconds to form a 120 nm-thick resist film. The obtained wafer was subjected to first exposure by using an ArF excimer laser scanner (PAS5500/1100, manufactured by ASML, NA: 0.75) through a 6% halftone mask having a 60-nm space 180-nm line pattern and further to second exposure through a mask having the same pattern as in the first mask by displacing the mask by 120 nm so as to locate the space between a space and a space at the first exposure. Thereafter, the resist film was heated at 130° C. for 60 seconds, developed with an aqueous tetramethylammonium hydroxide solution (2.38 mass %) for 30 seconds, rinsed with pure water and spin-dried to obtain a resist pattern.

(Exposure Condition (4): Immersion Double Exposure)

An organic antireflection film, ARC29A (produced by Nissan Chemical Industries, Ltd.), was applied on a silicon wafer and baked at 205° C. for 60 seconds to form a 78 nm-thick antireflection film, and the positive resist composition prepared was applied thereon and baked at 130° C. for 60 seconds to form a 120 nm-thick resist film. The obtained wafer was subjected to first exposure by using an ArF excimer laser immersion scanner (PAS5500/1250i, manufactured by ASML, NA: 0.85) through a 6% halftone mask having a 50-nm space 150-nm line pattern and further to second exposure through a mask having the same pattern as in the first mask by displacing the mask by 100 nm so as to locate the space between a space and a space at the first exposure. The immersion liquid used was ultrapure water. Thereafter, the resist film was heated at 130° C. for 60 seconds, developed with an aqueous tetramethylammonium hydroxide solution (2.38 mass %) for 30 seconds, rinsed with pure water and spin-dried to obtain a resist pattern.

When the addition mode of the surface hydrophobizing resin (FIR) is "TC", the following operation was performed after the formation of the resist film.

<Topcoat Forming Method>

The surface hydrophobizing resin (FIR) shown in Tables 7 and 8 was dissolved in a solvent and applied by a spin coater on the resist film above, and the wafer was dried by heating at 115° C. for 60 seconds to form a 0.05 µm-thick topcoat. At this time, the topcoat was observed whether coating unevenness was present or not, and it was confirmed that the topcoat was uniformly applied without coating unevenness.

The abbreviations of the solvents are as follows.
SL-1: 2-ethylbutanol
SL-2: perfluorobutyltetrahydrofuran Pattern Profile:

The pattern profile was observed through a scanning microscope (S-4800, manufactured by Hitachi, Ltd.). A rectangular profile was rated A, and others were rated B.

Pattern Collapse:

The exposure dose for reproducing a line-and-space 1:1 mask pattern in a target dimension is taken as an optimal exposure dose, and the line width (nm) at which a line-and-space 1:1 dense pattern is resolved without collapse to a finer mask size than that when exposed with the optimal exposure amount, is defined as a limiting pattern collapse line width. A smaller value indicates that a finer pattern is resolved without collapse and pattern collapse is less liable to occur.

TABLE 7

| Example | Acid-Increasing Agent | (g) | Acid Generator | (g) | Resin (10 g) | Basic Compound | (g) | Surfactant (0.03 g) | Solvent | (ratio by mass) | Dissolution Inhibiting Compound (g) | Hydrophobizing Resin (HR) | Mode of Addition | (g) or (solvent) |
|---|---|---|---|---|---|---|---|---|---|---|---|---|---|---|
| 32 | II-1 | (1.0) | z38 | (0.1) | 1a | PEA | (0.02) | W-4 | A1/B1 | (80/20) | | HR-22 | added | (0.1) |
| 33 | II-2 | (2.0) | z78 | (0.2) | 2a | TOA | (0.02) | W-4 | A1/B1 | (60/40) | | HR-5 | added | (0.2) |
| 34 | II-3 | (1.0) | z60 | (0.2) | 3a | TBAH | (0.02) | W-6 | A1/B1 | (80/20) | | HR-80 | added | (0.2) |
|  |  |  | z68 | (0.2) |  |  |  |  |  |  |  |  |  |  |
| 35 | II-4 | (1.0) | z68 | (0.4) | 4a | PEA | (0.02) | W-4 | A1/B1 | (60/40) | | HR-11 | added | (0.1) |
|  |  |  |  |  |  |  |  |  |  |  |  | HR-73 |  | (0.05) |
| 36 | II-5 | (2.0) | z63 | (0.1) | 5a | PBI | (0.01) | W-4 | A1 | (100) | LCB (0.2) | HR-51 | added | (0.2) |
| 37 | II-6 | (4.5) | z78 | (0.3) | 6a | PEA | (0.02) | W-1 | A1/B1 | (60/40) | | HR-65 | added | (0.2) |
| 38 | II-7 | (2.0) | z38 | (0.3) | 7a | PEA | (0.01) | W-4 | A1/B1 | (80/20) | | HR-37 | added | (0.4) |
|  |  |  |  |  |  | DIA | (0.005) |  |  |  |  |  |  |  |
| 39 | II-8 | (0.6) | z69 | (0.1) | 8a | PEA | (0.01) | W-4 | A1/B1 | (80/20) | | HR-30 | added | (0.3) |
| 40 | II-9 | (2.0) | z66 | (0.2) | 9a | PEA | (0.01) | W-4 | A1 | (100) | | HR-47 | added | (0.1) |

TABLE 7-continued

| | | | | | | | | | | | | | | |
|---|---|---|---|---|---|---|---|---|---|---|---|---|---|---|
| 41 | II-10 | (0.5) | z60 | (0.2) | 10a | TBAH | (0.02) | W-5 | A1 | (100) | | HR-51 | added | (0.2) |
| | | | z68 | (0.2) | | | | | | | | | | |
| 42 | II-11 | (0.6) | z69 | (0.1) | 11a | PEA | (0.02) | W-4 | A1/B1 | (80/20) | | HR-66 | added | (0.4) |
| 43 | II-12 | (1.0) | z66 | (0.2) | 12a | PEA | (0.01) | W-6 | A1 | (100) | | HR-44 | added | (0.1) |
| 44 | II-13 | (0.3) | z50 | (0.2) | 13a | TMEA | (0.02) | W-4 | A1/B1 | (80/20) | | HR-63 | added | (0.3) |
| 45 | II-14 | (1.0) | z61 | (0.2) | 14a | PEA | (0.02) | W-2 | A1/B1 | (80/20) | | HR-83 | TC | (SL-2) |
| 46 | II-15 | (0.5) | z72 | (0.2) | 15a | PEA | (0.02) | W-4 | A1/B1 | (80/20) | LCB (0.3) | HR-80 | added | (0.2) |
| 47 | II-16 | (2.0) | z38 | (0.2) | 16a | TOA | (0.01) | W-6 | A1/B2 | (60/40) | | HR-80 | added | (0.2) |
| 48 | II-17 | (1.0) | z69 | (0.2) | 17a | PBI | (0.02) | W-4 | A1/B1 | (80/20) | | HR-80 | added | (0.2) |
| 49 | II-18 | (0.5) | z60 | (0.1) | 18a | PEA | (0.01) | W-4 | A1/B1 | (60/40) | | HR-11 | added | (0.1) |
| | | | z38 | (0.05) | | DIA | (0.005) | | | | | HR-73 | | (0.05) |
| 50 | II-19 | (2.0) | z60 | (0.2) | 19a | TOA | (0.005) | W-6 | A1 | (100) | | HR-15 | added | (0.2) |
| 51 | II-20 | (1.0) | z64 | (0.3) | 20a | PEA | (0.01) | W-4 | A1 | (100) | | HR-20 | added | (0.2) |
| 52 | II-21 | (0.3) | z70 | (0.2) | 21a | PEA | (0.01) | W-4 | A1/A3 | (60/40) | | HR-83 | TC | (SL-2) |
| | | | | | | DIA | (0.01) | | | | | | | |
| 53 | II-22 | (0.3) | z72 | (0.4) | 22a | PEA | (0.02) | W-2 | A1/B1 | (80/20) | | HR-83 | TC | (SL-2) |
| 54 | II-23 | (0.5) | z60 | (0.2) | 23a | PEA | (0.02) | W-4 | A1/B2 | (60/40) | | HR-53 | TC | (SL-1) |
| | | | z68 | (0.2) | | | | | | | | | | |

| | Exposure Condition (1) | | Exposure Condition (2) | | Exposure Condition (3) | | Exposure Condition (4) | |
|---|---|---|---|---|---|---|---|---|
| Example | Pattern Profile | Pattern Collapse (nm) | Pattern Profile | Pattern Collapse (nm) | Pattern Profile | Pattern Collapse (nm) | Pattern Profile | Pattern Collapse (nm) |
| 32 | rectangular | 36.0 | rectangular | 37.2 | rectangular | 33.2 | rectangular | 21.5 |
| 33 | rectangular | 29.4 | rectangular | 37.6 | rectangular | 34.4 | rectangular | 38.4 |
| 34 | rectangular | 26.8 | rectangular | 36.0 | rectangular | 36.0 | rectangular | 24.8 |
| 35 | rectangular | 33.0 | rectangular | 27.6 | rectangular | 27.9 | rectangular | 25.4 |
| 36 | rectangular | 22.4 | rectangular | 28.4 | rectangular | 26.5 | rectangular | 32.7 |
| 37 | rectangular | 20.3 | rectangular | 32.0 | rectangular | 27.0 | rectangular | 31.2 |
| 38 | rectangular | 29.6 | rectangular | 27.6 | rectangular | 23.5 | rectangular | 18.9 |
| 39 | rectangular | 25.5 | rectangular | 33.6 | rectangular | 24.4 | rectangular | 25.0 |
| 40 | rectangular | 21.2 | rectangular | 32.0 | rectangular | 27.2 | rectangular | 28.8 |
| 41 | rectangular | 21.8 | rectangular | 39.2 | rectangular | 24.8 | rectangular | 25.3 |
| 42 | rectangular | 24.2 | rectangular | 36.8 | rectangular | 26.4 | rectangular | 20.8 |
| 43 | rectangular | 29.4 | rectangular | 28.8 | rectangular | 27.9 | rectangular | 28.6 |
| 44 | rectangular | 35.0 | rectangular | 30.8 | rectangular | 29.4 | rectangular | 20.6 |
| 45 | rectangular | 32.1 | rectangular | 32.4 | rectangular | 27.2 | rectangular | 26.2 |
| 46 | rectangular | 29.6 | rectangular | 24.0 | rectangular | 25.6 | rectangular | 23.3 |
| 47 | rectangular | 25.6 | rectangular | 28.2 | rectangular | 28.6 | rectangular | 24.5 |
| 48 | rectangular | 29.1 | rectangular | 31.8 | rectangular | 27.6 | rectangular | 23.0 |
| 49 | rectangular | 26.8 | rectangular | 29.1 | rectangular | 29.4 | rectangular | 26.2 |
| 50 | rectangular | 30.0 | rectangular | 29.6 | rectangular | 30.2 | rectangular | 19.2 |
| 51 | rectangular | 31.6 | rectangular | 24.4 | rectangular | 30.6 | rectangular | 20.9 |
| 52 | rectangular | 23.2 | rectangular | 31.6 | rectangular | 36.3 | rectangular | 22.6 |
| 53 | rectangular | 30.1 | rectangular | 29.2 | rectangular | 21.5 | rectangular | 20.5 |
| 54 | rectangular | 31.8 | rectangular | 28.0 | rectangular | 33.0 | rectangular | 20.6 |

TABLE 8

| Comparative Example | Acid-Increasing Agent (g) | Acid Generator | (g) | Resin (10 g) | Basic Compound | (g) | Surfactant (0.03 g) | Solvent | (ratio by mass) | Dissolution Inhibiting Compound (g) | Hydrophobizing Resin (HR) | Mode of Addition | (g) or (solvent) |
|---|---|---|---|---|---|---|---|---|---|---|---|---|---|
| 6 | —(—) | z38 | (0.15) | 1a | PEA | (0.03) | W-4 | A1/B1 | (60/40) | | HR-22 | added | (0.15) |
| 7 | —(—) | z60 | (0.4) | 2a | PEA | (0.01) | W-2 | A1/B1 | (80/20) | LCB (0.2) | HR-66 | added | (0.4) |
| | | | | | DIA | (0.005) | | | | | | | |
| 8 | —(—) | z38 | (0.2) | 10a | DIA | (0.03) | W-4 | A1 | (100) | | HR-83 | TC | (SL-2) |
| 9 | —(—) | z78 | (0.2) | 5a | TBAH | (0.04) | W-6 | A1/A3 | (60/40) | | HR-47 | added | (0.4) |
| 10 | —(—) | z38 | (0.4) | 22a | PBI | (0.01) | W-4 | A1 | (100) | | HR-65 | added | (0.2) |

| | Exposure Condition (1) | | Exposure Condition (2) | | Exposure Condition (3) | | Exposure Condition (4) | |
|---|---|---|---|---|---|---|---|---|
| Comparative Example | Pattern Profile | Pattern Collapse (nm) | Pattern Profile | Pattern Collapse (nm) | Pattern Profile | Pattern Collapse (nm) | Pattern Profile | Pattern Collapse (nm) |
| 6 | tapered | 58.5 | tapered | 80.8 | tapered | 67.5 | tapered | 79.6 |
| 7 | reverse tapered | 61.1 | tapered | 97.6 | tapered | 91.2 | reverse tapered | 76.3 |
| 8 | reverse tapered | 83.2 | tapered | 78.4 | tapered | 98.4 | tapered | 84.2 |

| | | | | | | | | |
|---|---|---|---|---|---|---|---|---|
| 9 | reverse tapered | 96.0 | tapered | 80.8 | tapered | 86.0 | tapered | 69.9 |
| 10 | reverse tapered | 88.8 | reverse tapered | 70.6 | tapered | 64.9 | tapered | 77.8 |

The denotations in the Tables are as follows.
[Basic Compound]
DIA: 2,6-diisopropylaniline
TBAH: tetrabutylammonium hydroxide
TMEA: tris(methoxyethoxyethyl)amine
PEA: N-phenyldiethanolamine
TOA: trioctylamine
PBI: 2-phenylbenzimidazole
[Surfactant]
W-1: Megaface F176 (produced by Dainippon Ink & Chemicals, Inc.) (fluorine-containing)
W-2: Megaface R08 (produced by Dainippon Ink & Chemicals, Inc.) (fluorine- and silicon-containing)
W-4: Troysol S-366 (produced by Troy Chemical)
W-5: PF656 (produced by OMNOVA, fluorine-containing)
W-6: PF6320 (produced by OMNOVA, fluorine-containing)
[Solvent]
A1: propylene glycol monomethyl ether acetate
A3: cyclohexanone
B1: propylene glycol monomethyl ether
B2: ethyl lactate
[Dissolution Inhibiting Compound]
LCB: tert-butyl lithocholate As seen from the results in Tables 7 and 8, the positive resist composition of the present invention exhibits good performance in terms of pattern profile and pattern collapse not only in normal exposure (dry exposure) but also in immersion exposure and at the same time exhibits good performance in terms of pattern profile and pattern collapse even in double exposure.

Synthesis Example 12

Synthesis of Compound (C-2)

7.01 g (51.5 mmol) of 1-p-tolylethanol and 503 mg (4.12 mmol) of N,N-dimethylaminopyridine were dissolved in 80 mL of tetrahydrofuran (THF), and the resulting solution was cooled to 0° C. under nitrogen flow. A solution prepared by dissolving 8.65 g (103 mmol) of diketene in 80 mL of THF was added dropwise to the solution above over 0.5 hours and then, the reaction was allowed to proceed at 0° C. for 1 hour. After adding 200 mL of ethyl acetate, the organic layer was washed, in order, twice with an aqueous saturated sodium hydrogencarbonate solution and twice with water, and dried over sodium sulfate. The solvent was concentrated, and the residue was purified by column chromatography ($SiO_2$, hexane/ethyl acetate-4/1) to obtain 8.9 g of 1-1-p-tolylethyl 3-oxobutanoate as a colorless transparent oil. Thereafter, 12.4 g (56.3 mmol) of the oil was dissolved in 40 mL of THF, and the resulting solution was added dropwise to a suspension containing 2.25 g (60 wt %, 56.3 mmol) of NaH and 80 mL of THF at 0° C. over 0.5 hours, followed by stirring for 0.5 hours. Furthermore, a solution containing 7.99 g (56.3 mmol) of MeI and 20 mL of THF was added dropwise over 0.5 hours, and the resulting mixture was stirred at 0° C. for 0.5 hours and further stirred at 25° C. for 5 hours. After adding 200 mL of ethyl acetate, the organic layer was washed, in order, twice with saturated brine and twice with water, and dried over sodium sulfate, and the solvent was concentrated to obtain 12.0 g of 1-p-tolylethyl 2-methyl-3-oxobutanoate as a colorless transparent oil. Subsequently, 45.9 g of an aqueous formalin solution was added to 13.23 g (56.5 mmol) of the oil. The resulting mixture was cooled to 0° C., and 7.81 g of potassium carbonate was added thereto. The obtained mixture was stirred at 0° C. for 1 hour and further stirred at 25° C. for 2 hours. After adding 200 mL of ethyl acetate, the organic layer was washed, in order, three times with an aqueous saturated sodium hydrogensulfite solution and twice with water, and dried over sodium sulfate, and the solvent was concentrated. The residue was recrystallized from hexane to obtain 13.4 g of 1-p-tolylethyl 2-(hydroxymethyl)-2-methyl-3-oxobutanoate us a white solid, and 6.0 g (22.7 mmol) of the solid was dissolved in 20 mL of pyridine. The resulting solution was cooled to 0° C., and 13.0 g of p-toluenesulfonyl chloride was added thereto. The mixture was stirred at 0° C. for 2 hours and then stirred at 30° C. for 6 hours. After adding 200 mL of ethyl acetate, the organic layer was washed, in order, three times with an aqueous saturated ammonium chloride solution and twice with water, and dried over sodium sulfate. The residue was purified by column chromatography ($SiO_2$, hexane/ethyl acetate=4/1) to obtain 5.17 g of a diastereomer mixture, that is, the objective Compound (C-2), as a colorless transparent oily product.

$^1$H-NMR (400 MHz, $CDCl_3$) δ 1.40, 1.43 (s, 3H), 1.47, 1.51 (s, 3H), 2.04 (s, 3H), 2.33, 2.44 (s, 3H), 2.44, 2.45 (s, 3H), 4.26-4.39 (m, 2H), 5.86 (m, 1H), 7.13-7.18 (m, 4H), 7.28, 7.34 (b, 2H), 7.69, 7.75 (d, 2H).

Synthesis Example 13

Synthesis of Compound (C-1)

Compound (C-1) was obtained as a colorless transparent oil in the same manner.

$^1$H-NMR (400 MHz, $CDCl_3$) δ 0.88-1.25 (m, 5H), 1.37 (s, 3H), 1.39 (s, 3H), 1.40 (s, 3H), 1.62-1.76 (m, 6H), 2.14 (s, 3H), 2.45 (s, 3H), 4.28 (AB quartet, 2H), 7.35 (d, 2H), 7.77 (d, 2H).

Synthesis Example 14

Synthesis of Compound (C-3)

Compound (C-3) was obtained as a white solid in the same manner.

$^1$H-NMR (400 MHz, $CDCl_3$) δ 1.44 (s, 3H), 1.56 (s, 2H), 1.57 (s, 3H), 1.69-1.94 (m, 10H), 2.17 (s, 3H), 2.24 (bs, 2H), 2.45 (s, 2H), 4.33 (AB quartet, 2H), 7.34 (d, 2H), 7.76 (d, 2H).

With respect to Acid-Decomposable Resins (A-1) to (A-7) used in Examples, the structure, compositional ratio, weight average molecular weight and polydispersity of each resin are shown below.
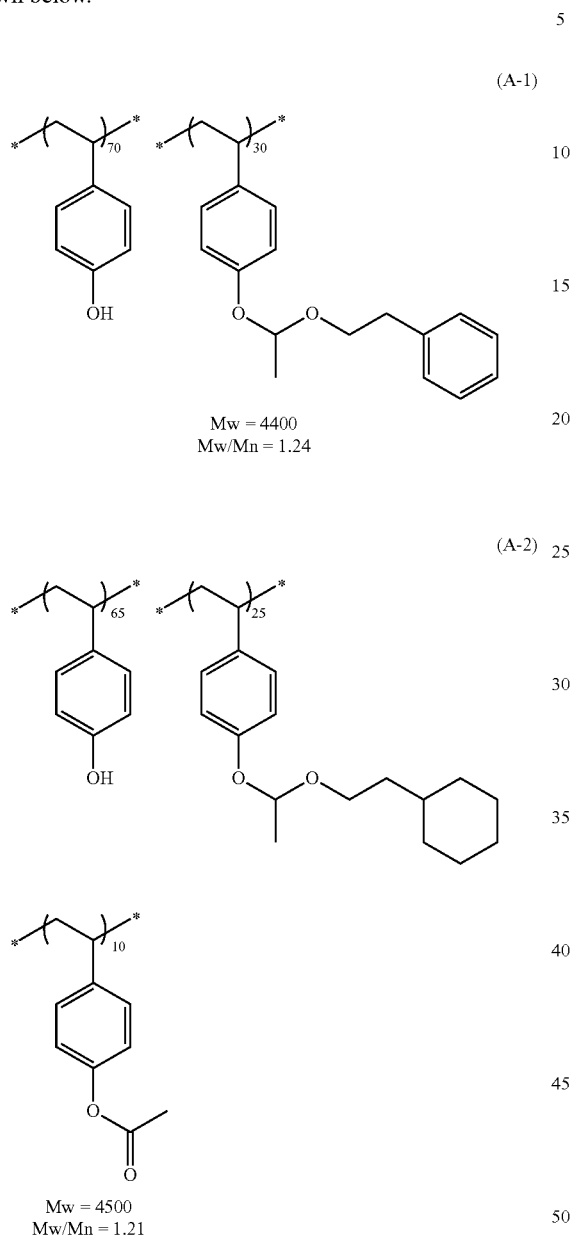
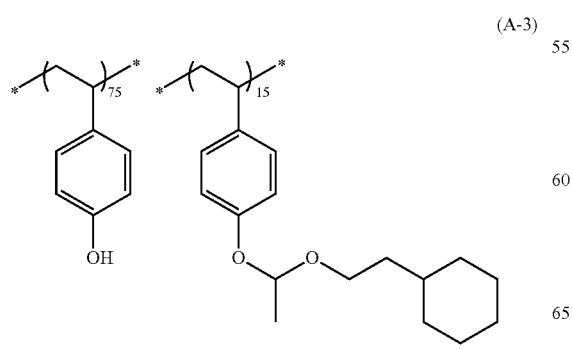
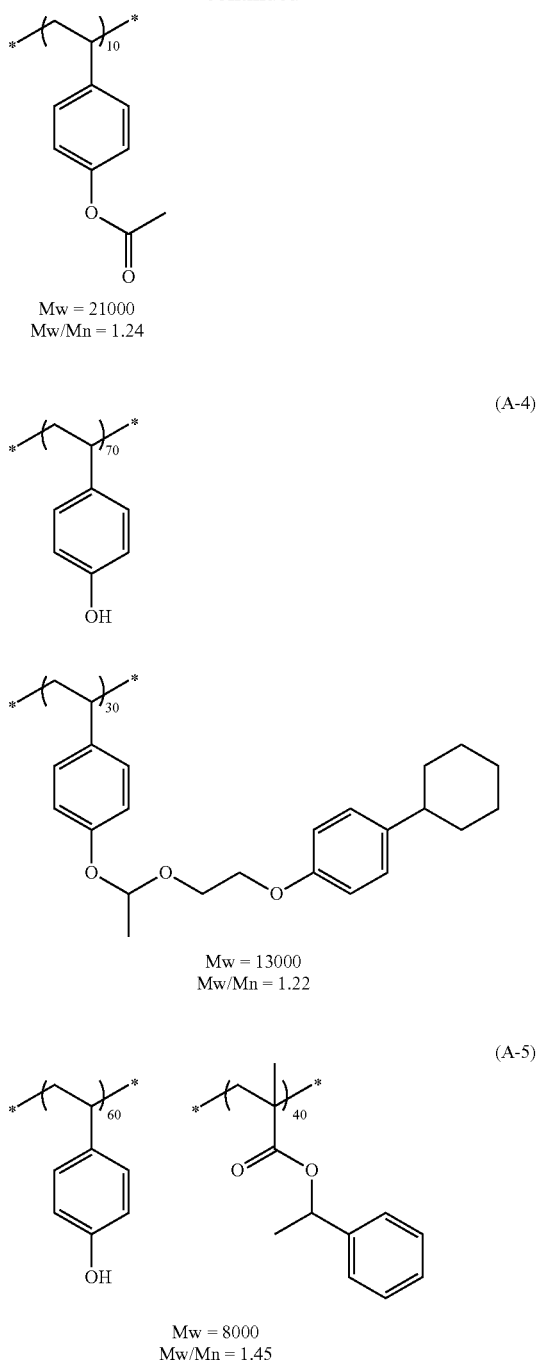

-continued

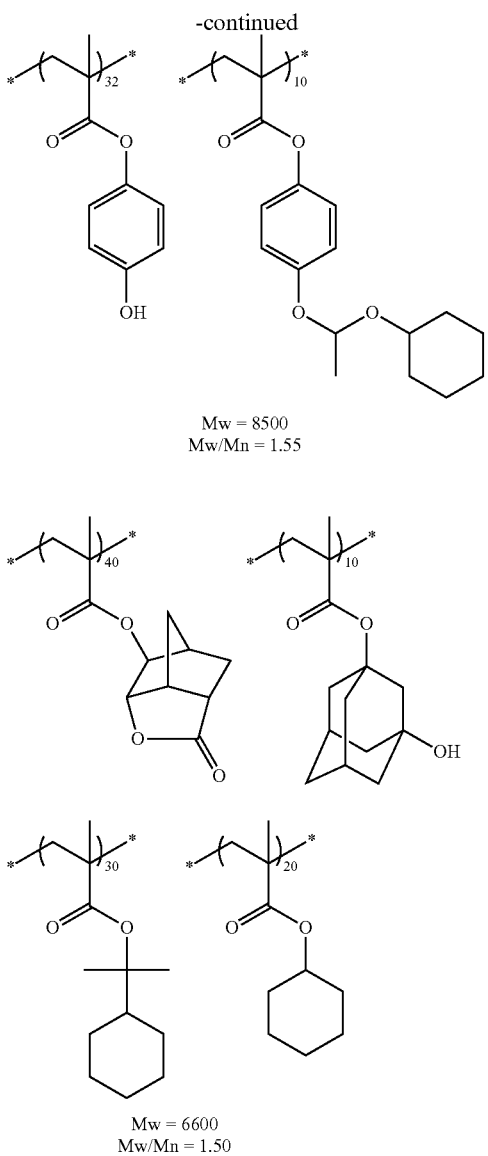

Mw = 8500
Mw/Mn = 1.55

(A-7)

Mw = 6600
Mw/Mn = 1.50

Examples 55 to 74 and Comparative Examples 11 and 12

<Preparation of Resist>

The components shown in Table 9 below were dissolved in a mixed solvent shown in Table 9, and the obtained solution was filtered through a polytetrafluoroethylene filter having a pore size of 0.1 μm to prepare a positive resist solution having an entire solid content concentration (mass %) shown in Table 9. The positive resist solutions prepared were evaluated as follows. In Table 9, the concentration (mass %) of each component is based on the entire solid content. The amount of the surfactant added is 0.1 mass % based on the entire solid content of the resist composition.

The solid content concentration of the acid-decomposable resin is an amount obtained by subtracting the amounts of acid generator, acid-increasing agent, basic compound and surfactant from the entire solid content of the positive resist composition.

<Evaluation of Resist (EB)>

The prepared positive resist solution was uniformly applied by a spin coater on a silicon substrate treated with hexamethyldisilazane, and dried by heating on a hot plate at 110° C. for 90 seconds to form a 100 nm-thick resist film.

This resist film was irradiated with electron beams by using an electron beam irradiation apparatus (HL750, manufactured by Hitachi Ltd., accelerating voltage: 50 KeV) and immediately after irradiation, heated on a hot plate at 110° C. for 90 seconds. Furthermore, the resist film was developed with an aqueous tetramethylammonium hydroxide solution in a concentration of 2.38 mass % at 23° C. for 60 seconds, rinsed with pure water for 30 seconds and then dried to form a line-and-space pattern. The obtained pattern was evaluated by the following methods.

[Sensitivity]

The cross-sectional profile of the pattern obtained was observed using a scanning electron microscope (S-9220, manufactured by Hitachi, Ltd.). The minimum irradiation energy for resolving a 100-nm line (line:space=1:1) was defined as the sensitivity.

[Resolution]

The limiting resolution (the line and space were separated and resolved) at the irradiation dose of giving the above-described sensitivity was defined as the resolution.

[Line Edge Roughness (LER)]

With respect to a range of 50 μm in the longitudinal direction of a 100-nm line pattern at the irradiation dose of giving the above-described sensitivity, the distance from the reference line where the edge should be present was measured at arbitrary 30 points by a scanning electron microscope (S-9220, manufactured by Hitachi Ltd.), and after determining the standard deviation, 3σ was computed.

[Pattern Profile]

The cross-sectional profile of a 100-nm line pattern at the irradiation dose of giving the above-described sensitivity was observed using a scanning electron microscope (S-4300, manufactured by Hitachi, Ltd.) and evaluated on a scale of three grades of rectangular, slightly tapered and tapered.

TABLE 9

| | (A) Resin | (B) Acid Generator | (B) Concentration | (C) Acid-Increasing Agent | (C) Concentration | (D) Organic Solvent | Ratio by Mass | (E) Basic Compound | (E) Concentration |
|---|---|---|---|---|---|---|---|---|---|
| Example 55 | A-1 | B-1 | 6 | C-1 | 15 | S1/S2 | 40/60 | E-3 | 2.5 |
| Example 56 | A-1 | B-2 | 10 | C-2 | 10 | S1/S2 | 40/60 | E-1 | 1.5 |
| Example 57 | A-1 | B-5 | 8 | C-3 | 15 | S1/S2 | 40/60 | E-3 | 2.5 |
| Example 58 | A-1 | B-6 | 8 | C-2 | 15 | S1/S2 | 40/60 | E-2 | 3.5 |
| Example 59 | A-2 | B-1 | 8 | C-1 | 15 | S1/S2 | 40/60 | E-3 | 2.5 |
| Example 60 | A-2 | B-3 | 6 | C-2 | 20 | S1/S2 | 40/60 | E-4 | 1.5 |

TABLE 9-continued

| | | | | | | | | | |
|---|---|---|---|---|---|---|---|---|---|
| Example 61 | A-2 | B-5 | 8 | C-3 | 15 | S1/S2 | 40/60 | E-3 | 3.5 |
| Example 62 | A-2 | B-6 | 8 | C-2 | 15 | S1/S2 | 40/60 | E-3 | 2.5 |
| Example 63 | A-2 | B-7 | 10 | C-2 | 10 | S1/S2 | 40/60 | E-5 | 1.5 |
| Example 64 | A-3 | B-1 | 12 | C-1 | 15 | S1/S2 | 40/60 | E-3 | 2.5 |
| Example 65 | A-3 | B-4 | 12 | C-3 | 10 | S1/S2 | 40/60 | E-6 | 1.5 |
| Example 66 | A-4 | B-1 | 8 | C-1 | 15 | S1/S2 | 40/60 | E-3 | 2.5 |
| Example 67 | A-4 | B-5 | 8 | C-2 | 15 | S1/S2 | 40/60 | E-3 | 2.5 |
| Example 68 | A-4 | B-7 | 10 | C-3 | 15 | S1/S2 | 40/60 | E-1 | 2.5 |
| Example 69 | A-5 | B-3 | 12 | C-1 | 10 | S1/S2 | 40/60 | E-3 | 2.5 |
| Example 70 | A-5 | B-6 | 12 | C-2 | 15 | S1/S2 | 40/60 | E-2 | 2.5 |
| Example 71 | A-6 | B-1 | 8 | C-2 | 15 | S1/S2 | 40/60 | E-3 | 2.5 |
| Example 72 | A-6 | B-5 | 10 | C-3 | 10 | S1/S2 | 40/60 | E-4 | 1.5 |
| Example 73 | A-7 | B-1 | 8 | C-1 | 15 | S1/S2 | 40/60 | E-5 | 2.0 |
| Example 74 | A-7 | B-4 | 12 | C-2 | 10 | S1/S2 | 40/60 | E-3 | 1.5 |
| Comparative Example 11 | A-1 | B-1 | 8 | — | — | S1/S2 | 40/60 | E-3 | 1.5 |
| Comparative Example 12 | A-1 | B-2 | 12 | — | — | S1/S2 | 40/60 | E-3 | 1.5 |

| | Surfactant | Entire Solid Content Concentration | Sensitivity (μC/cm²) | Resolution (nm) | Pattern Profile | LER (nm) |
|---|---|---|---|---|---|---|
| Example 55 | W-1 | 4.0 | 10.5 | 55 | rectangular | 6.5 |
| Example 56 | W-1 | 4.0 | 9.0 | 60 | rectangular | 6.5 |
| Example 57 | W-2 | 4.0 | 11.5 | 55 | rectangular | 6 |
| Example 58 | W-1 | 4.0 | 11.6 | 50 | rectangular | 6.5 |
| Example 59 | W-1 | 4.0 | 13.0 | 55 | rectangular | 6.3 |
| Example 60 | W-2 | 4.0 | 10.5 | 60 | rectangular | 6.6 |
| Example 61 | W-1 | 4.0 | 11.5 | 50 | rectangular | 6 |
| Example 62 | W-3 | 4.0 | 11.5 | 55 | rectangular | 6.2 |
| Example 63 | W-1 | 4.0 | 9.0 | 50 | rectangular | 6.5 |
| Example 64 | W-3 | 4.0 | 13.5 | 75 | rectangular | 8.2 |
| Example 65 | W-1 | 4.0 | 10.0 | 75 | rectangular | 8.7 |
| Example 66 | W-1 | 4.0 | 11.5 | 65 | rectangular | 7.9 |
| Example 67 | W-1 | 4.0 | 11.5 | 60 | rectangular | 7.7 |
| Example 68 | W-2 | 4.0 | 12.5 | 60 | rectangular | 7.8 |
| Example 69 | W-3 | 4.0 | 11.0 | 65 | rectangular | 7.8 |
| Example 70 | W-1 | 4.0 | 13.5 | 65 | rectangular | 7.9 |
| Example 71 | W-1 | 4.0 | 11.5 | 60 | rectangular | 8 |
| Example 72 | W-2 | 4.0 | 9.0 | 60 | rectangular | 7.8 |
| Example 73 | W-1 | 4.0 | 15.5 | 70 | rectangular | 8.1 |
| Example 74 | W-3 | 4.0 | 14.5 | 70 | rectangular | 8.3 |
| Comparative Example 11 | W-1 | 4.0 | 32.0 | 85 | tapered | 13.1 |
| Comparative Example 12 | W-1 | 4.0 | 27.5 | 75 | tapered | 12.5 |

The concentration of each component is the concentration (mass %) based on the entire solid content concentration.

Acid generators, acid-increasing agents and basic compounds used in Examples are shown below.

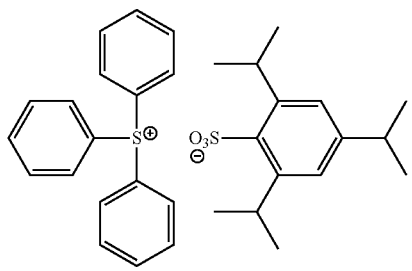

(B-1)

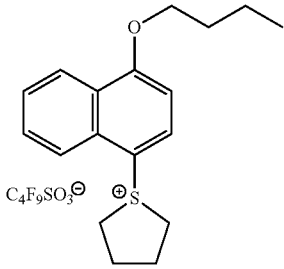

(B-3)

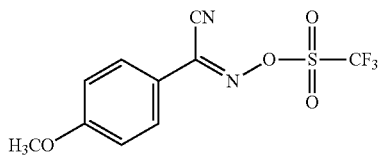

(B-2)

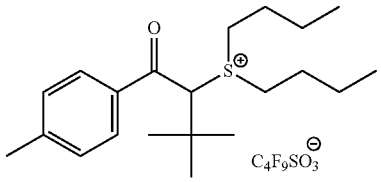

(B-4)

(B-5)
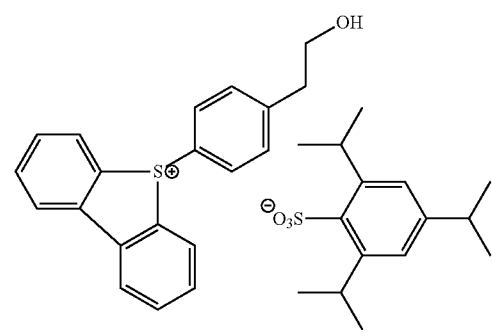
(B-6)
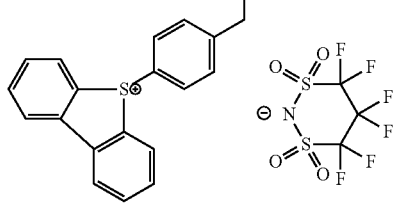
(B-7)
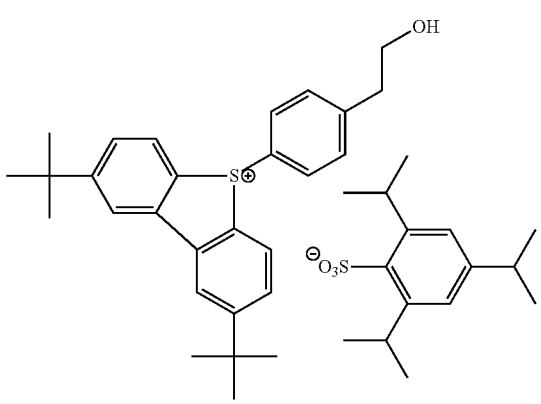
(C-1)
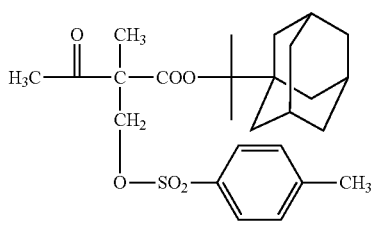
(C-2)
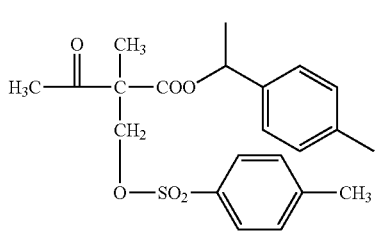
(C-3)
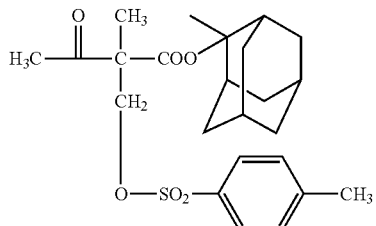
(E-1)
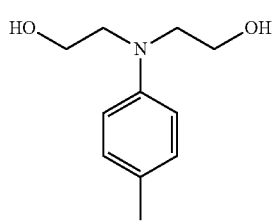
(E-2)
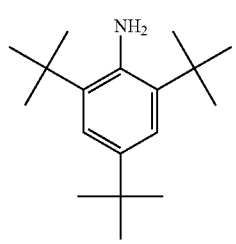
(E-3)
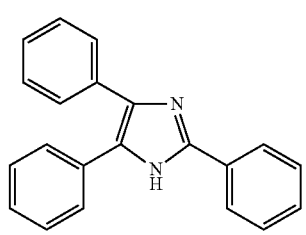
(E-4)
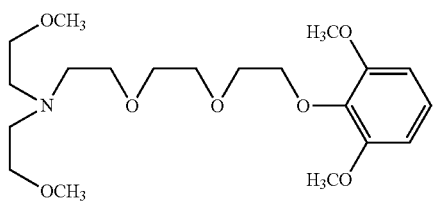
(E-5)
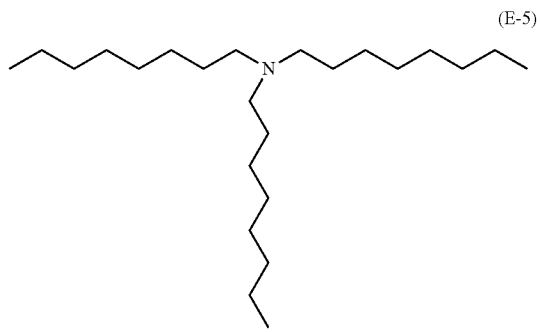

-continued

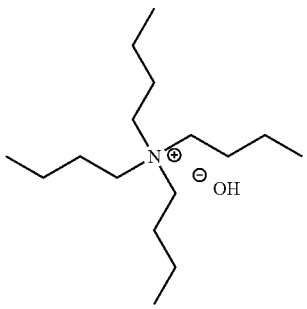
(E-6)

Surfactants and solvents used in Examples are shown below.
W-1: Megaface F-176 (produced by Dainippon Ink & Chemicals, Inc., fluorine-containing)
W-2: Megaface R08 (produced by Dainippon Ink & Chemicals, Inc., fluorine- and silicon-containing)
W-3: Polysiloxane Polymer (produced by Shin-Etsu Chemical Co., Ltd., silicon-containing)
S1: Propylene glycol monomethyl ether acetate
S2: Propylene glycol monomethyl ether As apparent from Table 9, the positive resist composition of the present invention satisfies all of high sensitivity, high resolution, good pattern profile and good line edge roughness at the same time.

<Evaluation of Resist (EUV Light)>

The prepared positive resist solution was uniformly applied by a spin coater on a silicon substrate treated with hexamethyldisilazane, and dried by heating on a hot plate at 110° C. for 90 seconds to form a 100 nm-thick resist film.

This resist film was irradiated by an EUV exposure apparatus (manufactured by Litho Tech Japan Corp., wavelength: 13 nm) and immediately after irradiation, heated on a hot plate at 110° C. for 90 seconds. Furthermore, the resist film was developed with an aqueous tetramethylammonium hydroxide solution in a concentration of 2.38 mass % at 23° C. for 60 seconds, rinsed with pure water for 30 seconds and then dried to form a line-and-space pattern. The obtained pattern was evaluated by the following methods.

[Sensitivity]

The cross-sectional profile of the pattern obtained was observed using a scanning electron microscope (S-9220, manufactured by Hitachi, Ltd.). The minimum irradiation energy for resolving a 100-nm line (line:space=1:1) was defined as the sensitivity.

[Pattern Profile]

The cross-sectional profile of a 100-nm line pattern at the irradiation dose of giving the above-described sensitivity was observed using a scanning electron microscope (S-4300, manufactured by Hitachi, Ltd.) and evaluated on a scale of three grades of rectangular, slightly tapered and tapered.

TABLE 10

| | (A) Resin | (B) Acid Generator | (B) Concentration | (C) Acid-Increasing Agent | (C) Concentration | (D) Organic Solvent | Ratio by Mass | (E) Basic Compound | (E) Concentration | Surfactant | Entire Solid Content Concentration | Sensitivity (mJ/cm²) | Pattern Profile |
|---|---|---|---|---|---|---|---|---|---|---|---|---|---|
| Example 75 | A-1 | B-1 | 6 | C-1 | 15 | S1/S2 | 40/60 | E-3 | 2.5 | W-1 | 4.0 | 15.6 | rectangular |
| Example 76 | A-1 | B-5 | 8 | C-3 | 15 | S1/S2 | 40/60 | E-3 | 2.5 | W-2 | 4.0 | 16.9 | rectangular |
| Example 77 | A-2 | B-1 | 8 | C-1 | 15 | S1/S2 | 40/60 | E-3 | 2.5 | W-1 | 4.0 | 18.0 | rectangular |
| Example 78 | A-2 | B-7 | 10 | C-2 | 10 | S1/S2 | 40/60 | E-5 | 1.5 | W-1 | 4.0 | 14.7 | rectangular |
| Example 79 | A-4 | B-5 | 8 | C-2 | 15 | S1/S2 | 40/60 | E-3 | 2.5 | W-1 | 4.0 | 15.2 | rectangular |
| Comparative Example 13 | A-1 | B-1 | 8 | — | — | S1/S2 | 40/60 | E-3 | 1.5 | W-1 | 4.0 | 55.0 | tapered |
| Comparative Example 14 | A-1 | B-2 | 12 | — | — | S1/S2 | 40/60 | E-3 | 1.5 | W-1 | 4.0 | 53.0 | tapered |

The concentration of each component is the concentration (mass %) based on the entire solid content concentration.

Examples 75 to 79 and Comparative Examples 13 and 14

<Preparation of Resist>

The components shown in Table 10 below were dissolved in a mixed solvent shown in Table 10, and the obtained solution was filtered through a polytetrafluoroethylene filter having a pore size of 0.1 μm to prepare a positive resist solution having an entire solid content concentration (mass %) shown in Table 10. The positive resist solutions prepared were evaluated as follows. In Table 10, the concentration (mass %) of each component is based on the entire solid content. The amount of the surfactant added is 0.1 mass % based on the entire solid content of the resist solution. Incidentally, separately from the surfactant shown in Table 10, polyoxyethylene lauryl ether was added in an amount of 0.1 mass % based on the entire solid content of the resist composition.

The solid content concentration of the acid-decomposable resin is an amount obtained by subtracting the amounts of acid generator, acid-increasing agent, basic compound and surfactant from the entire solid content of the positive resist composition.

The denotations of compounds used in Table 10 are the same as those in Table 9.

As apparent from Table 10, the positive resist composition of the present invention satisfies both high sensitivity and good pattern profile at the same time.

Industrial Applicability

The positive resist composition of the present invention exhibits good performance in terms of pattern profile, line edge roughness, pattern collapse, sensitivity and resolution in normal exposure (dry exposure), immersion exposure and double exposure.

Also, according to the present invention, a positive resist composition for electron beam, X-ray or EUV light, satisfying all of high sensitivity, high resolution, good pattern profile and good line edge roughness at the same time, particularly, in electron beam, X-ray or EUV exposure, and a pattern forming method using the composition can be provided.

The positive resist composition of the present invention is suitably used in the process of producing a semiconductor such as IC, in the production of a circuit board for liquid crystal, thermal head and the like, in other photo-fabrication processes, or in a lithographic printing plate or an acid-curable composition.

While the invention has been described in detail and with reference to specific embodiments thereof, it will be apparent to one skilled in the art that various changes and modifications can be made therein without departing from the spirit and scope thereof.

This application is based on Japanese Patent Application (Patent Application No. 2007-209034) filed on Aug. 10, 2007, Japanese Patent Application (Patent Application No. 2007-245331) filed on Sep. 21, 2007, Japanese Patent Application (Patent Application No. 2008-005705) filed on Jan. 15, 2008, and Japanese Patent Application (Patent Application No. 2008-074740) filed on Mar. 21, 2008, the contents of which are incorporated herein by way of reference.

The invention claimed is:

1. A positive resist composition, comprising:
(A) a compound capable of generating an acid upon irradiation with an actinic ray or radiation;
(B) a resin capable of increasing a solubility of the resin (B) in an alkali developer by an action of an acid; and
(C) a compound represented by the following formula (I), which decomposes by an action of an acid to generate an acid:

wherein $R_1$ represents an alkyl group, a cycloalkyl group, an alkoxy group, an aryl group or an aryloxy group;
$R_2$ represents an alkyl group or a cycloalkyl group;
$R_1$ and $R_2$ may combine with each other to form a monocyclic or polycyclic hydrocarbon structure;
each of $R_3$ and $R_4$ independently represents a hydrogen atom or an alkyl group;
$R_5$ represents a group capable of leaving by an action of an acid;
X represents —$SO_2$13 , —SO— or —CO—; and
Z represents a residue of an organic acid represented by ZH;
wherein the compound represented by formula (I) is a compound represented by the following formula (Ia):

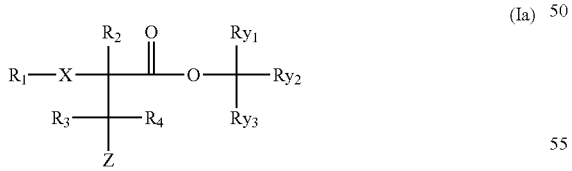

wherein $R_1$ represents an alkyl group, a cycloalkyl group, an alkoxy group, an aryl group or an aryloxy group;
$R_2$ represents an alkyl group or a cycloalkyl group;
$R_1$ and $R_2$ may combine with each other to form a monocyclic or polycyclic hydrocarbon structure;
each of $R_3$ and $R_4$ independently represents a hydrogen atom or an alkyl group;
X represents —$SO_2$—, —SO— or —CO—;
Z represents a residue of an organic acid represented by ZH; and each of $Ry_1$ to $Ry_3$ independently represents an alkyl group or a cycloalkyl group, and at least two members out of $Ry_1$ to $Ry_3$ may combine with each other to form a monocyclic or polycyclic hydrocarbon structure, provided that at least one of $Ry_1$ to $Ry_3$ represents a cycloalkyl group or at least two members out of $Ry_1$ to $Ry_3$ are combined to form a monocyclic or polycyclic hydrocarbon structure.

2. The positive resist composition according to claim 1, wherein ZH is an organic acid selected from the group consisting of a sulfonic acid, a carboxylic acid, an imide acid and a methide acid.

3. The positive resist composition according to claim 1, which further comprises:
a hydrophobic resin.

4. A pattern forming method, comprising:
forming a resist film from the positive resist composition according to claim 1; and subjecting the resist film to exposure and development.

5. The pattern forming method according to claim 4, wherein the exposure is immersion exposure.

6. The pattern forming method according to claim 5, further comprising:
forming a hydrophobic resin-containing topcoat on the resist film before subjecting the resist film to the immersion exposure and the development.

7. The positive resist composition according to claim 1, wherein the resin (B) capable of increasing the solubility of the resin (B) in an alkali developer by an action of an acid is an acid-decomposable resin containing hydroxystyrene as a repeating unit.

8. The positive resist composition according to claim 7, wherein the resin (B) contains a repeating unit represented by the following formula (III) and a repeating unit represented by the following formula (IV):

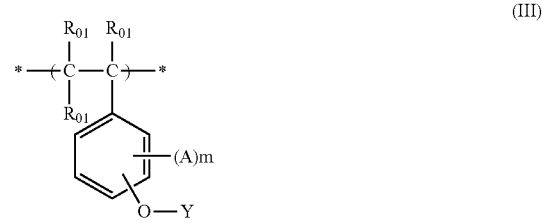

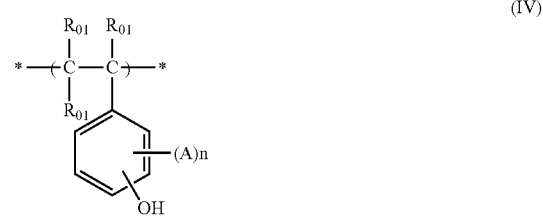

wherein in formulae (III) and (VI), each $R_{01}$ independently represents a hydrogen atom, an alkyl group, a cycloalkyl group, a halogen atom, a cyano group or an alkoxycarbonyl group;
Y represents a group capable of leaving by the action of an acid;
A represents a halogen atom, a cyano group, an acyl group, an alkyl group, an alkoxy group, an acyloxy group or an alkoxycarbonyl group;
m represents an integer of 0 to 4; and
n represents an integer of 0 to 4.

9. The positive resist composition according to claim 7, which further comprises:
a hydrophobic resin.

10. A positive resist composition, comprising:
(A) a compound capable of generating an acid upon irradiation with an actinic ray or radiation;
(B) a resin capable of increasing a solubility of the resin (B) in an alkali developer by an action of an acid; and
(C) a compound represented by the following formula (I), which decomposes by an action of an acid to generate an acid:

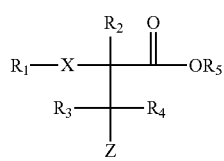
(I)

wherein $R_1$ represents an alkyl group, a cycloalkyl group, an alkoxy group, an aryl group or an aryloxy group;
$R_2$ represents an alkyl group or a cycloalkyl group;
$R_1$ and $R_2$ may combine with each other to form a monocyclic or polycyclic hydrocarbon structure;
each of $R_3$ and $R_4$ independently represents a hydrogen atom or an alkyl group;
$R_5$ represents a group capable of leaving by an action of an acid;
X represents —$SO_2$—, —SO— or —CO—; and
Z represents a residue of an organic acid represented by ZH;
wherein the compound represented by formula (I) is a compound represented by the following formula (II):

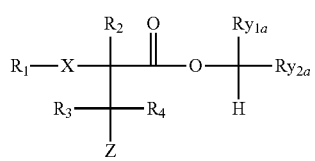
(II)

wherein $R_1$ represents an alkyl group, a cycloalkyl group, an alkoxy group, an aryl group or an aryloxy group;
$R_2$ represents an alkyl group or a cycloalkyl group;
$R_1$ and $R_2$ may combine with each other to form a monocyclic or polycyclic hydrocarbon structure;
each of $R_3$ and $R_4$ independently represents a hydrogen atom or an alkyl group;
$Ry_{1a}$ represents a hydrogen atom, an alkyl group, a cycloalkyl group, an alkoxy group, or an alkylene group bonded to $Ry_{2a}$;
$Ry_{2a}$ represents an aryl group or an aryloxy group;
X represents —$SO_2$—, —SO— or —CO—; and
Z represents a residue of an organic acid represented by ZH.

11. The positive resist composition according to claim 10, wherein the compound represented by formula (II) is a compound represented by the following formula (IIa) or (IIb):

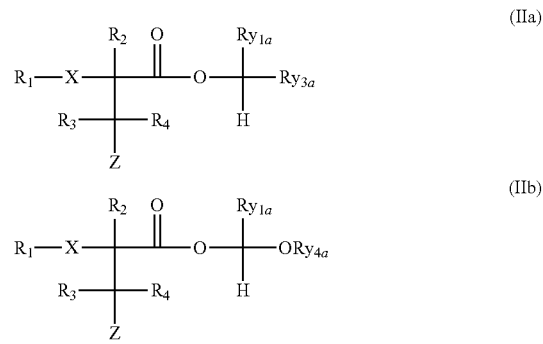

wherein $R_1$ represents an alkyl group, a cycloalkyl group, an alkoxy group, an aryl group or an aryloxy group;
$R_2$ represents an alkyl group or a cycloalkyl group;
$R_1$ and $R_2$ may combine with each other to form a monocyclic or polycyclic hydrocarbon structure;
each of $R_3$ and $R_4$ independently represents a hydrogen atom or an alkyl group;
$Ry_{1a}$ represents a hydrogen atom, an alkyl group, a cycloalkyl group, an alkoxy group, or an alkylene group bonded to $Ry_{3a}$ or $Ry_{4a}$;
$Ry_{3a}$ represents an aryl group;
$Ry_{4a}$ represents an aryl group;
X represents —$SO_2$—, —SO— or —CO—; and
Z represents a residue of an organic acid represented by ZH.

12. The positive resist composition according to claim 10, wherein ZH is an organic acid selected from the group consisting of a sulfonic acid, a carboxylic acid, an imide acid and a methide acid.

13. The positive resist composition according to claim 10, which further comprises:
a hydrophobic resin.

14. The positive resist composition according to claim 10, wherein $Ry_{1a}$ represents a hydrogen atom, an alkyl group, or a cycloalkyl group.

15. A compound represented by the following:
formula (II):

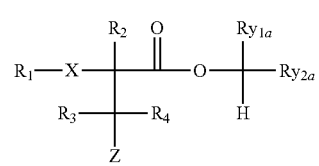
(II)

wherein $R_1$ represents an alkyl group, a cycloalkyl group, an alkoxy group, an aryl group or an aryloxy group;
$R_2$ represents an alkyl group or a cycloalkyl group;
$R_1$ and $R_2$ may combine with each other to form a monocyclic or polycyclic hydrocarbon structure;
each of $R_3$ and $R_4$ independently represents a hydrogen atom or an alkyl group;
$Ry_{1a}$ represents a hydrogen atom, an alkyl group, a cycloalkyl group, an alkoxy group, or an alkylene group bonded to $Ry_{2a}$;
$Ry_{2a}$ represents an aryl group or an aryloxy group;
X represents —$SO_2$—, —SO— or —CO—; and
Z represents a residue of an organic acid represented by ZH.

16. The compound according to claim 15, which is a compound represented by the following formula (IIa) or (IIb):

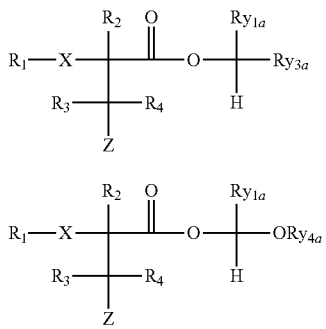

(IIa)

(IIb)

wherein $R_1$ represents an alkyl group, a cycloalkyl group, an alkoxy group, an aryl group or an aryloxy group;
$R_2$ represents an alkyl group or a cycloalkyl group;
$R_1$ and $R_2$ may combine with each other to form a monocyclic or polycyclic hydrocarbon structure;
each of $R_3$ and $R_4$ independently represents a hydrogen atom or an alkyl group;
$Ry_{1a}$ represents a hydrogen atom, an alkyl group, a cycloalkyl group, an alkoxy group, or an alkylene group bonded to $Ry_{3a}$ or $Ry_{4a}$;
$Ry_{3a}$ represents an aryl group;
$Ry_{4a}$ represents an aryl group;
X represents —$SO_2$—, —SO— or —CO—; and
Z represents a residue of an organic acid represented by ZH.

17. The compound according to claim 15,
wherein ZH is an organic acid selected from the group consisting of a sulfonic acid, an imide acid and a methide acid.

18. The compound according to claim 15, wherein $Ry_{1a}$ represents a hydrogen atom, an alkyl group, or a cycloalkyl group.

* * * * *